United States Patent
Bogen et al.

(10) Patent No.: US 11,680,060 B2
(45) Date of Patent: Jun. 20, 2023

(54) BICYCLOHEPTANE PYRROLIDINE OREXIN RECEPTOR AGONISTS

(71) Applicant: Merck Sharp & Dohme LLC, Rahway, NJ (US)

(72) Inventors: Stephane L. Bogen, Somerset, NJ (US); Dane James Clausen, Rahway, NJ (US); Deodial Guy Guiadeen, Chesterfield, NJ (US); Jinsong Hao, Belle Meade, NJ (US); Shishi Lin, Somerset, NJ (US); Michael T. Rudd, Collegeville, PA (US); Lan Wei, N. Berkeley Heights, NJ (US); Li Xiao, Cranbury, NJ (US); Dexi Yang, Livingston, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 0 days.

(21) Appl. No.: 17/402,932

(22) Filed: Aug. 16, 2021

(65) Prior Publication Data
US 2022/0056017 A1    Feb. 24, 2022

Related U.S. Application Data

(60) Provisional application No. 63/226,798, filed on Jul. 29, 2021, provisional application No. 63/066,908, filed on Aug. 18, 2020.

(51) Int. Cl.
| | | |
|---|---|---|
| *C07D 403/14* | (2006.01) | |
| *C07D 207/14* | (2006.01) | |
| *C07D 401/12* | (2006.01) | |
| *C07D 403/12* | (2006.01) | |
| *C07D 405/14* | (2006.01) | |
| *C07D 417/12* | (2006.01) | |
| *C07D 491/048* | (2006.01) | |

(52) U.S. Cl.
CPC ......... *C07D 403/14* (2013.01); *C07D 207/14* (2013.01); *C07D 401/12* (2013.01); *C07D 403/12* (2013.01); *C07D 405/14* (2013.01); *C07D 417/12* (2013.01); *C07D 491/048* (2013.01)

(58) Field of Classification Search
None
See application file for complete search history.

(56) References Cited

U.S. PATENT DOCUMENTS

| | | |
|---|---|---|
| 9,527,807 B2 | 12/2016 | Fukumoto et al. |
| 10,287,305 B2 | 5/2019 | Fujimoto et al. |
| 10,428,023 B2 | 10/2019 | Kajita et al. |
| 10,508,083 B2 | 12/2019 | Fujimoto et al. |
| 2017/0226137 A1 | 8/2017 | Fujimoto et al. |
| 2020/0255403 A1 | 8/2020 | Bogen et al. |
| 2021/0198240 A1 | 7/2021 | Oda et al. |
| 2021/0269420 A1 | 9/2021 | Fujimoto et al. |
| 2022/0017514 A1 | 1/2022 | Kajita et al. |

FOREIGN PATENT DOCUMENTS

| | | |
|---|---|---|
| EP | 3594202 A1 | 1/2020 |
| EP | 3594203 A1 | 1/2020 |
| EP | 3663281 A1 | 6/2020 |
| EP | 3895707 A1 | 10/2021 |
| WO | 2012137982 A2 | 10/2012 |
| WO | 2017135306 A1 | 8/2017 |
| WO | 2018164191 A1 | 9/2018 |
| WO | 2018164192 A1 | 9/2018 |
| WO | 2019027003 A1 | 2/2019 |
| WO | 2019027058 A1 | 2/2019 |
| WO | 2020004536 A1 | 1/2020 |
| WO | 2020004537 A1 | 1/2020 |
| WO | 2020122092 A1 | 6/2020 |
| WO | 2020122093 A1 | 6/2020 |
| WO | 2020158958 A1 | 8/2020 |

OTHER PUBLICATIONS

Chemelli, Richard M. et al., Narcolepsy in orexin Knockout Mice: Molecular Genetics of Sleep Regulation, Cell, 1999, 437-451, 98.
Harris, Glenda C. et al., Arousal and reward: a dichotomy in orexin function, Trends in Neurosciences, 2006, 571-577, 29(10).
Peyron, Christelle et al., Neurons Containing Hypocretin (Orexin) Project to Multiple Neuronal Systems, The Journal of Neuroscience, 1998, 9996-100150, 18(23).
Sakurai, Takeshi et al., Orexins and Orexin Receptors: A Family of Hypothalamic Neuropeptides and G Protein-Coupled Receptors that Regulate Feeding Behavior, Cell, 1998, 573-585, 92.

*Primary Examiner* — Samantha L Shterengarts
(74) *Attorney, Agent, or Firm* — John C. Todaro; Dianne Pecoraro

(57) ABSTRACT

The present invention is directed to bicyclo[4.1.0]heptane pyrrolidine compounds which are agonists of orexin receptors. The present invention is also directed to uses of the compounds described herein in the potential treatment or prevention of neurological and psychiatric disorders and diseases in which orexin receptors are involved. The present invention is also directed to compositions comprising these compounds. The present invention is also directed to uses of these compositions in the potential prevention or treatment of such diseases in which orexin receptors are involved.

37 Claims, No Drawings

BICYCLOHEPTANE PYRROLIDINE OREXIN RECEPTOR AGONISTS

BACKGROUND OF THE INVENTION

The orexins (hypocretins) comprise two neuropeptides produced in the hypothalamus: orexin A (OX-A) (a 33 amino acid peptide) and the orexin B (OX-B) (a 28 amino acid peptide) (Sakurai T. et al., Cell, 1998, 92, 573-585). Orexins regulate states of sleep and wakefulness opening potentially novel therapeutic approaches for narcolepsy, idiopathic hypersomnia, excessive daytime sleepiness, shift work disorder, obstructive sleep apnea and insomnia (Chemelli R. M. et al., Cell, 1999, 98, 437-451). Orexins are found to stimulate food consumption in rats suggesting a physiological role for these peptides as mediators in the central feedback mechanism that regulates feeding behavior (Sakurai T. et al., Cell, 1998, 92, 573-585). Orexins have also been indicated as playing a role in arousal, emotion, energy homeostasis, reward, learning and memory (Peyron, et al., Journal Neurosci., 1998, 18(23):9996-100150, Harris, et al., Trends Neurosci., 2006, 29 (10), 571-577). Two orexin receptors have been cloned and characterized in mammals. They belong to the super family of G-protein coupled receptors (Sakurai T. et al., Cell, 1998, 92, 573-585): the orexin-1 receptor (OX or OX1R) is partially selective for OX-A and the orexin-2 receptor (OX2 or OX2R) is capable of binding OX-A as well as OX-B with similar affinity. The physiological actions in which orexins are presumed to participate are thought to be expressed via one or both of OX1 receptor and OX2 receptor as the two subtypes of orexin receptors.

SUMMARY OF THE INVENTION

The present invention is directed to bicyclo[4.1.0]heptane pyrrolidine compounds which are agonists of orexin receptors. The present invention is also directed to uses of the compounds described herein in the potential treatment or prevention of neurological and psychiatric disorders and diseases in which orexin receptors are involved. The present invention is also directed to compositions comprising these compounds. The present invention is also directed to uses of these compositions in the potential prevention or treatment of such diseases in which orexin receptors are involved.

DETAILED DESCRIPTION OF THE INVENTION

The present invention is directed to compounds of the formula I:

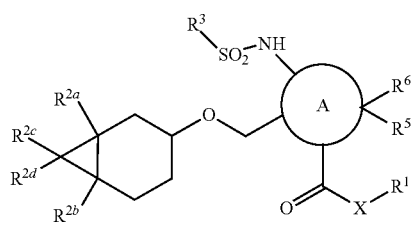

wherein:

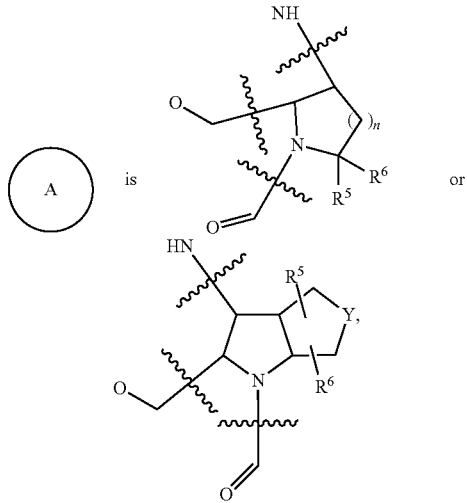

wherein n is 0 or 1;
X is —O— or —NH—, or X may be a direct bond to $R^1$;
Y is O or $CH_2$;
$R^1$ is selected from:
  (1) —$C_{1-6}$alkyl, where the alkyl is unsubstituted or substituted with one to six substituents independently selected from $R^4$,
  (2) —$C_{3-6}$cycloalkyl, where the cycloalkyl is unsubstituted or substituted with one to six substituents independently selected from $R^4$; and
  (3) -heterocyclyl, where the heterocyclyl is unsubstituted or substituted with one to three substituents independently selected from $R^4$;
$R^{2a}$ and $R^{2b}$ are selected from:
  (1) hydrogen,
  (2) —$C_{1-6}$alkyl, where the alkyl is unsubstituted or substituted with one to six substituents independently selected from $R^4$,
  (3) —$C_{3-6}$cycloalkyl, where the cycloalkyl is unsubstituted or substituted with one to six substituents independently selected from $R^4$,
  (4) -phenyl, where the phenyl is unsubstituted or substituted with one to three substituents independently selected from $R^4$, and
  (5) -heteroaryl, where the heteroaryl is selected from: pyridyl, pyrimidinyl, benzothiazolyl, thiazolyl and pyrazinyl, and the heteroaryl is unsubstituted or substituted with one to three substituents independently selected from $R^4$,
Provided that at least one of $R^{2a}$ and $R^{2b}$ is hydrogen;
$R^{2c}$ and $R^{2d}$ are independently selected from:
  (1) hydrogen, and
  (2) fluoro;
$R^3$ is selected from:
  (1) —$C_{1-6}$alkyl, where the alkyl is unsubstituted or substituted with one to six substituents independently selected from $R^4$,
  (2) —$C_{3-6}$cycloalkyl, where the cycloalkyl is unsubstituted or substituted with one to six substituents independently selected from $R^4$,
  (3) -phenyl, where the phenyl is unsubstituted or substituted with one to three substituents independently selected from $R^4$,
  (4) —$NR^{10}R^{11}$, wherein $R^{10}$ and $R^{11}$ are independently selected from:

(a) hydrogen, and
(b) $C_{1-6}$alkyl, which is unsubstituted or substituted with one to six $R^4$,
(5) -heterocyclyl, where the heterocyclyl is unsubstituted or substituted with one to three substituents independently selected from $R^4$,
(6) —$CHF_2$, and
(7) —$CF_3$;

$R^4$ is independently selected from:
(1) hydroxyl,
(2) halogen,
(3) $C_{1-6}$alkyl, which is unsubstituted or substituted with one to six substituents independently selected from $R^7$,
(4) $C_{2-4}$alkenyl,
(5) $C_{2-4}$alkynyl,
(6) —$C_{3-6}$cycloalkyl, which is unsubstituted or substituted with one to six substituents independently selected from $R^7$,
(7) —O—$C_{1-6}$alkyl, where the alkyl is unsubstituted or substituted with one to six substituents independently selected from $R^7$,
(8) —O(C=O)—$C_{1-6}$alkyl,
(9) —$NH_2$,
(10) —NH—$C_{1-6}$alkyl,
(11) —$NO_2$,
(12) phenyl,
(13) —$CO_2H$,
(14) —$SO_2$—$C_{1-6}$alkyl,
(15) —$C_{3-5}$cycloalkyl($SO_2$),
(16) —CN,
(17) -heterocyclyl, where the heterocyclyl is unsubstituted or substituted with one to three substituents independently selected from $R^7$,
(18) —$CHF_2$, and
(19) —$CF_3$;

$R^5$ and $R^6$ are independently selected from:
(1) hydrogen,
(2) $C_{1-6}$alkyl, where the alkyl is unsubstituted or substituted with one to six substituents independently selected from $R^4$, and
(3) —$C_{3-6}$cycloalkyl, where the cycloalkyl is unsubstituted or substituted with one to six substituents independently selected from $R^4$,
or $R^5$ and $R^6$ are joined together with the carbon atoms to which they are attached to form a —$C_{3-6}$cycloalkyl ring, where the cycloalkyl is unsubstituted or substituted with one to six substituents independently selected from $R^4$;

$R^7$ is independently selected from:
(1) halogen,
(2) $C_{1-6}$alkyl, which is unsubstituted or substituted with one to six substituents independently selected from halo, phenyl or cycloalkyl,
(3) —$CHF_2$, and
(4) —$CF_3$;

or a pharmaceutically acceptable salt thereof.

The present invention is directed to compounds of the formula IA:

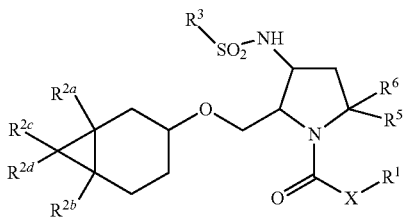

wherein:
X is —O— or —NH—, or X may be a direct bond to $R^1$;
$R^1$ is selected from:
(1) —$C_{1-6}$alkyl, where the alkyl is unsubstituted or substituted with one to six substituents independently selected from $R^4$, and
(2) —$C_{3-6}$cycloalkyl, where the cycloalkyl is unsubstituted or substituted with one to six substituents independently selected from $R^4$;

$R^{2a}$ and $R^{2b}$ are selected from:
(1) hydrogen,
(2) —$C_{1-6}$alkyl, where the alkyl is unsubstituted or substituted with one to six substituents independently selected from $R^4$,
(3) —$C_{3-6}$cycloalkyl, where the cycloalkyl is unsubstituted or substituted with one to six substituents independently selected from $R^4$,
(4) -phenyl, where the phenyl is unsubstituted or substituted with one to three substituents independently selected from $R^4$, and
(5) -heteroaryl, where the heteroaryl is selected from: pyridyl, pyrimidinyl, and pyrazinyl, and the heteroaryl is unsubstituted or substituted with one to three substituents independently selected from $R^4$,
Provided that at least one of $R^{2a}$ and $R^{2b}$ is hydrogen;

$R^{2c}$ and $R^{2d}$ are independently selected from:
(1) hydrogen, and
(2) fluoro;

$R^3$ is selected from:
(1) —$C_{1-6}$alkyl, where the alkyl is unsubstituted or substituted with one to six substituents independently selected from $R^4$,
(2) —$C_{3-6}$cycloalkyl, where the cycloalkyl is unsubstituted or substituted with one to six substituents independently selected from $R^4$,
(3) -phenyl, where the phenyl is unsubstituted or substituted with one to three substituents independently selected from $R^4$, and
(4) —$NR^{10}R^{11}$, wherein $R^{10}$ and $R^{11}$ are independently selected from:
(a) hydrogen, and
(b) $C_{1-6}$alkyl, which is unsubstituted or substituted with one to six $R^4$;

$R^4$ is selected from:
(1) hydroxyl,
(2) halogen,
(3) $C_{1-6}$alkyl, which is unsubstituted or substituted with one to six fluoro,
(4) $C_{2-4}$alkenyl,
(5) $C_{2-4}$alkynyl,
(6) —$C_{3-6}$cycloalkyl,
(7) —O—$C_{1-6}$alkyl,
(8) —O(C=O)—$C_{1-6}$alkyl,
(9) —$NH_2$,
(10) —NH—$C_{1-6}$alkyl,

(11) —NO$_2$,
(12) phenyl,
(13) —CO$_2$H,
(14) —SO$_2$—C$_{1-6}$alkyl,
(15) —C$_{3-5}$cycloalkyl(SO$_2$), and
(16) —CN;

R$^5$ and R$^6$ are independently selected from:
(1) hydrogen,
(2) C$_{1-6}$alkyl, where the alkyl is unsubstituted or substituted with one to six substituents independently selected from R$^4$, and
(3) —C$_{3-6}$cycloalkyl, where the cycloalkyl is unsubstituted or substituted with one to six substituents independently selected from R$^4$,
or R$^5$ and R$^6$ are joined together with the carbon atoms to which they are attached to form a —C$_{3-6}$cycloalkyl ring, where the cycloalkyl is unsubstituted or substituted with one
to six substituents independently selected from R$^4$;
or a pharmaceutically acceptable salt thereof.

An embodiment of the present invention includes compounds of the formula IB:

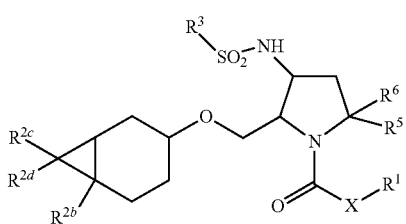

IB wherein X, R$^1$, R$^{2b}$, R$^{2c}$, R$^{2d}$, R$^3$, R$^5$ and R$^6$ are defined herein; or a pharmaceutically acceptable salt thereof.

An embodiment of the present invention includes compounds of the formula IC:

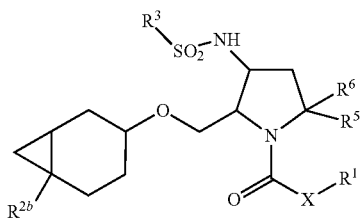

IC wherein X, R$^1$, R$^{2b}$, R$^3$, R$^5$ and R$^6$ are defined herein; or a pharmaceutically acceptable salt thereof.

An embodiment of the present invention includes compounds of the formula IC':

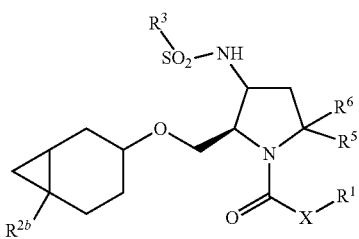

IC' wherein X, R$^1$, R$^2$, R$^3$, R$^5$ and R$^6$ are defined herein; or a pharmaceutically acceptable salt thereof.

An embodiment of the present invention includes compounds of the formula IC":

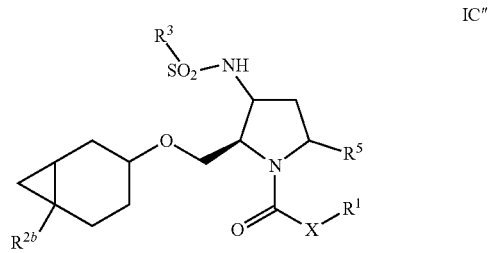

IC"

wherein X, R$^1$, R$^{2b}$, R$^3$ and R$^5$ are defined herein; or a pharmaceutically acceptable salt thereof.

An embodiment of the present invention includes compounds of the formula IC''':

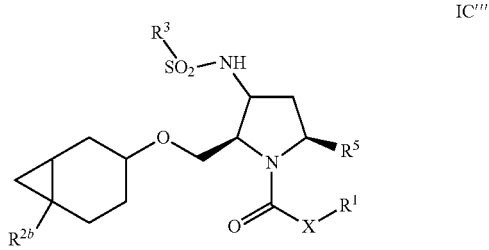

IC''' wherein X, R$^1$, R$^{2b}$, R$^3$ and R$^5$ are defined herein; or a pharmaceutically acceptable salt thereof.

An embodiment of the present invention includes compounds of the formula ID:

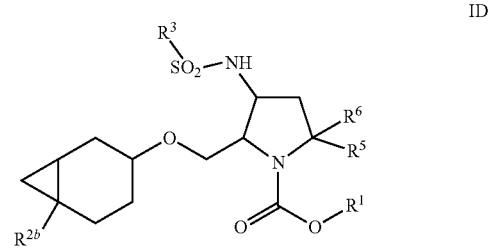

ID wherein R$^1$, R$^{2b}$, R$^3$, R$^5$ and R$^6$ are defined herein; or a pharmaceutically acceptable salt thereof.

An embodiment of the present invention includes compounds of the formula ID':

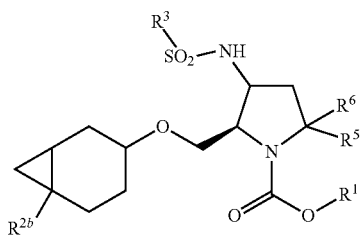

wherein $R^1$, $R^2$, $R^3$, $R^5$ and $R^6$ are defined herein; or a pharmaceutically acceptable salt thereof.

An embodiment of the present invention includes compounds of the formula ID'':

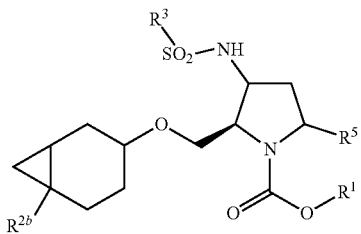

wherein $R^1$, $R^{2b}$, $R^3$ and $R^5$ are defined herein; or a pharmaceutically acceptable salt thereof.

An embodiment of the present invention includes compounds of the formula ID''':

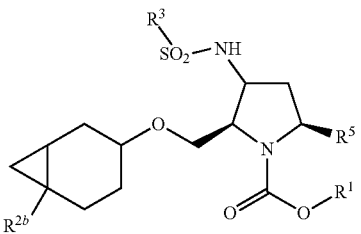

wherein $R^1$, $R^{2b}$, $R^3$ and $R^5$ are defined herein; or a pharmaceutically acceptable salt thereof.

An embodiment of the present invention includes compounds of the formula IE:

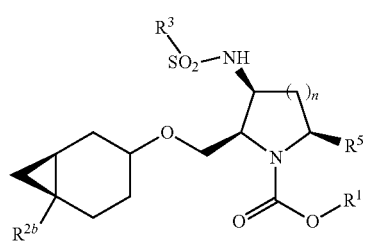

wherein n, $R^1$, $R^{2b}$, $R^3$ and $R^5$ are defined herein; or a pharmaceutically acceptable salt thereof.

An embodiment of the present invention includes compounds of the formula IE wherein n is 0.

An embodiment of the present invention includes compounds wherein

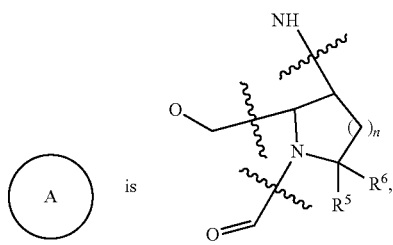

wherein n is 0 or 1. An embodiment of the present invention includes compounds wherein

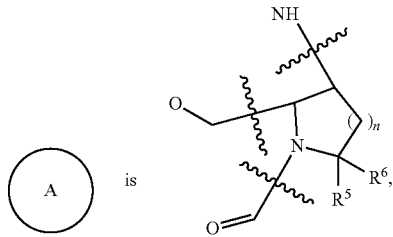

and n is 0.

An embodiment of the present invention includes compounds wherein $R^1$ is selected from:
(1) —$C_{1-6}$alkyl, where the alkyl is unsubstituted or substituted with one to three substituents independently selected from $R^4$,
(2) —$C_{3-6}$cycloalkyl, where the cycloalkyl is unsubstituted or substituted with one to three substituents independently selected from $R^4$, and
(3) -heterocyclyl, where the heterocyclyl is unsubstituted or substituted with one to three substituents independently selected from $R^4$.

An embodiment of the present invention includes compounds wherein $R^1$ is selected from:
(1) —$C_{1-6}$alkyl, which is unsubstituted or substituted with fluoro or —O(C=O)—$C_{1-6}$alkyl,
(2) —$C_{3-6}$cycloalkyl, and
(3) —$CH_2$—$C_{3-6}$cycloalkyl.

An embodiment of the present invention includes compounds wherein $R^1$ is —$C_{1-6}$alkyl, which is unsubstituted or substituted with one to four substituents independently selected from $R^4$.

An embodiment of the present invention includes compounds wherein $R^1$ is selected from:
(1) methyl,
(2) ethyl,
(3) —$CH_2OH$,
(4) —$CH_2CF_3$,
(5) —$CH_2CHF_2$,
(6) —$CH(CH_3)_2$,
(7) —$CH_2CH_2CH_2F$,
(8) cyclopropyl,
(9) —$CH_2$-cyclopropyl,
(10) —$CH_2$-cyclobutyl, and
(11) —$CH_2O(C=O)CH_3$.

An embodiment of the present invention includes compounds wherein $R^1$ is methyl.

An embodiment of the present invention includes compounds wherein X is —O—. An embodiment of the present invention includes compounds wherein X is —O— and $R^1$ is methyl. An embodiment of the present invention includes compounds wherein X is —O— and $R^1$ is ethyl. An embodiment of the present invention includes compounds wherein X is —O— and $R^1$ is —CH(CH$_3$)$_2$.

An embodiment of the present invention includes compounds wherein $R^{2a}$ and $R^{2b}$ are selected from:
(1) hydrogen,
(2) —C$_{1-6}$alkyl, where the alkyl is unsubstituted or substituted with one to three substituents independently selected from $R^4$,
(3) -phenyl, where the phenyl is unsubstituted or substituted with one to three substituents independently selected from $R^4$, and
(4) -heteroaryl, where the heteroaryl is selected from: pyridyl, pyrimidinyl, benzothiazolyl, thiazolyl and pyrazinyl, and the heteroaryl is unsubstituted or substituted with one to three substituents independently selected from $R^4$;
Provided that at least one of $R^{2a}$ and $R^{2b}$ is hydrogen.

An embodiment of the present invention includes compounds wherein $R^{2a}$ and $R^{2b}$ are selected from:
(1) hydrogen,
(2) —C$_{1-6}$alkyl, where the alkyl is unsubstituted or substituted with one to three fluoro,
(3) phenyl, which is unsubstituted or substituted with one to three fluoro, —CN, or —C$_{1-6}$alkyl, where the alkyl is unsubstituted or substituted with one to three fluoro, and
(4) heteroaryl, where the heteroaryl is selected from: pyridyl, pyrimidinyl, benzothiazolyl, thiazolyl and pyrazinyl, and the heteroaryl is unsubstituted or substituted with one to three substituents selected from halo, —C$_{3-6}$cycloalkyl, —O—C$_{1-6}$alkyl, CN, or —C$_{1-6}$alkyl, where the alkyl is unsubstituted or substituted with one to three fluoro;
Provided that at least one of $R^{2a}$ and $R^{2b}$ is hydrogen.

An embodiment of the present invention includes compounds wherein $R^{2a}$ and $R^{2b}$ are selected from:
(1) hydrogen,
(2) —CH$_2$(CH$_3$)$_2$,
(3) —CF$_3$,
(4) —CH$_2$CHF$_2$,
(5) —CH$_2$CF$_3$,
(6) pyridyl,
(7) pyrimidinyl,
(8) pyrazinyl,
(9) phenyl,
(10) benzothiazolyl, and
(11) thiazolyl,
Wherein said pyridyl, pyrimidinyl, pyrazinyl, phenyl, benzothiazolyl or thiazolyl is unsubstituted or substituted with halo, —C$_{3-6}$cycloalkyl, —O—C$_{1-6}$alkyl, CN, or —C$_{1-6}$alkyl, where the alkyl is unsubstituted or substituted with one to three fluoro;
Provided that at least one of $R^{2a}$ and $R^{2b}$ is hydrogen.

An embodiment of the present invention includes compounds wherein $R^{2a}$ and $R^{2b}$ are selected from:
(1) hydrogen,
(2) phenyl, which is unsubstituted or substituted with one to three substituents independently selected from $R^4$, and
(3) pyrimidinyl, which is unsubstituted or substituted with one to three substituents independently selected from $R^4$,
Provided that at least one of $R^{2a}$ and $R^{2b}$ is hydrogen.

An embodiment of the present invention includes compounds wherein $R^{2a}$ and $R^{2b}$ are selected from:
(1) hydrogen,
(2) —CH$_2$(CH$_3$)$_2$,
(3) —CF$_3$,
(4) —CH$_2$CHF$_2$,
(5) —CH$_2$CF$_3$,
(6) phenyl,
(7) phenyl-CF$_3$,
(8) phenyl-CH$_2$CF$_3$,
(9) fluorophenyl,
(10) difluorophenyl,
(11) trifluorophenyl,
(12) phenyl-CN,
(13) pyridyl,
(14) pyrimidinyl, wherein said pyrimidinyl is unsubstituted or substituted with halo, C$_{3-6}$cycloalkyl, —O—C$_{1-6}$alkyl, CN, or —C$_{1-6}$alkyl, where the alkyl is unsubstituted or substituted with one to three fluoro, and
(15) pyrazinyl,
Provided that at least one of $R^{2a}$ and $R^{2b}$ is hydrogen.

An embodiment of the present invention includes compounds wherein $R^{2a}$ and $R^{2b}$ are selected from:
(1) hydrogen, and
(2) pyrimidinyl, wherein said pyrimidinyl is unsubstituted or substituted with halo, —C$_{3-6}$cycloalkyl, —O—C$_{1-6}$alkyl, CN, or —C$_{1-6}$alkyl, where the alkyl is unsubstituted or substituted with one to three fluoro,
Provided that at least one of $R^{2a}$ and $R^{2b}$ is hydrogen.

An embodiment of the present invention includes compounds wherein $R^{2a}$ is hydrogen.

An embodiment of the present invention includes compounds wherein $R^{2b}$ is hydrogen.

An embodiment of the present invention includes compounds wherein $R^{2c}$ is hydrogen and $R^{2d}$ is hydrogen. An embodiment of the present invention includes compounds wherein $R^{2c}$ is hydrogen and $R^{2d}$ is fluoro. An embodiment of the present invention includes compounds wherein $R^{2c}$ is fluoro and $R^{2d}$ is fluoro.

An embodiment of the present invention includes compounds wherein $R^3$ is selected from:
(1) —C$_{1-6}$alkyl, where the alkyl is unsubstituted or substituted with one to four substituents independently selected from $R^4$,
(2) —C$_{3-6}$cycloalkyl, where the cycloalkyl is unsubstituted or substituted with one to four substituents independently selected from $R^4$,
(3) -phenyl, where the phenyl is unsubstituted or substituted with one to three substituents independently selected from $R^4$,
(4) —NR$^{10}$R$^{11}$, wherein R$^{10}$ and R$^{11}$ are independently selected from:
(a) hydrogen, and
(b) C$_{1-6}$alkyl, which is unsubstituted or substituted with one to four $R^4$,
(5) -heterocyclyl, where the heterocyclyl is azetidinyl or oxetanyl and is unsubstituted or substituted with one to three substituents independently selected from $R^4$,
(6) —CHF$_2$, and
(7) —CF$_3$.

An embodiment of the present invention includes compounds wherein $R^3$ is selected from:
(1) —C$_{1-6}$alkyl, where the alkyl is unsubstituted or substituted with one to three fluoro,
(2) —C$_{3-6}$cycloalkyl, (3) —NH$_2$,
(4) —NH(C$_{1-6}$alkyl),
(5) —N(C$_{1-6}$alkyl)(C$_{1-6}$alkyl), and
(6) -phenyl.

An embodiment of the present invention includes compounds wherein R$^3$ is selected from:
(1) methyl,
(2) —CF$_3$,
(3) —CHF$_2$,
(4) —CH$_2$F,
(5) ethyl,
(6) cyclopropyl,
(7) —CH(CH$_3$)$_2$,
(8) —NH(CH$_3$),
(9) —N(CH$_3$)$_2$, and
(10) -phenyl.

An embodiment of the present invention includes compounds wherein R$^3$ is selected from:
(1) methyl, and
(2) —N(CH$_3$)$_2$.

An embodiment of the present invention includes compounds wherein R$^3$ is —C$_{1-6}$alkyl, where the alkyl is unsubstituted or substituted with one to three fluoro.

An embodiment of the present invention includes compounds wherein R$^5$ and R$^6$ are independently selected from:
(1) hydrogen,
(2) methyl,
(3) ethyl,
(4) —CHF$_2$,
(5) —CF$_3$,
(6) —CH$_2$OH,
(7) —CH$_2$OCH$_3$, and
(8) cyclopropyl.

An embodiment of the present invention includes compounds wherein R$^5$ is C$_{1-6}$alkyl, where the alkyl is unsubstituted or substituted with one to six substituents independently selected from R$^4$, and R$^6$ is hydrogen. An embodiment of the present invention includes compounds wherein R$^5$ is C$_{1-6}$alkyl, where the alkyl is unsubstituted or substituted with one to six substituents independently selected from halo or —O—C$_{1-6}$alkyl, and R$^6$ is hydrogen. An embodiment of the present invention includes compounds wherein R$^5$ is methyl and R$^6$ is hydrogen. An embodiment of the present invention includes compounds wherein R$^5$ is hydrogen and R$^6$ is hydrogen. An embodiment of the present invention includes compounds wherein R$^5$ is ethyl and R$^6$ is hydrogen. An embodiment of the present invention includes compounds wherein R$^5$ is ethyl and R$^6$ is ethyl. An embodiment of the present invention includes compounds wherein R$^5$ and R$^6$ are joined together with the carbon atoms to which they are attached to form a cyclopropyl ring.

Certain embodiments of the present invention include a compound which is selected from the group consisting of the subject compounds of the Examples herein or a pharmaceutically acceptable salt thereof.

Certain embodiments of the present invention include a compound which is selected from:
Methyl (2R,3S,5R)-5-methyl-3-(methylsulfonamido)-2-(((6-phenylbicyclo[4.1.0]heptan-3-yl)oxy)methyl)pyrrolidine-1-carboxylate; (Ex No. 1 & 2)
methyl (2R,3S,5R)-3-((N,N-dimethylsulfamoyl)amino)-2-(((6-(3-fluorophenyl)bicyclo[4.1.0]heptan-3-yl)oxy)methyl)-5-methylpyrrolidine-1-carboxylate; (3);
methyl (2R,3S,5R)-2-(((6-(3,5-difluorophenyl)bicyclo[4.1.0]heptan-3-yl)oxy)methyl)-3-((N,N-dimethylsulfamoyl)amino)-5-methylpyrrolidine-1-carboxylate; (4)
methyl (2R,3S,5R)-2-(((6-(4-cyanophenyl)bicyclo[4.1.0]heptan-3-yl)oxy)methyl)-3-((N,N-dimethylsulfamoyl)amino)-5-methylpyrrolidine-1-carboxylate; (5)
methyl (2R,3S,5R)-3-((N,N-dimethylsulfamoyl)amino)-5-methyl-2-(((6-(pyrimidin-2-yl)bicyclo[4.1.0]heptan-3-yl)oxy)methyl)pyrrolidine-1-carboxylate; (6)
methyl (2R,3S,5R)-2-(((7,7-difluoro-6-(pyrimidin-2-yl)bicyclo[4.1.0]heptan-3-yl)oxy)methyl)-3-((N,N-dimethylsulfamoyl)amino)-5-methylpyrrolidine-1-carboxylate; (7)
isopropyl (2R,3S,5R)-3-((N,N-dimethylsulfamoyl)amino)-5-methyl-2-(((6-(pyrimidin-2-yl)bicyclo[4.1.0]heptan-3-yl)oxy)methyl)pyrrolidine-1-carboxylate; (8)
methyl (2R,3S,5R)-3-((N,N-dimethylsulfamoyl)amino)-5-methyl-2-(((6-(pyridin-2-yl)bicyclo[4.1.0]heptan-3-yl)oxy)methyl)pyrrolidine-1-carboxylate; (9)
methyl (2R,3S,5R)-3-((N,N-dimethylsulfamoyl)amino)-5-methyl-2-(((6-(pyrazin-2-yl)bicyclo[4.1.0]heptan-3-yl)oxy)methyl)pyrrolidine-1-carboxylate; (10)
methyl (2R,3S,5R)-3-((N,N-dimethylsulfamoyl)amino)-5-methyl-2-(((6-(pyrazin-2-yl)bicyclo[4.1.0]heptan-3-yl)oxy)methyl)pyrrolidine-1-carboxylate; (11)
methyl (2R,3S,5R)-3-((N,N-dimethylsulfamoyl)amino)-5-methyl-2-(((6-(pyrazin-2-yl)bicyclo[4.1.0]heptan-3-yl)oxy)methyl)pyrrolidine-1-carboxylate; (13)
methyl (2R,3S,5R)-3-((N,N-dimethylsulfamoyl)amino)-5-methyl-2-(((6-(pyrazin-2-yl)bicyclo[4.1.0]heptan-3-yl)oxy)methyl)pyrrolidine-1-carboxylate; (14)
methyl (2R,3S,5R)-5-methyl-3-(methylsulfonamido)-2-(((6-(pyrimidin-2-yl)bicyclo[4.1.0]heptan-3-yl)oxy)methyl)pyrrolidine-1-carboxylate; (16)
methyl (2R,3S,5R)-5-methyl-3-(methylsulfonamido)-2-(((6-(pyrimidin-2-yl)bicyclo[4.1.0]heptan-3-yl)oxy)methyl)pyrrolidine-1-carboxylate; (17)
methyl (2R,3S,5R)-5-methyl-3-(methylsulfonamido)-2-((((1S,3S,6R)-6-(pyrimidin-2-yl)bicyclo[4.1.0]heptan-3-yl)oxy)methyl)pyrrolidine-1-carboxylate; (19)
methyl (2R,3S,5R)-5-methyl-3-(methylsulfonamido)-2-((((1R,3R,6S)-6-(pyrimidin-2-yl)bicyclo[4.1.0]heptan-3-yl)oxy)methyl)pyrrolidine-1-carboxylate; (20)
methyl (2R,3S)-3-(methylsulfonamido)-2-(((6-(pyrimidin-2-yl)bicyclo[4.1.0]heptan-3-yl)oxy)methyl)pyrrolidine-1-carboxylate; (21);
methyl (2R,3S)-3-(methylsulfonamido)-2-((((1S,3S,6R)-6-(pyrimidin-2-yl)bicyclo[4.1.0]heptan-3-yl)oxy)methyl)pyrrolidine-1-carboxylate; (24)
methyl (2R,3S)-3-(methylsulfonamido)-2-((((1R,3R,6S)-6-(pyrimidin-2-yl)bicyclo[4.1.0]heptan-3-yl)oxy)methyl)pyrrolidine-1-carboxylate; (25)
isopropyl (2R,3S,5R)-2-(((6-(5-fluoropyrimidin-2-yl)bicyclo[4.1.0]heptan-3-yl)oxy)methyl)-5-methyl-3-(methylsulfonamido)pyrrolidine-1-carboxylate; (26);
isopropyl (2R,3S,5R)-2-((((1S,3S,6R)-6-(5-fluoropyrimidin-2-yl)bicyclo[4.1.0]heptan-3-yl)oxy)methyl)-5-methyl-3-(methylsulfonamido)pyrrolidine-1-carboxylate; (28)
isopropyl (2R,3S,5R)-2-((((1R,3R,6S)-6-(5-fluoropyrimidin-2-yl)bicyclo[4.1.0]heptan-3-yl)oxy)methyl)-5-methyl-3-(methylsulfonamido)pyrrolidine-1-carboxylate; (29)
methyl (2R,3S,5R)-3-((fluoromethyl)sulfonamido)-2-((((1S,3S,6R)-6-(5-fluoropyrimidin-2-yl)bicyclo[4.1.0]heptan-3-yl)oxy)methyl)-5-methylpyrrolidine-1-carboxylate; (30)

methyl (2R,3S,5R)-2-((((1S,3S,6R)-6-(5-fluoropyrimidin-2-yl)bicyclo[4.1.0]heptan-3-yl)oxy)methyl)-5-methyl-3-((trifluoromethyl)sulfonamido)pyrrolidine-1-carboxylate; (31)

methyl (2R,3S,5R)-2-((((1S,3S,6R)-6-(5-fluoropyrimidin-2-yl)bicyclo[4.1.0]heptan-3-yl)oxy)methyl)-5-methyl-3-((2,2,2-trifluoroethyl)sulfonamido)pyrrolidine-1-carboxylate; (32)

methyl (2R,3S,5R)-2-((((1S,3S,6R)-6-(5-fluoropyrimidin-2-yl)bicyclo[4.1.0]heptan-3-yl)oxy)methyl)-5-methyl-3-(propylsulfonamido)pyrrolidine-1-carboxylate; (33)

methyl (2R,3S,5R)-2-((((1S,3S,6R)-6-(5-fluoropyrimidin-2-yl)bicyclo[4.1.0]heptan-3-yl)oxy)methyl)-5-methyl-3-((phenylmethyl)sulfonamido)pyrrolidine-1-carboxylate; (34)

methyl (2R,3S,5R)-2-((((1S,3S,6R)-6-(5-fluoropyrimidin-2-yl)bicyclo[4.1.0]heptan-3-yl)oxy)methyl)-5-methyl-3-((2-methylpropyl)sulfonamido)pyrrolidine-1-carboxylate; (35)

methyl (2R,3S,5R)-3-(ethylsulfonamido)-2-((((1S,3S,6R)-6-(5-fluoropyrimidin-2-yl)bicyclo[4.1.0]heptan-3-yl)oxy)methyl)-5-methylpyrrolidine-1-carboxylate; (36)

methyl (2R,3S,5R)-3-((chloromethyl)sulfonamido)-2-((((1S,3S,6R)-6-(5-fluoropyrimidin-2-yl)bicyclo[4.1.0]heptan-3-yl)oxy)methyl)-5-methylpyrrolidine-1-carboxylate; (37)

methyl (2R,3S,5R)-2-((((1S,3S,6R)-6-(5-fluoropyrimidin-2-yl)bicyclo[4.1.0]heptan-3-yl)oxy)methyl)-5-methyl-3-((1-methylethyl)sulfonamido)pyrrolidine-1-carboxylate; (38)

methyl (2R,3S,5R)-3-(azetidine-1-sulfonamido)-2-((((1S,3S,6R)-6-(5-fluoropyrimidin-2-yl)bicyclo[4.1.0]heptan-3-yl)oxy)methyl)-5-methylpyrrolidine-1-carboxylate; (39)

methyl (2R,3S,5R)-2-((((1S,3S,6R)-6-(5-fluoropyrimidin-2-yl)bicyclo[4.1.0]heptan-3-yl)oxy)methyl)-5-methyl-3-(oxetane-3-sulfonamido)pyrrolidine-1-carboxylate; (40)

methyl (2R,3S,5R)-2-((((1S,3S,6R)-6-(5-fluoropyrimidin-2-yl)bicyclo[4.1.0]heptan-3-yl)oxy)methyl)-5-methyl-3-((1-methylpropyl)sulfonamido)pyrrolidine-1-carboxylate; (41)

methyl (2R,3S,5R)-3-(cyclopropanesulfonamido)-2-((((1S,3S,6R)-6-(5-fluoropyrimidin-2-yl)bicyclo[4.1.0]heptan-3-yl)oxy)methyl)-5-methylpyrrolidine-1-carboxylate; (42)

methyl (2R,3S,5R)-3-(azetidine-1-sulfonamido)-2-((((1R,3R,6S)-6-(5-fluoropyrimidin-2-yl)bicyclo[4.1.0]heptan-3-yl)oxy)methyl)-5-methylpyrrolidine-1-carboxylate; (43)

methyl (2R,3S,5R)-2-((((1R,3R,6S)-6-(5-fluoropyrimidin-2-yl)bicyclo[4.1.0]heptan-3-yl)oxy)methyl)-5-methyl-3-((trifluoromethyl)sulfonamido)pyrrolidine-1-carboxylate; (44)

methyl (2R,3S,5R)-2-((((1R,3R,6S)-6-(5-fluoropyrimidin-2-yl)bicyclo[4.1.0]heptan-3-yl)oxy)methyl)-5-methyl-3-((phenylmethyl)sulfonamido)pyrrolidine-1-carboxylate; (45)

methyl (2R,3S,5R)-2-((((1R,3R,6S)-6-(5-fluoropyrimidin-2-yl)bicyclo[4.1.0]heptan-3-yl)oxy)methyl)-5-methyl-3-((1-methylethyl)sulfonamido)pyrrolidine-1-carboxylate; (46)

methyl (2R,3S,5R)-3-(ethylsulfonamido)-2-((((1R,3R,6S)-6-(5-fluoropyrimidin-2-yl)bicyclo[4.1.0]heptan-3-yl)oxy)methyl)-5-methylpyrrolidine-1-carboxylate; (47)

methyl (2R,3S,5R)-3-((difluoromethyl)sulfonamido)-2-((((1S,3S,6R)-6-(5-fluoropyrimidin-2-yl)bicyclo[4.1.0]heptan-3-yl)oxy)methyl)-5-methylpyrrolidine-1-carboxylate; (48)

(3-fluorocyclobutyl)methyl (2R,3S,5R)-2-((((1S,3S,6R)-6-(5-fluoropyrimidin-2-yl)bicyclo[4.1.0]heptan-3-yl)oxy)methyl)-5-methyl-3-(methylsulfonamido)pyrrolidine-1-carboxylate; (49)

1,1-difluorobutan-2-yl (2R,3S,5R)-2-((((1S,3S,6R)-6-(5-fluoropyrimidin-2-yl)bicyclo[4.1.0]heptan-3-yl)oxy)methyl)-5-methyl-3-(methylsulfonamido)pyrrolidine-1-carboxylate; (50)

((1R,2R)-2-fluorocyclopropyl)methyl (2R,3S,5R)-2-((((1S,3S,6R)-6-(5-fluoropyrimidin-2-yl)bicyclo[4.1.0]heptan-3-yl)oxy)methyl)-5-methyl-3-(methylsulfonamido)pyrrolidine-1-carboxylate; (51)

3,3-difluoropropyl (2R,3S,5R)-2-((((1S,3S,6R)-6-(5-fluoropyrimidin-2-yl)bicyclo[4.1.0]heptan-3-yl)oxy)methyl)-5-methyl-3-(methylsulfonamido)pyrrolidine-1-carboxylate; (52)

(1-fluorocyclobutyl)methyl (2R,3S,5R)-2-((((1S,3S,6R)-6-(5-fluoropyrimidin-2-yl)bicyclo[4.1.0]heptan-3-yl)oxy)methyl)-5-methyl-3-(methylsulfonamido)pyrrolidine-1-carboxylate; (53)

2-cyclobutyl-2-fluoroethyl (2R,3S,5R)-2-((((1S,3S,6R)-6-(5-fluoropyrimidin-2-yl)bicyclo[4.1.0]heptan-3-yl)oxy)methyl)-5-methyl-3-(methylsulfonamido)pyrrolidine-1-carboxylate; (54)

((1R,3S)-2,2-difluoro-3-methylcyclopropyl)methyl (2R,3S,5R)-2-((((1S,3S,6R)-6-(5-fluoropyrimidin-2-yl)bicyclo[4.1.0]heptan-3-yl)oxy)methyl)-5-methyl-3-(methylsulfonamido)pyrrolidine-1-carboxylate; (55)

(3S,4S)-4-fluorotetrahydrofuran-3-yl (2R,3S,5R)-2-((((1S,3S,6R)-6-(5-fluoropyrimidin-2-yl)bicyclo[4.1.0]heptan-3-yl)oxy)methyl)-5-methyl-3-(methylsulfonamido)pyrrolidine-1-carboxylate; (56)

(2,2-difluoro-1-methylcyclopropyl)methyl (2R,3S,5R)-2-((((1S,3S,6R)-6-(5-fluoropyrimidin-2-yl)bicyclo[4.1.0]heptan-3-yl)oxy)methyl)-5-methyl-3-(methylsulfonamido)pyrrolidine-1-carboxylate; (57)

2-fluoropropyl (2R,3S,5R)-2-((((1S,3S,6R)-6-(5-fluoropyrimidin-2-yl)bicyclo[4.1.0]heptan-3-yl)oxy)methyl)-5-methyl-3-(methylsulfonamido)pyrrolidine-1-carboxylate; (58)

(2,2-difluorocyclopropyl)methyl (2R,3S,5R)-2-((((1S,3S,6R)-6-(5-fluoropyrimidin-2-yl)bicyclo[4.1.0]heptan-3-yl)oxy)methyl)-5-methyl-3-(methylsulfonamido)pyrrolidine-1-carboxylate; (59)

2,2-difluorobutyl (2R,3S,5R)-2-((((1S,3S,6R)-6-(5-fluoropyrimidin-2-yl)bicyclo[4.1.0]heptan-3-yl)oxy)methyl)-5-methyl-3-(methylsulfonamido)pyrrolidine-1-carboxylate; (60)

(1-fluorocyclopropyl)methyl (2R,3S,5R)-2-((((1S,3S,6R)-6-(5-fluoropyrimidin-2-yl)bicyclo[4.1.0]heptan-3-yl)oxy)methyl)-5-methyl-3-(methylsulfonamido)pyrrolidine-1-carboxylate; (61)

2-Fluoroethyl (2R,3S,5R)-2-((((1S,3S,6R)-6-(5-fluoropyrimidin-2-yl)bicyclo[4.1.0]heptan-3-yl)oxy)methyl)-5-methyl-3-(methylsulfonamido)pyrrolidine-1-carboxylate; (62)

1,1-Difluoropropan-2-yl (2R,3S,5R)-2-((((1S,3S,6R)-6-(5-fluoropyrimidin-2-yl)bicyclo[4.1.0]heptan-3-yl)oxy)methyl)-5-methyl-3-(methylsulfonamido)pyrrolidine-1-carboxylate; (63)

2,2-difluoropropyl (2R,3S,5R)-2-((((1S,3S,6R)-6-(5-fluoropyrimidin-2-yl)bicyclo[4.1.0]heptan-3-yl)oxy)methyl)-5-methyl-3-(methylsulfonamido)pyrrolidine-1-carboxylate; (64)

2,2,2-trifluoroethyl (2R,3S,5R)-2-((((1S,3S,6R)-6-(5-fluoropyrimidin-2-yl)bicyclo[4.1.0]heptan-3-yl)oxy)methyl)-5-methyl-3-(methylsulfonamido)pyrrolidine-1-carboxylate; (65)

2,2-difluoroethyl (2R,3S,5R)-2-((((1S,3S,6R)-6-(5-fluoropyrimidin-2-yl)bicyclo[4.1.0]heptan-3-yl)oxy)methyl)-5-methyl-3-(methylsulfonamido)pyrrolidine-1-carboxylate; (65)

methyl (2R,3S,5R)-3-((difluoromethyl)sulfonamido)-5-methyl-2-(((6-(pyrimidin-2-yl)bicyclo[4.1.0]heptan-3-yl)oxy)methyl)pyrrolidine-1-carboxylate; (67);

methyl (2R,3S,5R)-3-((difluoromethyl)sulfonamido)-5-methyl-2-((((1S,3S,6R)-6-(pyrimidin-2-yl)bicyclo[4.1.0]heptan-3-yl)oxy)methyl)pyrrolidine-1-carboxylate; (68);

methyl (2R,3S,5R)-3-((difluoromethyl)sulfonamido)-5-methyl-2-((((1R,3R,6S)-6-(pyrimidin-2-yl)bicyclo[4.1.0]heptan-3-yl)oxy)methyl)pyrrolidine-1-carboxylate; (69);

methyl (2R,3S,5R)-2-(((6-(5-chloro-4-methoxypyrimidin-2-yl)bicyclo[4.1.0]heptan-3-yl)oxy)methyl)-5-methyl-3-(methylsulfonamido)pyrrolidine-1-carboxylate; (70);

methyl (2R,3S,5R)-2-(((6-(4,7-difluorobenzo[d]thiazol-2-yl)bicyclo[4.1.0]heptan-3-yl)oxy)methyl)-5-methyl-3-(methylsulfonamido)pyrrolidine-1-carboxylate; (71)

methyl (2R,3S,5R)-2-(((6-(5-chloro-4-(trifluoromethyl)pyrimidin-2-yl)bicyclo[4.1.0]heptan-3-yl)oxy)methyl)-5-methyl-3-(methylsulfonamido)pyrrolidine-1-carboxylate; (72)

methyl (2R,3S,5R)-2-(((6-(4-(difluoromethyl)-5-fluoropyrimidin-2-yl)bicyclo[4.1.0]heptan-3-yl)oxy)methyl)-5-methyl-3-(methylsulfonamido)pyrrolidine-1-carboxylate; (73)

methyl (2R,3S,5R)-2-(((6-(4-cyclopropyl-5-fluoropyrimidin-2-yl)bicyclo[4.1.0]heptan-3-yl)oxy)methyl)-5-methyl-3-(methylsulfonamido)pyrrolidine-1-carboxylate; (74)

methyl (2R,3S,5R)-2-(((6-(5-(difluoromethoxy)-4-methylpyrimidin-2-yl)bicyclo[4.1.0]heptan-3-yl)oxy)methyl)-5-methyl-3-(methylsulfonamido)pyrrolidine-1-carboxylate; (75)

methyl (2R,3S,5R)-2-(((6-(5-fluoro-4-methoxypyrimidin-2-yl)bicyclo[4.1.0]heptan-3-yl)oxy)methyl)-5-methyl-3-(methylsulfonamido)pyrrolidine-1-carboxylate; (76)

methyl (2R,3S,5R)-2-(((6-(5-fluoro-4-methylpyrimidin-2-yl)bicyclo[4.1.0]heptan-3-yl)oxy)methyl)-5-methyl-3-(methylsulfonamido)pyrrolidine-1-carboxylate; (77)

methyl (2R,3S,5R)-2-((((1S,3S,6R)-6-(5-chloropyrimidin-2-yl)bicyclo[4.1.0]heptan-3-yl)oxy)methyl)-3-((difluoromethyl)sulfonamido)-5-methylpyrrolidine-1-carboxylate; (78)

methyl (2R,3S,5R)-2-((((1S,3S,6R)-6-(5-chloropyrimidin-2-yl)bicyclo[4.1.0]heptan-3-yl)oxy)methyl)-3-((fluoromethyl)sulfonamido)-5-methylpyrrolidine-1-carboxylate; (79)

isopropyl (2R,3S,5R)-2-((((1S,3S,6R)-6-(5-chloropyrimidin-2-yl)bicyclo[4.1.0]heptan-3-yl)oxy)methyl)-3-((difluoromethyl)sulfonamido)-5-methylpyrrolidine-1-carboxylate; (81)

isopropyl (2R,3S,5R)-2-(((6-(5-chloropyrimidin-2-yl)bicyclo[4.1.0]heptan-3-yl)oxy)methyl)-3-((difluoromethyl)sulfonamido)-5-methylpyrrolidine-1-carboxylate; (82)

methyl (2R,3S,5R)-2-((((1S,3S,6R)-6-(5-fluoro-4-methoxypyrimidin-2-yl)bicyclo[4.1.0]heptan-3-yl)oxy)methyl)-3-((fluoromethyl)sulfonamido)-5-methylpyrrolidine-1-carboxylate; (83)

methyl (2R,3S,5R)-2-((((1S,3S,6R)-6-(5-chloro-4-methoxypyrimidin-2-yl)bicyclo[4.1.0]heptan-3-yl)oxy)methyl)-3-((fluoromethyl)sulfonamido)-5-methylpyrrolidine-1-carboxylate; (84)

methyl (2R,3S,5R)-2-(((6-(5-fluoro-4-methoxypyrimidin-2-yl)bicyclo[4.1.0]heptan-3-yl)oxy)methyl)-3-((fluoromethyl)sulfonamido)-5-methylpyrrolidine-1-carboxylate; (85)

methyl (2R,3S,5R)-2-(((6-(5-chloro-4-methoxypyrimidin-2-yl)bicyclo[4.1.0]heptan-3-yl)oxy)methyl)-3-((fluoromethyl)sulfonamido)-5-methylpyrrolidine-1-carboxylate; (86)

methyl (2R,3S,5R)-2-((((1S,3S,6R)-6-(5-bromopyrimidin-2-yl)bicyclo[4.1.0]heptan-3-yl)oxy)methyl)-3-((fluoromethyl)sulfonamido)-5-methylpyrrolidine-1-carboxylate; (87)

methyl (2R,3S,5R)-2-(((6-(5-bromopyrimidin-2-yl)bicyclo[4.1.0]heptan-3-yl)oxy)methyl)-3-((fluoromethyl)sulfonamido)-5-methylpyrrolidine-1-carboxylate; (89)

isopropyl (2R,3S,5R)-3-((difluoromethyl)sulfonamido)-2-((((1S,3S,6R)-6-(5-fluoropyrimidin-2-yl)bicyclo[4.1.0]heptan-3-yl)oxy)methyl)-5-methylpyrrolidine-1-carboxylate; (90)

isopropyl (2R,3S,5R)-3-((difluoromethyl)sulfonamido)-2-((((1R,3R,6S)-6-(5-fluoropyrimidin-2-yl)bicyclo[4.1.0]heptan-3-yl)oxy)methyl)-5-methylpyrrolidine-1-carboxylate; (91)

isopropyl (2R,3S,5R)-3-((difluoromethyl)sulfonamido)-2-(((6-(5-fluoropyrimidin-2-yl)bicyclo[4.1.0]heptan-3-yl)oxy)methyl)-5-methylpyrrolidine-1-carboxylate; (92)

isopropyl (2R,3S,5R)-3-((difluoromethyl)sulfonamido)-2-(((6-(5-fluoropyrimidin-2-yl)bicyclo[4.1.0]heptan-3-yl)oxy)methyl)-5-methylpyrrolidine-1-carboxylate; (93)

methyl (2R,3S,5R)-2-(((6-(5-chloropyrimidin-2-yl)bicyclo[4.1.0]heptan-3-yl)oxy)methyl)-3-((fluoromethyl)sulfonamido)-5-methylpyrrolidine-1-carboxylate; (94)

isopropyl (2R,3S,5R)-2-((((1S,3S,6R)-6-(5-chloropyrimidin-2-yl)bicyclo[4.1.0]heptan-3-yl)oxy)methyl)-3-((fluoromethyl)sulfonamido)-5-methylpyrrolidine-1-carboxylate; (95)

isopropyl (2R,3S,5R)-2-((((1R,3R,6S)-6-(5-chloropyrimidin-2-yl)bicyclo[4.1.0]heptan-3-yl)oxy)methyl)-3-((fluoromethyl)sulfonamido)-5-methylpyrrolidine-1-carboxylate; (96)

isopropyl (2R,3S,5R)-3-((fluoromethyl)sulfonamido)-2-((((1R,3R,6S)-6-(5-fluoropyrimidin-2-yl)bicyclo[4.1.0]heptan-3-yl)oxy)methyl)-5-methylpyrrolidine-1-carboxylate; (99)

isopropyl (2R,3S,5R)-3-((fluoromethyl)sulfonamido)-2-((((1S,3S,6R)-6-(5-fluoropyrimidin-2-yl)bicyclo[4.1.0]heptan-3-yl)oxy)methyl)-5-methylpyrrolidine-1-carboxylate; (100)

isopropyl (2R,3S,5R)-2-((((1S,3S,6R)-6-(5-bromopyrimidin-2-yl)bicyclo[4.1.0]heptan-3-yl)oxy)methyl)-3-((fluoromethyl)sulfonamido)-5-methylpyrrolidine-1-carboxylate; (103)

isopropyl (2R,3S,5R)-2-((((1R,3R,6S)-6-(5-bromopyrimidin-2-yl)bicyclo[4.1.0]heptan-3-yl)oxy)methyl)-3-((fluoromethyl)sulfonamido)-5-methylpyrrolidine-1-carboxylate; (104)

isopropyl (2R,3S,5R)-2-(((6-(5-bromopyrimidin-2-yl)bicyclo[4.1.0]heptan-3-yl)oxy)methyl)-3-((fluoromethyl)sulfonamido)-5-methylpyrrolidine-1-carboxylate; (105)

isopropyl (2R,3S,5R)-2-(((6-(5-chloropyrimidin-2-yl)bicyclo[4.1.0]heptan-3-yl)oxy)methyl)-3-((fluoromethyl)sulfonamido)-5-methylpyrrolidine-1-carboxylate; (107)

isopropyl (2R,3S,5R)-2-(((6-(5-bromopyrimidin-2-yl)bicyclo[4.1.0]heptan-3-yl)oxy)methyl)-3-((fluoromethyl)sulfonamido)-5-methylpyrrolidine-1-carboxylate; (108)

isopropyl (2R,3S,5R)-3-((difluoromethyl)sulfonamido)-2-(((6-(5-fluoropyrimidin-2-yl)bicyclo[4.1.0]heptan-3-yl)oxy)methyl)-5-methylpyrrolidine-1-carboxylate; (109)

isopropyl (2R,3S,5R)-3-((fluoromethyl)sulfonamido)-2-(((6-(5-fluoropyrimidin-2-yl)bicyclo[4.1.0]heptan-3-yl)oxy)methyl)-5-methylpyrrolidine-1-carboxylate; (111)

methyl (2R,3S,5S)-5-(difluoromethyl)-3-((difluoromethyl)sulfonamido)-2-((((1S,3S,6R)-6-(5-fluoropyrimidin-2-yl)bicyclo[4.1.0]heptan-3-yl)oxy)methyl)pyrrolidine-1-carboxylate; (112)

methyl (2R,3S,5S)-5-(difluoromethyl)-3-((fluoromethyl)sulfonamido)-2-((((1S,3S,6R)-6-(5-fluoropyrimidin-2-yl)bicyclo[4.1.0]heptan-3-yl)oxy)methyl)pyrrolidine-1-carboxylate; (113)

methyl (2R,3S,5S)-2-((((1S,3S,6R)-6-(5-chloropyrimidin-2-yl)bicyclo[4.1.0]heptan-3-yl)oxy)methyl)-5-(difluoromethyl)-3-(ethylsulfonamido)pyrrolidine-1-carboxylate; (114)

methyl (2R,3S,5S)-2-((((1S,3S,6R)-6-(5-chloropyrimidin-2-yl)bicyclo[4.1.0]heptan-3-yl)oxy)methyl)-5-(difluoromethyl)-3-((fluoromethyl)sulfonamido)pyrrolidine-1-carboxylate; (115) methyl (2R,3S,5S)-3-(cyclopropanesulfonamido)-5-(difluoromethyl)-2-(((6-(5-fluoropyrimidin-2-yl)bicyclo[4.1.0]heptan-3-yl)oxy)methyl)pyrrolidine-1-carboxylate; (116)

methyl (2R,3S,5S)-5-(difluoromethyl)-3-(ethylsulfonamido)-2-(((6-(5-fluoropyrimidin-2-1)bicyclo[4.1.0]heptan-3-yl)oxy)methyl)pyrrolidine-1-carboxylate; (117)

isopropyl (2R,3S,5S)-5-(difluoromethyl)-3-(ethylsulfonamido)-2-((((1S,3S,6R)-6-(5-fluoropyrimidin-2-yl)bicyclo[4.1.0]heptan-3-yl)oxy)methyl)pyrrolidine-1-carboxylate; (118)

isopropyl (2R,3S,5S)-5-(difluoromethyl)-2-((((1S,3S,6R)-6-(5-fluoropyrimidin-2-yl)bicyclo[4.1.0]heptan-3-yl)oxy)methyl)-3-(methylsulfonamido)pyrrolidine-1-carboxylate; (119)

methyl (2R,3S,5S)-5-(difluoromethyl)-2-(((6-(5-fluoropyrimidin-2-yl)bicyclo[4.1.0]heptan-3-yl)oxy)methyl)-3-((1-methylethyl)sulfonamido)pyrrolidine-1-carboxylate; (120)

isopropyl (2R,3S)-3-((difluoromethyl)sulfonamido)-2-((((1S,3S,6R)-6-(5-fluoropyrimidin-2-yl)bicyclo[4.1.0]heptan-3-yl)oxy)methyl)piperidine-1-carboxylate; (121)

isopropyl (2R,3S)-3-(cyclopropanesulfonamido)-2-(((6-(5-fluoropyrimidin-2-yl)bicyclo[4.1.0]heptan-3-yl)oxy)methyl)piperidine-1-carboxylate; (122)

isopropyl (2R,3S)-2-(((6-(5-fluoropyrimidin-2-yl)bicyclo[4.1.0]heptan-3-yl)oxy)methyl)-3-((trifluoromethyl)sulfonamido)piperidine-1-carboxylate; (123)

isopropyl (2R,3S)-3-((fluoromethyl)sulfonamido)-2-((((1S,3S,6R)-6-(5-fluoropyrimidin-2-yl)bicyclo[4.1.0]heptan-3-yl)oxy)methyl)piperidine-1-carboxylate; (124)

isopropyl (2R,3S)-2-((((1S,3S,6R)-6-(5-fluoropyrimidin-2-yl)bicyclo[4.1.0]heptan-3-yl)oxy)methyl)-3-(methylsulfonamido)piperidine-1-carboxylate; (125)

isopropyl (2R,3S)-3-(ethylsulfonamido)-2-(((6-(5-fluoropyrimidin-2-yl)bicyclo[4.1.0]heptan-3-yl)oxy)methyl)piperidine-1-carboxylate; (126)

methyl (2R,3S,5S)-5-(difluoromethyl)-2-((((1S,3S,6R)-6-(5-fluoropyrimidin-2-yl)bicyclo[4.1.0]heptan-3-yl)oxy)methyl)-3-(methylsulfonamido)pyrrolidine-1-carboxylate; (127)

methyl (2R,3S,3aS,6aR)-3-(cyclopropanesulfonamido)-2-(((6-(5-fluoropyrimidin-2-yl)bicyclo[4.1.0]heptan-3-yl)oxy)methyl)hexahydrocyclopenta[b]pyrrole-1(2H)-carboxylate; (128)

methyl (2R,3S,3aS,6aR)-3-(ethylsulfonamido)-2-(((6-(5-fluoropyrimidin-2-yl)bicyclo[4.1.0]heptan-3-yl)oxy)methyl)hexahydrocyclopenta[b]pyrrole-1(2H)-carboxylate; (129)

methyl (2R,3S,3aS,6aR)-3-((fluoromethyl)sulfonamido)-2-(((6-(5-fluoropyrimidin-2-yl)bicyclo[4.1.0]heptan-3-yl)oxy)methyl)hexahydrocyclopenta[b]pyrrole-1(2H)-carboxylate; (130)

methyl (2R,3S,3aS,6aR)-2-((((1S,3S,6R)-6-(5-fluoropyrimidin-2-yl)bicyclo[4.1.0]heptan-3-yl)oxy)methyl)-3-(methylsulfonamido)hexahydrocyclopenta[b]pyrrole-1(2H)-carboxylate; (131)

methyl (2R,3S,5S)-2-((((1S,3S,6R)-6-(5-fluoropyrimidin-2-yl)bicyclo[4.1.0]heptan-3-yl)oxy)methyl)-5-(methoxymethyl)-3-(methylsulfonamido)pyrrolidine-1-carboxylate; (132)

methyl (2R,3S,5S)-2-((((1S,3S,6R)-6-(5-fluoropyrimidin-2-yl)bicyclo[4.1.0]heptan-3-yl)oxy)methyl)-3-(methylsulfonamido)-5-(trifluoromethyl)pyrrolidine-1-carboxylate; (133)

Methyl (2R,3aS,6aS)-2-(((6-(5-fluoropyrimidin-2-yl)bicyclo[4.1.0]heptan-3-yl)oxy)methyl)-3-(methylsulfonamido)hexahydro-1H-furo[3,4-b]pyrrole-1-carboxylate; (134)

methyl (2R,3S,5R)-2-(((6-(5-fluoropyrimidin-2-yl)bicyclo[4.1.0]heptan-3-yl)oxy)methyl)-5-methyl-3-(methylsulfonamido)pyrrolidine-1-carboxylate; (135)

methyl (2R,3S,5R)-2-((((1R,3R,6S)-6-(5-fluoropyrimidin-2-yl)bicyclo[4.1.0]heptan-3-yl)oxy)methyl)-5-methyl-3-(methylsulfonamido)pyrrolidine-1-carboxylate; (136)

methyl (2R,3S,5R)-2-((((1S,3S,6R)-6-(5-fluoropyrimidin-2-yl)bicyclo[4.1.0]heptan-3-yl)oxy)methyl)-5-methyl-3-(methylsulfonamido)pyrrolidine-1-carboxylate (137)

methyl (2R,3S,5R)-2-(((6-(5-chloropyrimidin-2-yl)bicyclo[4.1.0]heptan-3-yl)oxy)methyl)-5-methyl-3-(methylsulfonamido)pyrrolidine-1-carboxylate; (140)

methyl (2R,3S,5R)-2-((((1R,3R,6S)-6-(5-chloropyrimidin-2-yl)bicyclo[4.1.0]heptan-3-yl)oxy)methyl)-5-methyl-3-(methylsulfonamido)pyrrolidine-1-carboxylate; (141)

methyl (2R,3S,5R)-2-((((1S,3S,6R)-6-(5-chloropyrimidin-2-yl)bicyclo[4.1.0]heptan-3-yl)oxy)methyl)-5-methyl-3-(methylsulfonamido)pyrrolidine-1-carboxylate; (142)

methyl (2R,3S,5R)-5-methyl-3-(methylsulfonamido)-2-((((1R,3R,6S)-6-(thiazol-2-yl)bicyclo[4.1.0]heptan-3-yl)oxy)methyl)pyrrolidine-1-carboxylate; (145)

methyl (2R,3S,5R)-5-methyl-3-(methylsulfonamido)-2-((((1S,3S,6R)-6-(thiazol-2-yl)bicyclo[4.1.0]heptan-3-yl)oxy)methyl)pyrrolidine-1-carboxylate; (146)

methyl (2R,3S,5R)-5-methyl-3-(methylsulfonamido)-2-(((6-(thiazol-2-yl)bicyclo[4.1.0]heptan-3-yl)oxy)methyl)pyrrolidine-1-carboxylate; (149)

isopropyl (2R,3S,5R)-2-((((1R,3R,6S)-6-(5-chloropyrimidin-2-yl)bicyclo[4.1.0]heptan-3-yl)oxy)methyl)-5-methyl-3-(methylsulfonamido)pyrrolidine-1-carboxylate; (150)

isopropyl (2R,3S,5R)-2-((((1S,3S,6R)-6-(5-chloropyrimidin-2-yl)bicyclo[4.1.0]heptan-3-yl)oxy)methyl)-5-methyl-3-(methylsulfonamido)pyrrolidine-1-carboxylate; (151)

isopropyl (2R,3S,5R)-2-(((6-(5-chloropyrimidin-2-yl)bicyclo[4.1.0]heptan-3-yl)oxy)methyl)-5-methyl-3-(methylsulfonamido)pyrrolidine-1-carboxylate; (154)

methyl (2R,3S,5R)-5-methyl-2-(((((1R,3R,6S)-6-(5-methylpyrimidin-2-yl)bicyclo[4.1.0]heptan-3-yl)oxy)methyl)-3-(methylsulfonamido)pyrrolidine-1-carboxylate; (155)

methyl (2R,3S,5R)-5-methyl-2-(((((1S,3S,6R)-6-(5-methylpyrimidin-2-yl)bicyclo[4.1.0]heptan-3-yl)oxy)methyl)-3-(methylsulfonamido)pyrrolidine-1-carboxylate; (156)

methyl (2R,3S,5R)-5-methyl-2-(((6-(5-methylpyrimidin-2-yl)bicyclo[4.1.0]heptan-3-yl)oxy)methyl)-3-(methylsulfonamido)pyrrolidine-1-carboxylate; (159)

isopropyl (2R,3S,5R)-3-((N,N-dimethylsulfamoyl)amino)-2-(((((1R,3R,6S)-6-(5-fluoropyrimidin-2-yl)bicyclo[4.1.0]heptan-3-yl)oxy)methyl)-5-methylpyrrolidine-1-carboxylate; (160)

isopropyl (2R,3S,5R)-3-((N,N-dimethylsulfamoyl)amino)-2-(((((1S,3S,6R)-6-(5-fluoropyrimidin-2-yl)bicyclo[4.1.0]heptan-3-yl)oxy)methyl)-5-methylpyrrolidine-1-carboxylate; (161)

isopropyl (2R,3S,5R)-3-((N,N-dimethylsulfamoyl)amino)-2-(((6-(5-fluoropyrimidin-2-yl)bicyclo[4.1.0]heptan-3-yl)oxy)methyl)-5-methylpyrrolidine-1-carboxylate; (164)

methyl (2R,3S,5R)-3-((N,N-dimethylsulfamoyl)amino)-2-(((((1R,3R,6S)-6-(5-fluoropyrimidin-2-yl)bicyclo[4.1.0]heptan-3-yl)oxy)methyl)-5-methylpyrrolidine-1-carboxylate; (165)

methyl (2R,3S,5R)-3-((N,N-dimethylsulfamoyl)amino)-2-(((((1S,3S,6R)-6-(5-fluoropyrimidin-2-yl)bicyclo[4.1.0]heptan-3-yl)oxy)methyl)-5-methylpyrrolidine-1-carboxylate; (166)

methyl (2R,3S,5R)-3-((N,N-dimethylsulfamoyl)amino)-2-(((6-(5-fluoropyrimidin-2-yl)bicyclo[4.1.0]heptan-3-yl)oxy)methyl)-5-methylpyrrolidine-1-carboxylate; (167)

methyl (2R,3S,5R)-3-((N,N-dimethylsulfamoyl)amino)-2-(((6-(5-fluoropyrimidin-2-yl)bicyclo[4.1.0]heptan-3-yl)oxy)methyl)-5-methylpyrrolidine-1-carboxylate; (169)

isopropyl (2R,3S,5R)-3-((N,N-dimethylsulfamoyl)amino)-5-methyl-2-(((((1R,3R,6S)-6-(pyrimidin-2-yl)bicyclo[4.1.0]heptan-3-yl)oxy)methyl)pyrrolidine-1-carboxylate; (170)

isopropyl (2R,3S,5R)-3-((N,N-dimethylsulfamoyl)amino)-5-methyl-2-(((((1S,3S,6R)-6-(pyrimidin-2-yl)bicyclo[4.1.0]heptan-3-yl)oxy)methyl)pyrrolidine-1-carboxylate; (171)

isopropyl (2R,3S,5R)-3-((N,N-dimethylsulfamoyl)amino)-5-methyl-2-(((6-(pyrimidin-2-yl)bicyclo[4.1.0]heptan-3-yl)oxy)methyl)pyrrolidine-1-carboxylate; (174)

methyl (2R,3S,3aS,6aR)-3-(methylsulfonamido)-2-(((6-(pyrimidin-2-yl)bicyclo[4.1.0]heptan-3-yl)oxy)methyl)hexahydrocyclopenta[b]pyrrole-1(2H)-carboxylate; (175)

methyl (2R,3S)-3-(methylsulfonamido)-2-(((((1R,3R,6S)-6-(pyrimidin-2-yl)bicyclo[4.1.0]heptan-3-yl)oxy)methyl)pyrrolidine-1-carboxylate; (176)

methyl (2R,3S)-3-(methylsulfonamido)-2-(((((1S,3S,6R)-6-(pyrimidin-2-yl)bicyclo[4.1.0]heptan-3-yl)oxy)methyl)pyrrolidine-1-carboxylate; (177)

methyl (2R,3S,5R)-5-methyl-3-(methylsulfonamido)-2-(((((1R,3R,6S)-6-(pyrimidin-2-yl)bicyclo[4.1.0]heptan-3-yl)oxy)methyl)pyrrolidine-1-carboxylate; (180)

methyl (2R,3S,5R)-5-methyl-3-(methylsulfonamido)-2-(((((1S,3S,6R)-6-(pyrimidin-2-yl)bicyclo[4.1.0]heptan-3-yl)oxy)methyl)pyrrolidine-1-carboxylate; (181)

methyl (2R,3S,5R)-5-methyl-3-(methylsulfonamido)-2-(((6-(pyrimidin-2-yl)bicyclo[4.1.0]heptan-3-yl)oxy)methyl)pyrrolidine-1-carboxylate; (184)

methyl (2R,3S)-3-(methylsulfonamido)-2-(((6-(pyrimidin-2-yl)bicyclo[4.1.0]heptan-3-yl)oxy)methyl)pyrrolidine-1-carboxylate; (185)

methyl (2R,3S,5R)-3-((N,N-dimethylsulfamoyl)amino)-5-methyl-2-(((6-(pyrimidin-2-yl)bicyclo[4.1.0]heptan-3-yl)oxy)methyl)pyrrolidine-1-carboxylate; (186)

methyl (2R,3S,5R)-2-(((6-(5-cyanopyrimidin-2-yl)bicyclo[4.1.0]heptan-3-yl)oxy)methyl)-5-methyl-3-(methylsulfonamido)pyrrolidine-1-carboxylate; (188)

methyl (2R,3S,5R)-2-(((((1S,3S,6R)-6-(5-cyanopyrimidin-2-yl)bicyclo[4.1.0]heptan-3-yl)oxy)methyl)-5-methyl-3-(methylsulfonamido)pyrrolidine-1-carboxylate (190)

or a pharmaceutically acceptable salt thereof.

Certain embodiments of the present invention include a compound which is selected from Example Numbers: 30, 31, 48, 68, 115, 124, 132, 133, 137, and 142 or a pharmaceutically acceptable salt thereof.

Certain embodiments of the present invention include a compound which is selected from Example Number: 30, 48, 68, 137, and 142 or a pharmaceutically acceptable salt thereof.

It is understood that reference to "Formula I" also encompasses compounds of Formula IA, Formula IA', Formula IA", Formula IA''', Formula IB, Formula IB', Formula IB", Formula IB''', Formula IC, Formula IC', Formula IC", Formula IC''', Formula ID and Formula IE, unless indicated otherwise.

The present invention includes compounds that may contain one or more asymmetric centers. Thus, compounds of the present invention include those that can occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. Likewise, the present invention includes tautomeric forms of the compounds disclosed herein. Formula I, as well as other Formulae herein (e.g. IA, IB, IC and ID), shows the structure of the class of compounds without specific stereochemistry. At least some of the chemical names of compounds of the invention as set forth in this application may have been generated on an automated basis by use of commercially available chemical naming software programs, and have not been independently verified.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. Absolute stereochemistry may also be elucidated through other techniques known in the art, such as cryogenic electron microscopy. Relative stereochemistry may be determined using nuclear magnetic resonance with methods known in the art. Stereochemistry may be assigned by analogy to a set of isomers based on their relative biological activity following the same trend established by a similar stereochemically defined group of isomers. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Compounds of the present invention may also be separated by supercritical fluid chromatography (SFC). Isomers are named according to the order they came off the column (PEAK 1, PEAK 2, etc.). For isomers that have a designation similar to "PEAK 2, part b" or "PEAK 2b", one with skill in the art would understand that sometimes the peaks may contain more than a single isomer and when cut in half or fractionated further result in a "part a" and a "part b" of one peak. Furthermore, some separations required multiple rounds of purifications by the same method of purification and/or an alternative purification system to resolve mixtures into single isomers (i.e., PEAK 2 was a mixture of multiple isomers after the initial purification that was resolved further to give PEAK 2A and PEAK 2B). Additionally, a mixture may be a mixture of 2 to 4 stereoisomers. Alternatively, any enantiomer of a compound may be obtained by stereoselective synthesis using optically pure starting materials or reagents of known configuration by methods well known in the art.

As appreciated by those of skill in the art, halogen or halo as used herein are intended to include fluoro, chloro, bromo and iodo. Similarly, $C_{1-6}$, as in $C_{1-6}$alkyl is defined to identify the group as having 1, 2, 3, 4, 5 or 6 carbons in a linear or branched arrangement, such that $C_{1-6}$alkyl specifically includes methyl, ethyl, n-propyl, iso-propyl, n-butyl, iso-butyl, tert-butyl, pentyl, and hexyl. Additionally, heterocyclyl, unless otherwise specified, means mono- and bicyclic saturated rings and ring systems containing at least one heteroatom selected from N, S and O, each of said rings having 3 to 10 atoms in which the point of attachment may be carbon or nitrogen. Examples of "heterocyclyl" include, but are not limited to, azetidinyl, oxetanyl, pyrrolidinyl, piperidinyl, piperazinyl, imidazolidinyl, tetrahydrofuranyl, 1,4-dioxanyl, morpholinyl, thiomorpholinyl, tetrahydrothienyl and the like. Heterocycles can also exist in tautomeric forms, e.g., 2- and 4-pyridones. In some embodiments, heterocyclyl is independently selected from azetidnyl, oxetanyl, piperidinyl, pyridyl, pyrrolidinyl or tetrahydrofuranyl. In an embodiment of instant invention, heterocyclyl in $R^1$ is tetrahydrofuranyl. In an embodiment of instant invention, heterocyclyl in $R^3$ is selected from azetidinyl or oxetanyl. A group which is designated as being independently substituted with substituents may be independently substituted with multiple numbers of such substituents.

The present invention also includes all pharmaceutically acceptable isotopic variations of a compound of the Formula I in which one or more atoms is replaced by atoms having the same atomic number, but an atomic mass or mass number different from the atomic mass or mass number usually found in nature. Such compounds are identical to those disclosed herein, but for the fact that one or more atoms are replaced by an atom having an atomic mass or mass number different from the atomic mass or mass number usually found in nature. Examples of isotopes suitable for inclusion in the compounds of the invention include isotopes of hydrogen such as $^2H$ and $^3H$, carbon such as $^{11}C$, $^{13}C$ and $^{14}C$, nitrogen such as $^{13}N$ and $^{15}N$, oxygen such as $^{15}O$, $^{17}O$ and $^{18}O$, phosphorus such as $^{32}P$, sulfur such as $^{35}S$, fluorine such as $^{18}F$, iodine such as $^{123}I$ and $^{125}I$, and chlorine such as $^{36}Cl$. Certain isotopically-labelled compounds of Formula I, for example those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy. An embodiment of the present invention includes compounds that are substituted with a positron emitting isotope. An embodiment of the present invention includes compounds that are substituted with a $^{11}C$ isotope. An embodiment of the present invention includes compounds that are substituted with an $^{18}F$ isotope. In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of the invention can be prepared without undue experimentation by conventional techniques well known to those skilled in the art or by processes analogous to those described in the schemes and examples herein using appropriate isotopically-enriched reagents and/or intermediates.

Where a wavy line terminates a conventional bond (as opposed to connecting two atoms within a structure) it indicates a point of bonding to a structure, e.g.:

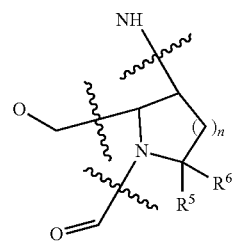

indicates the heterocyclyl shown is bonded to the rest of the structure of Formula I via the bonds terminated with the wavy line. Where an alphabetical notation is used to depict a substituent moiety, a dash is employed to indicate the point of bonding to the indicated substrate, e.g.: —CH$_2$—C(O)—CH$_2$Cl indicates the acetyl chloride moiety is bonded via the methylene portion of the moiety.

When any variable (e.g., $R^4$, $R^7$, etc.) occurs more than one time in any substituent or in Formula I, its definition on each occurrence is independent of its definition at every other occurrence unless otherwise specified at the point of definition. One of ordinary skill in the art will recognize that choice of combinations of the various substituents defined in a structural representation, i.e. $R^4$, $R^7$, etc., are to be chosen in conformity with well-known principles of chemical structure connectivity and stability, and combinations of substituents and/or variables are permissible only if such combinations result in stable compounds.

A "stable" compound is a compound which can be prepared and isolated and whose structure and properties remain or can be caused to remain essentially unchanged for a period of time sufficient to allow use of the compound for the purposes described herein (e.g., therapeutic administration to a subject). The compounds of the present invention are limited to stable compounds embraced by Formula I.

Those skilled in the art will recognize those instances in which the compounds of the invention may form salts. In such instances, another embodiment provides pharmaceutically acceptable salts of the compounds of the invention. Thus, reference to a compound of the invention herein is understood to include reference to salts thereof, unless otherwise indicated. The term "pharmaceutically acceptable salts" refers to salts prepared from pharmaceutically acceptable non-toxic bases or acids including inorganic or organic bases and inorganic or organic acids. In addition, when a compound of the invention contains both a basic moiety, such as, but not limited to a pyridine or imidazole, and an acidic moiety, such as, but not limited to a carboxylic acid, zwitterions ("inner salts") may be formed and are included within the present invention. Salts derived from inorganic bases include aluminum, ammonium, calcium, copper, ferric, ferrous, lithium, magnesium, manganic salts, manganous, potassium, sodium, zinc, and the like. Particular embodiments include the ammonium, calcium, magnesium, potassium, and sodium salts. Salts in the solid form may exist in more than one crystal structure, and may also be in the form of hydrates or solvates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments include the citric, hydrobromic, hydrochloric, maleic, phosphoric, sulfuric, fumaric, and tartaric acids. It will be understood that, as used herein, references to the compounds of Formula I are meant to also include the pharmaceutically acceptable salts. Salts of the compounds of the invention may be formed by methods known to those of ordinary skill in the art, for example, by reacting a compound of the invention with an amount of acid or base, such as an equivalent amount, in a medium such as one in which the salt precipitates or in an aqueous medium followed by lyophilization.

Exemplifying the invention is the use of the compounds disclosed in the Examples and herein. Specific compounds within the present invention include a compound which is selected from the compounds disclosed in the following Examples and pharmaceutically acceptable salts thereof and individual enantiomers or diastereomers thereof.

The present invention is also directed to the use of the compounds disclosed herein as agonists of orexin receptor activity. The subject compounds and pharmaceutically acceptable salts thereof are useful in a method of agonizing orexin receptor activity in a subject such as a mammal comprising the administration of an amount of the compound. In addition to primates, especially humans, a variety of other mammals may be administered with a compound of the present invention. The present invention is directed to a compound of the present invention or a pharmaceutically acceptable salt thereof that could be useful in therapy. The present invention may further be directed to a use of a compound of the present invention or a pharmaceutically acceptable salt thereof for the manufacture of a medicament for agonizing orexin receptor activity or treating the disorders and diseases noted herein in humans and animals.

A subject administered with a compound of the present invention, or a pharmaceutically acceptable salt thereof, is generally a mammal, such as a human being, male or female. The amount of compound administered to the subject is an amount sufficient to agonize the orexin receptor in the subject. In an embodiment, the amount of compound can be an "effective amount", wherein the subject compound is administered in an amount that will elicit the biological or medical response of a tissue, system, animal or human that is being sought by the researcher, veterinarian, medical doctor or other clinician. An effective amount does not necessarily include considerations of toxicity and safety related to the administration of the compound. It is recognized that one skilled in the art may affect neurological and psychiatric disorders associated with orexin receptor activation by treating a subject presently afflicted with the disorders, or by prophylactically treating a subject likely to be afflicted with the disorders, with an effective amount of a compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a subject that is predisposed to such disease or disorder. The terms "administration of" and or "administering a" compound should be understood to mean providing a compound of the invention or a prodrug of a compound of the invention to the subject.

The term "composition" as used herein is intended to encompass a product comprising the specified ingredients in the specified amounts, as well as any product which results, directly or indirectly, from combination of the specified ingredients in the specified amounts. Such term is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The utility of the compounds in accordance with the present invention as orexin receptor OX1R and/or OX2R agonists may be readily determined without undue experimentation by methodology well known in the art. Both the OX1R and/or OX2R G-coupled protein receptors (GPCRs) couple through the Gαq signaling pathway, which ultimately promotes calcium mobilization via inositol triphosphate (IP3) production. The half-life of IP-3 is relatively short, being rapidly metabolized to inositol monophosphate (IP-1), which can be readily detected using a commercially available assay kit (IP-One; Cisbio; cat #621PAPEC) coupled with a cell line expressing the target receptor(s) of interest. The utility of the compounds in accordance with the present invention as orexin receptor OX1R and/or OX2R agonists may be determined utilizing this assay.

In a typical experiment, the OX1 and OX2 receptor agonist activity is determined in accordance with the following general experimental method. Chinese hamster ovary (CHO) cells expressing human OX1R and/or the human OX2R were grown in Iscove's modified DMEM containing glutaMAX™, 1% G418, 100 U/mL penicillin, 100 µg/mL streptomycin and 10% heat-inactivated qualified fetal bovine serum (FBS). The OX2R cells were seeded at 10,000 cells/well/50 µL and the OX1R cells were seeded at 20,000 cells/well/50 µL into 384-well white tissue culture plates (Greiner; cat #781080). All cell/media reagents were from GIBCO-Invitrogen Corp. The seeded cell plate(s) were incubated at 37° C. with 5% $CO_2$ and 85% humidity for 20-24 hours. On the day of the assay, assay-ready compound plates were prepared using an acoustic liquid handler (ECHO; Labcyte), which dispensed sufficient volume of test compound stock (10 mM in DMSO) or 100% DMSO to prepare 10 point, ½-log dilutions in a final volume of 202.5 nL/well in all test wells of a 384-well diamond plate (Labcyte). Following completion of assay-ready plates, importantly, the next three steps were performed with minimal delay: 1) 20 µl of 1× stimulation buffer was added to the compound plate using a Multidrop Combi (small cassette, Thermo Fisher Scientific cat #24073290); 2) culture medium was removed from the cell plate using the Bluewasher plate washer (gentle spin; BlueCatBio); 3) 14 µl of compound/stimulation buffer mixture was added to the cell plate using a Bravo liquid handler (Agilent) prior to incubating cell plates at 37° C. with 5% $CO_2$ and 85% humidity for 1 or 2 hours (OX1R and OX2R, respectively). During this incubation, IP-one detection reagents were prepared (38:1:1 lysis buffer:D2:AB-cryptate reagents). Six µL of mixed detection reagents were added to the cell plate using a Multidrop Combi (small cassette, Thermo Fisher Scientific cat #24073290) and incubated 60 minutes at room temperature in the dark. Fluorescence signal was detected using an Envision plate reader (Perkin Elmer) [LANCE/DELFIA Dual Enh (Em: APC 665; Ex: Cy5 620)].

For each compound, data were fit to a four parameter logistic fit (ActivityBase software) and the $EC_{50}$ was reported as the inflection point of the resulting curve. Percent effect for each test compound was determined as the percentage of sample raw value/mean max effect, where the mean max effect was derived from the mean raw value of 32 control wells per assay plate (using Orexin A (cat #003-30) at 1 µM for human OX1R and a reference compound at 1 uM with 100% activity previously established by comparison to Orexin A for human OX2R). The intrinsic orexin receptor agonist activity of a compound which may be used in the present invention may be determined by these assays.

All of the final compounds of the following examples had activity in agonizing the human orexin-2 receptor in the aforementioned IPOne assay with an $EC_{50}$ of about 0.01 nM to 5000 nM. Additional data is provided in the following Examples. Such a result is indicative of the intrinsic activity of the compounds in use as agonists of orexin-1 receptor and/or the orexin-2 receptor. In general, one of ordinary skill in the art would appreciate that a substance is considered to effectively agonize the orexin receptor if it has an $EC_{50}$ in the IPOne assay of less than about 50 µM, or more specifically less than about 1000 nM.

The orexin receptors have been implicated in a wide range of biological functions. This has suggested a potential role for these receptors in a variety of disease processes in humans or other species. The compounds of the present invention could therefore potentially have utility in treating, preventing, ameliorating, controlling or reducing the risk of a variety of disorders associated with orexin receptors, including one or more of the following conditions or diseases: narcolepsy, narcolepsy syndrome accompanied by narcolepsy-like symptoms, cataplexy in narcolepsy, excessive daytime sleepiness (EDS) in narcolepsy, hypersomnia, idiopathic hypersomnia, repeatability hypersomnia, intrinsic hypersomnia, hypersomnia accompanied by daytime hypersomnia, interrupted sleep, sleep apnea, wakefulness, nocturnal myoclonus, disturbances of consciousness, such as coma, REM sleep interruptions, jet-lag, excessive daytime sleepiness, shift workers' sleep disturbances, dyssomnias, sleep disorders, sleep disturbances, hypersomnia associated with depression, emotional/mood disorders, Alzheimer's disease or cognitive impairment, Parkinson's disease, Guillain-Barre syndrome, Kleine Levin syndrome, and sleep disorders which accompany aging; Alzheimer's sundowning; conditions associated with circadian rhythmicity as well as mental and physical disorders associated with travel across time zones and with rotating shift-work schedules; fibromyalgia; cardiac failure; diseases related to bone loss; sepsis; syndromes which are manifested by non-restorative sleep and muscle pain or sleep apnea which is associated with respiratory disturbances during sleep; conditions which result from a diminished quality of sleep; and other diseases related to general orexin system dysfunction.

Thus, in certain embodiments the present invention may provide methods for: treating or controlling narcolepsy, narcolepsy syndrome accompanied by narcolepsy-like symptoms, cataplexy in narcolepsy, excessive daytime sleepiness (EDS) in narcolepsy, hypersomnia, idiopathic hypersomnia, repeatability hypersomnia, intrinsic hypersomnia, hypersomnia accompanied by daytime hypersomnia, interrupted sleep, sleep apnea, disturbances of consciousness, REM sleep interruptions, jet-lag, shiftworkers' sleep disturbances, dyssomnias, night terror, insomnias associated with depression, emotional/mood disorders, Alzheimer's disease or cognitive impairment; treating or controlling sleep disturbances associated with diseases such as neurological disorders including neuropathic pain and restless leg syndrome; treating or controlling addiction disorders; treating or controlling psychoactive substance use and abuse; enhancing cognition; increasing memory retention; treating or controlling obesity; treating or controlling diabetes and appetite, taste, eating, or drinking disorders; treating or controlling insulin resistance syndrome; treating or controlling hypothalamic diseases; treating or controlling depression; treating, controlling, ameliorating or reducing the risk of epilepsy, including absence epilepsy; treating or controlling pain, including neuropathic pain; treating or controlling Parkinson's disease; treating or controlling Guillain-Barre syndrome; treating or controlling Klein Levin syndrome; treating or controlling psychosis; treating or controlling dysthymic, mood, psychotic and anxiety disorders; treating side effects or complications due to anesthesia; reversal of anesthesia; reversal of anesthesia following surgery; treating or controlling depression, including major depression and major depression disorder; treating or controlling bipolar disorder; or treating, controlling, ameliorating or reducing the risk of schizophrenia, in a mammalian subject which comprises administering to the subject a compound of the present invention.

The compounds of the present invention may also potentially have utility in treating, preventing, ameliorating, controlling or reducing the risk of a variety of other disorders associated with orexin receptors, including one or more of the following conditions or diseases including enhancing sleep quality, improving sleep quality, increasing sleep efficiency, augmenting sleep maintenance; increasing the value which is calculated from the time that a subject sleeps divided by the time that a subject is attempting to sleep; improving sleep initiation; decreasing sleep latency or onset (the time it takes to fall asleep); decreasing difficulties in falling asleep; increasing sleep continuity; decreasing the number of awakenings during sleep; decreasing intermittent wakings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; decreasing nocturnal arousals, especially early morning awakenings; increasing daytime alertness; reducing daytime drowsiness; treating or reducing excessive daytime sleepiness; increasing satisfaction with the intensity of sleep; increasing sleep maintenance; idiopathic insomnia; sleep problems; insomnia; night terror, insomnias associated with depression, emotional/mood disorders, Alzheimer's disease or cognitive impairment, as well as sleep walking and enuresis, and sleep disorders which accompany aging; Alzheimer's sundowning; conditions associated with circadian rhythmicity as well as mental and physical disorders associated with travel across time zones and with rotating shift-work schedules, conditions due to drugs which cause reductions in REM sleep as a side effect; fibromyalgia; syndromes which are manifested by non-restorative sleep and muscle pain or sleep apnea which is associated with respiratory disturbances during sleep; conditions which result from a diminished quality of sleep; increasing learning; augmenting memory; increasing retention of memory; eating disorders associated with excessive food intake and complications associated therewith, compulsive eating disorders, obesity (due to any cause, whether genetic or environmental), obesity-related disorders overeating, anorexia, bulimia, cachexia, dysregulated appetite control, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, lung disease, abnormal heart rhythms and arrythmias, myocardial infarction, congestive heart failure, coronary heart disease, acute and congestive heart failure; hypotension; hypertension; urinary retention; osteoporosis; angina pectoris; myocardinal infarction; ischemic or haemorrhagic stroke; subarachnoid haemorrhage; ulcers; allergies; benign prostatic hypertrophy; chronic renal failure; renal disease; impaired glucose tolerance; sudden death, polycystic ovary disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g., children with acute lymphoblastic leukemia, metabolic syndrome, also known as syndrome X, insulin resistance syndrome, reproductive hormone abnormalities, sexual and reproductive dysfunction, such as impaired fertility, infertility, hypogonadism in males and hirsutism in females, fetal defects associated with maternal obesity, gastrointestinal motility disorders, intestinal motility dyskinesias, obesity-related gastro-esophageal reflux, hypothalmic diseases, hypophysis diseases, respiratory disorders, such as obesity-hypoventilation syndrome (Pickwickian syndrome), breathlessness, cardiovascular disorders, inflammation, such as systemic inflammation of the vasculature, arteriosclerosis, hypercholesterolemia, hyperuricaemia, lower back pain, gallbladder disease, gout, kidney cancer, increased anesthetic risk, reducing the risk of secondary outcomes of obesity, such as reducing the risk of left ventricular hypertrophy; diseases or disorders where abnormal oscillatory activity occurs in the brain, including depression, migraine, neuropathic pain, Parkinson's disease, psychosis and schizophrenia, as well as diseases or disorders where there is abnormal coupling of activity, particularly through the thalamus; enhancing cognitive function, including cognitive dysfunctions that comprise deficits in all types of attention, learning and memory functions occurring transiently or chronically in the normal, healthy, young, adult or aging population, and also occurring transiently or chronically in psychiatric, neurologic, cardiovascular and immune disorders; treating or controlling Guillain-Barre syndrome; treating or controlling Klein Levin syndrome; treating or controlling psychosis; treating or controlling dysthymic, mood, psychotic and anxiety disorders; treating complications due to anesthesia; enhancing memory; increasing memory retention; increasing immune response; increasing immune function; hot flashes; night sweats; extending life span; schizophrenia; muscle-related disorders that are controlled by the excitation/relaxation rhythms imposed by the neural system such as cardiac rhythm and other disorders of the cardiovascular system; conditions related to proliferation of cells such as vasodilation or vasorestriction and blood pressure; cancer; cardiac arrhythmia; hypertension; congestive heart failure; conditions of the genital/urinary system; disorders of sexual function and fertility; adequacy of renal function; responsivity to anesthetics; mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder, mood disorders due to a general medical condition, and substance-induced mood disorders; affective neurosis; depressive neurosis; anxiety neurosis; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; acute neurological and psychiatric disorders such as cerebral deficits subsequent to cardiac bypass surgery and grafting, stroke, ischemic stroke, cerebral ischemia, spinal cord trauma, head trauma, perinatal hypoxia, cardiac arrest, hypoglycemic neuronal damage; Huntington's Chorea; Huntington's disease and Tourette syndrome; Cushing's syndrome/disease; basophile adenoma; prolactinoma; hyperprolactinemia; hypophysis tumor/adenoma; hypothalamic diseases; inflammatory bowel disease; gastric diskinesia; gastric ulcers; Froehlich's syndrome; adrenohypophysis disease; hypophysis disease; adrenohypophysis hypofunction; adrenohypophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth deficiency; dwarfism; gigantism; acromegaly; amyotrophic lateral sclerosis; multiple sclerosis; ocular damage; retinopathy; cognitive disorders; idiopathic and drug-induced Parkinson's disease; muscular spasms and disorders associated with muscular spasticity including tremors, epilepsy, convulsions, seizure disorders, absence seisures, complex partial and generalized seizures; Lennox-Gastaut syndrome; cognitive disorders including dementia (associated with Alzheimer's disease, ischemia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder; dissociative disorders including multiple personality syndromes and psychogenic amnesias; substance-related disorders, substance use, substance abuse, substance seeking, substance reinstatement, all types of psychological and physical addictions and addictive behaviors, reward-related behaviors (including substance-induced delirium, persisting dementia, persisting amnestic disorder, psychotic disorder or anxiety disorder; tolerance, addictive feeding, addictive feeding behaviors, binge/purge feeding behaviors, dependence, withdrawal or relapse from substances including alcohol, amphetamines, cannabis, cocaine, hallucinogens, inhalants, morphine, nicotine, opioids, phencyclidine, sedatives, hypnotics or anxiolytics); appetite, taste, eating or drinking disorders; movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), chronic fatigue syndrome, fatigue, including Parkinson's fatigue, multiple sclerosis fatigue, fatigue caused by a sleep disorder or a circadian rhythm disorder, medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, and dyskinesias [including tremor (such as rest tremor, essential tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), restless leg syndrome and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia); neurodegenerative disorders including nosological entities such as disinhibition-dementia-parkinsonism-amyotrophy complex; pallido-ponto-nigral degeneration; epilepsy; seizure disorders; attention deficit/hyperactivity disorder (ADHD); conduct disorder; migraine (including migraine headache); headache; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; emesis, nausea, vomiting; gastric dyskinesia; gastric ulcers; Kallman's syndrome (anosmia); asthma; cancer; conditions associated with visceral pain such as irritable bowel syndrome, and angina; eating disorders; urinary incontinence; substance tolerance, substance withdrawal (including, substances such as opiates, nicotine, tobacco products, alcohol, benzodiazepines, cocaine, sedatives, hypnotics, etc.); psychosis; schizophrenia; anxiety (including generalized anxiety disorder, panic disorder, and obsessive compulsive disorder); mood disorders (including depression, mania, bipolar disorders); trigeminal neuralgia; hearing loss; tinnitus; neuronal damage including ocular damage; retinopathy; macular degeneration of the eye; emesis; brain edema; pain, including acute and chronic pain states, severe pain, intractable pain, inflammatory pain, neuropathic pain, post-traumatic pain, bone and joint pain (osteoarthritis), repetitive motion pain, dental pain, cancer pain, myofascial pain (muscular injury, fibromyalgia), perioperative pain (general surgery, gynecological), chronic pain, neuropathic pain, post-traumatic pain, trigeminal neuralgia, migraine and migraine headache and other diseases related to general orexin system dysfunction.

The subject compounds could further be of potential use in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to subjects (animals and human) in need of such treatment in dosages that will provide optimal pharmaceutical efficacy. The selected dosage depends upon the desired therapeutic effect, on the route of administration, and on the duration of the treatment. The dose will vary from subject to subject depending upon the nature and severity of disease, the subject's weight, special diets then being followed by a subject, concurrent medication, and other factors which those skilled in the art will recognize.

Generally, dosage levels of between 0.0001 to 100 mg/kg. of body weight daily are administered to the subject, e.g., humans, adolescent humans and elderly humans, to obtain effective agonism of orexin receptors. The dosage range will generally be about 0.5 mg to 10.0 g. per subject per day which may be administered in single or multiple doses. In one embodiment, the dosage range will be about 0.5 mg to 500 mg per subject per day; in another embodiment about 0.5 mg to 200 mg per subject per day; and in yet another embodiment about 5 mg to 50 mg per subject per day.

Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 30 mg, 50 mg, 80 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the subject to be treated. The compounds may be administered on a regimen of 1 to 4 times per day, such as once or twice per day. The compounds may be administered once or multiple times during the day. The compounds may be administered upon awakening or otherwise in the morning, or during waking hours. For example, the compounds may be administered about 1 hour after awakening, about 30 minutes after awakening or immediately after awakening.

The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention is contemplated. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The compounds of the present invention may be administered in combination with compounds which are known in the art to be useful for treating or controlling narcolepsy, including e.g., methylphenidate, amphetamine, pemoline, phenelzine, protriptyline, gamma-hydroxybutyric acid, sodium oxybate, or other oxybate salts, modafinil, armodafinil, caffeine, and salts thereof, and combinations thereof, and the like, The compounds of the present invention may be administered in combination with compounds which are known in the art to be useful for preventing and treating sleep disorders and sleep disturbances, including e.g., sedatives, hypnotics, anxiolytics, antipsychotics, antianxiety agents, antihistamines, benzodiazepines, barbiturates, cyclopyrrolones, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, orexin antagonists, other orexin agonists, prokineticin agonists and antagonists, pyrazolopyrimidines, T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, omortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

In another embodiment, the subject compound may be employed in combination with other compounds which are known in the art, either administered separately or in the same pharmaceutical compositions, including, but are not limited to: insulin sensitizers including (i) PPARγ antagonists such as glitazones (e.g. ciglitazone; darglitazone; englitazone; isaglitazone (MCC-555); pioglitazone; rosiglitazone; troglitazone; tularik; BRL49653; CLX-0921; 5-BTZD), GW-0207, LG-100641, and LY-300512, and the like); (iii) biguanides such as metformin and phenformin; (b) insulin or insulin mimetics, such as biota, LP-100, novarapid, insulin detemir, insulin lispro, insulin glargine, insulin zinc suspension (lente and ultralente); Lys-Pro insulin, GLP-1 (73-7) (insulintropin); and GLP-1 (7-36)-NH$_2$); (c) sulfonylureas, such as acetohexamide; chlorpropamide; diabinese; glibenclamide; glipizide; glyburide; glimepiride;

gliclazide; glipentide; gliquidone; glisolamide; tolazamide; and tolbutamide; (d) α-glucosidase inhibitors, such as acarbose, adiposine; camiglibose; emiglitate; miglitol; voglibose; pradimicin-Q; salbostatin; CKD-711; MDL-25,637; MDL-73,945; and MOR 14, and the like; (e) cholesterol lowering agents such as (i) HMG-CoA reductase inhibitors (atorvastatin, itavastatin, fluvastatin, lovastatin, pravastatin, rivastatin, rosuvastatin, simvastatin, and other statins), (ii) bile acid absorbers/sequestrants, such as cholestyramine, colestipol, dialkylaminoalkyl derivatives of a cross-linked dextran; Colestid®; LoCholest®, and the like, (ii) nicotinyl alcohol, nicotinic acid or a salt thereof, (iii) proliferator-activator receptor a agonists such as fenofibric acid derivatives (gemfibrozil, clofibrate, fenofibrate and benzafibrate), (iv) inhibitors of cholesterol absorption such as stanol esters, beta-sitosterol, sterol glycosides such as tiqueside; and azetidinones such as ezetimibe, and the like, and (acyl CoA: cholesterol acyltransferase (ACAT)) inhibitors such as avasimibe, and melinamide, (v) anti-oxidants, such as probucol, (vi) vitamin E, and (vii) thyromimetics; (f) PPARα agonists such as beclofibrate, benzafibrate, ciprofibrate, clofibrate, etofibrate, fenofibrate, and gemfibrozil; and other fibric acid derivatives, such as Atromid®, Lopid® and Tricor®, and the like, and PPARα agonists as described in WO 97/36579; (g) PPARδ agonists, such as those disclosed in WO 97/28149; (h) PPAR α/δ agonists, such as muraglitazar, and the compounds disclosed in U.S. Pat. No. 6,414, 002; (i) anti-obesity agents, such as (1) growth hormone secretagogues, growth hormone secretagogue receptor agonists/antagonists, such as NN703, hexarelin, MK-0677, SM-130686, CP-424,391, L-692,429, and L-163,255, and such as those disclosed in U.S. Pat. Nos. 5,536,716, and 6,358,951, U.S. Patent Application Nos. 2002/049196 and 2002/022637, and PCT Application Nos. WO 01/56592 and WO 02/32888; (2) protein tyrosine phosphatase-IB (PTP-1B) inhibitors; (3) cannabinoid receptor ligands, such as cannabinoid $CB_1$ receptor antagonists or inverse agonists, such as rimonabant, taranabant, AMT-251, and SR-14778 and SR 141716A (Sanofi Synthelabo), SLV-319 (Solvay), BAY 65-2520 (Bayer) and those disclosed in U.S. Pat. Nos. 5,532,237, 4,973,587, 5,013,837, 5,081,122, 5,112,820, 5,292,736, 5,624,941, 6,028,084, PCT Application Nos. WO 96/33159, WO 98/33765, WO 98/43636, WO 98/43635, WO 01/09120, WO 98/31227, WO 98/41519, WO 98/37061, WO 00/10967, WO 00/10968, WO97/29079, WO99/02499, WO 01/58869, WO 01/64632, WO 01/64633, WO 01/64634, WO 02/076949, WO 03/007887, WO 04/048317, and WO 05/000809; (4) anti-obesity serotonergic agents, such as fenfluramine, dexfenfluramine, phentermine, and sibutramine; (5) β3-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, SR 59119A; (6) pancreatic lipase inhibitors, such as orlistat (Xenical®), Triton WR1339, RHC80267, lipstatin, tetrahydrolipstatin, teasaponin, diethylumbelliferyl phosphate, and those disclosed in PCT Application No. WO 01/77094; (7) neuropeptide Y1 antagonists, such as BIBP3226, J-115814, BIBO 3304, LY-357897, CP-671906, GI-264879A, and those disclosed in U.S. Pat. No. 6,001, 836, and PCT Patent Publication Nos. WO 96/14307, WO 01/23387, WO 99/51600, WO 01/85690, WO 01/85098, WO 01/85173, and WO 01/89528; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104, and those disclosed in U.S. Pat. Nos. 6,057,335; 6,043,246; 6,140,354; 6,166,038; 6,180,653; 6,191,160; 6,313,298; 6,335,345; 6,337,332; 6,326,375; 6,329,395; 6,340,683; 6,388,077; 6,462,053; 6,649,624; and 6,723,847, European Patent Nos. EP-01010691, and EP-01044970; and PCT International Patent Publication Nos. WO 97/19682, WO 97/20820, WO 97/20821, WO 97/20822, WO 97/20823, WO 98/24768; WO 98/25907; WO 98/25908; WO 98/27063, WO 98/47505; WO 98/40356; WO 99/15516; WO 99/27965; WO 00/64880, WO 00/68197, WO 00/69849, WO 01/09120, WO 01/14376; WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/22592, WO 0248152, and WO 02/49648; WO 02/094825; WO 03/014083; WO 03/10191; WO 03/092889; WO 04/002986; and WO 04/031175; (9) melanin-concentrating hormone (MCH) receptor antagonists, such as those disclosed in WO 01/21577 and WO 01/21169; (10) melanin-concentrating hormone 1 receptor (MCH1R) antagonists, such as T-226296 (Takeda), and those disclosed in PCT Patent Application Nos. WO 01/82925, WO 01/87834, WO 02/051809, WO 02/06245, WO 02/076929, WO 02/076947, WO 02/04433, WO 02/51809, WO 02/083134, WO 02/094799, WO 03/004027; (11) melanin-concentrating hormone 2 receptor (MCH2R) agonist/antagonists; (12) orexin receptor antagonists, such as SB-334867-A, and those disclosed in patent publications herein; (13) serotonin reuptake inhibitors such as fluoxetine, paroxetine, and sertraline; (14) melanocortin agonists, such as Melanotan II; (15) Mc4r (melanocortin 4 receptor) agonists, such as CHIR86036 (Chiron), ME-10142, and ME-10145 (Melacure), CHIR86036 (Chiron); PT-141, and PT-14 (Palatin); (16) 5HT-2 agonists; (17) 5HT2C (serotonin receptor 2C) agonists, such as BVT933, DPCA37215, WAY161503, R-1065, and those disclosed in U.S. Pat. No. 3,914,250, and PCT Application Nos. WO 02/36596, WO 02/48124, WO 02/10169, WO 01/66548, WO 02/44152, WO 02/51844, WO 02/40456, and WO 02/40457; (18) galanin antagonists; (19) CCK agonists; (20) CCK-A (cholecystokinin-A) agonists, such as AR-R 15849, GI181771, JMV-180, A-71378, A-71623 and SR14613, and those described in U.S. Pat. No. 5,739,106; (21) GLP-1 agonists; (22) corticotropin-releasing hormone agonists; (23) histamine receptor-3 (H3) modulators; (24) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, GT2394 (Gliatech), and O-[3-(1H-imidazol-4-yl)propanol]-carbamates; (25) β-hydroxy steroid dehydrogenase-1 inhibitors (β-HSD-1); (26) PDE (phosphodiesterase) inhibitors, such as theophylline, pentoxifylline, zaprinast, sildenafil, amrinone, milrinone, cilostamide, rolipram, and cilomilast; (27) phosphodiesterase-3B (PDE3B) inhibitors; (28) NE (norepinephrine) transport inhibitors, such as GW 320659, despiramine, talsupram, and nomifensine; (29) ghrelin receptor antagonists, such as those disclosed in PCT Application Nos. WO 01/87335, and WO 02/08250; (30) leptin, including recombinant human leptin (PEG-OB, Hoffman La Roche) and recombinant methionyl human leptin (Amgen); (31) leptin derivatives; (32) BRS3 (bombesin receptor subtype 3) agonists such as [D-Phe6, beta-Ala11,Phe13,Nle14]Bn(6-14) and [D-Phe6,Phe13]Bn (6-13)propylamide, and those compounds disclosed in Pept. Sci. 2002 August; 8(8): 461-75); (33) CNTF (Ciliary neurotrophic factors), such as GI-181771 (Glaxo-SmithKline), SR146131 (Sanofi Synthelabo), butabindide, PD170,292, and PD 149164 (Pfizer); (34) CNTF derivatives, such as axokine (Regeneron); (35) monoamine reuptake inhibitors, such as sibutramine; (36) UCP-1 (uncoupling protein-1), 2, or 3 activators, such as phytanic acid, 4-[(E)-2-(5,6,7,8-tetrahydro-5,5,8,8-tetramethyl-2-napthalenyl)-1-propenyl] benzoic acid (TTNPB), retinoic acid; (37) thyroid hormone β agonists, such as KB-2611 (KaroBioBMS); (38) FAS (fatty acid synthase) inhibitors, such as Cerulenin and C75; (39) DGAT1 (diacylglycerol acyltransferase 1) inhibitors; (40) DGAT2 (diacylglycerol acyltransferase 2) inhibitors; (41) ACC2 (acetyl-CoA carboxylase-2) inhibitors; (42) glucocorticoid antagonists; (43) acyl-estrogens, such as oleoyl-estrone, disclosed in del Mar-Grasa, M. et al., Obesity Research, 9:202-9 (2001); (44) dipeptidyl peptidase IV (DP-IV) inhibitors, such as isoleucine thiazolidide, valine pyrrolidide, NVP-DPP728, LAF237, P93/01, TSL 225, TMC-2A/2B/2C, FE 999011, P9310/K364, VIP 0177, SDZ 274-444, sitagliptin; and the compounds disclosed in U.S. Pat. No. 6,699,871, WO 03/004498; WO 03/004496; EP 1 258 476; WO 02/083128; WO 02/062764; WO 03/000250; WO 03/002530; WO 03/002531; WO 03/002553; WO 03/002593; WO 03/000180; and WO 03/000181; (46) dicarboxylate transporter inhibitors; (47) glucose transporter inhibitors; (48) phosphate transporter inhibitors; (49) Metformin (Glucophage®); (50) Topiramate (Topimax®); (50) peptide YY, PYY 3-36, peptide YY analogs, derivatives, and fragments such as BIM-43073D, BIM-43004C (Olitvak, D. A. et al., Dig. Dis. Sci. 44(3):643-48 (1999)); (51) Neuropeptide Y2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (52) Neuropeptide Y4 (NPY4) agonists such as pancreatic peptide (PP), and other Y4 agonists such as 1229U91; (54) cyclooxygenase-2 inhibitors such as etoricoxib, celecoxib, valdecoxib, parecoxib, lumiracoxib, BMS347070, tiracoxib or JTE522, ABT963, CS502 and GW406381; (55) Neuropeptide Y1 (NPY1) antagonists such as BIBP3226, J-115814, BIBO 3304, LY-357897, CP-671906, GI-264879A; (56) Opioid antagonists such as nalmefene (Revex®), 3-methoxynaltrexone, naloxone, naltrexone; (57) 11β HSD-1 (11-beta hydroxy steroid dehydrogenase type 1) inhibitors such as BVT 3498, BVT 2733, and those disclosed in WO 01/90091, WO 01/90090, WO 01/90092, U.S. Pat. No. 6,730,690 and US 2004-0133011; (58) aminorex; (59) amphechloral; (60) amphetamine; (61) benzphetamine; (62) chlorphentermine; (63) clobenzorex; (64) cloforex; (65) clominorex; (66) clortermine; (67) cyclexedrine; (68) dextroamphetamine; (69) diphemethoxidine, (70) N-ethylamphetamine; (71) fenbutrazate; (72) fenisorex; (73) fenproporex; (74) fludorex; (75) fluminorex; (76) furfurylmethylamphetamine; (77) levamfetamine; (78) levophacetoperane; (79) mefenorex; (80) metamfepramone; (81) methamphetamine; (82) norpseudoephedrine; (83) pentorex; (84) phendimetrazine; (85) phenmetrazine; (86) picilorex; (87) phytopharm 57; and (88) zonisamide, (89) neuromedin U and analogs or derivatives thereof, (90) oxyntomodulin and analogs or derivatives thereof, and (91) Neurokinin-1 receptor antagonists (NK-1 antagonists) such as the compounds disclosed in: U.S. Pat. Nos. 5,162,339, 5,232,929, 5,242,930, 5,373,003, 5,387,595, 5,459,270, 5,494,926, 5,496,833, and 5,637,699.

In another embodiment, the subject compound may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-HT$_{1A}$ agonists or antagonists, especially 5-HT$_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; citalopram, duloxetine, fluoxetine, fluvoxamine, paroxetine and sertraline; isocarboxazid, phenelzine, tranylcypromine and selegiline; moclobemide: venlafaxine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

In another embodiment, the subject compound may be employed in combination with anti-Alzheimer's agents; beta-secretase inhibitors, such as verubecestat; gamma-secretase inhibitors; growth hormone secretagogues; recombinant growth hormone; HMG-CoA reductase inhibitors; NSAID's including ibuprofen; vitamin E; anti-amyloid antibodies; CB-1 receptor antagonists or CB-1 receptor inverse agonists; antibiotics such as doxycycline and rifampin; N-methyl-D-aspartate (NMDA) receptor antagonists, such as memantine; cholinesterase inhibitors such as galantamine, rivastigmine, donepezil, and tacrine; growth hormone secretagogues such as ibutamoren, ibutamoren mesylate, and capromorelin; histamine H$_3$ antagonists; AMPA agonists; PDE IV inhibitors; GABA$_A$ inverse agonists; or neuronal nicotinic agonists.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amitriptyline, amobarbital, amoxapine, bentazepam, benzoctamine, brotizolam, bupropion, busprione, butabarbital, butalbital, capuride, carbocloral, chloral betaine, chloral hydrate, chlordiazepoxide, clomipramine, clonazepam, cloperidone, clorazepate, clorethate, clozapine, cyprazepam, desipramine, dexclamol, diazepam, dichloralphenazone, divalproex, diphenhydramine, doxepin, estazolam, ethchlorvynol, etomidate, fenobam, flunitrazepam, flurazepam, fluvoxamine, fluoxetine, fosazepam, glutethimide, halazepam, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, reclazepam, roletamide, secobarbital, sertraline, suproclone, temazepam, thioridazine, tracazolate, tranylcypromaine, trazodone, triazolam, trepipam, tricetamide, triclofos, trifluoperazine, trimetozine, trimipramine, uldazepam, venlafaxine, zaleplon, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with acetophenazine, alentemol, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, risperidone, sulpiride, tetrabenazine, trihexyphenidyl, thioridazine, thiothixene or trifluoperazine.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone.

In another embodiment, the subject compound may be employed in combination with a nicotine agonist or a nicotine receptor partial agonist such as varenicline, opioid antagonists (e.g., naltrexone (including naltrexone depot), antabuse, and nalmefene), dopaminergic agents (e.g., apomorphine), ADD/ADHD agents (e.g., methylphenidate hydrochloride (e.g., Ritalin® and Concerta®), atomoxetine (e.g., Strattera®), a monoamine oxidase inhibitor (MAOI), amphetamines (e.g., Adderall®)) and anti-obesity agents, such as apo-B/MTP inhibitors, 11Beta-hydroxy steroid dehydrogenase-1 (11Beta-HSD type 1) inhibitors, peptide YY3-36 or analogs thereof, MCR-4 agonists, CCK-A agonists, monoamine reuptake inhibitors, sympathomimetic agents, β3 adrenergic receptor agonists, dopamine receptor agonists, melanocyte-stimulating hormone receptor analogs, 5-HT2c receptor agonists, melanin concentrating hormone receptor antagonists, leptin, leptin analogs, leptin receptor agonists, galanin receptor antagonists, lipase inhibitors, bombesin receptor agonists, neuropeptide-Y receptor antagonists (e.g., NPY Y5 receptor antagonists), thyromimetic agents, dehydroepiandrosterone or analogs thereof, glucocorticoid receptor antagonists, orexin receptor antagonists, such as suvorexant, other orexin agonists, glucagon-like peptide-1 receptor agonists, ciliary neurotrophic factors, human agouti-related protein antagonists, ghrelin receptor antagonists, histamine 3 receptor antagonists or inverse agonists, and neuromedin U receptor agonists, and pharmaceutically acceptable salts thereof.

In another embodiment, the subject compound may be employed in combination with an agent such as aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; selective serotonin reuptake inhibitor (SSRI); halogenated amphetamine derivatives, including chlorphentermine, cloforex, clortermine, dexfenfluramine, fenfluramine, picilorex and sibutramine; and pharmaceutically acceptable salts thereof.

In another embodiment, the subject compound may be employed in combination with an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the subject compound may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention may be effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives. Pharmaceutical compositions of the present compounds may be in the form of a sterile injectable aqueous or oleagenous suspension. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

Several methods for preparing the compounds of this invention are illustrated in the following Schemes and Examples. Starting materials are made according to procedures known in the art or as illustrated herein. The following abbreviations are used herein: Me: methyl; Et: ethyl; t-Bu: tert-butyl; Ar: aryl; Ph: phenyl; BINAP: 2,2'-bis(diphenylphosphino)-1,1'-binaphthyl; Bn: benzyl; Ac: acetyl; ACN: acetonitrile; Boc: tert-butyloxy carbonyl; BSA: bovine serum albumin; Cbz: benzyloxycarbonyl; CbzCl: benzylchloroformate; CDI: carbonyl diimidazole; DCM ($CH_2Cl_2$): dichloromethane; DCE: dichloroethane; DEAD: diethylazodicarboxylate; DIPEA: N,N-diisopropylethylamine; DMAP: 4-dimethylaminopyridine; DMF: N,N-dimethylformamide; DMSO: dimethylsulfoxide; EDC: N-(3-Dimethylaminopropyl)-N'-ethylcarbodiimide; $Et_3N$: triethylamine; EtOAc: ethyl acetate; EtOH: ethanol; HCl: hydrogen chloride; HOAt: 1-hydroxy-7-aza-benzotriazole; HOBT: hydroxybenzotriazole hydrate; HPLC: high performance liquid chromatography; Hunig's base: N,N-diisopropylethylamine; (iPr)3SiH: triisopropylsilane; MeOH: methanol; $MgSO_4$: magnesium sulfate; Ms: methanesulfonyl; MsCl: methanesulfonyl chloride; MTBE: methyl tert-butyl ether; $NaHCO_3$: sodium bicarbonate; NaOH: sodium hydroxide; NMM: N-methylmorpholine; $Pd(dppf)Cl_2$: [1,1'-bis(diphenylphosphino) ferrocene]palladium(II) dichloride; PMB: p-methoxybenzyl; $PMBNH_2$: 4-methoxybenzylamine; $PtO_2$: platinum oxide; PyClu: 1-(chloro-1-pyrrolidinyl-methylene)-pyrrolidinium hexafluorophosphate; rt: room temperature; $SOCl_2$: thionyl chloride; SFC: supercritical fluid chromatography; STAB: sodium triacetoxyborohydride T3P: 2,4,6-tripropyl-1,3,5,2,4,6-trioxatriphosphorinane-2,4,6-trioxide; TBAF-tetra-n-butylammonium fluoride; TBS: tert-butyldimethylsilyl; TBSCl-tert-butyldimethylsilyl chloride; TEA-triethylamine; TES: triethylsilyl; TESCl: chlorotriethylsilane; TFAA: trifluoroacetic anhydride; THF: tetrahydrofuran; TFA: trifluoroacetic acid; TMSOTf: trimethylsilyl trifluoromethanesulfonate; X-Phos: 2-(dicyclohexyl-phosphino)-2',4',6'-triisopropylbiphenyl.

The compounds of the present invention can be prepared in a variety of fashions. In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

Intermediate A

Benzyl (2R,3S,5R)-3-((N,N-dimethylsulfamoyl)(4-methoxybenzyl)amino)-5-methyl-2-(((triethylsilyl)oxy)methyl)pyrrolidine-1-carboxylate

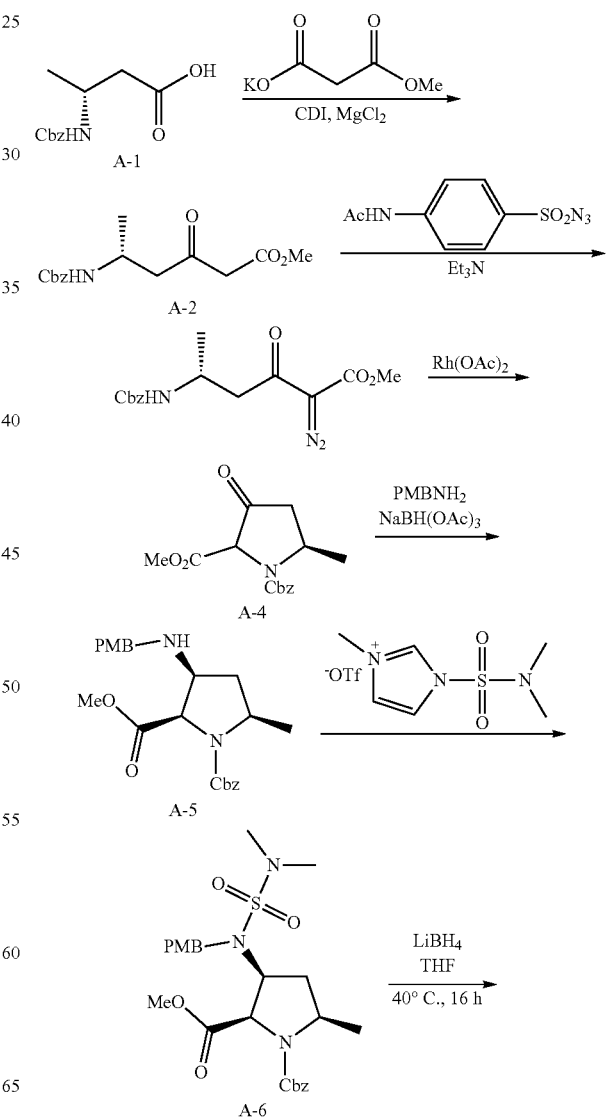

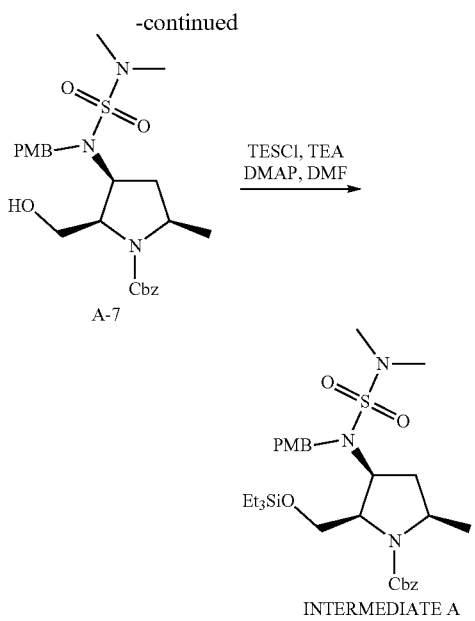

Step 1: methyl (R)-5-(((benzyloxy)carbonyl)amino)-3-oxohexanoate (A-2)

To a solution of (R)-3-(((benzyloxy)carbonyl)amino)butanoic acid (A-1) (6.25 g, 26.3 mmol) in anhydrous THF (100 ml) under $N_2$ was added di(1H-imidazol-1-yl)methanone (6.41 g, 39.5 mmol). After stirring at rt for 1 h, pre-mixed $MgCl_2$ (4.64 ml, 52.7 mmol) and potassium 3-methoxy-3-oxopropanoate (8.23 g, 52.7 mmol) was added. The resulting mixture was stirred at rt for additional 18 h under $N_2$. The solvent was evaporated and the residue was dissolved in ethyl acetate (100 mL) and washed with brine (20 mL). The organic layer was dried over $MgSO_4$, filtered and concentrated in vacuo. The residue was purified by column chromatography (silica gel, 0-100% EtOAc in hexanes) to afford the title compound. LC-MS 294 (M+1).

Step 2: methyl (R)-5-(((benzyloxy)carbonyl)amino)-2-diazo-3-oxohexanoate (A-3)

To a solution of methyl (R)-5-(((benzyloxy)carbonyl)amino)-3-oxohexanoate (A-2) (6.2 g, 21.14 mmol) in $CH_2Cl_2$ (200 ml) was added $Et_3N$ (6.42 g, 63.4 mmol) and 4-acetamidobenzene-sulfonyl azide (5.08 g, 21.14 mmol) at rt under $N_2$. The reaction mixture was stirred for 12 h. LC-MS shown reaction completed. The crude was diluted with 200 ml of DCM, then was washed with 50 ml of $H_2O$. The organic phase was collected and dried over $MgSO_4$, concentrated and chromatographed over silica gel (0-100% Ethyl acetate in hexanes) to give the title compound. LC-MS 320 (M+1).

Step 3: 1-benzyl 2-methyl (5R)-5-methyl-3-oxopyrrolidine-1,2-dicarboxylate (A-4)

To a solution of methyl (R)-5-(((benzyloxy)carbonyl)amino)-2-diazo-3-oxohexanoate (A-3) (2.0 g, 6.26 mmol) in toluene (50 ml) was added diacetoxyrhodium (0.138 g, 0.313 mmol) under $N_2$ at rt. The reaction mixture was degassed for 10 min, then was stirred at 80° C. for 2 h. LC-MS shown reaction completed. The reaction mixture was concentrated and chromatographed over silica gel (0-100% EtOAc in hexanes) to give the title compound. LC-MS 292.28 (M+1).

Step 4: methyl (R)-5-(((benzyloxy)carbonyl)amino)-3-oxohexanoate (A-5)

To a solution of 1-benzyl 2-methyl (5R)-5-methyl-3-oxopyrrolidine-1,2-dicarboxylate (A-4) (5000 mg, 17.16 mmol) in DCM (100 mL) was added 4-methoxybenzylamine (2.467 mL, 18.88 mmol) and catalytic amount of acetic acid (0.049 mL, 0.858 mmol). The mixture was stirred at rt for 30 mins, then sodium triacetoxyborohydride (4.37 g, 20.6 mmol) was added to the mixture. The reaction was stirred at rt overnight. The reaction was quenched with sat. aq. $NaHCO_3$ (50 mL), extracted with DCM (3×50 mL). The combined organic phases were dried over $MgSO_4$, filtered and concentrated. The residue was purified by column chromatography on silica gel (EtOAc in Hexane 0-100%) to afford the title compound. LC-MS 413 (M+1).

Step 5: 1-benzyl 2-methyl (2R,3S,5R)-3-((N,N-dimethylsulfamoyl)(4-methoxybenzyl)amino)-5-methylpyrrolidine-1,2-dicarboxylate (A-6)

Into a 2000-mL 4-necked round-bottom flask, was placed DCM (450 ml), 1-benzyl 2-methyl (5R)-3-((4-methoxybenzyl)amino)-5-methylpyrrolidine-1,2-dicarboxylate (A-5) (150 g, 1 eq) and 1-(N,N-dimethylsulfamoyl)-3-methyl-1H-imidazol-3-ium trifluoromethanesulfonate (370 g, 3 equiv), The resulting solution was stirred for 3 d at 80° C. in an oil bath. The reaction mixture was cooled to room temperature and concentrated. The residue was applied onto a silica gel column with ethyl acetate/petroleum ether (1/5-1/4) to give the desired product.

Step 6: benzyl (2R,3S,5R)-3-((N,N-dimethylsulfamoyl)(4-methoxybenzyl)amino)-2-(hydroxymethyl)-5-methylpyrrolidine-1-carboxylate (A-7)

Into a 2000-mL 3-necked round-bottom flask purged and maintained with an inert atmosphere of nitrogen, was placed a solution of 1-benzyl 2-methyl (2R,3S,5R)-3-((N,N-dimethylsulfamoyl)(4-methoxybenzyl)amino)-5-methylpyrrolidine-1,2-dicarboxylate (A-6) (40 g, 80 mmol) in THF (400 ml). This was followed by the addition of LiBH4 (7 g, 315 mmol) with stirring at 0° C. The resulting solution was stirred at 40° C. for 16 h. The reaction was then quenched by the addition of water/ice. The resulting solution was extracted with 3×500 ml of EA and the organic layers combined and dried over $Na_2SO_4$ and concentrated to give the desired product. (ESI, m/z): $(M+Na)^+$: 514

Step 7: benzyl (2R,3S,5R)-3-((N,N-dimethylsulfamoyl)(4-methoxybenzyl)amino)-5-methyl-2-(((triethylsilyl)oxy)methyl)pyrrolidine-1-carboxylate (Intermediate A)

Into a 1000-mL 3-necked round-bottom flask purged and maintained with an inert atmosphere of nitrogen, was placed a solution of benzyl (2R,3S,5R)-3-((N,N-dimethylsulfamoyl)(4-methoxybenzyl)amino)-2-(hydroxymethyl)-5-methylpyrrolidine-1-carboxylate (A-7) (34 g, 69 mmol) in DMF (340 ml) was added TEA (8.36 g, 83 mmol) at r.t under N2. Then add DMAP (1.68 g, 14 mmol) to the system. This was followed by the addition of TESCl (12.5 g, 83 mmol) dropwise with stirring at 0° C. The resulting solution was stirred at 25° C. for 3 h. The reaction was then quenched by the addition of water/ice. The resulting solution was extracted with 2×300 mL of EA. The organic layer was washed with 200 mL of brine and the organic layers combined and dried over Na$_2$SO$_4$ and concentrated. The residue was applied onto a silica gel column with petroleum ether/ethyl acetate (15/1) to give the desired product. (ESI, m/z): (M+Na)$^+$:606.

Intermediate B

Benzyl (2R,3S,5R)-3-(N-(4-methoxybenzyl)methylsulfonamido)-5-methyl-2-(((triethylsilyl)oxy)methyl)pyrrolidine-1-carboxylate

INTERMEDIATE B

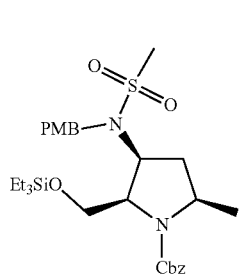

Benzyl (2R,3S,5R)-3-(N-(4-methoxybenzyl)methylsulfonamido)-5-methyl-2-(((triethylsilyl)oxy)methyl)pyrrolidine-1-carboxylate (INTERMEDIATE B) was prepared according to the same procedure provided in INTERMEDIATE A by substituting the appropriate reagent with methyl sulfonyl chloride.

Intermediate C 6-phenylbicyclo[4.1.0]heptan-3-one

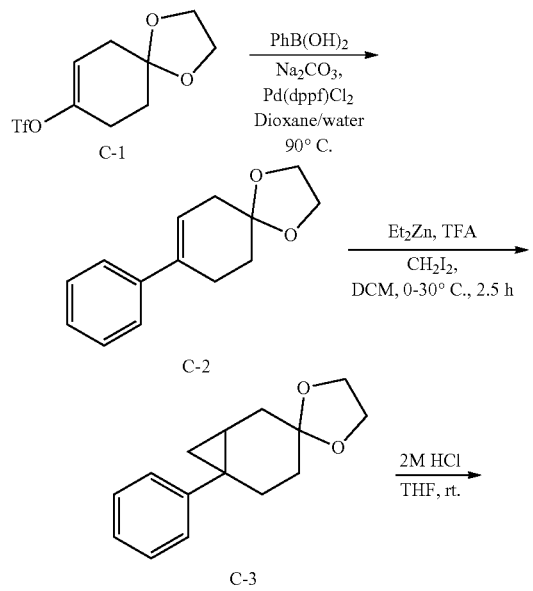

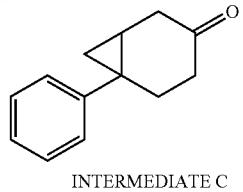

INTERMEDIATE C

Step 1: 8-phenyl-1,4-dioxaspiro[4.5]dec-7-ene (C-2)

To a solution of C-1 (10 g, 34.7 mmol) in 1,4-Dioxane (100 mL) and Water (20.00 mL) was added phenylboronic acid (4.65 g, 38.2 mmol), Na$_2$CO$_3$ (7.35 g, 69.4 mmol) and Pd(dppf)Cl$_2$ (2.54 g, 3.47 mmol) under N$_2$. The mixture was stirred at 90° C. for 2 h. The reaction mixture was poured into water (300 mL), extracted with EtOAc (100 mL×3). The combined organic phases were washed with brine (300 mL), and dried over Na$_2$SO$_4$. After filtration and concentration, the residue was purified by flash silica gel chromatography (6% EtOAc/Pet.ether gradient) to give the title compound. $^1$H NMR (400 MHz, CDCl$_3$): δ 7.42-7.35 (m, 3H), 7.33-7.20 (m, 2H), 5.98 (tt, J=1.8, 3.7 Hz, 1H), 4.08-3.98 (m, 4H), 2.75-2.60 (m, 2H), 2.48 (br d, J=0.8 Hz, 2H), 1.93 (t, J=6.5 Hz, 2H).

Step 2: 6-phenylspiro[bicyclo[4.1.0]heptane-3,2'-[1,3]dioxolane] (C-3)

To a solution of diethylzinc (13.87 mL, 13.87 mmol) (1.0 M in hexane) in DCM (250 mL) was added a solution of TFA (3.31 mL, 43.0 mmol) in dry DCM (20 mL) over the course of 30 minutes at 0° C. The reaction mixture was stirred at 0° C. for 30 min. Then diiodomethane (3.24 mL, 40.2 mmol) was added to above solution, and a solution of C-2 (3 g, 13.87 mmol) in DCM (20 mL) was added over 5 minutes. After complete addition, the resulting solution was warmed to 30° C., stirred for additional 50 minutes. LCMS showed the desired product was formed and the red solution was quenched with 1 M HCl (250 mL). The organic layer was washed with water (200 mL×3), dried over Na$_2$SO$_4$ and filtered. The filtrate was concentrated and purified by reversed MPLC (0%~61% MeCN\H$_2$O (0.5‰ TFA) gradient) to give the title compound. LCMS m/z (M+H): 231.2 required. 231.2 found.

Step 3: 6-phenylbicyclo[4.1.0]heptan-3-one (Intermediate C)

To a solution of C-3 (1.1 g, 4.78 mmol) in THF (12 mL) was added hydrogen chloride (3 mL, 6.00 mmol) (2.0 M) and stirred at 25° C. for 3 hours. LCMS showed the reaction was completed. The reaction mixture was poured into water (20 mL), extracted with EtOAc (10 mL×3). The organic layer was washed with brine (20 mL), dried over Na$_2$SO$_4$ and filtered. The filtrate was concentrated and purified by reversed MPLC (0%~25% MeCN\H$_2$O (0.5‰ TFA)) to give the title compound. $^1$H NMR (500 MHz, CDCl$_3$): δ 7.32-7.22 (m, 4H), 7.20-7.12 (m, 1H), 2.81 (dd, J=5.0, 18.6 Hz, 1H), 2.71-2.58 (m, 1H), 2.49-2.32 (m, 2H), 2.28-2.12 (m, 2H), 1.45 (dtd, J=2.6, 5.3, 8.2 Hz, 1H), 1.05 (dd, J=5.8, 9.0 Hz, 1H), 0.99-0.90 (m, 1H).

Intermediate D

6-(3-fluorophenyl)bicyclo[4.1.0]heptan-3-one

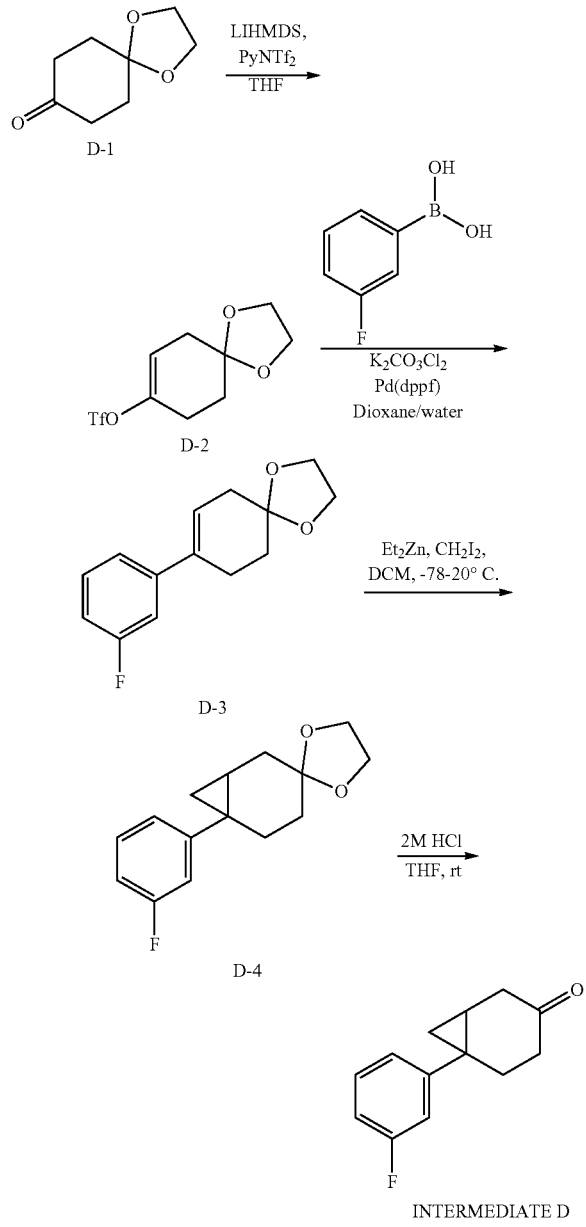

INTERMEDIATE D

Step 1: 1,4-dioxaspiro[4.5]dec-7-en-8-yl trifluoromethanesulfonate (D-2)

To a solution of D-1 (20 g, 128 mmol) and N,N-bis(trifluoromethylsulfonyl)aniline (50.3 g, 141 mmol) in anhydrous THF (300 mL) at −78° C. was added lithium bis(trimethylsilyl)amide (141 mL, 141 mmol)(1 M in THF) under $N_2$ at −78° C. The mixture was stirred at −78° C. for 30 minutes and warmed to 25° C. for 3 h. The reaction mixture was poured into water (500 mL), extracted with EtOAc (200 mL×3), the combined organic phases were washed with brine (500 mL), dried over $Na_2SO_4$. After filtration and concentration. The residue was purified by flash silica gel chromatography (0~10% ethyl acetate/pet. ether) to give the title compound. $^1$H NMR (400 MHz, $CDCl_3$): δ 5.63 (t, J=4.0 Hz, 1H), 4.01-3.92 (m, 4H), 2.55-2.47 (m, 2H), 2.40-2.35 (m, 2H), 1.88 (t, J=6.6 Hz, 2H)

Step 2: 8-(3-fluorophenyl)-1,4-dioxaspiro[4.5]dec-7-ene (D-3)

To a solution of D-2 (9.2 g, 31.9 mmol) in 1,4-Dioxane (85 mL) and Water (17 mL) was added (3-fluorophenyl)boronic acid (4.91 g, 35.1 mmol), $K_2CO_3$ (8.82 g, 63.8 mmol) and $PdCl_2$(dppf) (2.335 g, 3.19 mmol) at 25° C. The mixture was stirred at 90° C. under $N_2$ for 2 h. Then the mixture was diluted with water (150 mL), extracted with EtOAc (100 mL×3), washed with brine (100 mL), dried over $Na_2SO_4$, filtered and concentrated. The residue was purified by flash silica gel chromatography (0~20% ethyl acetate/pet. ether) to give the title compound. $^1$H NMR (400 MHz, $CDCl_3$) δ 7.26-7.19 (m, 1H), 7.16-7.11 (m, 1H), 7.06 (td, J=2.0, 10.9 Hz, 1H), 6.92-6.85 (m, 1H), 6.02-5.98 (m, 1H), 4.00 (s, 4H), 2.61 (ddd, J=1.7, 4.5, 8.4 Hz, 2H), 2.45 (br s, 2H), 1.90 (t, J=6.6 Hz, 2H).

Step 3: 6-(3-fluorophenyl)spiro[bicyclo[4.1.0]heptane-3,2'-[1,3]dioxolane] (D-4)

To a solution of diethylzinc (40.1 mL, 40.1 mmol) (1.0 M) in DCM (26 mL) was added $CH_2I_2$ (6.45 mL, 80 mmol) at −78° C. The reaction mixture was stirred at 0° C. for 15 min. Then a solution of D-3 (4.7 g, 20.06 mmol) in DCM (10 mL) was added over 5 minutes. After complete addition, the resulting solution was warmed to 25° C., stirred for additional 15 h. LCMS showed the desired product was formed and the solution was quenched with 1 M HCl (100 mL), extracted with EtOAc (50 mL×3). The organic layer was washed with brine (100 mL), dried over $Na_2SO_4$ and filtered. The filtrate was concentrated and purified by flash silica gel chromatography (0~10% ethyl acetate/pet. ether) to give the title compound. LCMS m/z (M+H): 249 required. 249.0 found. $^1$H NMR (400 MHz, $CDCl_3$) δ 7.25-7.16 (m, 1H), 7.05 (d, J=7.8 Hz, 1H), 6.99 (br d, J=10.5 Hz, 1H), 6.87-6.79 (m, 1H), 4.02-3.83 (m, 4H), 2.37-2.09 (m, 3H), 1.80 (dd, J=1.0, 14.4 Hz, 1H), 1.69-1.58 (m, 1H), 1.51-1.38 (m, 1H), 1.30-1.18 (m, 1H), 1.01 (dd, J=4.9, 9.3 Hz, 1H), 0.77 (t, J=5.3 Hz, 1H).

Step 4: 6-(3-fluorophenyl)bicyclo[4.1.0]heptan-3-one (Intermediate D)

To a solution of D-4 (2 g, 8.06 mmol) in acetone (80 mL) was added HCl (16 mL, 32.0 mmol) (2 M in water) and the solution was stirred at 20° C. for 3 h. Then the mixture was basified with NaOH (150 mL) (1M in Water) extracted with EtOAc (100 mL×3 L). The mixture was washed with brine (150 mL), dried over $Na_2SO_4$ and filtered. The filtrate was concentrated and purified by silica chromatography (0~15% ethyl acetate/pet. ether) to give the title compound. $^1$H NMR (400 MHz, $CDCl_3$) δ 7.34-7.20 (m, 1H), 7.04 (d, J=7.6 Hz, 1H), 6.96 (td, J=2.0, 10.5 Hz, 1H), 6.92-6.82 (m, 1H), 2.89-2.77 (m, 1H), 2.72-2.62 (m, 1H), 2.52-2.34 (m, 2H), 2.31-2.13 (m, 2H), 1.54-1.41 (m, 1H), 1.11-0.94 (m, 2H).

Intermediate E, F, and G 6-(pyrimidin-2-yl)bicyclo[4.1.0]heptan-3-one (Intermediate E), 6-(pyrimidin-2-yl)bicyclo[4.1.0]heptan-3-one (Intermediate F), and 6-(pyrimidin-2-yl)bicyclo[4.1.0]heptan-3-one (Intermediate G)

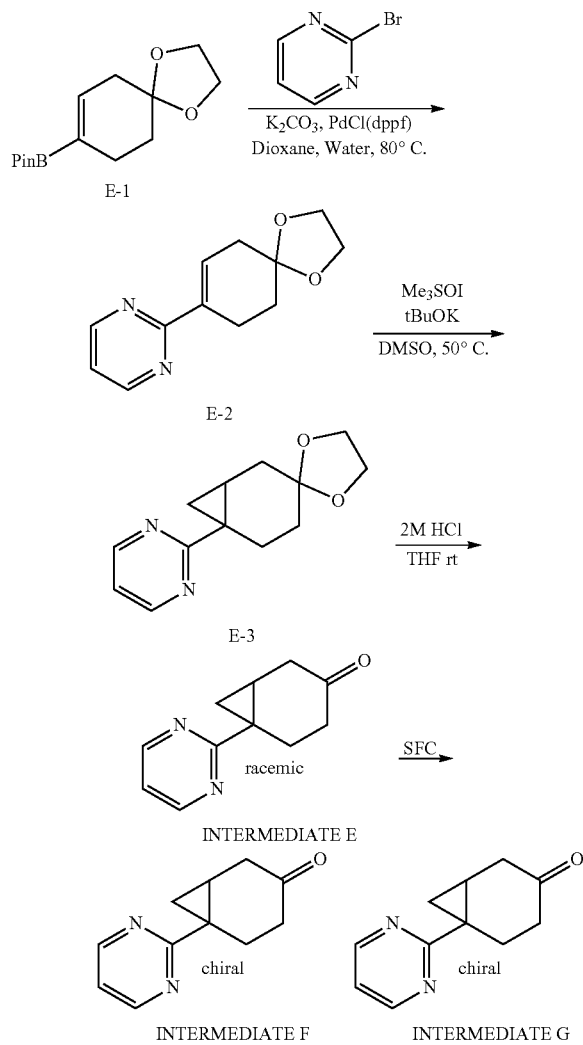

Step 1: 2-(1,4-dioxaspiro[4.5]dec-7-en-8-yl)pyrimidine (E-2)

To a solution of 2-bromopyrimidine (12 g, 75 mmol) in dioxane (240 mL) and water (80 mL) were added E-1 (22.10 g, 83 mmol), $K_2CO_3$ (20.86 g, 151 mmol) and $PdCl_2$(dppf) (5.52 g, 7.55 mmol). Then the mixture was stirred at 80° C. for 3 hours. LCMS showed the desired product was formed. The reaction mixture was poured into water (300 mL), extracted with EtOAc (100 mL×3). The organic layer was washed with brine (200 mL), dried over $Na_2SO_4$ and filtered. The filtrate was concentrated and purified by flash silica gel chromatography (0~40% ethyl acetate/pet. ether) to give the title compound.

Step 2: 2-(spiro[bicyclo[4.1.0]heptane-3,2'-[1,3]dioxolan]-6-yl)pyrimidine (E-3)

To a solution of trimethylsulfoxonium iodide (11.95 g, 54.3 mmol) in DMSO (160 mL) was added potassium tert-butoxide (5.78 g, 51.5 mmol) and stirred at 50° C. for 50 mins. E-2 (3 g, 13.75 mmol) in DMSO (20 mL) was added and stirred at 50° C. for 12 hours. LCMS showed the desired product was formed. The reaction mixture was poured into water (300 mL), extracted with EtOAc (150 mL×3). The organic layer was washed with brine (100 mL), dried over $Na_2SO_4$ and filtered. The filtrate was concentrated and purified by flash silica gel chromatography (0~14% ethyl acetate/pet. ether) to give the title compound. $^1$H NMR (500 MHz, $CDCl_3$) δ 8.58 (d, J=5.1 Hz, 2H), 7.00 (t, J=4.7 Hz, 1H), 4.00-3.88 (m, 4H), 3.10 (ddd, J=5.7, 10.3, 14.2 Hz, 1H), 2.28-2.12 (m, 2H), 1.91 (d, J=14.5 Hz, 1H), 1.87-1.78 (m, 1H), 1.71 (dtd, J=2.0, 5.8, 13.4 Hz, 1H), 1.61-1.48 (m, 2H), 1.04 (dd, J=3.9, 6.3 Hz, 1H).

Step 3: 6-(pyrimidin-2-yl)bicyclo[4.1.0]heptan-3-one (Intermediate E)

To a solution of E-3 (3 g, 12.92 mmol) in THF (60 mL) was added hydrogen chloride (25.8 mL, 51.7 mmol) (2.0 M in $H_2O$) and stirred at 30° C. for 2 hours. LCMS showed the reaction was completed. The reaction mixture was poured into sat. $NaHCO_3$ (100 mL), extracted with EtOAc (50 mL×3). The organic layer was washed with brine (50 mL), dried over $Na_2SO_4$ and filtered. The filtrate was concentrated to give the title compound.

Step 4: 6-(pyrimidin-2-yl)bicyclo[4.1.0]heptan-3-one (Intermediate F) and 6-(pyrimidin-2-yl)bicyclo[4.1.0]heptan-3-one (Intermediate G)

INTERMEDIATE E (2.3 g, 12.22 mmol) was separated by SFC to give INTERMEDIATE F (RT=3.350) and INTERMEDIATE G (RT=4.593).

SFC condition:

Column: DAICEL CHIRALPAK AD (250 mm*50 mm, 10 um)

Condition: 0.1% $NH_3H_2O$ ETOH

Begin B: 40%

End B: 40%

FlowRate (ml/min): 200

INTERMEDIATE F: $^1$H NMR (400 MHz, $CDCl_3$) δ 8.60 (d, J=5.1 Hz, 2H), 7.06 (t, J=4.9 Hz, 1H), 2.99 (ddd, J=5.5, 10.4, 14.3 Hz, 1H), 2.81 (dd, J=5.5, 18.4 Hz, 1H), 2.66-2.56 (m, 1H), 2.54-2.45 (m, 1H), 2.36 (td, J=5.7, 14.1 Hz, 1H), 2.31-2.20 (m, 1H), 1.90 (dtd, J=3.1, 5.8, 8.8 Hz, 1H), 1.72 (dd, J=4.7, 9.0 Hz, 1H), 1.14 (t, J=5.3 Hz, 1H).

INTERMEDIATE G: $^1$H NMR (400 MHz, $CDCl_3$) δ 8.60 (d, J=4.7 Hz, 2H), 7.06 (t, J=4.9 Hz, 1H), 2.99 (ddd, J=5.7, 10.2, 14.3 Hz, 1H), 2.86-2.76 (m, 1H), 2.66-2.57 (m, 1H), 2.55-2.45 (m, 1H), 2.36 (td, J=5.5, 14.1 Hz, 1H), 2.31-2.19 (m, 1H), 1.90 (dtd, J=3.1, 5.6, 8.8 Hz, 1H), 1.72 (dd, J=5.1, 9.0 Hz, 1H), 1.14 (t, J=5.3 Hz, 1H).

Intermediate H

6-(3,5-difluorophenyl)bicyclo[4.1.0]heptan-3-one

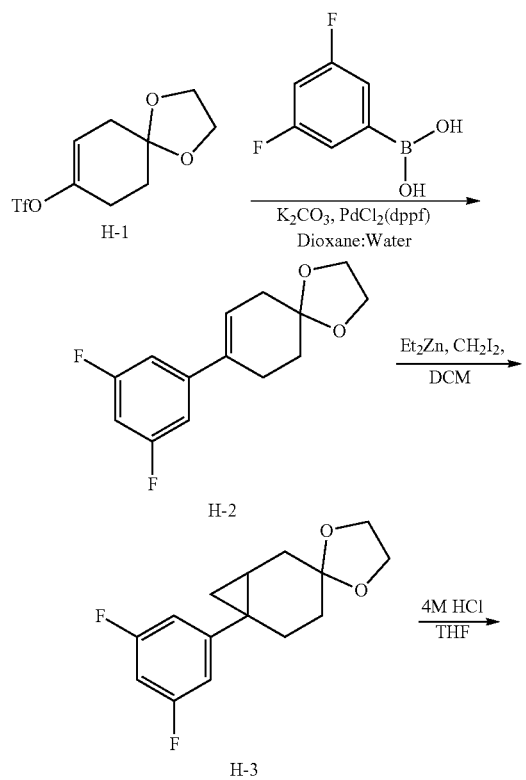

INTERMEDIATE H

Step 1: 8-(3,5-difluorophenyl)-1,4-dioxaspiro[4.5]dec-7-ene (H-2)

To a mixture of H-1 (6.7 g, 23.24 mmol) in 1,4-Dioxane (85 mL) and Water (15 mL) were added (3,5-difluorophenyl)boronic acid (4.04 g, 25.6 mmol), $K_2CO_3$ (6.43 g, 46.5 mmol) and $PdCl_2(dppf)$ (0.850 g, 1.162 mmol) at 25° C. The mixture was stirred at 90° C. under $N_2$ protection for 2 h. The mixture was extracted with EtOAc (100 mL×3), washed with brine (50 mL×3). The organic layer was dried over $Na_2SO_4$, filtered and the filtrate was concentrated. The crude product was purified by flash silica gel chromatography (10% EtOAc/Pet.ether) to give the title compound. LCMS m/z (M+H): 253.3 found, 253.1 required.

Step 2: 6-(3,5-difluorophenyl)spiro[bicyclo[4.1.0]heptane-3,2'-[1,3]dioxolane] (H-3)

To a solution of diethylzinc (39.6 mL, 39.6 mmol) (1.0 M in hexane) in DCM (30 mL) was added a solution of diiodomethane (6.38 mL, 79 mmol) in dry DCM (5 mL) at −78° C. Then the reaction mixture was stirred at 0° C. for 15 mins. Then H-2 (5 g, 19.82 mmol) in DCM (5 mL) was added to the mixture over 5 minutes. After complete addition, the resulting solution was warmed to 25° C., stirred for additional 16 h. The red solution was quenched with $NaHCO_3$ (10 mmol, 50 mL). The mixture was extracted with EtOAc (50 mL×3), washed with brine (100 mL). The organic layer was dried over $Na_2SO_4$, filtered and the filtrate was concentrated. The crude product was purified by flash silica gel chromatography (5% EtOAc/Pet.ether) to give the title compound. LCMS m/z (M+H): 267.1 required, 267.3 found.

Step 3: 6-(3,5-difluorophenyl)bicyclo[4.1.0]heptan-3-one (Intermediate H)

To a solution of 11-3 (2 g, 7.51 mmol) in THF (20 mL) was added HCl (7.45 mL, 29.8 mmol) (4 M in water) and the solution was stirred at 20° C. for 5 h. Then the mixture was basified with NaOH (1M in Water) (50 mL). The acidic aqueous phase was extracted with EtOAc (3×50 mL). The mixture was washed with brine (100 mL). The organic layer dried over $Na_2SO_4$. The filtrate was concentrated and purified by prep-HPLC (H2O/MeCN with TFA modifier) to give the title compound. LCMS m/z (M+H+41): 264.09 required. 264.3 found. $^1$H NMR (400 MHz, $CDCl_3$) δ 6.80 (dd, J=2.2, 8.8 Hz, 2H), 6.72-6.62 (m, 1H), 2.91-2.77 (m, 1H), 2.77-2.59 (m, 1H), 2.55-2.37 (m, 2H), 2.35-2.14 (m, 2H), 1.59-1.44 (m, 1H), 1.17-1.00 (m, 2H).

Intermediate I

4-(4-oxobicyclo[4.1.0]heptan-1-yl)benzonitrile

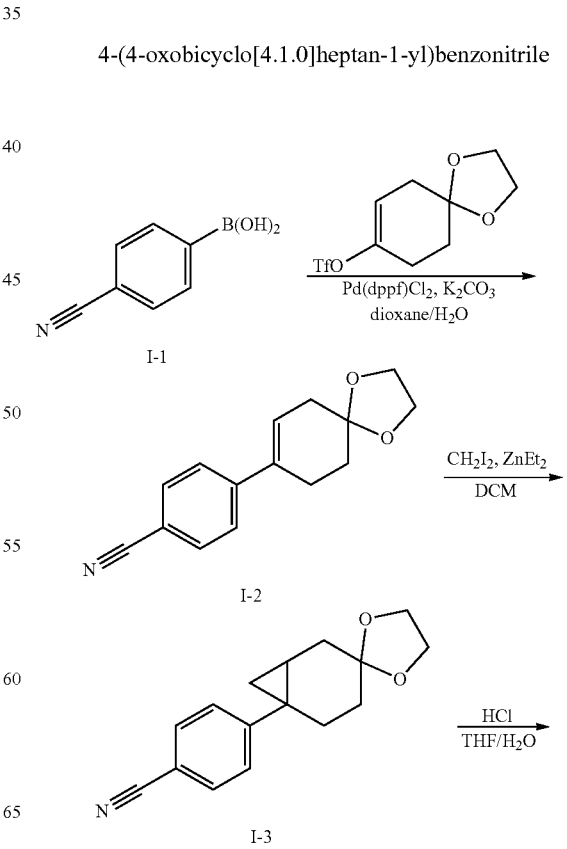

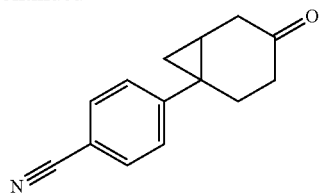

INTERMEDIATE I

Step 1: 4-(1,4-dioxaspiro[4.5]dec-7-en-8-yl)benzonitrile (I-2)

To a mixture of 1,4-dioxaspiro[4.5]dec-7-en-8-yl trifluoromethanesulfonate (5 g, 17.35 mmol) in 1,4-Dioxane (85 mL) and water (15 mL) were added I-1 (2.80 g, 19.08 mmol), $K_2CO_3$ (4.79 g, 34.7 mmol) and $PdCl_2(dppf)$ (0.635 g, 0.867 mmol) at 25° C. The mixture was stirred at 90° C. under $N_2$ protection for 2 h. The mixture was extracted with EtOAc (100 mL×3), washed with brine (50 mL×3). The organic layer was dried over $Na_2SO_4$, filtered and the filtrate was concentrated. The crude product was purified by flash silica gel chromatography (10% EtOAc/Pet.ether) to give the title compound. LCMS m/z (M+H+41): 283.3 found, 283.1 required.

Step 2: 4-(spiro[bicyclo[4.1.0]heptane-3,2'-[1,3]dioxolan]-6-yl)benzonitrile (I-3)

To a solution of diethylzinc (20.72 mL, 20.72 mmol) (1.0 M in hexane) in DCM (15 mL) was added a solution of diiodomethane (11.10 g, 41.4 mmol) in dry DCM (5 mL) at −78° C. Then the reaction mixture was stirred at 0° C. for 15 min. Then I-2 (2.5 g, 10.36 mmol) in DCM (5 mL) was added over 5 minutes. After complete addition, the resulting solution was warmed to 25° C., and stirred for additional 16 h. The yellow solution was quenched with $NaHCO_3$ (100 mL). The mixture was extracted with EtOAc (100 mL×3), washed with brine (100 mL). The organic layer dried over $Na_2SO_4$, filtered and the filtrate was concentrated. The crude product was purified by flash silica gel chromatography (0~30% ethyl acetate/pet. ether) to give the title compound. LCMS m/z (M+H): 256.1 required. 256.3 found.

Step 3: 4-(4-oxobicyclo[4.1.0]heptan-1-yl)benzonitrile (Intermediate I)

To a mixture of 1-3 (300 mg, 1.175 mmol) in THF (3 mL) was added HCl (1.166 mL, 4.66 mmol) (4 M in water) and the solution was stirred at 25° C. for 2 h. Then the mixture was basified with NaOH (1M in water) (5 mL). The aqueous phase was extracted with EtOAc (3×10 mL). The mixture was washed with brine (20 mL). The organic layer was dried over $Na_2SO_4$, filtered and the filtrate was concentrated. The crude product was purified by flash silica gel chromatography (0~20% ethyl acetate/pet. ether) to give the title compound. LCMS m/z (M+H): 212.1 required. 212.3 found. $^1H$ NMR (400 MHz, $CDCl_3$) δ 7.62 (d, 2H), 7.39 (d, 2H), 2.87 (dd, 1H), 2.72 (dd, 1H), 2.54-2.42 (m, 2H), 2.37-2.20 (m, 2H), 1.59-1.52 (m, 1H), 1.26-1.11 (m, 2H).

Intermediate J

Methyl (2R,3S,5R)-3-((N,N-dimethylsulfamoyl)(4-methoxybenzyl)amino)-5-methyl-2-(((triethylsilyl)oxy)methyl)pyrrolidine-1-carboxylate

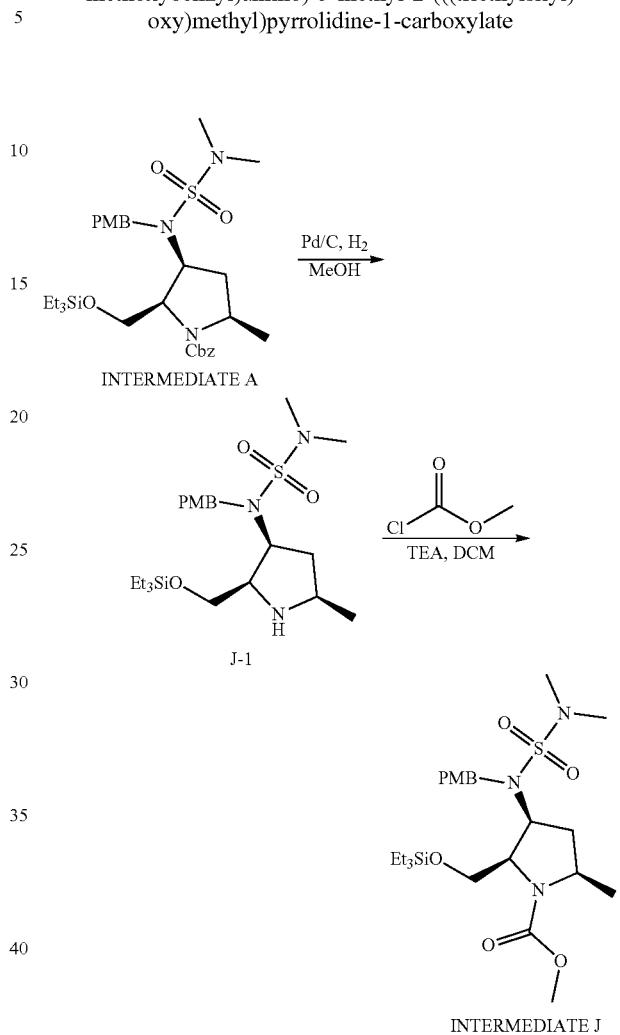

Step 1: J-1

To a solution of INTERMEDIATE A (250 mg, 0.413 mmol) in MeOH (5 mL) was added Pd—C (43.9 mg, 0.413 mmol) and the solution was stirred at 20° C. for 1 h under $H_2$ (15 psi). The mixture was filtered and concentrated to give the title compound. LCMS m/z (M+H): 472.3 required, 472.3 found.

Step 2: Methyl (2R,3S,5R)-3-((N,N-dimethylsulfamoyl)(4-methoxybenzyl)amino)-5-methyl-2-(((triethylsilyl)oxy)methyl)pyrrolidine-1-carboxylate (Intermediate J)

To a solution of J-1 (195 mg, 0.413 mmol) in $CH_2Cl_2$ (5 mL) were added TEA (0.115 mL, 0.827 mmol) and methyl carbonochloridate (46.9 mg, 0.496 mmol) at 0° C. The mixture was stirred at 0° C. for 30 min. LCMS showed the desired mass was formed. The mixture was poured into water (5 mL), extracted with DCM (5 mL×3). The combined organic phases were washed with brine (10 mL), and dried over Na$_2$SO$_4$. After filtration and concentration, the residue was purified by flash silica gel chromatography (80% ethyl acetate/pet. ether) to give the title compound. LCMS m/z (M+H): 530.3 required, 530.3 found.

Intermediate K methyl (2R,3S,5R)-3-(N-(4-methoxybenzyl)methyl-sulfonamido)-5-methyl-2-(((triethylsilyl)oxy)methyl) pyrrolidine-1-carboxylate

INTERMEDIATE K

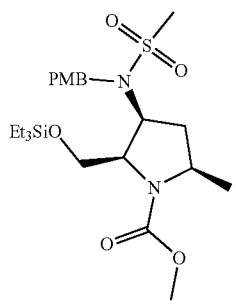

Methyl (2R,3S,5R)-3-(N-(4-methoxybenzyl)methylsulfonamido)-5-methyl-2-(((triethylsilyl)oxy)methyl)pyrrolidine-1-carboxylate (INTERMEDIATE K) was prepared according to the same procedure provided in INTERMEDIATE J by starting with INTERMEDIATE B.

Intermediate L

Isopropyl (2R,3S,5R)-3-((N,N-dimethylsulfamoyl)(4-methoxybenzyl)amino)-5-methyl-2-(((triethylsilyl)oxy)methyl)pyrrolidine-1-carboxylate

INTERMEDIATE L

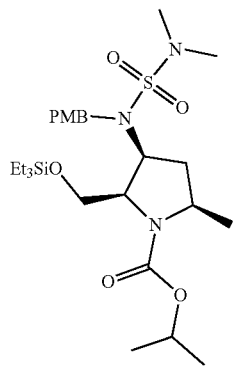

Isopropyl (2R,3S,5R)-3-((N,N-dimethylsulfamoyl)(4-methoxybenzyl)amino)-5-methyl-2-(((triethylsilyl)oxy)methyl)pyrrolidine-1-carboxylate (INTERMEDIATE L) was prepared according to the same procedure provided in INTERMEDIATE J by substituting the appropriate reagent with isopropyl chloroformate.

Intermediate M 7,7-difluoro-6-(pyrimidin-2-yl)bicyclo[4.1.0]heptan-3-one

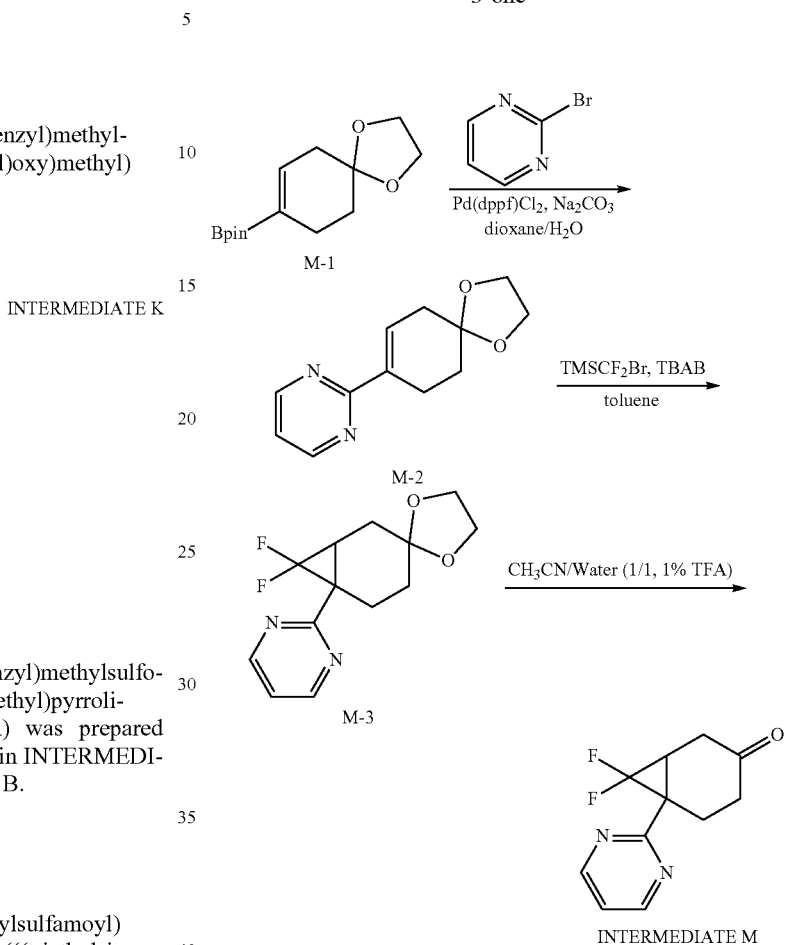

INTERMEDIATE M

Step 1: 2-(1,4-dioxaspiro[4.5]dec-7-en-8-yl)pyrimidine (M-2)

To a solution of 2-bromopyrimidine (5 g, 31.4 mmol) in Dioxane (100 mL) and Water (35 mL) were added M-1 (9.21 g, 34.6 mmol), K$_2$CO$_3$ (8.69 g, 62.9 mmol) and Pd(dppf)Cl$_2$ (2.301 g, 3.14 mmol). The mixture was stirred at 80° C. for 4 h. LCMS showed the desired product was formed. The reaction mixture was poured into water (200 mL), extracted with EtOAc (100 mL×3). The organic layer was washed with brine (200 mL), dried over Na$_2$SO$_4$ and filtered. The filtrate was concentrated and purified by flash silica gel chromatography (0~40% ethyl acetate/pet. ether) to give the title compound. LCMS m/z (M+H): 219.2 required, 219.1 found.

Step 2: 2-(7,7-difluorospiro[bicyclo[4.1.0]heptane-3,2'-[1,3]dioxolan]-6-yl)pyrimidine (M-3)

To a solution of M-2 (2 g, 9.16 mmol) in Toluene (2 mL) was added tetrabutylammonium bromide (1.477 g, 4.58 mmol) and (bromodifluoromethyl) trimethylsilane (7.10 ml, 45.8 mmol). The mixture was stirred at 110° C. for 2 hours. LCMS showed product was formed. The reaction was poured into water (30 mL), extracted with EtOAc (30 ml×3).

The combined organic phase was dried over $Na_2SO_4$, filtered. The filtrate was concentrated and purified by TLC (Pet. Ether:EtOAc=1:1) to give the title compound. LCMS m/z (M+H): 269.2 required, 269.3 found.

Step 3: 7,7-difluoro-6-(pyrimidin-2-yl)bicyclo[4.1.0]heptan-3-one (Intermediate M)

To a solution of M-3 (500 mg, 1.864 mmol) in acetonitrile (5 mL) and water (1% TFA, W %) (5 ml) and the solution was stirred at 40° C. for 4 h. LCMS showed product was formed. The reaction was purified by HPLC (TEA) to give the title compound. LCMS m/z (M+H): 225.2 required, 225.3 found.

Intermediate N

6-(pyridin-2-yl)bicyclo[4.1.0]heptan-3-one

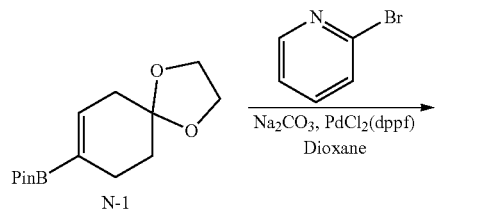

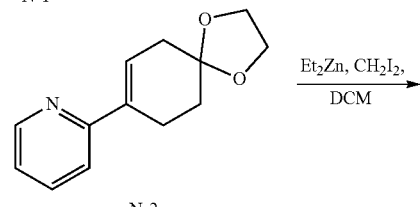

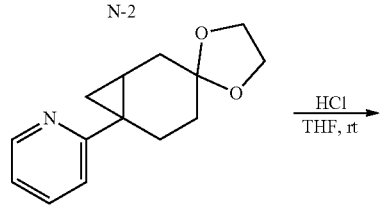

INTERMEDIATE N

Step 1: 2-(1,4-dioxaspiro[4.5]dec-7-en-8-yl)pyridine (N-2)

To a solution of N-1 (1.718 g, 6.46 mmol) in Dioxane (20 mL) and water (4 mL) were added 2-bromopyridine (0.85 g, 5.38 mmol), $Na_2CO_3$ (1.711 g, 16.14 mmol) and Pd(dppf)$Cl_2$ (0.394 g, 0.538 mmol). The mixture was stirred at 90° C. for 16 h. LCMS showed the desired mass was formed. The mixture was poured into water (20 mL), extracted with EtOAc (20 mL×3). The combined organic phases were washed with brine (20 mL) and dried over $Na_2SO_4$. After filtration and concentration, the residue was purified by flash silica gel chromatography (60% ethyl acetate/pet. ether) to give the title compound. LCMS m/z (M+H): 218.2 required, 218.2 found.

Step 2: 2-(spiro[bicyclo[4.1.0]heptane-3,2'-[1,3]dioxolan]-6-yl)pyridine (N-3)

To a solution of diethylzinc (7.36 mL, 7.36 mmol) (1.0 M in hexane) in DCM (10 mL) was added $CH_2I_2$ (1.185 mL, 14.73 mmol) in dry DCM (5 mL) over the course of 30 minutes at −78° C. The reaction mixture was stirred at 0° C. for 15 min. Then N-2 (800 mg, 3.68 mmol) in DCM (5 mL) was added over 5 minutes. After complete addition, the resulting solution was warmed to 20° C., and stirred for 2 h. LCMS showed the desired product was formed. The solution was quenched with $H_2O$ (10 mL), extracted with EtOAc (10 mL×3). The organic layer was washed with brine (10 mL), dried over $Na_2SO_4$ and filtered. The filtrate was concentrated and purified by flash silica gel chromatography (30% EtOAc/Pet.ether) to afford the title compound. LCMS m/z (M+H): 232.1 required. 232.1 found.

Step 3: 6-(pyridin-2-yl)bicyclo[4.1.0]heptan-3-one (Intermediate N)

To a solution of N-3 (100 mg, 0.432 mmol) in THF (2 mL) was added HCl (1.081 mL, 4.32 mmol) (4 M in water) and the solution was stirred at 20° C. for 16 h. LCMS showed the desired product was formed. The mixture was concentrated in vacuo and extracted with EtOAc (2×10 mL). The combined organic layer was washed with water (2×10 mL), brine (10 mL), dried over $Na_2SO_4$ and filtered. The filtrate was concentrated to give the title compound. LCMS m/z (M+H): 188.1 required. 188.1 found. $^1H$ NMR (500 MHz, $CDCl_3$) δ 8.51 (td, J=0.9, 4.0 Hz, 1H), 7.62 (dt, J=1.8, 7.8 Hz, 1H), 7.28-7.26 (m, 1H), 7.16-7.01 (m, 1H), 2.88-2.78 (m, 1H), 2.75-2.69 (m, 2H), 2.55-2.46 (m, 1H), 2.44-2.37 (m, 1H), 2.34-2.24 (m, 1H), 1.82 (dtd, J=3.0, 5.5, 8.5 Hz, 1H), 1.48 (dd, J=5.4, 9.1 Hz, 1H), 1.10 (t, J=5.5 Hz, 1H).

Intermediate O and Intermediate P

6-(pyrazin-2-yl)bicyclo[4.1.0]heptan-3-one (Intermediate O) and 6-(pyrazin-2-yl)bicyclo[4.1.0]heptan-3-one (Intermediate P)

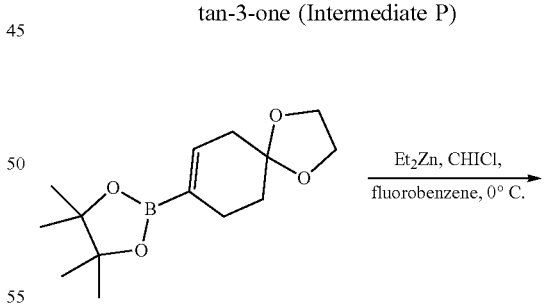

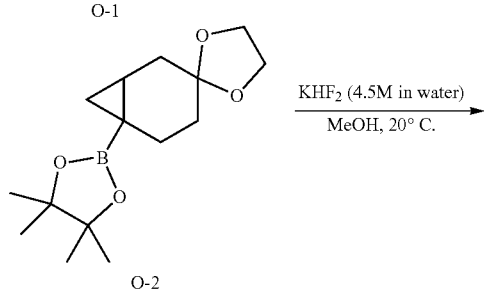

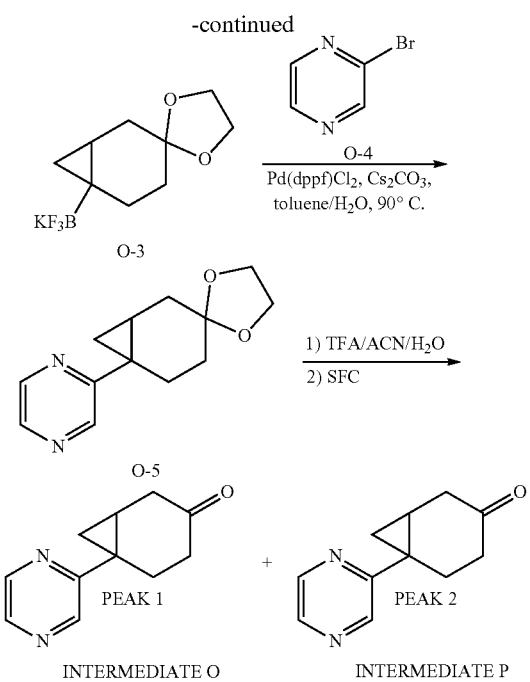

Step 1: 4,4,5,5-tetramethyl-2-(spiro[bicyclo[4.1.0]heptane-3,2'-[1,3]dioxolan]-6-yl)-1,3,2-dioxaborolane (O-2)

To a solution of O-1 (12 g, 45.1 mmol) in Fluorine benzene (120 mL) was added diethylzinc (180 mL, 180 mmol) (1M in Tol) over the course of 15 minutes at −5° C. The reaction mixture was stirred at −5° C. for 15 min. Then a solution of chloroiodomethane (63.6 g, 361 mmol) in Fluorine benzene (56 mL) was added over 15 minutes. The reaction was stirred for 2 h at −5° C. The solution was quenched with aq. NH$_4$Cl (200 mL) and extracted with EtOAc (200 mL×3). The organic layer was washed with brine (200 mL), dried over Na$_2$SO$_4$ and filtered. The filtrate was concentrated and purified by flash silica gel chromatography (40% ethyl acetate/pet. ether) to give the title compound. $^1$H NMR (400 MHz, CDCl$_3$) δ 3.95-3.79 (m, 4H), 2.31-2.19 (m, 1H), 2.03-1.97 (m, 1H), 1.91-1.83 (m, 1H), 1.72-1.65 (m, 1H), 1.49-1.34 (m, 2H), 1.23-1.12 (m, 13H), 0.86-0.79 (m, 1H), 0.58-0.48 (m, 1H).

Step 2: trifluoro(spiro[bicyclo[4.1.0]heptane-3,2'-[1,3]dioxolan]-6-yl)-14-borane, potassium salt (O-3)

To a solution of O-2 (12 g, 42.8 mmol) in MeOH (150 mL) was added potassium hydrogen fluoride (46.8 g, 600 mmol) (4.5 M in water) over the course of 10 minutes at 20° C. The reaction mixture was stirred at 20° C. for 32 h. The mixture was concentrated under vacuo and lyophilized. The solid was re-suspended in MTBE (100 mL) and filtered. The precipitate was collected and re-suspended in hot acetone, filtered. The filtrate was concentrated to give the title compound.

Step 3: 2-(spiro[bicyclo[4.1.0]heptane-3,2'-[1,3]dioxolan]-6-yl)pyrazine (O-5)

To a solution of O-3 (3 g, 11.53 mmol) in Toluene (60 mL) and Water (12 mL) was added 2-bromopyrazine (2.200 g, 13.84 mmol), Cs$_2$CO$_3$ (11.27 g, 34.6 mmol) and Pd(dppf)Cl$_2$ (0.844 g, 1.153 mmol). The mixture was stirred at 90° C. for 16 h. LCMS showed the desired mass was formed. The mixture was poured into water (50 mL), extracted with EtOAc (50 mL×3). The combined organic phases were washed with brine (10 mL), and dried over Na$_2$SO$_4$. After filtration and concentration, the residue was purified by flash silica gel chromatography (60% ethyl acetate/pet. ether) to the title compound. LCMS m/z (M+H): 233.0 required, 233.0 found.

Step 4: 6-(pyrazin-2-yl)bicyclo[4.1.0]heptan-3-one (Intermediate O) and 6-(pyrazin-2-yl)bicyclo[4.1.0]heptan-3-one (Intermediate P)

To a solution of O-5 (1.3 g, 5.60 mmol) in ACN (10 mL) and Water (10 mL) was added TFA (1.294 mL, 16.79 mmol) and the solution was stirred at 20° C. for 3 h. LCMS showed the desired product was formed, then the mixture was filtered and purified by HPLC (C18, H2O/MeCN with TFA modifier) to the title compound. LCMS m/z (M+H): 189.2 required. 189.2 found. The mixture was separated by SFC to give INTERMEDIATE O (PEAK 1) and INTERMEDIATE O (PEAK 2).

SFC condition:
Column: Chiralcel OD-3 150*4.6 mm I.D., 3 um
Mobile phase: A: CO$_2$ B: ethanol (0.05% DEA)
Gradient: from 5% to 40% of B in 5 min and hold 40% for 2.5 min, then 5% of B for 2.5 min, Flow rate: 2.5 mL/min, Column temp.: 35° C., ABPR: 1500 psi.

Intermediate Q tert-butyl (2R,3S)-3-amino-2-(((tert-butyldimethylsilyl)oxy)methyl)pyrrolidine-1-carboxylate

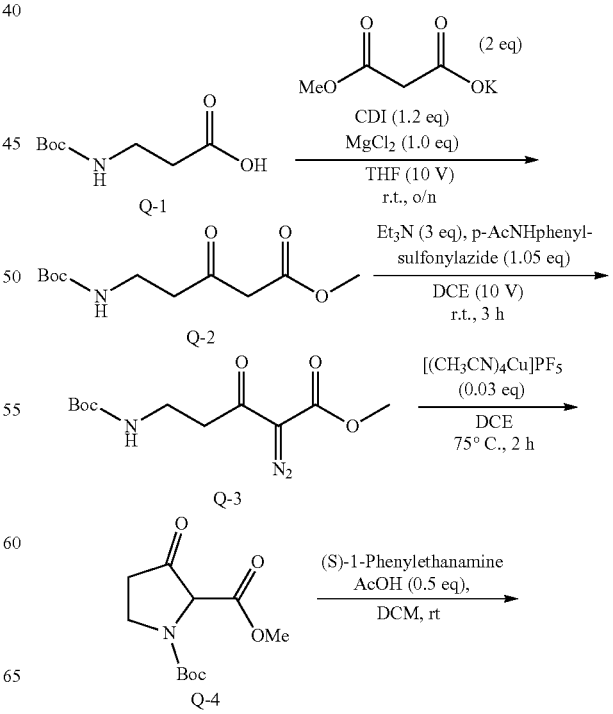

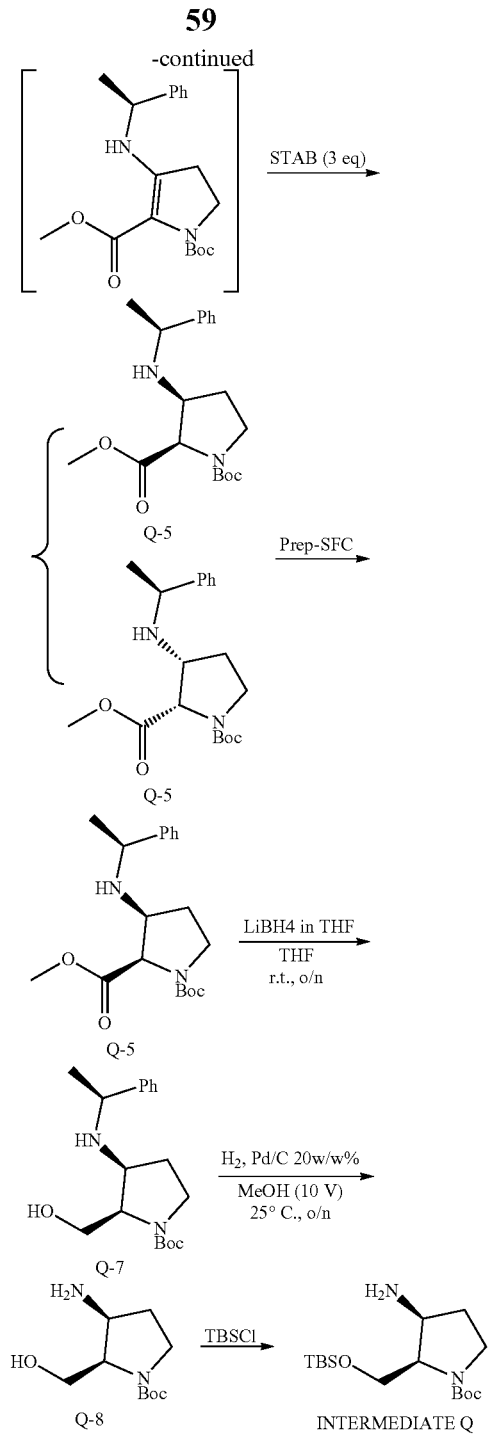

Step 1: methyl 5-[[(tert-butoxy)carbonyl]amino]-3-oxopentanoate (Q-2)

Into a 20-L 4-necked round-bottom flask purged and maintained with an inert atmosphere of nitrogen, was placed CDI (514 g, 1.2 equiv) in THF (5 L). This was followed by the addition of 3-[[(tert-butoxy)carbonyl]amino]propanoic acid (500 g, 1 equiv). The mixture was stirred for 3 h at room temperature. To this was added 1-methyl 3-potassium propanedioate (825 g, 2 equiv) and MgCl2 (250 g, 1 equiv). The resulting solution was stirred for overnight at room temperature. The resulting solution was diluted with 10 L of EA. The pH value of the solution was adjusted to 4 with aqueous KHSO4 (5%). The organic layer was separated and washed with aqueous NaHCO$_3$ (3 L), then H2O (3 L). The EA layer was dried over anhydrous sodium sulfate and concentrated to give the title compound.

Step 2: methyl 5-[[(tert-butoxy)carbonyl]amino]-2-diazo-3-oxopentano-ate (Q-3)

Into a 20-L 4-necked round-bottom flask purged and maintained with an inert atmosphere of nitrogen, was placed methyl 5-[[(tert-butoxy)carbonyl]amino]-3-oxopentanoate (Q-2) (650 g, 1 equiv) in DCE (6.5 L). Then, 4-acetamido-benzene-1-sulfonyl azide (669 g, 1.05 equiv) was added. This was followed by the addition of triethylamine (805 g, 3 equiv) dropwise with stirring in 1 hr at 5 C. The resulting solution was stirred for 2 h at 25 C. The solids were filtered out. The pH value of the solution was adjusted to 2 with aqueous HCl (1 mol/L). The resulting solution was extracted with of DCE and the organic layers combined. The resulting mixture was washed with 2 L of aqueous NaHCO3 and 2 L of aqueous NH4Cl. The mixture was dried over anhydrous sodium sulfate and used for next step directly.

Step 3: 1-tert-butyl 2-methyl 3-oxopyrrolidine-1,2-dicarboxylate (Q-4)

Into a 10-L 4-necked round-bottom flask purged and maintained with an inert atmosphere of nitrogen, was placed [(CH3CN)4Cu]PF6 (12 g, 0.012 equiv) in DCE (150 ml). The mixture was warmed to 75 C. Followed by the addition of the solution of methyl 5-[[(tert-butoxy)carbonyl]amino]-2-diazo-3-oxopentano-ate (Q-3) (719 g, 1 equiv) in DCE (7.5 L) dropwise with stirring. The resulting solution was stirred for 2 h at 75 C. Concentrated and the residue was purified by column chromatography with EA:PE=15% to afford the title compound.

Step 4: 1-(tert-butyl) 2-methyl (2R,3S)-3-(((S)-1-phenylethyl)amino)pyrrolidine-1,2-dicarboxylate (Q-5) and 1-(tert-butyl) 2-methyl (2S,3R)-3-(((S)-1-phenylethyl)amino)pyrrolidine-1,2-dicarboxylate (Q-6)

Into a 2 L four-neck round flask purged and maintained with nitrogen was charged 1-tert-butyl 2-methyl 3-oxopyrrolidine-1,2-dicarboxylate (Q-3) (80 g, 0.33 mol, 1 equiv) in DCM (800 ml). (S)-1-phenylethan-1-amine (43 g, 0.36 mol, 1.1 equiv) and AcOH (9.9 g, 0.165 mol, 0.5 equiv) were added at room temperature. The mixture was stirred for 30 min. Then STAB (206 g, 0.99 mol, 3 equiv) was added. The mixture was stirred for another 2 h. The solution was quenched by 1 L water and exacted with DCM (2×1 L). The organic layer was washed with brine (300 ml) and dried with Na2SO4 and concentrated. The residue was purified by column with (EA:PE=0%-30%) to give a mixture of the title compounds.

Step 5: 1-(tert-butyl) 2-methyl (2R,3S)-3-(((S)-1-phenylethyl)amino)pyrrolidine-1,2-dicarboxylate (Q-5)

The mixture of compound Q-5 and Q-6 (50 g) was separated by Prep-SFC (column: CHIRALPAK IG5*25 cm, 10 um; CO2: IPA (2 mM NH3-MeOH)=80:20; Flow Rate=160 g/min). This gave pure Q-5.

Step 6: tert-butyl (2R,3S)-2-(hydroxymethyl)-3-(((S)-1-phenylethyl)amino)pyrrolidine-1-carboxylate (Q-7)

Into a 1 L four-neck round flask purged and maintained with nitrogen was charged 1-(tert-butyl) 2-methyl (2R,3S)-3-(((S)-1-phenylethyl)amino)pyrrolidine-1,2-dicarboxylate (Q-5) (27 g, 76 mmol, 1 equiv) in THF (257 ml). LiBH4 in THF (110.5 ml, 2 mol/L, 221 mmol, 2 equiv) was added dropwise at room temperature. The mixture was stirred for overnight. The solution was quenched by 257 ml MeOH. Concentrated and the residue was dissolved with EA (2×200 mL). The organic layer was washed with H2O (100 ml) and brine (30 ml), dried with Na2SO4 and concentrated. The residue was purified by column with (EA:PE=20%-50%) to give the title compound.

Step 7: tert-butyl (2R,3S)-3-amino-2-(hydroxymethyl)pyrrolidine-1-carboxylate (Q-8)

Into a 500 mL 3-neck round flask purged was charged tert-butyl (2R,3S)-2-(hydroxymethyl)-3-(((S)-1-phenylethyl)amino)pyrrolidine-1-carboxylate (Q-7) (20 g, 62.5 mmol, 1 equiv) in MeOH (200 ml). Pd/C (4 g, 20 w/w %) was added. Then, the hydrogen was through in. Then the mixture was stirred for overnight under hydrogen. The mixture was filtered and the filtration was concentrated to give the title compound. LC-MS: (m/z): 239.1 [M+Na]+. 1H-NMR: (400 MHz, DMSO-d6, ppm): δ 3.61-3.62 (m, 2H), 3.11-3.44 (m, 6H), 1.88-1.90 (m, 1H), 1.62-1.71 (m, 1H), 1.39 (s, 9H).

Step 8: tert-butyl (2R,3S)-3-amino-2-[[(tert-butyldimethylsilyl)oxy]methyl]pyrrolidine-1-carboxylate (Intermediate Q)

Into a 500-mL 3-necked round-bottom flask purged and maintained with an inert atmosphere of nitrogen, was placed tert-butyl (2R,3S)-3-amino-2-(hydroxymethyl)pyrrolidine-1-carboxylate (Q-8) (37.00 g, 171.074 mmol, 1.00 equiv), DMF (111.00 mL). Then add imidazole (23.29 g, 342.147 mmol, 2.00 equiv) at 0 degrees C. This was followed by the addition of a solution of TBSCl (25.78 g, 171.074 mmol, 1.00 equiv) in DMF (74 mL) dropwise with stirring at 0 degrees C. in 30 min. The resulting solution was allowed to react, with stirring, for an additional 16 min at 25 degrees C. The reaction was then quenched by the addition of 500 mL of water/ice. The resulting solution was extracted with 2×500 mL of MTBE and the organic layers combined. The resulting mixture was washed with 3×300 ml of Water. The organic was dried by Na2SO4. The crude product was applied onto a silica gel column with dichloromethane/methanol (10/1) to afford the title compound. LC-MS: (ES, m/z): 331.15 [M+H]+. 1H NMR: (300 MHz, Chloroform-d, ppm): δ 4.16-3.81 (m, 2H), 3.74-3.16 (m, 4H), 2.06 (q, J=10.4, 7.0 Hz, 1H), 1.91 (p, J=10.4 Hz, 1H), 1.47 (s, 11H), 0.90 (s, 9H), 0.06 (d, J=1.9 Hz, 6H).

Intermediate R

Methyl (2R,3S)-2-(((tert-butyldimethylsilyl)oxy)methyl)-3-(N-(4-methoxybenzyl)methylsulfonamido)pyrrolidine-1-carboxylate

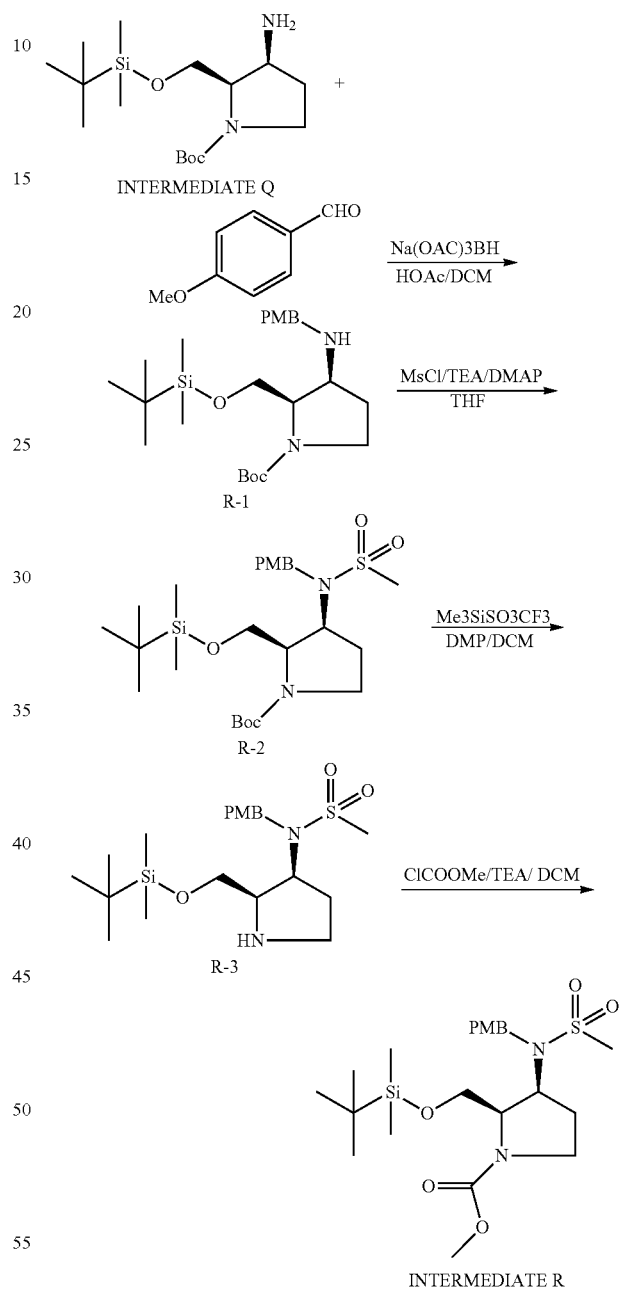

INTERMEDIATE R

Step 1: Tert-butyl (2R,3S)-2-(((tert-butyldimethylsilyl)oxy)methyl)-3-((4-methoxybenzyl)amino)pyrrolidine-1-carboxylate (R-1)

To a solution of tert-butyl (2R,3S)-3-amino-2-(((tert-butyldimethylsilyl)oxy)methyl)pyrrolidine-1-carboxylate (INTERMEDIATE Q) (750 mg, 2.269 mmol) in DCM (25 ml) was added 4-methoxybenzaldehyde (371 mg, 2.72 mmol) and catalytic amount of ACETIC ACID (65 μl, 1.134 mol) and magnesium sulfate (0.8 g). The mixture was stirred at rt for 1 hr, then SODIUM TRIACETOXYBOROHYDRIDE (625 mg, 2.95 mmol) was added to the mixture. The reaction was stirred at rt for 3 days. The reaction was quenched with saturated NaHCO₃ solution, extracted with DCM (3×5 ml). The combined organic was dried over MgSO₄. Filtered and concentrated to leave yellow oil. The residue was purified by column chromatography on silica (0% to 50% EtOAc/hexanes) to afford the title compound. MS: 452.6 (M+1).

Step 2: Tert-butyl (2R,3S)-2-(((tert-butyldimethylsilyl)oxy)methyl)-3-(N-(4-methoxy benzyl)methylsulfonamido)pyrrolidine-1-carboxylate (R-2)

To a solution of tert-butyl (2R,3S)-2-(((tert-butyldimethylsilyl)oxy)methyl)-3-((4-methoxybenzyl)amino)pyrrolidine-1-carboxylate (R-1, 917 mg, 2.035 mmol) in THF (20.00 ml) was added Et3N (0.851 ml, 6.10 mmol) at 0° C. under N2, followed by addition of Ms-Cl (0.190 ml, 2.442 mmol) and DMAP (19.89 mg, 0.163 mmol). The resulting mixture was stirred at 0° C. for 1 hr, then warmed up to room temperature and stirred at rt overnight. The reaction was quenched with water, extracted with CH2Cl2 (2×10 ml). The combined organic phases were dried over MgSO4, filtered, and the filtrate was concentrated in vacuo. The residue was purified by column chromatography on silica (0% to 40% EtOAc/hexanes) to afford the title compound. MS: 530.4 (M+1).

Step 3: N-((2R,3S)-2-(((tert-butyldimethylsilyl)oxy)methyl)pyrrolidin-3-yl)-N-(4-methoxybenzyl)methanesulfonamide (R-3)

To a solution of tert-butyl (2R,3S)-2-(((tert-butyldimethylsilyl)oxy)methyl)-3-(N-(4-methoxybenzyl)methylsulfonamido)pyrrolidine-1-carboxylate (R-2, 477 mg, 0.902 mmol) in DCM (7 ml) at 0° C. was added 2,6-dimethylpyridine (0.841 ml, 7.22 mmol) followed by trimethylsilyl trifluoromethanesulfonate (0.490 ml, 2.71 mmol). The reaction mixture was stirred at 0° C. under nitrogen for 15 mins. The reaction was quenched with sat. NaHCO₃, extracted with DCM (×3). The combined organic fractions were washed with brine, dried over MgSO4, filtered and the solvent was evaporated under reduced pressure. The residue was purified by prep silica gel TLC eluent with 3% 7N NH3 in MeOH/DCM to afford the title compound. MS: 430.2 (M+1).

Step 4: Methyl (2R,3S)-2-(((tert-butyldimethylsilyl)oxy)methyl)-3-(N-(4-methoxybenzyl)methylsulfonamido)pyrrolidine-1-carboxylate (Intermediate R)

To a solution of N-((2R,3S)-2-(((tert-butyldimethylsilyl)oxy)methyl)pyrrolidin-3-yl)-N-(4-methoxybenzyl)methanesulfonamide (R-3, 340 mg, 0.793 mmol) in DCM (6 ml) at 0° C. was added TEA (332 μl, 2.379 mmol) followed by methyl chloroformate (74 μl, 0.952 mmol). The reaction mixture was stirred at 0° C. for 30 mins. The reaction was quenched with MeOH. The residue was purified by prep silica gel TLC eluent with 2% MeOH/DCM to afford the title compound. MS: 487.2 (M+1).

Intermediate S benzyl (2R,3S,3aS,6aR)-3-(N-benzyl-2,2,2-trifluoroacetamido)-2-(((triethylsilyl)oxy)methyl)hexahydrocyclopenta[b]pyrrole-1(2H)-carboxylate

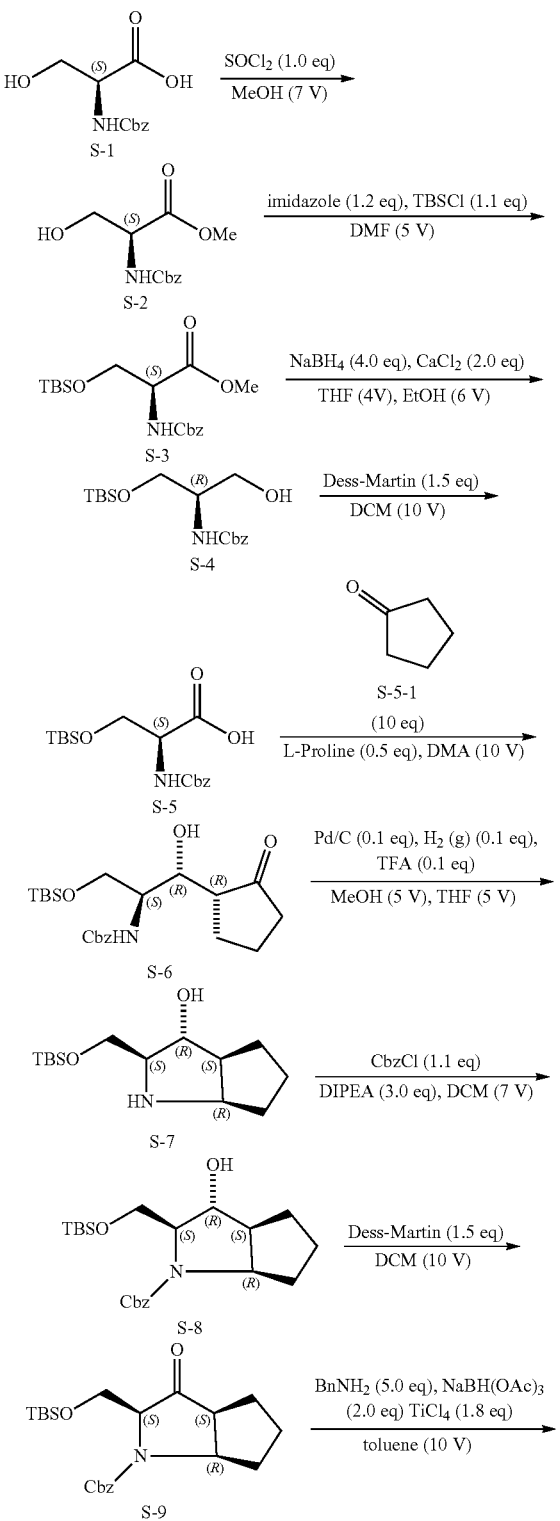

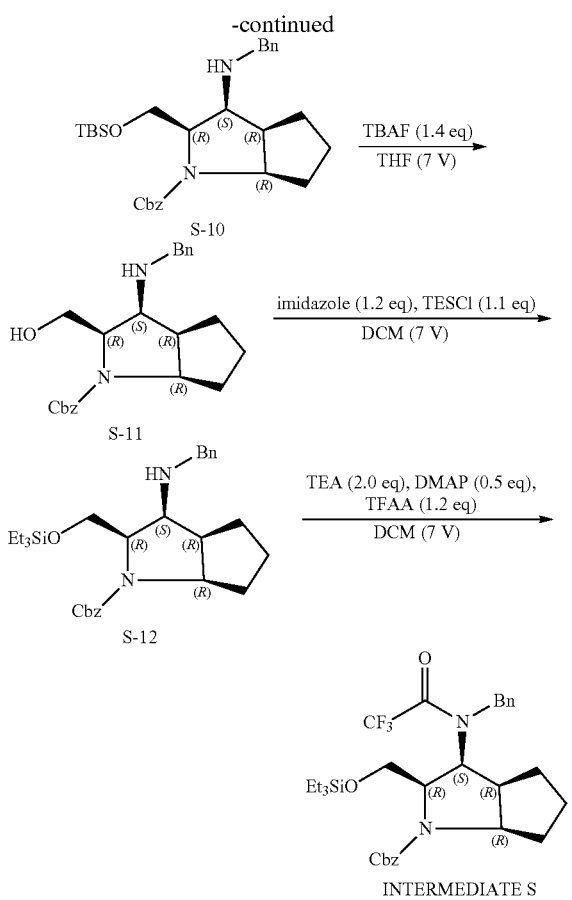

Step 1: methyl ((benzyloxy)carbonyl)-L-serinate (S-2)

Add compound S-1 (500 g, 2.09 mol, 1.00 eq) in MeOH (3.5 L) at 10~20° C. Add SOCl₂ (248 g, 2.09 mol, 151 mL, 1.00 eq) to the mixture drop-wise at 0-5° C. Stir the mixture at 70~80° C. for 2 hrs. Concentrated the mixture to give the title compound.

Step 2: methyl N-((benzyloxy)carbonyl)-O-(tert-butyldimethylsilyl)-L-serinate (S-3)

Add compound S-2 (480 g, 1.90 mol, 1.00 eq) in DMF (2.4 L) at 10~20° C. Add imidazole (154 g, 2.27 mol, 1.20 eq) to the mixture. Add TBSCl (314 g, 2.08 mol, 255 mL, 1.10 eq) to the mixture at 0° C. Stir the mixture at 10~20° C. for 12 hrs. Pour the mixture to ice water (3.5 L) and diluted with EtOAc (3 L). Separate the organic layer and extract the aqueous phase with EtOAc (1 L) and wash the combined organic layer with saturated brine (2 L) and concentrate under reduced pressure to give the title compound.

Step 3: benzyl (R)-(1-((tert-butyldimethylsilyl)oxy)-3-hydroxypropan-2-yl)carbamate (S-4)

Add compound S-3 (620 g, 1.69 mol, 1.00 eq) in THF (2.48 L) and EtOH (3.72 L) at 10~20° C. Add CaCl₂ (374 g, 3.37 mol, 2.00 eq) to the mixture. Add NaBH₄ (255 g, 6.75 mol, 4.00 eq) to the mixture at 0° C. Stir the mixture for 3 hrs at 20~30° C. Pour the mixture to ice 0.5 M HCl solution (4 L) and diluted with EtOAc (4 L). Separate the organic layer and extract the aqueous phase with EtOAc (2 L) and wash the combined organic layer with NaHCO₃ solution (4 L) and saturated brine (4 L) and concentrate under reduced pressure to give the title compound.

Step 4: benzyl (S)-(1-((tert-butyldimethylsilyl)oxy)-3-oxopropan-2-yl)carbamate (S-5)

Add compound S-4 (510 g, 1.50 mol, 1.00 eq) in DCM (5.1 L). Add Dess-Martin (955 g, 2.25 mol, 697 mL, 1.50 eq) to the mixture. Stir the mixture at 20~30° C. for 3 hrs. Filter the mixture to give the filtrate. Wash the filtrate with Na₂CO₃ solution (3 L). Separate the organic layer and concentrate under reduced pressure to give the title compound.

Step 5: benzyl ((1R,2S)-3-((tert-butyldimethylsilyl)oxy)-1-hydroxy-1-((R)-2-oxocyclopentyl)propan-2-yl)carbamate (S-6)

Add compound S-5 (440 g, 1.30 mol, 1.00 eq) in DMA (4.4 L). Add compound S-5-1 (1100 g, 13.0 mol, 10.0 eq) and L-Proline (75.0 g, 0.65 mol, 0.50 eq) to the mixture. Stir the mixture at 10~20° C. for 12 hrs. Pour the mixture to ice water (5 L) and diluted with EtOAc (4 L). Separate the organic layer and extract the aqueous phase with EtOAc (2 L) and wash the combined organic layer with saturated brine (5 L) and concentrate under reduced pressure to give the crude product. Purify the crude product by silica gel chromatography (Petroleum ether/Ethyl acetate=100/1~1/1) to give the title compound. ¹HNMR: (400 MHz, CDCl₃) δ: 7.30-7.39 (m, 5H), 5.19-5.21 (m, 1H), 5.11-5.14 (m, 2H), 4.10-4.17 (m, 1H), 4.00-4.03 (m, 1H), 3.80-3.88 (m, 1H), 3.74-3.77 (m, 1H), 2.86-2.88 (m, 2H), 2.29-2.33 (m, 1H), 2.08-2.14 (m, 2H), 2.05-2.07 (m, 1H), 1.76-1.78 (m, 1H), 0.77-0.92 (m, 9H), 0.07-0.10 (m, 6H).

Step 6: (2S,3R,3aS,6aR)-2-(((tert-butyldimethylsilyl)oxy)methyl)octahydrocyclopenta[b]pyrrol-3-ol (S-7)

Add Pd/C (15.5 g, 10% purity) in MeOH (775 mL) and THF (775 mL). Add compound S-6 (155 g, 367 mmol, 1.00 eq) and TFA (4.19 g, 36.7 mmol, 0.10 eq) to the mixture. Stir the mixture for 12 hrs at 25° C. under H2. Workup and filter the mixture to give the filtrate and concentrate the filtrate to give the title compound.

Step 7: benzyl (2S,3R,3aS,6aR)-2-(((tert-butyldimethylsilyl)oxy)methyl)-3-hydroxyhexahydrocyclopenta[b]pyrrole-1(2H)-carboxylate (S-8)

Add compound S-7 (170 g, 0.62 mol, 1.00 eq) in DCM (1.19 L). Add DIPEA (242 g, 1.88 mol, 3.00 eq) to the mixture. Add CbzCl (117 g, 0.68 mol, 1.10 eq) to the mixture drop-wise at 0-10° C. Stir the mixture at 10~20° C. for 2 hrs. Pour the mixture to ice water (1 L) and adjust the mixture to pH=4-5 with 1.0 M HCl solution (1 L) and diluted with DCM (1 L). Separate the organic layer and extract the aqueous phase with DCM (500 mL) and wash the combined organic layer with NaHCO₃ solution (2 L) and saturated brine (2 L) and concentrate under reduced pressure to give the crude product. Purify the crude product by silica gel chromatography (Petroleum ether/Ethyl acetate=100/1~1/1) to give the title compound.

Step 8: benzyl (2S,3aS,6aR)-2-(((tert-butyldimethylsilyl)oxy)methyl)-3-oxohexahydrocyclopenta[b]pyrrole-1(2H)-carboxylate (S-9)

Add compound S-8 (160 g, 394 mmol, 1.00 eq) in DCM (1.6 L). Add Dess-Martin (250 g, 591 mmol, 1.50 eq) to the mixture. Stir the mixture at 20~30° C. for 3 hrs. Filter the mixture to give the filtrate and wash the filtrate with $Na_2CO_3$ solution (2 L). Separate the organic layer and concentrate under reduced pressure to give the crude product. Purify the crude product by silica gel chromatography (Petroleum ether/Ethyl acetate=100/1~1/1) to give the title compound. $^1$HNMR: (400 MHz, $CDCl_3$) δ: 7.32-7.39 (m, 5H), 5.14-5.26 (m, 2H), 4.61-4.63 (m, 1H), 4.10-4.21 (m, 1H), 3.96-4.02 (m, 1H), 2.90-2.96 (m, 1H), 2.05-2.10 (m, 1H), 1.90-1.97 (m, 2H), 1.74-1.88 (m, 1H), 1.70-1.73 (m, 1H), 1.50-1.52 (m, 1H), 1.54-1.59 (m, 1H), 0.85 (s, 9H), 0.00 (s, 6H).

Step 9: benzyl (2R,3S,3aR,6aR)-3-(benzylamino)-2-(((tert-butyldimethylsilyl)oxy)methyl)hexahydrocyclopenta[b]pyrrole-1(2H)-carboxylate (S-10)

Add compound S-9 (135 g, 334 mmol, 1.00 eq) in toluene (1.35 L) at 10~20° C. Add $TiCl_4$ (1.00 M, 602 mL, 1.80 eq) to the mixture drop-wise at −10~−5° C. Add $BnNH_2$ (179 g, 1670 mmol, 5.00 eq) to the mixture drop-wise at −5~0° C., and stir the mixture at −5° C. for 0.5 hr. Add $NaBH(OAc)_3$ (141 g, 669 mmol, 2.00 eq) to the mixture at −5° C. Stir the mixture at 20~30° C. for 2 hrs. Pour the mixture to $Na_2CO_3$ solution (1.5 L) and diluted with EtOAc (2 L), and filter the mixture to give the filtrate. Separate the organic layer and extract the aqueous phase with EtOAc (1 L) and wash the combined organic layer with saturated brine (3 L) and concentrate under reduced pressure to give the crude product. Purify the crude product by silica gel chromatography (Petroleum ether/Ethyl acetate=50/1~1/1) to give the title compound.

Step 10: benzyl (2R,3S,3aR,6aR)-3-(benzylamino)-2-(hydroxymethyl)hexahydrocyclopenta[b]pyrrole-1(2H)-carboxylate (S-11)

Add compound 10 (80.0 g, 161 mmol, 1.00 eq) in THF (560 mL) at 10~20° C. Add TBAF (59.2 g, 226 mmol, 1.40 eq) to the mixture at 0-10° C. Stir the mixture at 10~20° C. for 3 hrs. Pour the mixture to $NH_4Cl$ solution (800 mL) and diluted with EtOAc (500 mL). Separate the organic layer and extract the aqueous phase with EtOAc (200 mL) and wash the combined organic layer with $NaHCO_3$ solution (600 mL) and concentrate under reduced pressure to give the title compound.

Step 11: benzyl (2R,3S,3aR,6aR)-3-(benzylamino)-2-(((triethylsilyl)oxy)methyl)hexahydrocyclopenta[b]pyrrole-1(2H)-carboxylate (S-12)

Add compound S-11 (60.0 g, 157 mmol, 1.00 eq) in DCM (420 mL) at 10~20° C. Add imidazole (12.8 g, 189 mmol, 1.20 eq) to the mixture. Add TESCl (26.1 g, 173 mmol, 29.5 mL, 1.10 eq) to the mixture at 0° C. Stir the mixture at 10~20° C. for 2 hrs. Pour the mixture to ice water (500 mL) and diluted with DCM (100 mL). Separate the organic layer and extract the aqueous phase with DCM (100 mL) and wash the combined organic layer with saturated brine (400 mL) and concentrate under reduced pressure to give the crude product. Purify the crude product by silica gel chromatography (Petroleum ether/Ethyl acetate=100/1~1/1) to give the title compound.

Step 12: benzyl (2R,3S,3aS,6aR)-3-(N-benzyl-2,2,2-trifluoroacetamido)-2-(((triethylsilyl)oxy)methyl)hexahydrocyclopenta[b]pyrrole-1 (2H)-carboxylate (Intermediate S)

Add compound S-12 (50.0 g, 101 mmol, 1.00 eq) in DCM (350 mL) at 10~20° C. Add TEA (20.4 g, 202 mmol, 28.1 mL, 2.00 eq) and DMAP (6.17 g, 50.5 mmol, 0.50 eq) to the mixture. Add TFAA (25.4 g, 121 mmol, 16.8 mL, 1.20 eq) to the mixture drop-wise at 0-10° C. Stir the mixture at 20~30° C. for 3 hrs. Pour the mixture to ice water (300 mL) and adjust the mixture to pH=4~5 with 0.5 M HCl solution (100 mL). Separate the organic layer and extract the aqueous phase with DCM (200 mL) and wash the combined organic layer with saturated $NaHCO_3$ solution (500 mL) and concentrate under reduced pressure to give the crude product. Purify the crude product by silica gel chromatography (Petroleum ether/Ethyl acetate=100/1~1/1) to give the title compound. $^1$HNMR: (400 MHz, $CDCl_3$) δ: 7.29-7.35 (m, 8H), 7.05-7.25 (m, 2H), 4.85-5.14 (m, 5H), 4.23-4.47 (m, 1H), 3.89-4.14 (m, 2H), 3.57-3.70 (m, 1H), 2.37-2.66 (m, 1H), 2.18-2.65 (m, 1H), 1.90-2.06 (m, 1H), 1.56-1.80 (m, 2H), 1.25-1.31 (m, 2H), 0.84-1.02 (m, 9H), 0.54-0.62 (m, 6H).

Intermediate T benzyl (2R,3S,5S)-5-(methoxymethyl)-2-(((triethylsilyl)oxy)methyl)-3-(2,2,2-trifluoro-N-(4-methoxybenzyl)acetamido)pyrrolidine-1-carboxylate

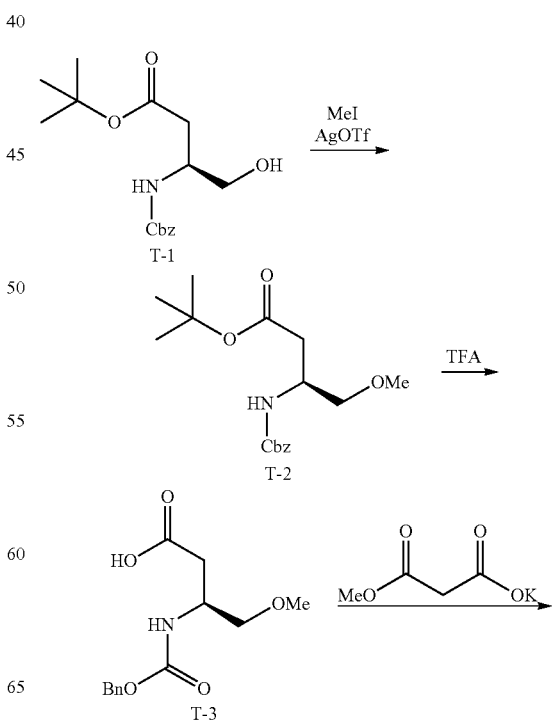

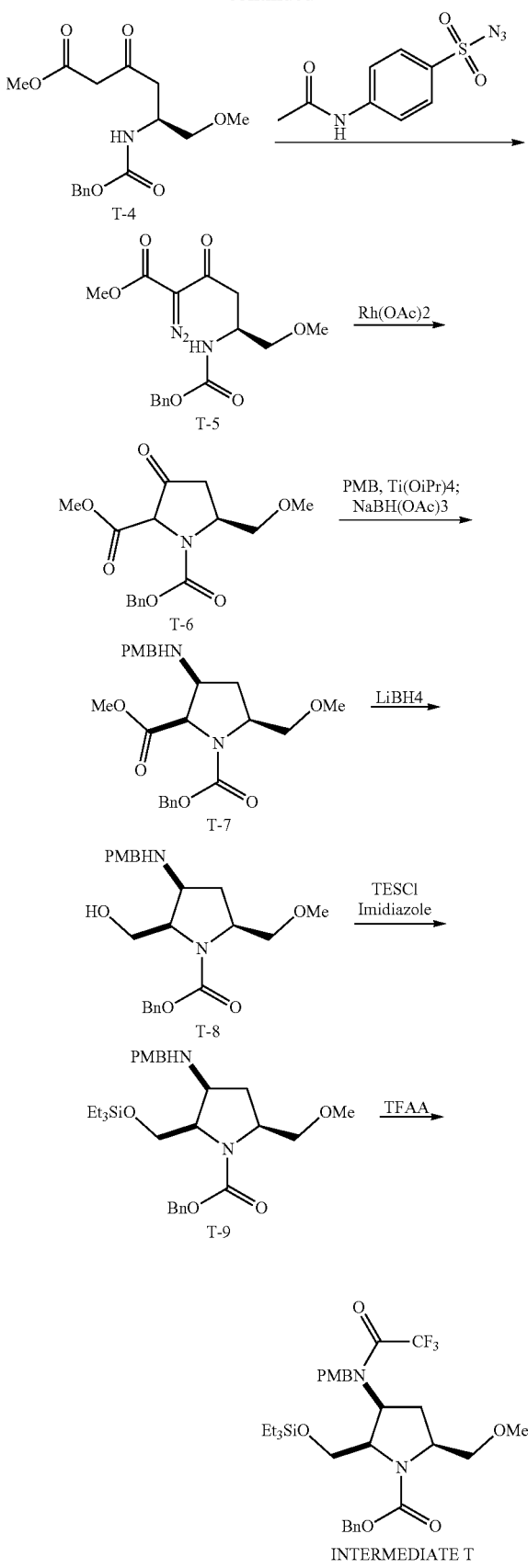

Step 1: tert-butyl (S)-3-(((benzyloxy)carbonyl) amino)-4-methoxybutanoate (T-2)

To a mixture of tert-butyl (S)-3-(((benzyloxy) carbonyl) amino)-4-hydroxybutanoate (T-1) (100 g, 0.324 mol, 1 equiv) in DCM (1 L) at 0° C. was added iodomethane (73.5 g, 0.518 mol, 1.6 equiv), 2,6-di-tert-butyl-4-methylpyridine (132.8 g, 0.648 mol, 2 equiv), and silver trifluoromethanesulfonate (133.1 g, 0.0.518 mol, 1.6 equiv). The mixture was allowed to warm to ambient temperature and stirred overnight. The resulting mixture was filtered through a pad of celite and concentrated. The resulting residue was purified with silica gel chromatography (2% to 75% EtOAc/PE) to obtain the title compound.

Step 2: (S)-3-(((benzyloxy)carbonyl)amino)-4-methoxybutanoic acid (T-3)

Into a 1-L 3-necked round-bottom flask purged and maintained with an inert atmosphere of nitrogen, was placed a solution of tert-butyl (S)-3-(((benzyloxy) carbonyl) amino)-4-methoxybutanoate (T-2) (66 g, 0.204 mol, 1.00 equiv) in DCM (330 mL). This was followed by the addition of TFA (30 g, 0.306 mol, 1.50 equiv) drop wise with stirring at room temperature. The resulting solution was stirred for 2 h at room temperature. The reaction was then quenched by the addition of 300 mL of water/ice. The resulting mixture was washed with 3×200 mL of H2O. The mixture was dried over anhydrous sodium sulfate and concentrated. The residue was applied onto a silica gel column (ethyl acetate/petroleum ether 0%-25%) to give the title compound.

Step 3: methyl S)-5-(((benzyloxy) carbonyl) amino)-6-methoxy-3-oxohexanoate (S-4)

Into a 500-mL 3-necked round-bottom flask purged and maintained with an inert atmosphere of nitrogen, was placed a solution of(S)-3-(((benzyloxy)carbonyl)amino)-4-methoxybutanoic acid (S-3) (26.7 g, 100 mmol, 1.00 equiv) in THF (267 mL). This was followed by the addition of CDI (21.0 g, 150 mmol, 1.50 equiv) dropwise with stirring at room temperature. The resulting solution was stirred for 3 h at room temperature. This was followed by the addition of $MgCl_2$ (19.0 g, 200 mmol, 2.00 equiv) and 1-methyl 3-potassium propanedioate (31.2 g, 200 mmol, 2.00 equiv) dropwise with stirring at room temperature. The resulting solution was allowed to react, with stirring, for an additional 2 days at room temperature. The resulting solution was diluted with 150 mL of EA. The reaction was then quenched by the addition of 100 mL of water/ice. The resulting mixture was washed with 2×200 mL of $NaHCO_3$. The resulting solution was extracted with 2×100 mL of ethyl acetate and the organic layers combined. The resulting mixture was washed with 1×200 mL of NaCl. The mixture was dried over anhydrous sodium sulfate and concentrated to give the title compound.

Step 4: methyl (S)-5-(((benzyloxy)carbonyl)amino)-2-diazo-6-methoxy-3-oxohexanoate (S-5)

Into a 500-mL 3-necked round-bottom flask purged and maintained with an inert atmosphere of nitrogen, was placed a solution of methyl (S)-5-(((benzyloxy)carbonyl)amino)-6-methoxy-3-oxohexanoate (S-4) (34.00 g, crude) in DCM (340 mL). This was followed by the addition of triethylamine (30.30 g, 300 mmol, 3 equiv) and 4-acetamidobenzenesulfonyl azide (24.00 g, 100 mmol, 1 equiv) dropwise with stirring at room temperature. The resulting solution was stirred overnight at room temperature. The solids were filtered out. The filtrate was washed with 2×100 mL of H₂O. The resulting mixture was washed with 1×100 mL of citric acid and 1×200 mL of NaCl. The mixture was dried over anhydrous sodium sulfate and concentrated to give the title compounds.

Step 5: methyl (S)-5-(((benzyloxy)carbonyl)amino)-2-diazo-6-methoxy-3-oxohexanoate (S-6)

Into a 500-mL 3-necked round-bottom flask purged and maintained with an inert atmosphere of nitrogen, was placed0 a solution of methyl methyl (S)-5-(((benzyloxy) carbonyl)amino)-2-diazo-6-methoxy-3-oxohexanoate (S-5) (34.00 g, crude) in toluene (340 mL), (acetyloxy)rhodio acetate (2.21 g, 10 mmol, 0.10 equiv). The resulting solution was stirred for 3 h at 80 degrees C. in an oil bath. The reaction mixture was cooled with a water bath. The solids were filtered out. The filtrate was concentrated. The residue was applied onto a silica gel column (ethyl acetate/petroleum ether 0%-20%) to obtain the title compound.

Step 6: 1-benzyl 2-methyl (2R,3S,5S)-3-((4-methoxybenzyl)amino)-5-(methoxymethyl)pyrrolidine-1,2-dicarboxylate (S-7)

Into a 500-mL 3-necked round-bottom flask purged and maintained with an inert atmosphere of nitrogen, was placed a solution of methyl (S)-5-(((benzyloxy)carbonyl)amino)-2-diazo-6-methoxy-3-oxohexanoate (S-6) (20.00 g, 62.3 mmol, 1.00 equiv) in THF (200 mL), (4-methoxyphenyl) methanamine (10.2 g, 74.8 mmol, 1.20 equiv). This was followed by the addition of Ti(Oi-Pr)₄ (17.7 g, 62.3 mmol, 1.00 equiv) dropwise with stirring at 0 degrees C. The resulting solution was stirred overnight at room temperature. To this was added STAB (92.45 g, 436.1 mmol, 7.00 equiv) in several batches. The resulting solution was allowed to react, with stirring, for an additional 2 days at room temperature. The resulting solution was diluted with 100 mL of EA. The reaction was then quenched by the addition of 200 mL of NaHCO₃. The solids were filtered out. The resulting solution was extracted with 2×100 mL of ethyl acetate and the organic layers combined. The resulting mixture was washed with 2×200 mL of NaCl. The mixture was dried over anhydrous sodium sulfate and concentrated. The residue was applied onto a silica gel column (ethyl acetate/petroleum ether 0%-45%) to obtain the title compound.

Step 7: benzyl (2R,3S,5S)-2-(hydroxymethyl)-3-((4-methoxybenzyl)amino)-5-(methoxymethyl)pyrrolidine-1-carboxylate (S-8)

Into a 100-mL 3-necked round-bottom flask purged and maintained with an inert atmosphere of nitrogen, was placed a solution of 1-benzyl 2-methyl (2R,3S,5S)-3-((4-methoxybenzyl)amino)-5-(methoxymethyl)pyrrolidine-1,2-dicarboxylate (S-7) (8.2 g, 18.569 mmol, 1.00 equiv) in THF (50 mL). This was followed by the addition of LiBH₄ (1.21 g, 55.708 mmol, 3.00 equiv) dropwise with stirring at room temperature. The resulting solution was stirred overnight at room temperature. The reaction was then quenched by the addition of 20 mL of EA. The resulting solution was diluted with 50 mL of H₂O/ice. The resulting solution was extracted with 2×20 mL of ethyl acetate and the organic layers combined. The resulting mixture was washed with 2×50 mL of Brine. The mixture was dried over anhydrous sodium sulfate and concentrated. The crude product was purified by Prep-HPLC (MeCN/H₂O 35%-57%) to give the title compound.

Step 8: benzyl(5S)-5-(methoxymethyl)-3-[[(4-methoxyphenyl)methyl]amino]-2-[[(triethylsilyl)oxy]methyl]pyrrolidine-1-carboxylate (S-9)

Into a 250-mL 3-necked round-bottom flask purged and maintained with an inert atmosphere of nitrogen, was placed a solution of benzyl (5S)-2-(hydroxymethyl)-5-(methoxymethyl)-3-[[(4-methoxyphenyl)methyl]amino] pyrrolidine-1-carboxylate (S-8) (10.00 g, 24.125 mmol, 1.00 equiv) in DCM (100 mL), TEA (3.17 g, 31.363 mmol, 1.30 equiv), DMAP (0.29 g, 2.413 mmol, 0.10 equiv). This was followed by the addition of chlorotriethylsilane (4.00 g, 26.538 mmol, 1.10 equiv) dropwise with stirring at 0 degrees C. The resulting solution was stirred for 2 h at room temperature. The reaction was then quenched by the addition of 100 mL of water/ice. The resulting solution was extracted with 2×50 mL of DCM and the organic layers combined. The resulting mixture was washed with 2×100 mL of NaCl. The mixture was dried over anhydrous sodium sulfate and concentrated to give the title compound.

Step 9: benzyl (5S)-5-(methoxymethyl)-2-[[(triethylsilyl)oxy]methyl]-3-[2,2,2-trifluoro-N-[(4-methoxyphenyl)methyl]acetamido]pyrrolidine-1-carboxylate (Intermediate T)

Into a 250-mL 3-necked round-bottom flask purged and maintained with an inert atmosphere of nitrogen, was placed a solution of benzyl (5S)-5-(methoxymethyl)-3-[[(4-methoxyphenyl)methyl]amino]-2-[[(triethylsilyl)oxy] methyl]pyrrolidine-1-carboxylate (S-9) (13.00 g, 24.586 mmol, 1.00 equiv) in DCM (130 mL), TEA (4.98 g, 49.171 mmol, 2.00 equiv). This was followed by the addition of TFAA (6.20 g, 29.503 mmol, 1.20 equiv) dropwise with stirring at 0 degrees C. The resulting solution was stirred for 2 h at room temperature. The resulting mixture was concentrated. The crude product was purified by Prep-HPLC (MeCN/H₂O 87%-100%) to obtain the title compound. LC-MS: (ES, m/z): 625 [M+1]⁺. H-NMR: (300 MHz, Chloroform-d, ppm): δ 7.36 (s, 5H), 7.03 (d, J=8.5 Hz, 2H), 6.90 (d, J=8.7 Hz, 2H), 5.26-5.00 (m, 2H), 4.94-4.80 (m, 2H), 4.67-4.37 (m, 2H), 3.98-3.71 (m, 6H), 3.60-3.44 (m, 1H), 3.40-3.15 (m, 4H), 2.42-2.07 (m, 1H), 1.85 (dt, J=12.9, 7.1 Hz, 1H), 0.96 (t, J=8.0 Hz, 9H), 0.71-0.52 (m, 6H).

Intermediate U, Intermediate V, and Intermediate W

6-(5-fluoropyrimidin-2-yl)bicyclo[4.1.0]heptan-3-one (Intermediate U), (1S,6R)-6-(5-fluoropyrimidin-2-yl)bicyclo[4.1.0]heptan-3-one (Intermediate V), and (1R,6S)-6-(5-fluoropyrimidin-2-yl)bicyclo[4.1.0]heptan-3-one (Intermediate W)

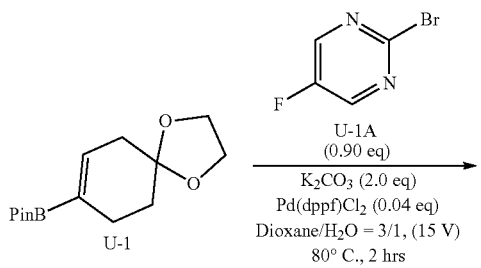

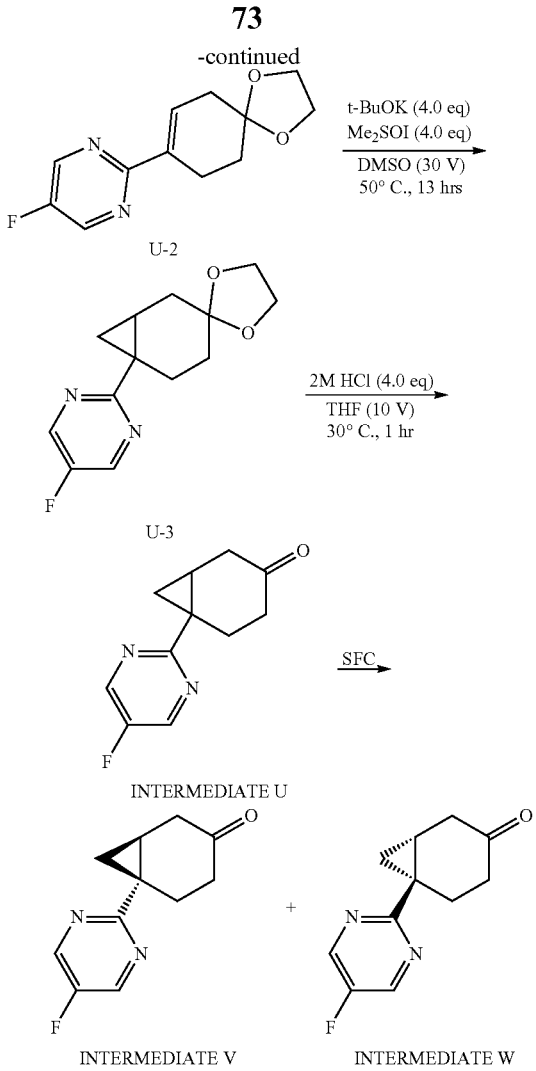

Step 1: 5-fluoro-2-(1,4-dioxaspiro[4.5]dec-7-en-8-yl)pyrimidine (U-2)

Add compound U-1 (100 g, 375 mmol, 1.0 eq) to Dioxane (1.50 L) and H₂O (500 mL) under N₂ at 25° C. Add compound 1A (44.8 g, 338 mmol, 41.9 mL, 0.9 eq) and K₂CO₃ (103 g, 751 mmol, 2.0 eq) to the mixture and purged with N₂ three times at 25° C. Add Pd(dppf)Cl₂ (11.0 g, 15.0 mmol, 0.04 eq) to the mixture, The reaction solution was purged with N₂ three times again and then warm the mixture to 80° C. Stir the mixture at 80° C. for 2 hrs. Pour the mixture into water (2.50 L), filter the mixture and wash the filter cake with ethyl acetate (500 mL×2), then extract the mixture with ethyl acetate (1.00 L× 2), combine the organic layers and wash it with brine (1.00 L), dry over Na₂SO₄ and concentrate in vacuum to give a residue. Purify the residue by column chromatography (SiO₂, petroleum ether:ethyl acetate=10:1 to 3:1) to give the title compound.

Step 2: 5-fluoro-2-(spiro[bicyclo[4.1.0]heptane-3,2'-[1,3]dioxolan]-6-yl)pyrimidine (U-3)

Add t-BuOK (38.0 g, 338 mmol, 4.0 eq) and Me₃SOI (74.5 g, 338 mmol, 4.0 eq) to DMSO (600 mL) the mixture at 25° C. Warm the mixture to 30° C. for 1 hr. Add compound U-2 (20.0 g, 84.6 mmol, 1.0 eq) in DMSO (80.0 mL) to the mixture at 30° C. Stir the mixture at 50° C. for 12 hrs. Cool the solution to 25° C., work-up: pour the mixture into sat. NH₄Cl (2.50 mL) with stirring, extract the mixture with ethyl acetate (1.50 mL×3), combine the organic layers and wash it with brine (1.50 mL), dry over Na₂SO₄ and concentrate in vacuum to give a residue. Purify the residue by column chromatography (SiO₂, petroleum ether:ethyl acetate=1:0 to 40:1) to obtain the title compound.

Step 3: 6-(5-fluoropyrimidin-2-yl)bicyclo[4.1.0]heptan-3-one (Intermediate U)

Add compound U-3 (32.0 g, 127 mmol, 1.0 eq) into THF (150 mL) at 30° C. Add aq. HCl (2 M, 255 mL, 4.0 eq) to the mixture at 30° C. Stir the mixture at 30° C. for 1 hr. Dilute the mixture with water (200 mL), adjust the mixture pH=8 with NaHCO₃ aq. with stirring. Extract the mixture with ethyl acetate (300 mL×2), combine the organic layers and extract the mixture with brine (100 mL), dry over with Na₂SO₄ and concentrate in vacuum to give the title compound. LCMS m/z (M+H): 207.2.

Step 4: (1S,6R)-6-(5-fluoropyrimidin-2-yl)bicyclo[4.1.0]heptan-3-one (Intermediate V) and (1R,6S)-6-(5-fluoropyrimidin-2-yl)bicyclo[4.1.0]heptan-3-one (Intermediate W)

Purify compound INTERMEDIATE U by SFC (column: DAICEL CHIRALPAK AD (250 mm*50 mm, 10 um); mobile phase: [Neu-EtOH]; B %: 40%-40%, 6 min).

INTERMEDIATE V: ¹HNMR: (400 MHz, CDCl₃) δ 8.46 (s, 2H), 2.95-2.96 (m, 1H), 2.77-2.78 (m, 1H), 2.62-2.63 (m, 1H), 2.57-2.58 (m, 1H), 2.38-2.50 (m, 2H), 1.85-1.87 (m, 1H), 1.66-1.69 (m, 1H), 1.13-1.15 (t, 1H).

INTERMEDIATE W: ¹HNMR (400 MHz, CDCl₃) δ 8.46 (s, 2H), 2.95-2.98 (m, 1H), 2.77-2.79 (m, 1H), 2.62-2.63 (m, 1H), 2.58-2.59 (m, 1H), 2.38-2.47 (m, 2H), 1.86-1.87 (m, 1H), 1.66-1.70 (m, 1H), 1.13-1.16 (t, 1H).

Intermediate X (+/−) benzyl (2R,3S,5S)-2-(((tert-butyldimethylsilyl)oxy)methyl)-5-(difluoromethyl)-3-(2,2,2-trifluoro-N-(4-methoxybenzyl)acetamido)pyrrolidine-1-carboxylate

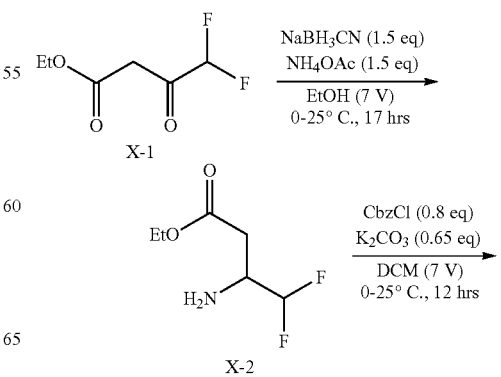

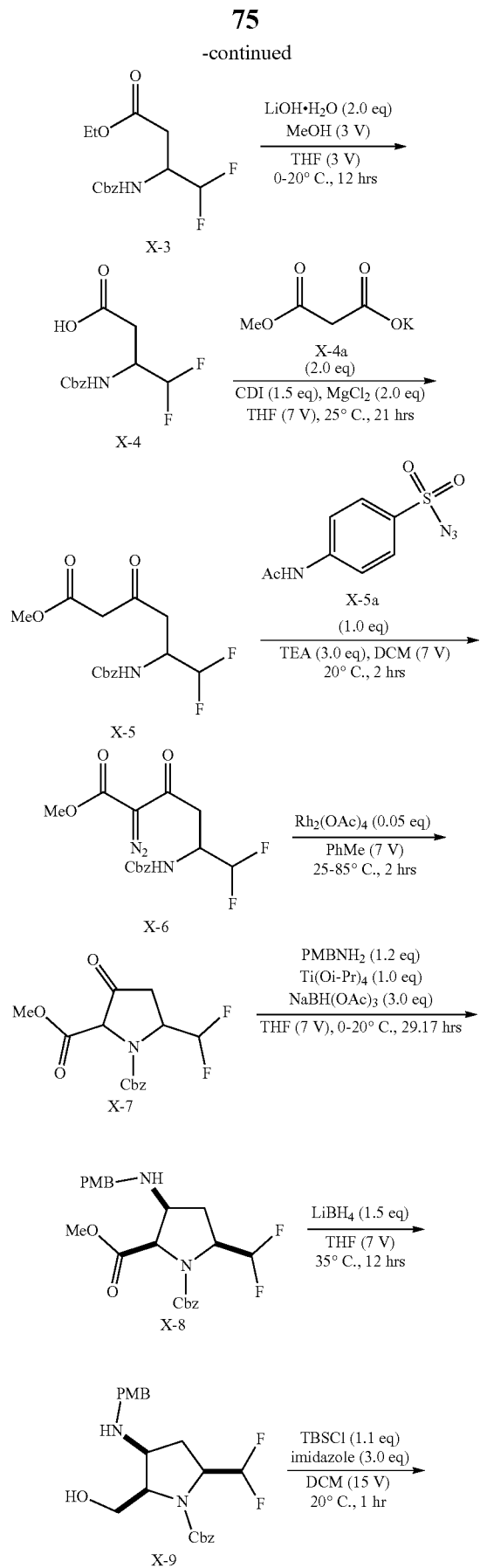
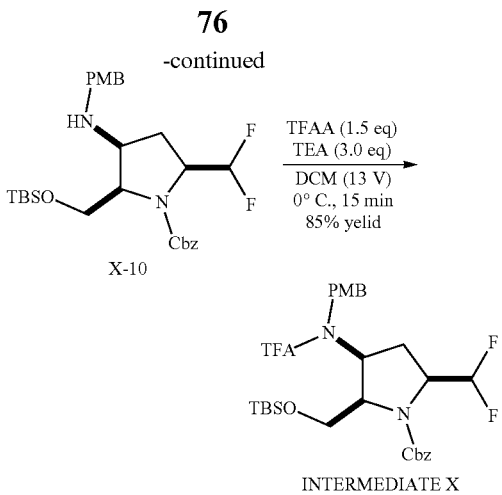

Step 1: ethyl 3-amino-4,4-difluorobutanoate (X-2)

Add compound X-1 (400 g, 2.41 mol, 1.00 eq), and NH$_4$OAc (278 g, 3.61 mol, 1.50 eq) to EtOH (2800 mL) at 25° C. Stir the mixture at 25° C. for 12 hrs. Cool the mixture to 0° C. Add NaBH$_3$CN (226 g, 3.61 mol, 1.50 eq) at 0° C. Warm the mixture to 25° C. Stir the mixture at 25° C. for 5 hrs. Concentrate the mixture at 45° C. to get crude product. Dissolve the mixture with ethyl acetate (1.50 L), wash with saturate Na$_2$CO$_3$ solution (1.00 L) and brine (1.00 L). Dry the mixture by Na$_2$SO$_4$ and concentrate to obtain the title compound. $^1$H NMR (400 MHz, CDCl$_3$) δ 5.59-6.18 (m, 1H), 4.82 (s, 1H), 4.12-4.19 (m, 1H), 3.39-3.43 (m, 1H), 2.61-2.65 (m, 1H), 2.45-2.61 (m, 1H), 2.39-2.43 (m, 1H), 2.02 (s, 1H), 1.86 (br s, 1H), 1.24 (t, J=0.01 Hz, 2H).

Step 2: ethyl 3-(((benzyloxy)carbonyl)amino)-4,4-difluorobutanoate (X-3)

Add compound X-2 (400 g, 2.39 mol, 1.00 eq) to DCM (2.80 L) at 25° C. Add K$_2$CO$_3$ (214 g, 1.56 mol, 0.65 eq) to the mixture to make the aqueous phase was adjusted from pH ~4 to pH ~9 (required 1.80 L of a 10% aq solution). Cool the mixture to 0° C. Add CbzCl (326 g, 1.91 mol, 272 mL, 0.80 eq) drop wise at 0° C. to the mixture for 0.5 hr. Warm the mixture to 25° C. Stir the mixture at 25° C. for 5 hrs. Quench with solution of NaHCO$_3$ (1.50 L). Extract with DCM (1.00 L). Dry over Na$_2$SO$_4$ and concentrate. The crude product was triturated with MTBE (1.30 L) at 20° C. for 30 mins. Filter and dry to give the title compound. $^1$HNMR: (400 MHz, CDCl$_3$) δ: 7.31-7.41 (m, 5H), 5.95-6.09 (m, 1H), 5.43 (d, J=8.00 Hz, 1H), 5.13 (s, 2H), 4.40 (br s, 1H), 4.15-4.20 (m, 2H), 2.68-2.70 (m, 2H), 1.25-1.29 (m, 3H).

Step 3: 3-(((benzyloxy)carbonyl)amino)-4,4-difluorobutanoic acid (X-4)

Add compound X-3 (460 g, 1.53 mol, 1.00 eq) to MeOH (1300 mL) and THF (1300 mL) at 20° C. Cool the mixture to 0° C. Add LiOH.H$_2$O (2M, 1.53 L, 2.00 eq) to the mixture at 0° C. Warm the mixture to 20° C. Stir the mixture at 20° C. for 12 hrs. Concentrating at 45° C. to give crude product. Pour the crude product into H$_2$O (10.0 L) and extract with EtOAc (4.00 L). Acidify the aqueous phase with 1M HCl to pH=5 at 0° C., and extract with MTBE (2.00 L x 2). Filter and concentrate to give the title compound. $^1$HNMR: (400

MHz, MeOH) δ: 7.33-7.38 (m, 5H), 5.77-6.05 (m, 1H), 5.13 (s, 2H), 4.37 (br s, 1H), 2.53-2.74 (m, 2H).

Step 4: methyl 5-(((benzyloxy)carbonyl)amino)-6,6-difluoro-3-oxohexanoate (X-5)

Add compound X-4 (360 g, 1.32 mol, 1.00 eq) and CDI (320 g, 1.98 mol, 1.50 eq) in THF (2500 mL) at 25° C. Stir at 25° C. for 1 hr. Then add compound X-4a (411 g, 2.64 mol, 2.00 eq) and $MgCl_2$ (250 g, 2.64 mol, 108 mL, 2.00 eq) to the mixture at 25° C. Stir at 25° C. for 20 hrs. Quench with a solution of $NaHCO_3$ (1.50 L). Extract with EtOAc (3.00 L). Wash the organic phase with the brine (1.50 L). Dry over $Na_2SO_4$. Concentrate to give product. The crude product was triturated with MTBE at 20° C. for 30 mins to obtain the title compound. $^1$HNMR: (400 MHz, MeOH) δ: 7.06-7.34 (m, 5H), 5.75-6.03 (m, 1H), 5.14-5.09 (m, 1H), 4.29 (br s, 1H), 3.69 (s, 2H), 2.97-2.83 (m, 1H).

Step 5: methyl 5-(((benzyloxy)carbonyl)amino)-2-diazo-6,6-difluoro-3-oxohexanoate (X-6)

Add compound X-5 (184 g, 0.28 mol, 1.00 eq) to DCM (1250 mL) at 20° C. Add TEA (339 g, 0.84 mol, 3.00 eq) and compound X-5a (165 g, 0.84 mol, 1.50 eq) to the mixture at 20° C. Stir the mixture at 20° C. for 2 hrs. Diluting with water (1.00 L). Extracting with DCM (2.00 L). Wash the organic with brine (500 mL). Drying over $Na_2SO_4$ and concentrating to give the crude product. The residue was purified by silica gel chromatography (Petroleum ether/ Ethyl acetate=50/1, 2/1) to afford the title compound. $^1$HNMR: (400 MHz, $CDCl_3$) δ: 7.22-7.29 (m, 5H), 5.82-6.11 (m, 1H), 5.03 (s, 2H), 5.37 (br s, 1H), 5.11 (s, 2H), 4.49 (br s, 1H) 3.85 (s, 3H), 2.43 (s, 1H).

Step 6: 1-benzyl 2-methyl 5-(difluoromethyl)-3-oxopyrrolidine-1,2-dicarboxylate (X-7)

Add compound S-6 (360 g, 1.01 mol, 1.00 eq) to toluene (2500 mL) at 25° C. Add $Rh_2(OAc)_4$ (22.39 g, 50.7 mmol, 0.05 eq) to the mixture at 25° C. Heat the mixture solution to 85° C. Stir the mixture solution at 85° C. for 2 hrs. Cool the mixture to the atmosphere temperature. Filter the mixture to removal of catalyst. Concentrate the mixture solution to obtain the title compound. $^1$HNMR: (400 MHz, $CDCl_3$) δ: 7.32-7.41 (m, 5H), 5.86-6.43 (m, 1H), 5.05-5.33 (m, 2H), 4.53-4.80 (m, 1H), 3.84 (d, J=0.01 Hz, 1H), 3.57 (s, 3H), 2.88 (s, 2H), 2.32-2.39 (m, 1H).

Step 7: 1-benzyl 2-methyl (2R,3S,5S)-5-(difluoromethyl)-3-((4-methoxybenzyl)amino)pyrrolidine-1,2-dicarboxylate (X-8)

Add compound X-7 (10.0 g, 458 mmol, 1.00 eq) to THF (900 mL) at 20° C. Cool the mixture to 0° C. Add $PMBNH_2$ (5.03 g, 360 mmol, 1.20 eq) at 0° C. Add Ti(Oi-Pr)$_4$ (8.68 g, 300 mmol, 1.00 eq) drop wise at 0° C. to the mixture for 10 mins. Warm the mixture to 20° C. and stir for 5 hrs. Cool the mixture to 0° C. Add NaBH(OAc)$_3$ (19.40 g, 1.37 mol, 3.00 eq) to the mixture at 0° C. Warm the mixture to 20° C. and stir for 12 hrs. Cool the mixture to 0° C. Add NaBH(OAc)$_3$ (19.40 g, 1.37 mol, 3.00 eq) to the mixture at 0° C. Warm the mixture to 20° C. and stir for 12 hrs Dilute the mixture solution with EtOAc (1.00 L). Quench the mixture with a solution of $NaHCO_3$ (1.00 L). Separate of liquid and extract the organic with EtOAc (1.00 L). Dry over $Na_2SO_4$. Concentrate to give crude product. The residue was purified by silica gel chromatography (Petroleum ether/Ethyl acetate=30/1, 1/1) to afford product. The crude product was triturated with MTBE (200 mL) at 20° C. for 30 mins to obtain the title compound. $^1$HNMR: (400 MHz, DMSO) δ 7.32-7.40 (m, 5H), 7.22 (d, J=8.0 Hz, 2H), 6.86 (d, J=8.0 Hz, 2H), 6.20-6.48 (m, 1H), 5.03-5.13 (m, 2H), 4.62 (d, J=8.0 Hz, 1H), 4.24 (br s, 1H), 3.72 (s, 3H), 3.63 (s, 5H), 3.52 (br s, 1H), 2.22 (m, 2H), 1.92-1.96 (m, 1H).

Step 8: benzyl (2R,3S,5S)-5-(difluoromethyl)-2-(hydroxymethyl)-3-((4-methoxybenzyl)amino)pyrrolidine-1-carboxylate (X-9)

Add compound X-9 (25.0 g, 55.7 mmol, 1.0 eq) to THF (150 mL) at 20° C. Purge with $N_2$ for 3 times. Cool the mixture to 0° C. and add $LiBH_4$ (2 M, 41.8 mL, 1.5 eq) in portions to the mixture. Warm the mixture to 20° C. and stir the mixture at 20° C. for 12 hrs. Add water (1000 mL) to the mixture, extract the mixture with EtOAc (500 mL×2), combine two the organic layers and wash the organic layers with brine (500 mL), dry over $Na_2SO_4$ and concentrate in vacuum to give a residue. The residue was purified by column chromatography ($SiO_2$, petroleum ether/ethyl acetate=30/1 to 0/1) to obtain the title compound. $^1$HNMR: (400 MHz, $CDCl_3$) δ 7.33-7.39 (m, 5H), 7.19-7.21 (d, J=8 Hz, 2H), 6.86-6.88 (d, J=8 Hz, 2H), 6.14-6.43 (t, J=60 Hz, 1H), 5.14 (s, 2H), 4.07-4.12 (m, 1), 3.77-3.83 (m, 8H), 3.44-3.46 (m, 1H), 2.28-2.30 (m, 1H), 2.25-2.28 (m, 1H).

Step 9: benzyl (2R,3S,5S)-2-(((tert-butyldimethylsilyl)oxy)methyl)-5-(difluoromethyl)-3-((4-methoxybenzyl)amino)pyrrolidine-1-carboxylate (X-10)

Add TBSCl (13.0 g, 86.3 mmol, 10.6 mL, 1.1 eq) to DCM (190 mL) at 20° C. Add compound X-9 (33.0 g, 78.5 mmol, 1.0 eq) imidazole (16.0 g, 235 mmol, 3.0 eq) to the mixture at 20° C. Stir the mixture at 20° C. for 1 hr. Concentrate the mixture in vacuum to give a residue. The residue was purified by column chromatography ($SiO_2$, Petroleum ether/ Ethyl acetate=30/1 to 5/1) to obtain the title compound. $^1$HNMR: (400 MHz, $CDCl_3$) δ: 7.34-7.37 (m, 5H), 7.23-7.25 (d, J=8 Hz, 2H), 6.85-6.87 (d, J=8 Hz, 2H), 6.12-6.45 (m, 1H), 5.15 (s, 2H), 4.02-4.05 (m, 2H), 3.73-3.87 (m, 7H), 3.37-3.73 (m, 2H), 2.05-2.23 (m, 2H), 0.90 (s, 9H), 0.01-0.11 (m, 6H).

Step 10: (+/−) benzyl (2R,3S,5S)-2-(((tert-butyldimethylsilyl)oxy)methyl)-5-(difluoromethyl)-3-(2,2,2-trifluoro-N-(4-methoxybenzyl)acetamido)pyrrolidine-1-carboxylate (Intermediate X)

Add compound X-10 (26.0 g, 48.6 mmol, 1.0 eq) to DCM (160 mL). Add TEA (14.7 g, 146 mmol, 20.3 mL, 3.0 eq) to the mixture. Cool the mixture to 0° C. Add TFAA (15.3 g, 72.9 mmol, 10.1 mL, 1.5 eq) to the mixture and keep the temperature at 0° C. for 0.5 hr. Add $NaHCO_3$ (150 mL) to the mixture to adjust pH=8, extract the mixture with DCM (100 mL×2), combine the organic layers and wash it with brine (100 mL), dry over $Na_2SO_4$ and concentrate in vacuum to give a residue. The residue was purified by column chromatography ($SiO_2$, petroleum ether:ethyl acetate from 30:1 to 0:1) to obtain the title compound. $^1$H NMR: (400 MHz, $CDCl_3$) δ; 7.33-7.39 (m, 5H), 7.03-7.05 (d, J=8 Hz 2H), 6.89-6.91 (d, J=8 Hz, 2H), 6.22-6.50 (t, J=64 Hz, 1H), 5.05-5.23 (m, 2H), 4.81-4.96 (m, 2H), 4.45-4.55 (m, 2H), 3.89-4.12 (m, 5H), 3.50-3.53 (m, 1H), 2.47-2.53 (m, 1H), 1.61-1.69 (m, 1H), 0.89 (s, 9H), 0.005-0.084 (m, 6H).
Intermediate Y
benzyl (2R,3S,5S)-2-(((tert-butyldimethylsilyl)oxy)methyl)-3-(2,2,2-trifluoro-N-(4-methoxybenzyl)acetamido)-5-(trifluoromethyl)pyrrolidine-1-carboxylate
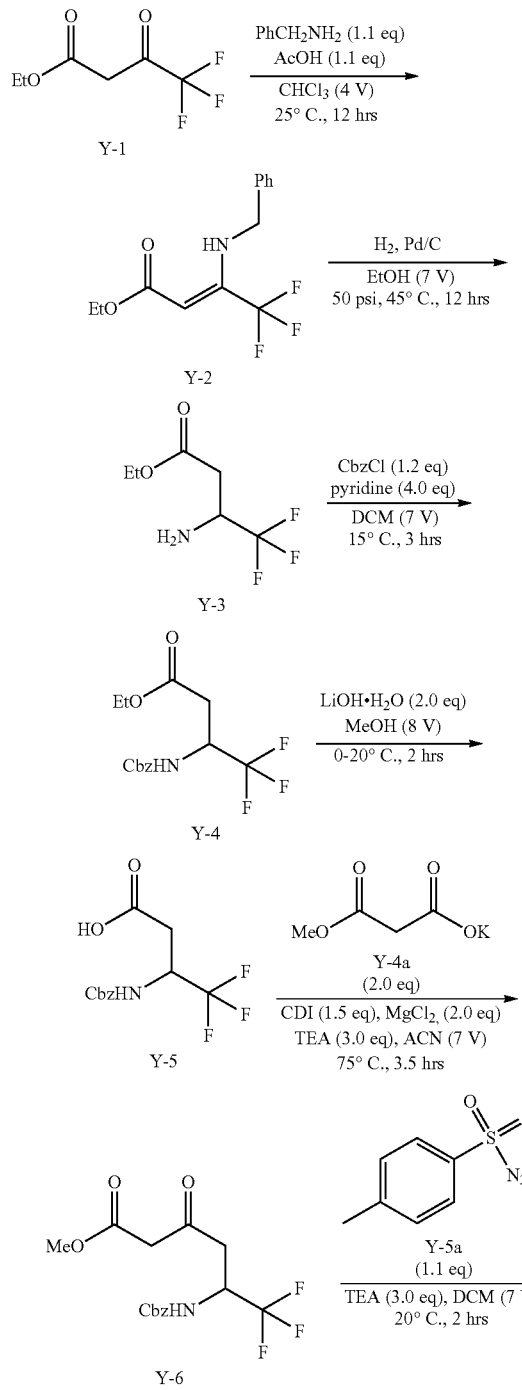
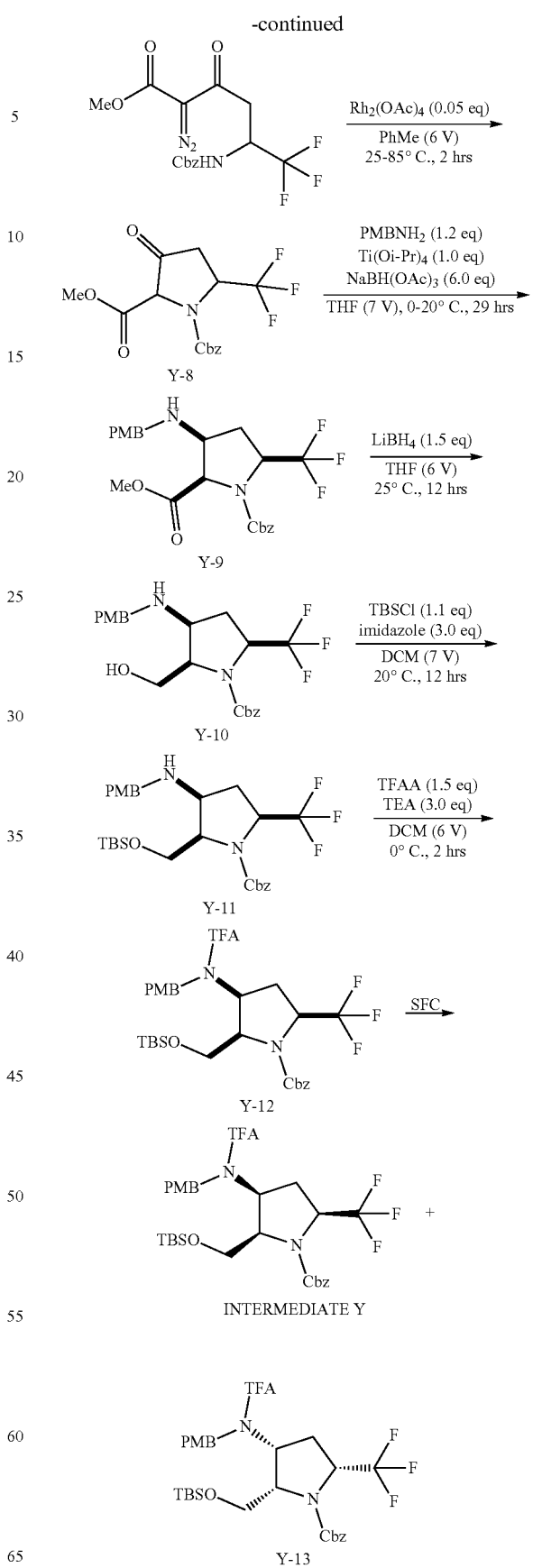

Step 1: ethyl (Z)-3-(benzylamino)-4,4,4-trifluorobut-2-enoate (Y-2)

Add compound Y-1 (500 g, 2.72 mol, 1.00 eq), PhCH$_2$NH$_2$ (325 g, 3.03 mol, 1.10 eq) and CH$_3$COOH (185 g, 3.08 mol, 1.10 eq) to EtOH (2.00 L) at 25° C. Stir the mixture at 25° C. for 12 hrs. Concentrate the mixture at 45° C. to get crude product. Dissolve the mixture with ethyl acetate (1.00 L), wash with saturate Na$_2$CO$_3$ solution (1.00 L) and brine (0.50 L). Dry the mixture by Na$_2$SO$_4$ and concentrate to give compound the title compound. $^1$HNMR: (400 MHz, CDCl$_3$). δ 8.46 (br s, 1H), 7.29-7.39 (m, 5H), 5.18 (s, 1H), 4.49 (d, J=6.4 Hz, 2H), 4.15 (q, J=7.2 Hz, 2H), 1.28 (t, J=7.2 Hz, 3H).

Step 2: ethyl 3-amino-4,4,4-trifluorobutanoate (Y-3)

Add compound Y-2 (90.0 g, 0.39 mol, 1.00 eq) to EtOH (0.60 L) at 15° C. Add Pd/C (16.0 g, 0.39 mol, 10% purity, 1.00 eq) under Ar. The suspension was degassed and purged with H2 for 12 times. The mixture was stirred under H2 (50 Psi) at 50° C. for 12 hrs. The reaction mixture filtered and concentrated under reduced pressure to give compound the title compound. $^1$HNMR: (400 MHz, CDCl$_3$). δ: 4.20 (q, J=6.8 Hz, 2H), 3.73-3.77 (m, 1H), 2.71-2.75 (m, 1H), 2.42-2.49 (m, 1H), 1.29 (t, J=7.2 Hz, 3H).

Step 3: ethyl 3-(((benzyloxy)carbonyl)amino)-4,4,4-trifluorobutanoate (Y-4)

Add compound Y-3 (360 g, 1.94 mol, 1.00 eq), CbzCl (398, 2.33 mol, 1.20 eq) and pyridine (615 g, 7.78 mol, 4.00 eq) in DCM (2.40 L) at 15° C. Stir the reaction mixture at 15° C. for 3 hrs. The aqueous phase with 1M HCl to pH=2 at 0° C. The mixture stirred for 30 min before quenching with solution of NaHCO$_3$ (1.00 L). Extract with DCM (1.00 L), dry over Na$_2$SO$_4$, and concentrating. The crude product was triturate with Petroleum ether (0.60 L) at 20° C. for 30 min. Filter and dry to give the title compound. $^1$HNMR: (400 MHz, CDCl$_3$) δ: 7.32-7.41 (m, 5H), 5.55 (d, J=9.6 Hz, 1H), 5.15 (s, 2H), 4.17 (q, J=7.2 Hz, 2H), 2.75-2.80 (m, 1H), 2.60-2.66 (m, 1H) 1.25 (t, J=7.2 Hz, 3H).

Step 4: 3-(((benzyloxy)carbonyl)amino)-4,4,4-trifluorobutanoic acid (Y-5)

Add compound Y-4 (350 g, 1.10 mol, 1.00 eq) to MeOH (2.80 L) at 20° C. Cool the mixture to 0° C. Add LiOH.H$_2$O (2 M, 1.10 L, 2.00 eq) to the mixture at 0° C. Warm the mixture to 20° C. Stir the mixture at 20° C. for 2 hrs. Concentrating at 45° C. to give crude product. Pour the crude product into H$_2$O (3.00 L) and extract with EtOAc (2.00 L). Acidify the aqueous phase with 1M HCl to pH=5 at 0° C., and extract with EtOAc (1.00 L×2). Dry over Na$_2$SO$_4$ and concentrate to give the title compound. $^1$HNMR: (400 MHz, MeOH). δ: 7.29-7.34 (m, 5H), 5.08-5.14 (m, 2H), 4.7-4.74 (m, 1H), 2.75-2.80 (m, 1H), 2.57-2.64 (m, 1H).

Step 5: methyl 5-(((benzyloxy)carbonyl)amino)-6,6,6-trifluoro-3-oxohexanoate (Y-6)

Add compound Y-5 (320 g, 1.10 mol, 1.00 eq) and CDI (196 g, 1.21 mol, 1.10 eq) in ACN (2.10 L) at 25° C. Stir at 25° C. for 1 hr. The compound Y-4a (343 g, 2.20 mol, 2.00 eq), TEA (334 g, 3.30 mol, 3.00 eq) and MgCl (261 g, 2.75 mol, 2.50 eq) to the mixture at 25° C. Stir at 75° C. for 2.5 hrs. Pour the crude product into H$_2$O (1.00 L). Acidify the aqueous phase with 1M HCl to pH=5 at 0° C., and extract with EtOAc (1.00 L×2). Dry over Na$_2$SO$_4$ and concentrate to give the title compound. $^1$HNMR: (400 MHz, CDCl$_3$) δ: 7.32-7.39 (m, 5H), 5.45 (d, J=9.2 Hz, 1H), 5.09-5.17 (m, 2H), 4.81-4.84 (m, 1H), 3.74 (s, 3H), 3.45-3.50 (m, 2H), 2.94-3.04 (m, 2H).

Step 6: methyl 5-(((benzyloxy)carbonyl)amino)-2-diazo-6,6,6-trifluoro-3-oxohexanoate (Y-7)

Add compound Y-6 (320 g, 0.94 mol, 1.00 eq), Compound Y-5a (266 g, 1.01 mol, 75% purity, 1.10 eq), TEA (279 g, 2.76 mol, 3.00 eq) to DCM (4.00 L) at 15° C. Stir the mixture at 20° C. for 2 hrs. Add water (1.00 L) to mixture at 25° C. Extract with DCM (1.00 L). Wash the organic with brine (1.00 L). Dry over Na$_2$SO$_4$ and concentrate to give the crude product. The crude product was triturating with MTBE (1.00 L) at 20° C. for 30 min. Filter and dry to give the title compound. $^1$HNMR: (400 MHz, CDCl$_3$) δ: 7.32-7.38 (m, 5H), 5.37 (d, J=9.2 Hz, 1H), 5.13 (s, 2H), 4.88 (br s, 1H), 3.85 (s, 3H), 3.28-3.34 (m, 1H), 3.16-3.21 (m, 1H).

Step 7: 1-benzyl 2-methyl 3-oxo-5-(trifluoromethyl)pyrrolidine-1,2-di carboxylate (Y-8)

Add compound Y-7 (237 g, 0.63 mol, 1.00 eq) to toluene (1.40 L) at 25° C. Add Rh$_2$(OAc)$_4$ (14.0 g, 0.03 mol, 0.05 eq) to the mixture at 25° C. Heat the mixture solution to 85° C. Stir the mixture solution at 85° C. for 2 hrs. Cool the mixture to the atmosphere temperature. Filter the mixture to removal of catalyst. Concentrate the mixture solution to obtain the title compound.

Step 8: 1-benzyl 2-methyl (2R,3S,5S)-3-((4-methoxybenzyl)amino)-5-(trifluoromethyl)pyrrolidine-1,2-dicarboxylate (Y-9)

Add compound Y-8 (190 g, 0.55 mol, 1.00 eq) to THF (1.30 L) at 20° C. Cool the mixture to 0° C. Add PMBNH$_2$ (91.0 g, 0.66 mol, 1.20 eq) at 0° C. Add Ti(Oi-Pr)$_4$ (156 g, 0.55 mol, 1.00 eq) dropwise at 0° C. Warm the mixture to 20° C. and stir for 5 hrs. Cool the mixture to 0° C. Add NaBH(OAc)$_3$ (349 g, 1.65 mol, 3.00 eq) to the mixture at 0° C. Warm the mixture to 20° C. and stir for 12 hrs. Cool the mixture to 0° C. Add NaBH(OAc)$_3$ (349 g, 1.65 mol, 3.00 eq) to the mixture at 0° C. Dilute the mixture solution with EtOAc (1.00 L). Quench the mixture with a solution of NaHCO$_3$ (1.00 L). Separate of liquid and extract the organic with EtOAc (1.00 L). Dry over Na$_2$SO$_4$. Concentrate to give crude product. The residue was purified by silica gel chromatography (Petroleum ether/Ethyl acetate, 30/1-1/1) to afford the title compound. $^1$HNMR: (400 MHz, MeOH) δ: 7.30-7.38 (m, 5H), 7.22 (d, J=8.4 Hz, 2H), 6.85 (d, J=8.4 Hz, 2H), 5.10-5.18 (m, 2H), 4.73 (d, J=8.0 Hz, 1H), 4.52-4.57 (m, 1H), 3.76 (s, 3H), 3.65-3.72 (m, 5H), 3.54-3.60 (m, 1H), 2.44-2.50 (m, 1H), 2.11-2.17 (m, 1H).

Step 9: benzyl (2R,3S,5S)-2-(hydroxymethyl)-3-((4-methoxybenzyl)amino)-5-(trifluoromethyl)pyrrolidine-1-carboxylate (Y-10)

Add compound Y-9 (35.5 g, 0.07 mol, 1.00 eq) to THF (0.20 L) at 15° C. Cool the mixture to 0° C. Add LiBH$_4$ (2 M, 52.2 mL, 1.40 eq) dropwise at 0° C. to the mixture for 1 min. Stir the mixture solution at 25° C. for 12 hrs. The mixture was cooled in ice bath. Add was water (200 mL) and the mixture was extract with ethyl acetate (2×200 mL). Wash the organic with brine (200 mL). Dry over Na$_2$SO$_4$ and concentrate to give the crude product. The residue was purified by silica gel chromatography (Petroleum ether/Ethyl acetate, 30/1-1/1) to afford the title compound.

Step 10: benzyl (2R,3S,5S)-2-(((tert-butyldimethylsilyl)oxy)methyl)-3-((4-methoxybenzyl)amino)-5-(trifluoromethyl)pyrrolidine-1-carboxylate (Y-11)

Add compound Y-10 (27.0 g, 61.5 mmol, 1.00 eq), TBSCl (10.2 g, 67.7 mmol, 1.10 eq) and imidazole (12.6 g, 185 mmol, 3.00 eq) to DCM (180 mL) at 15° C. Stir the mixture solution at 20° C. for 12 hrs. Dilute the mixture solution with DCM (200 mL). Quench the mixture with a solution of H$_2$O (150 mL). Separate of liquid and extract the organic with DCM (200 mL). Dry over Na$_2$SO$_4$. Concentrate to give the title compound. $^1$HNMR: (400 MHz, CDCl$_3$) δ 7.32-7.39 (m, 5H), 7.22 (d, J=8.0 Hz, 2H), 6.86 (d, J=8.0 Hz, 2H), 5.15 (s, 1H), 4.20-4.36 (m, 2H), 3.90-3.94 (m, 1H), 3.76-3.81 (m, 6H), 3.30-3.35 (m, 1H), 2.42-2.45 (m, 1H), 2.01-2.06 (m, 1H), 0.90 (s, 9H), 0.08 (s, 6H).

Step 11: benzyl (2R,3S,5S)-2-(((tert-butyldimethylsilyl)oxy)methyl)-3-(2,2,2-trifluoro-N-(4-methoxybenzyl)acetamido)-5-(trifluoromethyl)pyrrolidine-1-carboxylate (Y-12)

Add compound Y-11 (34.0 g, 61.5 mmol, 1.00 eq) and TEA (18.7 g, 184 mmol, 3.00 eq) to DCM (200 mL) at 15° C. Cool the mixture to 0° C. Add TFAA (19.4 g, 92.3 mmol, 1.50 eq) to mixture at 0° C. The mixture was stirred at 0° C. for 2 hrs. Dilute the mixture solution with DCM (100 mL). Quench the mixture with a solution of H$_2$O (100 mL). Separate of liquid and extract the organic with DCM (100 mL). Dry over Na$_2$SO$_4$. Concentrate to give crude product. The residue was purified by silica gel chromatography (Petroleum ether/Ethyl acetate, 30/1-1/1) to afford the title compound. $^1$HNMR: (400 MHz, DMSO) δ: 7.33-7.39 (m, 5H), 7.05 (d, J=8.0 Hz, 2H), 6.90 (d, J=8.0 Hz, 2H), 5.09-5.22 (m, 2H), 4.79-4.91 (m, 2H), 4.55 (br s, 1H), 4.41 (br s, 1H), 4.26 (br s, 1H), 3.81 (br s, 1H) 3.80 (s, 3H), 3.60 ((d, J=12 Hz, 1H)), 2.59 (br s, 1H), 1.85-2.05 (m, 1H), 0.90 (s, 9H), 0.05 (s, 6H).

Step 12: benzyl (2R,3S,5S)-2-(((tert-butyldimethylsilyl)oxy)methyl)-3-(2,2,2-trifluoro-N-(4-methoxybenzyl)acetamido)-5-(trifluoromethyl)pyrrolidine-1-carboxylate (Intermediate Y) and benzyl (2S,3R,5R)-2-(((tert-butyldimethylsilyl)oxy)methyl)-3-(2,2,2-trifluoro-N-(4-methoxybenzyl)acetamido)-5-(trifluoromethyl)pyrrolidine-1-carboxylate (Y-13)

Compound Y-12 (39.0 g, 60.1 mmol, 1.00 eq) was separated by SFC (column: REGIS (s,s) WHELK-01 (250 mm×50 mm, 10 um); mobile phase: [0.1% NH$_3$H$_2$O ETOH]; B %: 40%-40%, 4.4 min. The organic layers were concentrated under reduced pressure.

INTERMEDIATE Y: $^1$HNMR: (400 MHz, CDCl$_3$) δ: 7.33-7.39 (m, 5H), 7.05 (d, J=8.0 Hz, 2H), 6.90 (d, J=8.0 Hz, 2H), 5.09-5.22 (m, 2H), 4.79-4.91 (m, 2H), 4.55 (br s, 1H), 4.41 (br s, 1H), 4.26 (br s, 1H), 3.81 (br s, 1H) 3.80 (s, 3H), 3.60 ((d, J=12 Hz, 1H)), 2.59 (br s, 1H), 1.85-2.05 (m, 1H), 0.90 (s, 9H), 0.05 (s, 6H).

Intermediate Z potassium ((1S,4R,6S)-4-(((2R,3S,5R)-1-((benzyloxy)carbonyl)-5-methyl-3-(2,2,2-trifluoro-N-(4-methoxybenzyl)acetamido)pyrrolidin-2-yl)methoxy)bicyclo[4.1.0]heptan-1-yl)trifluoroborate

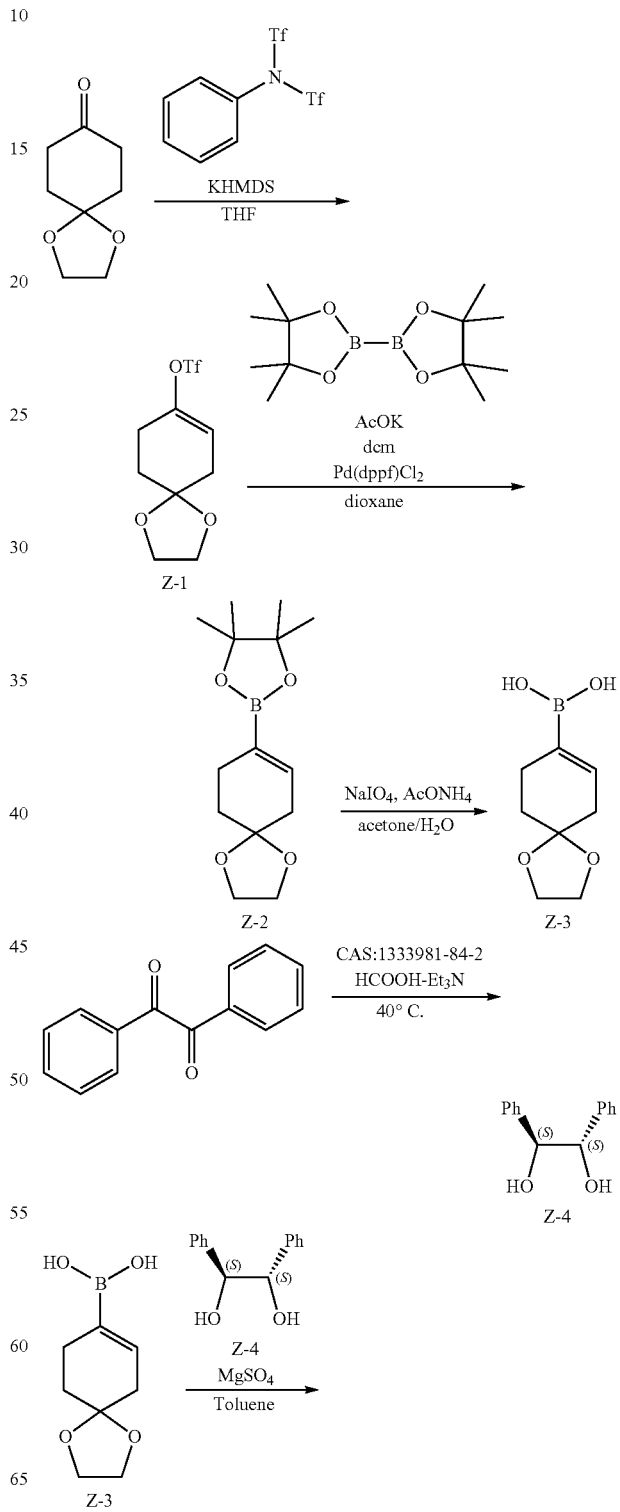

85

-continued

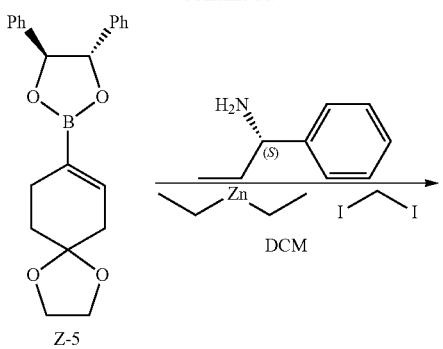

Z-5

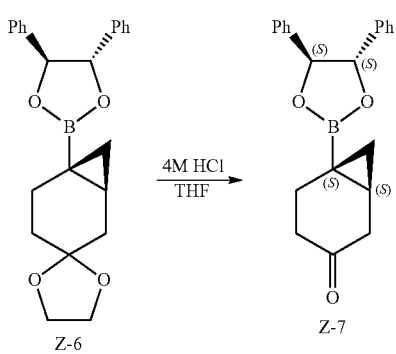

Z-6 → Z-7

4M HCl
THF

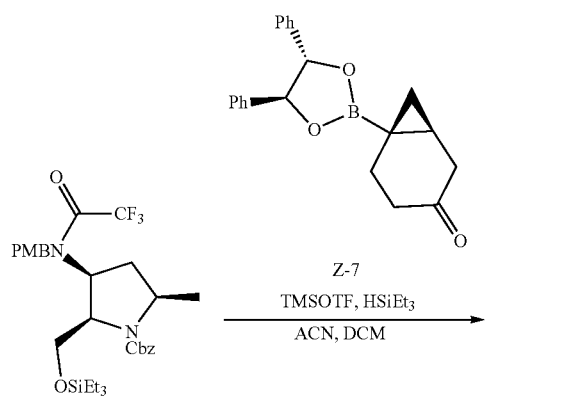

Intermediate CC + Z-7

TMSOTF, HSiEt₃
─────────────
ACN, DCM

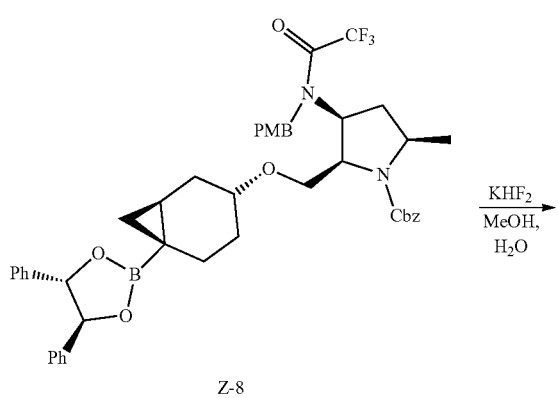

Z-8

KHF₂
─────
MeOH,
H₂O

86

-continued

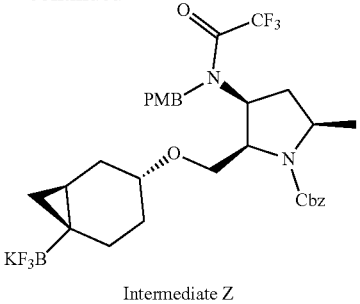

Intermediate Z

Step 1: 1,4-dioxaspiro[4.5]dec-7-en-8-yl trifluoromethanesulfonate (Z-1)

Into a 20-L 4-necked round-bottom flask purged and maintained with an inert atmosphere of nitrogen were added tetrahydrofuran (5 L), 1,4-dioxaspiro[4.5]decan-8-one (1 kg, 6.40 mol, 1.00 eq.) and 1,1,1-trifluoro-N-phenyl-N-trifluoromethanesulfonylmethanesulfonamide (2.40 kg, 6.72 mol, 1.05 eq.). To the above mixture was added KHMDS (6.8 L, 1 mol/L, 1.05 eq.) dropwise over 1 h at −25° C. The resulting mixture was stirred for additional 2 h at 25° C. The reaction was quenched by the addition of 10 L ice water at 0° C. and stirred for additional 30 minutes. The resulting mixture was extracted with PE (3×10 L). The combined organic layers were washed with brine (2×10 L), dried over anhydrous Na₂SO₄. After filtration, the filtrate was concentrated under reduced pressure to obtain the title compound.

Step 2: 2-{1,4-dioxaspiro[4.5]dec-7-en-8-yl}-4,4,5,5-tetramethyl-1,3,2-dioxaborolane (Z-2)

Into a 20-L 4-necked round-bottom flask purged and maintained with an inert atmosphere of nitrogen were added Dioxane (12 L), 1,4-dioxaspiro[4.5]dec-7-en-8-yl trifluoromethanesulfonate (Z-1) (1.6 kg, 5.55 mol, 1.00 eq.), bis(pinacolato)diboron (1.83 kg, 7.22 mol, 1.3 eq.), KOAc (1.63 kg, 16.6 mol, 3 eq.) and Pd(dppf)Cl₂.CH₂Cl₂ (45.22 g, 55.5 mmol, 0.01 eq.). The above mixture was heated to 100° C. under N₂ atmosphere for 3 h. The mixture was allowed to cool down to 25° C. The resulting mixture was concentrated under reduced pressure. The resulting mixture was diluted with brine (15 L). The resulting mixture was extracted with PE (2×15 L). The combined organic layers were washed with brine (2×10 L), dried over anhydrous Na₂SO₄. After filtration, the filtrate was concentrated under reduced pressure. Then let stand over night at 0° C. and filtered to obtain the title compound.

Step 3: 1,4-dioxaspiro[4.5]dec-7-en-8-ylboronic acid (Z-3)

Into a 2*20-L 4-necked round-bottom flask purged and maintained with an inert atmosphere of nitrogen were added 2-{1,4-dioxaspiro[4.5]dec-7-en-8-yl}-4,4,5,5-tetramethyl-1,3,2-dioxaborolane (Z-2) (2*600 g, 4.51 mol, 1.00 eq.) Acetone (2*6.00 L), NH₄OAc (2*521 g, 13.5 mol, 3 eq.), NaIO₄ (2*1.45 Kg, 13.5 mol, 3 eq.) and H₂O (2*6.00 L). The above mixture was stirred for 6 h at 25° C. The resulting mixture was filtered, the filter cake was washed with EA (2×5 L). The filtrate was concentrated under reduced pressure. The resulting mixture was extracted with EA (3×10 L). The combined organic layers were washed with brine (2×10

L), dried over anhydrous Na₂SO₄. After filtration, the filtrate was concentrated under reduced pressure. The residue was slurried with Et₂O:PE (1:1) (1×4.8 L). The precipitated solids were collected to afford the title compound.

Step 4: (1S,2S)-1,2-diphenylethane-1,2-diol (Z-4)

Into a 5-L 4-necked round-bottom flask purged and maintained with an inert atmosphere of nitrogen were added TEA (2.12 Kg, 20.93 mol, 4.4 eq.). To the above mixture was added HCOOH (963 g, 20.93 mol, 4.4 eq.) dropwise over 30 minutes at −20° C. The resulting mixture was stirred for 30 minutes at 0° C. under N₂ atmosphere. To the above mixture was added benzil (1 Kg, 4.76 mol, 1.00 eq.) and RuCl(p-cymene)[(R,R)-Ts-DENEB (3.1 g, 4.769 mmol) at 0° C. under N₂ atmosphere. The resulting mixture was stirred for additional 15 h at 40° C. under N₂. The resulting mixture was concentrated under reduced pressure. The resulting mixture was diluted with H₂O (10 L) and stirred for 1 h. The precipitated solids were collected by filtration and washed with H₂O (1×3 L). The resulting wet cake was dried by natural air. The crude product was re-crystallized from EtOH (3 L) to afford the title compound.

Step 5: (4S,5S)-2-{1,4-dioxaspiro[4.5]dec-7-en-8-yl}-4,5-diphenyl-1,3,2-dioxaborolane (Z-5)

Into a 20-L 4-necked round-bottom flask purged and maintained with an inert atmosphere of nitrogen were added 1,4-dioxaspiro[4.5]dec-7-en-8-ylboronic acid (Z-3) (500 g, 2.72 mol, 1.00 eq.), (1S,2S)-1,2-diphenylethane-1,2-diol (Z-4) (640 g, 2.99 mol, 1.1 eq.), MgSO₄ (1.64 g, 13.6 mol, 5 eq.) and Toluene (15 L). The resulting mixture was stirred overnight at 25° C. under N₂ atmosphere. The resulting mixture was filtered, the filter cake was washed with EA (1 L). The filtrate was concentrated under reduced pressure. The crude product was slurried by PE (1.5 L). The precipitated solids were collected by filtration to obtain the title compound.

Step 6: (4S,5S)-4,5-diphenyl-2-[(1S,6S)-spiro[bicyclo[4.1.0]heptane-3,2'-[1,3]dioxolan]-6-yl]-1,3,2-dioxaborolane (Z-6)

Into a 20-L 4-necked round-bottom flask purged and maintained with an inert atmosphere of nitrogen were added (4S,5S)-2-{1,4-dioxaspiro[4.5]dec-7-en-8-yl}-4,5-diphenyl-1,3,2-dioxaborolane (Z-5) (800 g, 2.21 mol, 1.00 eq.), (1S)-1-phenylpropan-1-amine (597.23 g, 4.42 mol, 2 eq.), DCM (8 L). To the above mixture was added diethylzinc (8.83 L, 8.83 mol, 4 eq.) dropwise over 2 h at −40° C. The resulting mixture was stirred for additional 30 minutes at −40° C. To the above mixture was added diiodomethane (3.55 Kg, 13.3 mol, 6 eq.) dropwise over 30 minutes at −20° C. The resulting mixture was stirred for additional 6 h at −20° C. The resulting mixture was stirred overnight at 10° C. under N₂ atmosphere. The resulting mixture was diluted with DCM (8 L). The reaction was quenched by the addition of NH₄Cl saturated aqueous solution (20 L). The resulting mixture was extracted with DCM (8 L). The aqueous layer was extracted with DCM (8 L). The combined organic layers were washed with brine (2×15 L), dried over anhydrous Na₂SO₄. After filtration, the filtrate was concentrated under reduced pressure. The residue was purified by silica gel column chromatography (PE:EA (Ratio from 10:1 to 4:1)) to afford 600 g crude product. The crude product was three times re-crystallized from n-hexane (3 L) to afford the title compound.

Step 7: (1S,6S)-6-[(4S,5S)-4,5-diphenyl-1,3,2-dioxaborolan-2-yl]bicyclo[4.1.0]heptan-3-one (Z-7)

Into a 3-L 4-necked round-bottom flask purged and maintained with an inert atmosphere of nitrogen were added (4S,5S)-4,5-diphenyl-2-[(1S,6S)-spiro[bicyclo[4.1.0]heptane-3,2'-[1,3]dioxolan]-6-yl]-1,3,2-dioxaborolane (Z-6) (280 g, 744 mmol, 1.00 eq.), tetrahydrofuran (1.4 L). To the above mixture was added hydrochloric acid aqueous solution (372 mL, 4 mol/L, 2 eq.) dropwise over 20 minutes at 0° C. The resulting mixture was stirred for additional 2 h at 25° C. The resulting mixture was extracted with Et₂O (2×1.5 L). The combined organic layers were washed with Saturated NaHCO₃ solution (3×1.5 L), dried over anhydrous Na₂SO₄. After filtration, the filtrate was concentrated under reduced pressure. The resulting oil was stand overnight at 25° C. to afford to obtain the title compound. H NMR: (400 MHz, Chloroform-d, ppm) δ 7.46-7.35 (m, 6H), 7.33-7.29 (m, 4H), 5.18 (s, 2H), 2.82 (dd, J=17.9, 5.6 Hz, 1H), 2.65-2.49 (m, 2H), 2.38 (dt, J=18.0, 6.0 Hz, 1H), 2.20 (ddd, J=18.1, 9.3, 6.0 Hz, 1H), 2.02 (dt, J=14.3, 6.1 Hz, 1H), 1.66-1.56 (m, 1H), 1.24 (dd, J=8.2, 4.7 Hz, 1H), 0.80 (t, J=4.9 Hz, 1H).

Step 8: benzyl (2R,3S,5R)-2-({[(1S,6S)-6-[(4S,5S)-4,5-diphenyl-1,3,2-dioxaborolan-2-yl]bicyclo[4.1.0]heptan-3-yl]oxy}methyl)-5-methyl-3-{2,2,2-trifluoro-N-[(4-methoxyphenyl)methyl]acetamido}pyrrolidine-1-carboxylate (Z-8)

To a stirred solution of benzyl (2R,3S,5R)-5-methyl-2-{[(triethylsilyl)oxy]methyl}-3-{2,2,2-trifluoro-N-[(4-methoxyphenyl)methyl]acetamido}pyrrolidine-1-carboxylate (INTERMEDIATE CC) (111 g, 187 mmol, 1 eq.) and (1S,6S)-6-[(4S,5S)-4,5-diphenyl-1,3,2-dioxaborolan-2-yl]bicyclo[4.1.0]heptan-3-one (Z-7) (74.4 g, 224 mmol, 1.2 eq.) in ACN (750 mL) DCM (250 mL) were added triethylsilane (26 g, 224 mmol, 1.2 eq.) in DCM (300 mL) and TMSOTF (20.7 g, 93.3 mmol, 0.5 eq.) in 300 mL (ACN:DCM=3:1) dropwise at −30° C. under N₂ atmosphere. The resulting mixture was stirred for 2 hours at −30° C. under N₂ atmosphere. The reaction was quenched with saturated NaHCO₃ at −30° C. The resulting mixture was extracted with EA (2×1 L). The combined organic layers were washed with NaCl (2×500 mL), dried over anhydrous Na₂SO₄. After filtration, the filtrate was concentrated under reduced pressure. The residue was purified by silica gel column chromatography (PE:EA 10:1) to afford the title compound.

Step 9: potassium ((1S,4R,6S)-4-(((2R,3S,5R)-1-((benzyloxy)carbonyl)-5-methyl-3-(2,2,2-trifluoro-N-(4-methoxybenzyl)acetamido)pyrrolidin-2-yl)methoxy)bicyclo[4.1.0]heptan-1-yl)trifluoroborate (Intermediate Z)

Into a 500 mL flask were added benzyl (2R,3S,5R)-2-({[(1S,6S)-6-[(4S,5S)-4,5-diphenyl-1,3,2-dioxaborolan-2-yl]bicyclo[4.1.0]heptan-3-yl]oxy}methyl)-5-methyl-3-{2,2,2-trifluoro-N-[(4-methoxyphenyl)methyl]acetamido}pyrrolidine-1-carboxylate (Z-8) (12 g, 15.1 mmol, 1 eq.) in MeOH (240 mL) and KHF₂ (4.71 g, 60.2 mmol, 4 eq.) in H₂O (24 mL) at 20° C. The resulting mixture was stirred for 16 hours at 20° C. under N₂ atmosphere. The resulting mixture was concentrated under vacuum. The resulting mixture was diluted with acetone (200 mL). The resulting mixture was filtered, the filter cake was washed with acetone (2×100 mL). The filtrate was concentrated under vacuum. The residue was purified by slurry with MTBE (200 mL) to obtain the title compound. LCMS: (ES, m/z): M+1:619. H-NMR: (300 MHz, Chloroform-d, ppm): δ 7.26 (s, 1H), 6.95 (d, J=8.4 Hz, 2H), 6.81 (d, J=8.5 Hz, 2H), 5.06 (s, 2H), 4.79 (s, 2H), 4.45 (s, 2H), 3.73 (s, 3H), 3.62 (s, 2H), 3.21 (s, 1H), 3.12 (s, 2H), 2.28 (s, 1H), 1.80 (s, 5H), 1.32 (s, 4H), 1.19 (s, 3H), 0.72 (s, 1H), 0.46 (s, 1H).

Intermediate AA benzyl (2R,3S,5R)-2-((((1S,3R,6R)-6-(5-fluoropyrimidin-2-yl)bicyclo[4.1.0]heptan-3-yl)oxy)methyl)-5-methyl-3-(2,2,2-trifluoro-N-(4-methoxybenzyl)acetamido)pyrrolidine-1-carboxylate

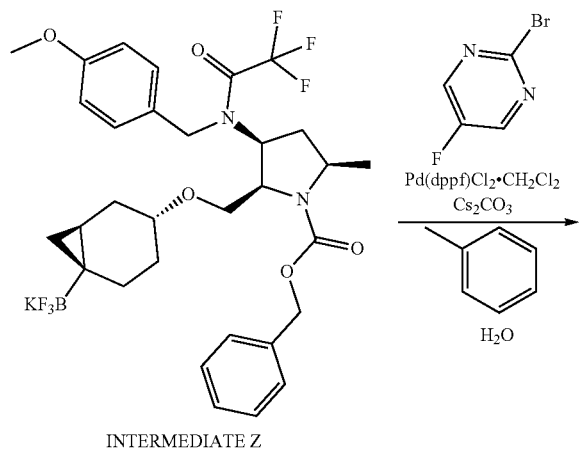

INTERMEDIATE Z

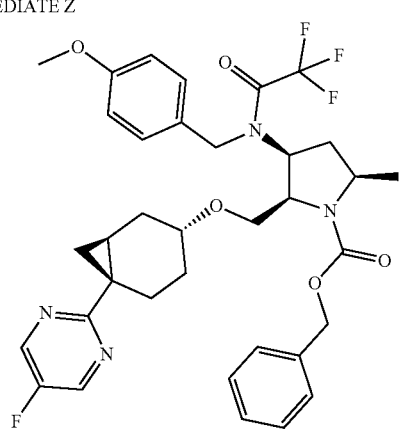

INTERMEDIATE AA

A solution of benzyl (2R,3S,5R)-5-methyl-3-{2,2,2-trifluoro-N-[(4-methoxyphenyl)methyl]acetamido}-2-({[(1S,3R,6S)-6-(trifluoro-lambda4-boranyl)bicyclo[4.1.0]heptan-3-yl]oxy}methyl)pyrrolidine-1-carboxylate potassium (INTERMEDIATE Z) (60 g, 88.2 mmol, 1 eq.) and 2-bromo-5-fluoropyrimidine (31.2 g, 176 mmol, 2 eq.) and Cs$_2$CO$_3$ (86.2 g, 264 mmol, 3 eq.) and Pd(dppf)Cl$_2$CH$_2$Cl$_2$ (14.4 g, 17.6 mmol, 0.2 eq.) in toluene (1.2 L) and H$_2$O (240 mL) was stirred for 16 hours at 88° C. under N$_2$ atmosphere. The mixture was allowed to cool down to 20° C. The resulting mixture was filtered, the filter cake was washed with EA. The resulting mixture was extracted with EA (1×1 L). The combined organic layers were washed with NaCl (1×500 mL), dried over anhydrous Na$_2$SO$_4$. After filtration, the filtrate was concentrated under reduced pressure. The residue was purified by silica gel column chromatography, (PE:EA 10:1) to afford the racemic product. The racemic product was purified by SFC(Column: OptiChiral-C9-10, 5*25 cm, 10 μm; Mobile Phase A: CO$_2$, Mobile Phase B: MeOH—Preparative; Flow rate: 200 mL/min; Gradient: isocratic 40% B; Column Temperature (° C.): 35; Back Pressure (bar): 100; Wave Length: 270 nm; RT1 (min): 4.53; RT2 (min): 5.37; Sample Solvent: MeOH—Preparative; Injection Volume: 10 mL; Number Of Runs: 25) to afford the title compound. LCMS: (ES, m/z): M+ 1:671. H-NMR: (400 MHz, Chloroform-d, ppm) δ 8.46 (s, 2H), 7.34 (d, J=5.7 Hz, 4H), 7.32-7.27 (m, 1H), 7.03 (d, J=8.4 Hz, 2H), 6.89 (d, J=8.5 Hz, 2H), 5.17 (d, J=14.6 Hz, 2H), 5.05 (d, J=12.6 Hz, 0H), 4.90 (d, J=17.8 Hz, 1H), 4.82 (s, 1H), 4.78 (s, 0H), 4.49 (d, J=13.2 Hz, 2H), 3.81 (s, 3H), 3.79 (s, 1H), 3.68 (s, 2H), 3.58 (d, J=10.7 Hz, 0H), 3.28 (d, J=11.2 Hz, 2H), 2.66 (s, 1H), 2.51 (s, 1H), 2.30 (d, J=14.0 Hz, 1H), 1.94 (d, J=10.8 Hz, 1H), 1.56 (d, J=10.7 Hz, 1H), 1.48 (dd, J=9.5, 4.0 Hz, 1H), 1.29 (s, 2H), 1.26-1.16 (m, 1H), 0.97 (t, J=5.2 Hz, 1H).

Intermediate BB

N-((2R,3S,5R)-2-((((1S,3S,6R)-6-(5-fluoropyrimidin-2-yl)bicyclo[4.1.0]heptan-3-yl)oxy)methyl)-5-methylpyrrolidin-3-yl)methanesulfonamide

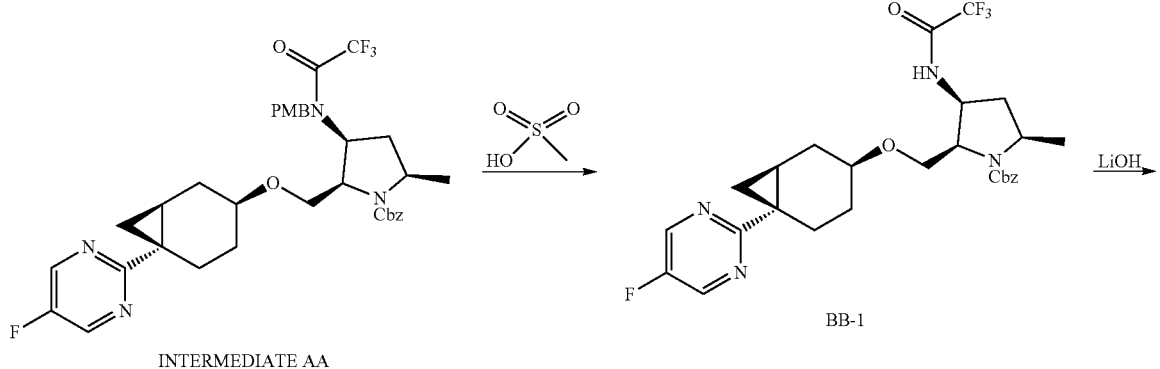

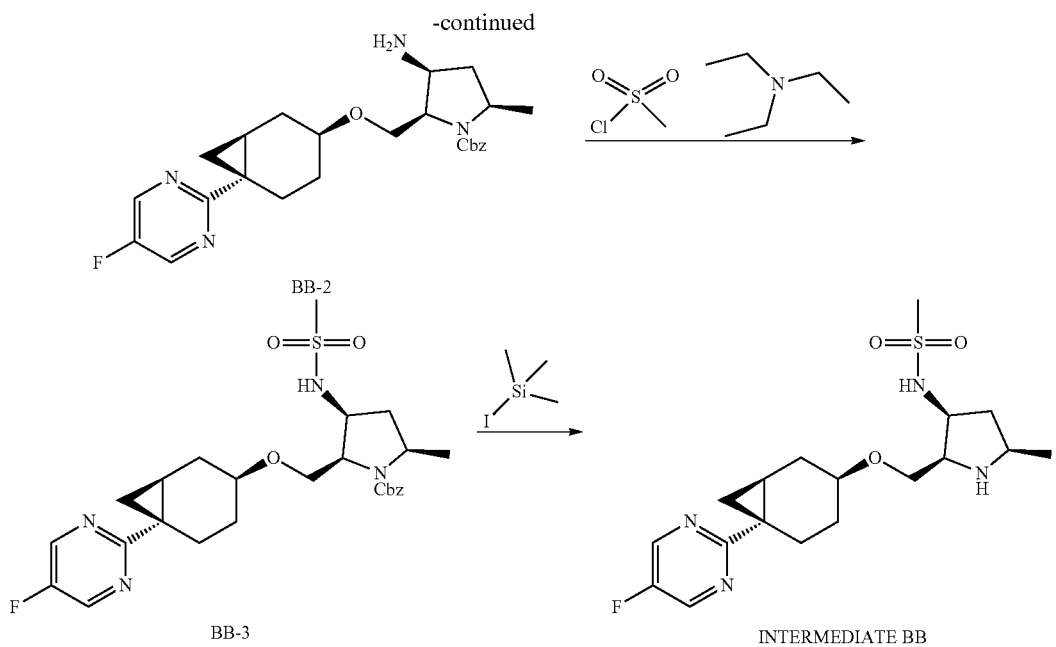

Step 1: benzyl (2R,3S,5R)-2-((((1S,3S,6R)-6-(5-fluoropyrimidin-2-yl)bicyclo[4.1.0]heptan-3-yl)oxy)methyl)-5-methyl-3-(2,2,2-trifluoroacetamido)pyrrolidine-1-carboxylate (BB-1)

Into a 100 mL rbf with a stir bar was added benzyl (2R,3S,5R)-2-((((1S,3S,6R)-6-(5-fluoropyrimidin-2-yl)bicyclo[4.1.0]heptan-3-yl)oxy)methyl)-5-methyl-3-(2,2,2-trifluoro-N-(4-methoxybenzyl)acetamido)pyrrolidine-1-carboxylate (INTERMEDIATE AA) (1 g, 1.491 mmol), CH2Cl2 (14.91 ml) and methanesulfonic acid (1.002 ml, 15.43 mmol). The reaction was stirred for 10 min. The reaction was quenched with NaHCO₃ (15 mL), extracted with CH2Cl2 (3×20 mL), washed with brine, dried over Na2SO4, and concentrated to afford the title compound. MS: 551.4 (M+H).

Step 2: benzyl (2R,3S,5R)-3-amino-2-((((1S,3S, 6R)-6-(5-fluoropyrimidin-2-yl)bicyclo[4.1.0]heptan-3-yl)oxy)methyl)-5-methylpyrrolidine-1-carboxylate (BB-2)

Into a 200 mL rbf with a stir bar was added BB-1 (821 mg, 1.491 mmol), LITHIUM HYDROXIDE (0.238 ml, 14.91 mmol), THF (1.565 ml), Methanol (12.74 ml) and Water (8.05 ml). The reaction was stirred at 50 degrees for 1 h. Most of the solvent was removed in vacuo. The residue was purified by column chromatography on silica (0% to 10% MeOH/DCM (with 1% NH₄OH)) to afford the title compound. MS: 455.4 (M+H).

Step 3: benzyl (2R,3S,5R)-2-((((1S,3S,6R)-6-(5-fluoropyrimidin-2-yl)bicyclo[4.1.0]heptan-3-yl)oxy)methyl)-5-methyl-3-(methylsulfonamido)pyrrolidine-1-carboxylate (BB-3)

Into a vial with a stir bar was added BB-2 (660 mg, 1.452 mmol) and CH2Cl2 (4400 µl). The reaction was cooled to 0 degrees and Triethylamine (805 µl, 5.81 mmol) and methanesulfonyl chloride (292 µl, 2.90 mmol) were added. The reaction was stirred at 0 degrees for 20 minutes. The solvent was removed in vacuo and the mixture directly purified by column chromatography on silica (5% to 50% 3:1 EtOAc: EtOH/hexanes) to afford the title compound. MS: 533.4 (M+H).

Step 4: N-((2R,3S,5R)-2-((((1S,3S,6R)-6-(5-fluoropyrimidin-2-yl)bicyclo[4.1.0]heptan-3-yl)oxy)methyl)-5-methylpyrrolidin-3-yl)methanesulfonamide (Intermediate BB)

Into a vial with a stir bar was added BB-3 (765 mg, 1.436 mmol) in Acetonitrile (2873 µl). The reaction was cooled to 0 degrees and IODOTRIMETHYLSILANE (307 µl, 2.154 mmol) was added dropwise. The reaction was stirred at 0 degrees for 30 min. The residue was purified directly by column chromatography on silica (0% to 15% MeOH/DCM (with 1% NH₄OH)) to afford the title compound. MS: 399.3 (M+H).

Intermediate CC benzyl (2R,3S,5R)-5-methyl-2-(((triethylsilyl)oxy)methyl)-3-(2,2,2-trifluoro-N-(4-methoxybenzyl)acetamido)pyrrolidine-1-carboxylate

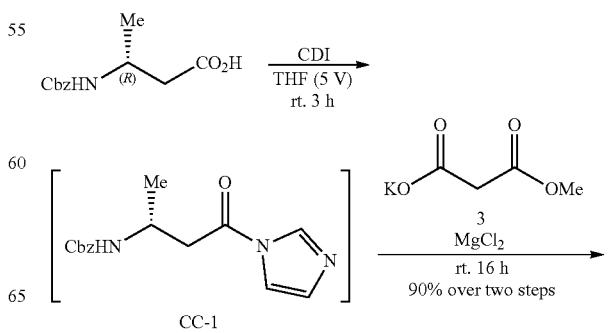

-continued

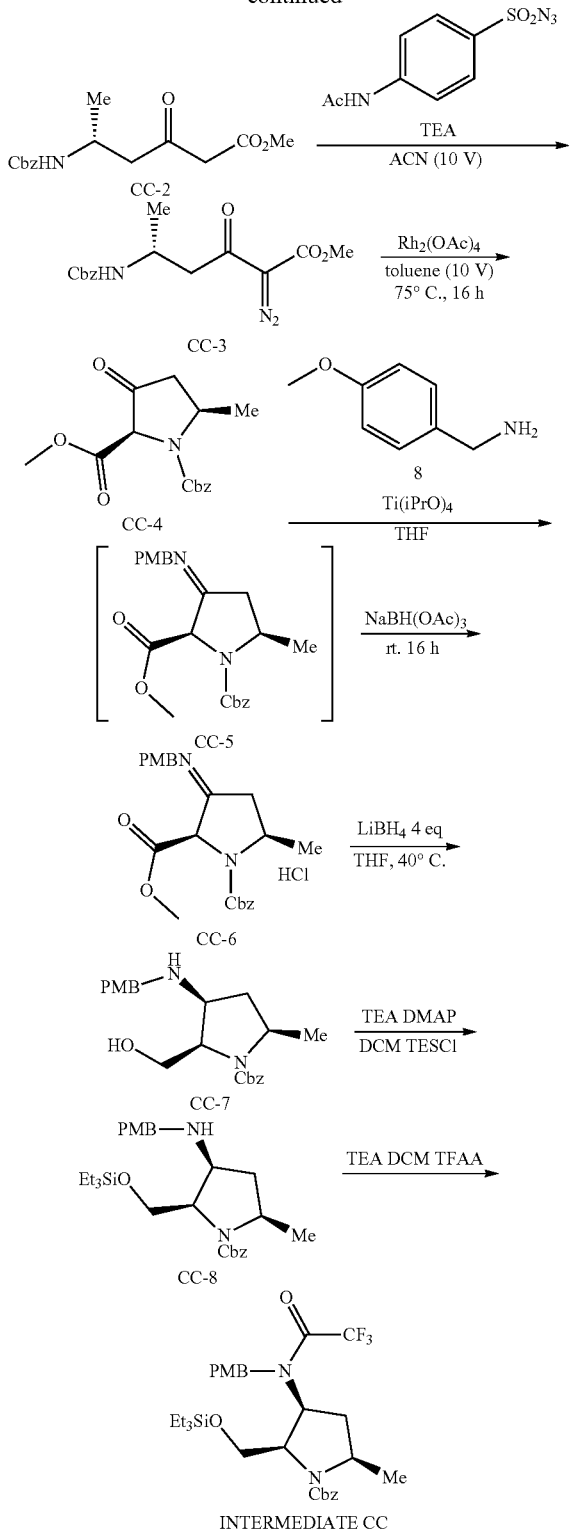

Step 1: benzyl (R)-(4-(1H-imidazol-1-yl)-4-oxobutan-2-yl)carbamate (CC-1)

Into a 5-L 4-necked round-bottom flask, was placed CDI (107.64 g, 663.83 mmol, 1.05 equiv), THF (750.00 mL). To this was added (3R)-3-[[(benzyloxy)carbonyl]amino]butanoic acid (150.00 g, 632.23 mmol, 1.00 equiv), in portions at 0-5° C. in 30 min. The resulting solution was stirred for 3 h at room temperature. Which was used in the next step without further purification.

Step 2: methyl (5R)-5-[[(benzyloxy)carbonyl]amino]-3-oxohexanoate (CC-2)

Into a 3-L 4-necked round-bottom flask, was placed 1-methyl 3-potassium propanedioate (147 g, 941.23 mmol, 1.50 equiv), THF (750 mL). This was followed by the addition of MgCl$_2$ (45 g, 470.61 mmol, 0.75 equiv), in portions at 25° C. The resulting solution was stirred for 4 h at 40° C. To this was added the solution in the step 1 at 25° C. The resulting solution was stirred for 16 h at 25° C. The reaction was then quenched by the addition of 1 L of water/ice. The pH value of the solution was adjusted to 4 with HCl (2 mol/L). The resulting solution was extracted with 2×2 L of ethyl acetate and the organic layer was combined. The resulting mixture was washed with 1×1 L of H$_2$O and 1×1 L of brine. The mixture was dried over anhydrous sodium sulfate and concentrated to give the title compound.

Step 3: methyl (5R)-5-[[(benzyloxy)carbonyl]amino]-2-diazo-3-oxohexanoate (CC-3)

Into a 5-L 4-necked round-bottom flask, was methyl (5R)-5-[[(benzyloxy)carbonyl]amino]-3-oxohexanoate (CC-2) (167.00 g, 569.34 mmol, 1.00 equiv), ACN (1.70 L) and 4-acetamidobenzenesulfonyl azide (136.78 g, 569.34 mmol, 1.00 equiv) at 0° C. Dropwise TEA (11.52 g, 113.84 mmol, 0.20 equiv) at 0° C. The flask was wrapped with aluminum foil and the resulting solution was stirred for 3 h at room temperature in a water/ice bath. The solids were filtrated out by filtration. The reaction was quenched with 2 L of water. The filtrate was extracted with EA (2×2.7 L) and the organic layers combined. The mixture was dried over anhydrous sodium sulfate and concentrated under vacuum to give the title compound.

Step 4: 1-benzyl 2-methyl (2R,5R)-5-methyl-3-oxopyrrolidine-1,2-dicarboxylate (CC-4)

Into a 5-L round-bottom flask, was placed methyl (5R)-5-[[(benzyloxy)carbonyl]amino]-2-diazo-3-oxohexanoate (CC-3) (140 g, 438.40 mmol, 1.00 equiv), toluene (1.40 L), 1,1,1-tris(acetyloxy)dirhodium-1-yl acetate (19.4 g, 43.84 mmol, 0.1 equiv). The resulting solution was stirred for 16 h at 75° C. The residue was applied onto a silica gel column (PE:THF=1:1) to obtain the title compound.

Step 5: 1-benzyl 2-methyl (2R,5R)-3-((4-methoxybenzyl)imino)-5-methylpyrrolidine-1,2-dicarboxylate (CC-5)

Into a 5-L 4-necked round-bottom flask, was placed 1-benzyl 2-methyl 5-methyl-3-oxopyrrolidine-1,2-dicarboxylate (CC-4) (95.00 g, 326.12 mmol, 1.00 equiv), THF (1.80 L), 4-methoxy-benzenemethanamine (44.74 g, 326.12 mmol, 1.00 equiv) and tetraisopropoxy(methyl)titanium (97.59 g, 326.12 mmol, 1.00 equiv). The resulting solution was stirred for overnight at r.t. The resulting solution was directly in the next step.

Step 6: benzyl 2-methyl (2R,3S,5R)-3-[[(4-methoxyphenyl)methyl]amino]-5-methylpyrrolidine-1,2-dicarboxylate hydrochloride (CC-6)

Into the step 5 mixture, was added bis(acetyloxy)(sodio)-lambda4-boranyl acetate (483 g, 2.28 mol, 7.00 equiv), once every half an hour, a total of 7 times are added. The resulting solution was stirred for overnight at 30° C. The reaction was then quenched by the addition of 5 L of water/ice and stir for 1 h. The resulting solution was extracted with 1×1.8 L of ethyl acetate. The organic layer was dried over anhydrous sodium sulfate and concentrated. Dissolve the product in 4 L of MTBE and added HCl (4 N in dioxane, 45 mL). After stirring for 5 h, the white solid collected by suction filtration to obtain the title compound.

Step 7: benzyl (2R,3S,5R)-2-(hydroxymethyl)-3-[[(4-methoxyphenyl)methyl]amino]-5-methylpyrrolidine-1-carboxylate (CC-7)

Into a 2-L round-bottom flask, added benzyl 2-methyl (2R,3S,5R)-3-[[(4-methoxyphenyl)methyl]amino]-5-methylpyrrolidine-1,2-dicarboxylate hydrochloride (CC-6) (72 g, 0.16 mol, 1.00 equiv) and EA (1 L), to this was added 40 mL of HCl in dioxane (4 N). The resulting solution was stirred for 16 h at r.t. Then the reaction was filtered, the filtrate was concentrated. This resulted in 60 g of 1-benzyl 2-methyl (2R,3S,5R)-3-[[(4-methoxyphenyl)methyl]amino]-5-methylpyrrolidine-1,2-dicarboxylate. Then into a 2-L 4-necked round-bottom flask, was placed 1-benzyl 2-methyl (2R,3S,5R)-3-[[(4-methoxyphenyl)methyl]amino]-5-methylpyrrolidine-1,2-dicarboxylate (60.00 g, 145.45 mmol, 1.00 equiv), THF (1200 mL). This was followed by the addition of lithio-lambda5-borane (12.67 g, 581.83 mmol, 4.00 equiv) in batches. The resulting solution was stirred for 16 h at 40° C. The reaction was then quenched by the addition of 3 L of water/ice. The resulting solution was extracted with EA (2×1.2 L), the organic layer was dried over anhydrous sodium sulfate and concentrated. The residue was applied onto a silica gel column (PE:EA=3:1) to obtain the title compound.

Step 8: benzyl (2R,3S,5R)-3-[[(4-methoxyphenyl)methyl]amino]-5-methyl-2-[[(triethylsilyl)oxy]methyl]pyrrolidine-1-carboxylate (CC-8)

Into a 1-L 3-necked round-bottom flask purged and maintained with an inert atmosphere of nitrogen, was placed benzyl (2R,3S,5R)-2-(hydroxymethyl)-3-[[(4-methoxyphenyl)methyl]amino]-5-methylpyrrolidine-1-carboxylate (CC-7) (40.00 g, 104.03 mmol, 1.00 equiv), triethanolamine (18.63 g, 124.87 mmol, 1.20 equiv.), DCM (300 mL), 4-dimethylaminopyridine (2.54 g, 20.79 mmol, 0.20 equiv.). To the mixture was added chlorotriethylsilane (18.82 g, 124.86 mmol, 1.20 equiv) dropwised at 0° C. The resulting solution was stirred for 1 h at room temperature. The reaction was then quenched by the addition of 1 L of water/ice. The resulting solution was extracted with DCM (2×200 mL), the organic layer was dried over anhydrous sodium sulfate and concentrated. The residue was applied onto a silica gel column (PE:THF=5:1~3:1) to obtain the title compound.

Step 9: benzyl (2R,3S,5R)-5-methyl-2-[[(triethylsilyl)oxy]methyl]-3-[2,2,2-trifluoro-N-[(4-methoxyphenyl)methyl]acetamido]pyrrolidine-1-carboxylate (Intermediate CC)

Into a 1-L 3-necked round-bottom flask, was placed benzyl (2R,3S,5R)-3-[[(4-methoxyphenyl)methyl]amino]-5-methyl-2-[[(triethylsilyl)oxy]methyl]pyrrolidine-1-carboxylate (CC-8) (42.0 g, 84.20 mmol, 1.0 equiv), triethanolamine (18.9 g, 88.40 mmol, 1.05 equiv) and methylene chloride (400 mL). To this was added trifluoro acetic acid (10.08 g, 88.4 mmol, 1.05 equiv) at 0° C. The resulting solution was stirred for 30 min at room temperature. The resulting mixture was washed with 1×200 mL of sat NaHCO₃ (aq). The resulting solution was extracted with DCM (2×400 mL), the organic layer was dried over anhydrous sodium sulfate and concentrated. The residue was applied onto a silica gel column (PE:EA=10:1) to obtain the title compound. LC-MS: (ES, m/z): 595 [M+H]⁺. ¹H-NMR: (300 MHz, CDCl₃, ppm) δ 7.36 (s, 5H), 7.03 (d, J=8.6 Hz, 2H), 6.91 (d, J=8.7 Hz, 2H), 5.28-4.99 (m, 2H), 4.98-4.80 (m, 2H), 4.63-4.38 (m, 2H), 4.08-3.63 (m, 5H), 3.56-3.43 (m, 1H), 2.06-1.91 (m, 1H), 1.77-1.63 (m, 1H), 1.37-1.22 (m, 3H), 0.98 (t, J=7.5 Hz, 10H), 0.64 (t, J=8.2 Hz, 7H).

Intermediate DD methyl (2R,3S,5R)-3-amino-5-methyl-2-(((6-(pyrimidin-2-yl)bicyclo[4.1.0]heptan-3-yl)oxy)methyl)pyrrolidine-1-carboxylate

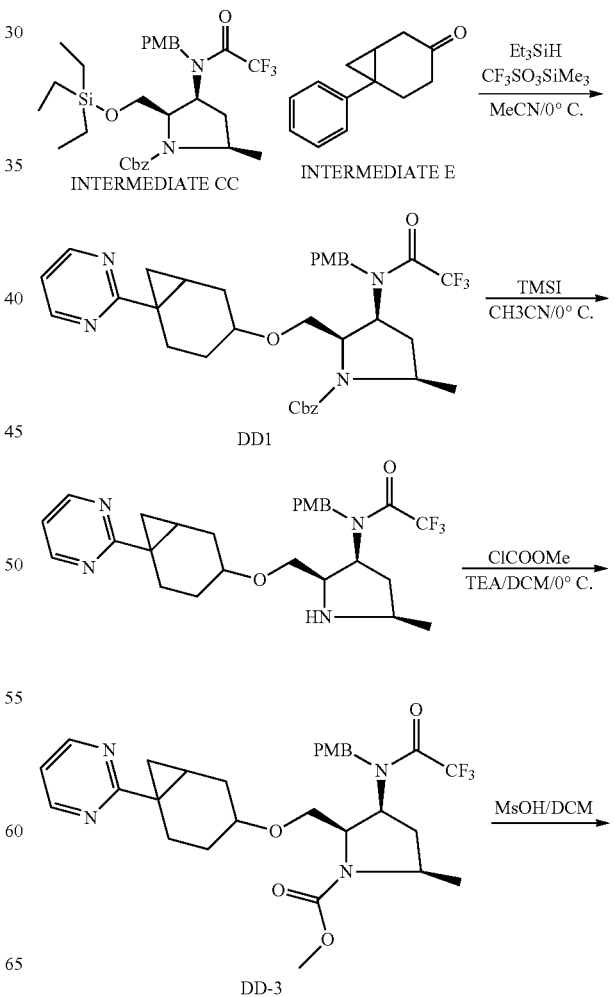

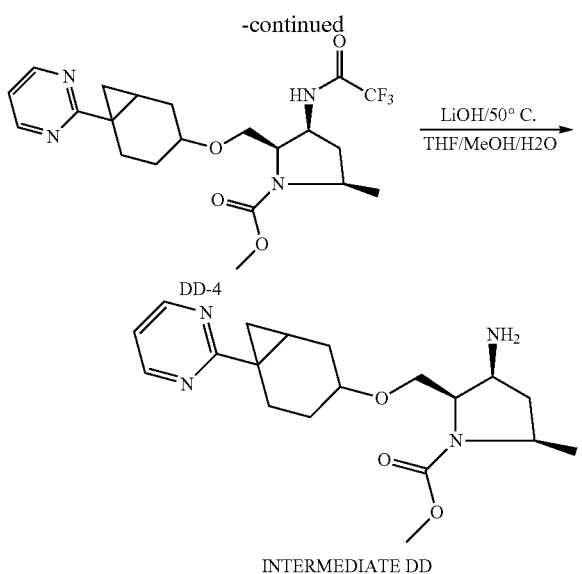

INTERMEDIATE DD

Step 1: benzyl (2R,3S,5R)-5-methyl-2-(((6-(pyrimidin-2-yl)bicyclo[4.1.0]heptan-3-yl)oxy)methyl)-3-(2,2,2-trifluoro-N-(4-methoxybenzyl)acetamido)pyrrolidine-1-carboxylate (DD-1)

To a solution of benzyl (2R,3S,5R)-5-methyl-2-(((triethylsilyl)oxy)methyl)-3-(2,2,2-trifluoro-N-(4-methoxybenzyl)acetamido)pyrrolidine-1-carboxylate (INTERMEDIATE CC) (100 mg, 0.168 mmol) in Acetonitrile (2.5 ml) at 0° C. was added 6-(pyrimidin-2-yl)bicyclo[4.1.0]heptan-3-one (INTERMEDIATE E) (41.1 mg, 0.219 mmol) followed by triethylsilane (0.081 ml, 0.504 mmol) under N2. After stirring 5 mins at 0° C., trimethylsilyl trifluoromethanesulfonate (0.183 ml, 1.009 mmol) was added. After stirring at 0° C. for 10 mins, the reaction mixture was quenched with sat. aq. NaHCO₃ in the ice bath. The reaction mixture was extracted by 2 portions of 10 ml of EtOAc. The combined organic phase was collected and concentrated. The residue was purified by column chromatography on C18 (5-95% MeCN/water with 0.05% TFA modifier) to afford the title compound. MS: 653.5 (M+1).

Step 2: 2,2,2-trifluoro-N-(4-methoxybenzyl)-N-42R,3S,5R)-5-methyl-2-(((6-(pyrimidin-2-yl)bicyclo[4.1.0]heptan-3-yl)oxy)methyl)pyrrolidin-3-yl)acetamide (DD-2)

To a solution benzyl (2R,3S,5R)-5-methyl-2-(((6-(pyrimidin-2-yl)bicyclo[4.1.0]heptan-3-yl)oxy)methyl)-3-(2,2,2-trifluoro-N-(4-methoxybenzyl)acetamido)pyrrolidine-1-carboxylate (DD-1, 320 mg, 0.490 mmol) in MeCN (5 ml) at 0° C. was added TMS-I (100 μl, 0.735 mmol). The mixture was stirred at 0° C. for 80 mins. The reaction was quenched with MeOH. The mixture was directly purified by prep silica gel TLC (eluent with 5% 7N NH3 in MeOH/DCM) to afford the title compound. MS: 519.5 (M+1).

Step 3: methyl (2R,3S,5R)-5-methyl-2-(((6-(pyrimidin-2-yl)bicyclo[4.1.0]heptan-3-yl)oxy)methyl)-3-(2,2,2-trifluoro-N-(4-methoxybenzyl)acetamido)pyrrolidine-1-carboxylate (DD-3)

To a solution of 2,2,2-trifluoro-N-(4-methoxybenzyl)-N-((2R,3S,5R)-5-methyl-2-(((6-(pyrimidin-2-yl)bicyclo[4.1.0]heptan-3-yl)oxy)methyl)pyrrolidin-3-yl)acetamide (DD-2, 205 mg, 0.395 mmol) in CH2Cl2 (4 ml) at 0° C. was added Et3N (0.165 ml, 1.186 mmol) followed by METHYL CHLOROFORMATE (0.040 ml, 0.514 mmol) under N2. The reaction mixture was stirred at 0° C. for 15 mins and then quenched with MeOH. The mixture was directly purified by prep silica gel TLC (eluent with 4% MeOH/DCM) to afford the title compound. MS: 577.5 (M+1).

Step 4: methyl (2R,3S,5R)-5-methyl-2-(((6-(pyrimidin-2-yl)bicyclo[4.1.0]heptan-3-yl)oxy)methyl)-3-(2,2,2-trifluoroacetamido)pyrrolidine-1-carboxylate (DD-4)

To a solution of methyl (2R,3S,5R)-5-methyl-2-(((6-(pyrimidin-2-yl)bicyclo[4.1.0]heptan-3-yl)oxy)methyl)-3-(2,2,2-trifluoro-N-(4-methoxybenzyl)acetamido)pyrrolidine-1-carboxylate (DD-3, 246 mg, 0.427 mmol) in DCM (4 ml) was added MsOH (0.416 ml, 6.40 mmol). The reaction mixture was stirred at rt for 40 mins. The reaction mixture was partitioned between water and DCM. The aqueous layer was extracted with DCM twice. The combined organic layer was washed with brine, dried with MgSO4, concentrated to afford the title compound. MS: 457.4 (M+1).

Step 5: methyl (2R,3S,5R)-3-amino-5-methyl-2-(((6-(pyrimidin-2-yl)bicyclo[4.1.0]heptan-3-yl)oxy)methyl)pyrrolidine-1-carboxylate (Intermediate DD)

To a stirred solution of methyl (2R,3S,5R)-5-methyl-2-(((6-(pyrimidin-2-yl)bicyclo[4.1.0]heptan-3-yl)oxy)methyl)-3-(2,2,2-trifluoroacetamido)pyrrolidine-1-carboxylate (DD-4, 195 mg, 0.427 mmol) in THF (0.5 ml) and MeOH (4.0 ml) was added LITHIUM HYDROXIDE (102 mg, 4.27 mmol) followed by water (2.5 ml). The mixture was heated at 50° C. for 20 mins. Removed most of solvent under reduce pressure. The residue was purified by prep silica gel TLC (eluent with 5% 7N NH3 in MeOH/DCM) to afford the title compound. MS: 361.3 (M+1).

Intermediate EE potassium trifluoro(4-(((2R,3S,5R)-3-(N-(4-methoxybenzyl)methylsulfonamido)-1-(methoxycarbonyl)-5-methylpyrrolidin-2-yl)methoxy)bicyclo[4.1.0]heptan-1-yl)borate

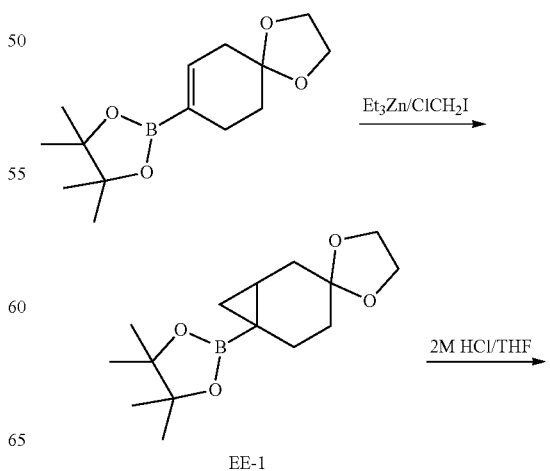

EE-1

-continued

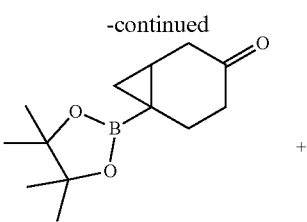

EE-2

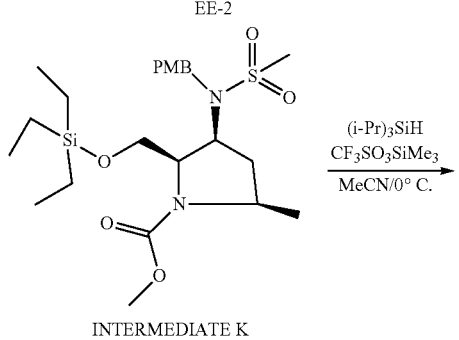

INTERMEDIATE K

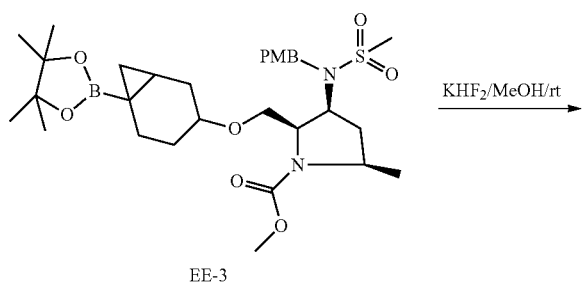

EE-3

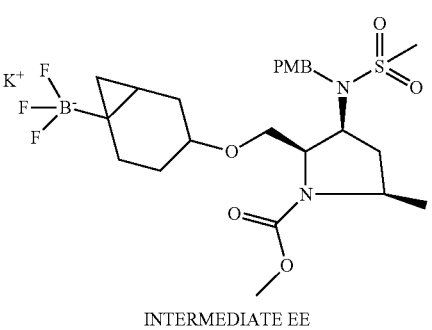

INTERMEDIATE EE

Step 1: 4,4,5,5-Tetramethyl-2-(spiro[bicyclo[4.1.0] heptane-3,2'-[1,3]dioxolan]-6-yl)-1,3,2-dioxaborolane (EE-1)

To a solution of 4,4,5,5-tetramethyl-2-(1,4-dioxaspiro[4.5]dec-7-en-8-yl)-1,3,2-dioxaborolane (9.0 g, 33.8 mmol) in Fluorobenzene (90 mL) at −5° C. was added diethylzinc (1.0 M in hexanes, 135 mL, 135 mmol) over the course of 15 minutes. The reaction mixture was stirred at −5° C. for 15 mins. Then a solution of chloroiodomethane (19.64 ml, 271 mmol) in fluorinebenzene (45 mL) was added over 15 minutes. The reaction was stirred for 2 h at −5° C. The reaction mixture was quenched with aq. NH$_4$Cl (150 mL) and extracted with EtOAc (150 mL×3). The organic layer was washed with brine (100 mL), dried over Na$_2$SO$_4$ and filtered. The filtrate was concentrated. The residue was purified by flash silica gel chromatography (0-20% EtOAc/hexanes gradient) to afford the title compound. MS: 280.2 (M).

Step 2: 6-(4,4,5,5-Tetramethyl-1,3,2-dioxaborolan-2-yl)bicyclo[4.1.0]heptan-3-one (EE-2)

To a solution of 4,4,5,5-tetramethyl-2-(spiro[bicyclo[4.1.0]heptane-3,2'-[1,3]dioxolan]-6-yl)-1,3,2-dioxaborolane (EE-1, 3.0 g, 10.71 mmol) in THF (48 mL) was added 2M HCl (21.42 mL, 42.8 mmol) and stirred at rt for 15 mins. The reaction mixture was quenched with sat. NaHCO$_3$ (120 ml) at 0° C. to PH=7, extracted with DCM (30 mL×3). The organic layer was washed with brine (20 mL), dried over MgSO$_4$ and filtered. The filtrate was concentrated and purified by flash silica gel chromatography (0~20% EtOAc in hexane) to afford the title compound. MS: 237.2 (M+1).

Step 3: methyl (2R,3S,5R)-3-(N-(4-methoxybenzyl) methylsulfonamido)-5-methyl-2-(((6-(4,4,5,5-tetramethyl-1,3,2-dioxaborolan-2-yl)bicyclo[4.1.0] heptan-3-yl)oxy)methyl)pyrrolidine-1-carboxylate (EE-3)

To a solution of methyl (2R,3S,5R)-3-(N-(4-methoxybenzyl)methylsulfonamido)-5-methyl-2-(((triethylsilyl)oxy) methyl)pyrrolidine-1-carboxylate (INTERMEDIATE K, 500 mg, 1.698 mmol) in Acetonitrile (16.0 ml) at 0° C. was added 6-(4,4,5,5-tetramethyl-1,3,2-dioxaborolan-2-yl)bicyclo[4.1.0]heptan-3-one (EE-2, 453 mg, 1.918 mmol) followed by triisopropylsilane (0.965 ml, 3.40 mmol) under N2. After stirring 5 mins at 0° C., trimethylsilyl trifluoromethanesulfonate (0.307 ml, 1.698 mmol) was added. The reaction mixture was continued to stir at 0° C. for 40 mins. The reaction mixture was quenched with sat. aq. NaHCO$_3$ in the ice bath. The reaction mixture was extracted by 2 portions of 30 ml of DCM. The combined organic phase was collected and concentrated. The residue was purified by prep silica gel TLC (eluent with 40% EtOAc/hexanes) to afford the title compound. MS: 607.5 (M+1).

Step 4: potassium trifluoro(4-(((2R,3S,5R)-3-(N-(4-methoxybenzyl)methylsulfonamido)-1-(methoxycarbonyl)-5-methylpyrrolidin-2-yl)methoxy)bicyclo [4.1.0]heptan-1-yl)borate (Intermediate EE)

To a solution of methyl (2R,3S,5R)-3-(N-(4-methoxybenzyl)methylsulfonamido)-5-methyl-2-(((6-(4,4,5,5-tetramethyl-1,3,2-dioxaborolan-2-yl)bicyclo[4.1.0]heptan-3-yl) oxy)methyl)pyrrolidine-1-carboxylate (EE-3, 775 mg, 1.278 mmol) in MeOH (17 mL) at rt was added potassium hydrogen fluoride (4.5 M in water, 2.56 ml, 11.50 mmol). The reaction mixture was stirred at rt overnight. The mixture was concentrated under vacuo to leave white solid. The solid was re-suspended in MTBE (60 mL) and filtered. The precipitate was collected and re-suspended in hot acetone, filtered. The filtrate was concentrated to afford the title compound. MS: 525.4 (M+1).

Intermediate FF methyl (2R,3S,5R)-3-amino-2-(((6-(5-chloropyrimi-din-2-yl)bicyclo[4.1.0]heptan-3-yl)oxy)methyl)-5-methylpyrrolidine-1-carboxylate

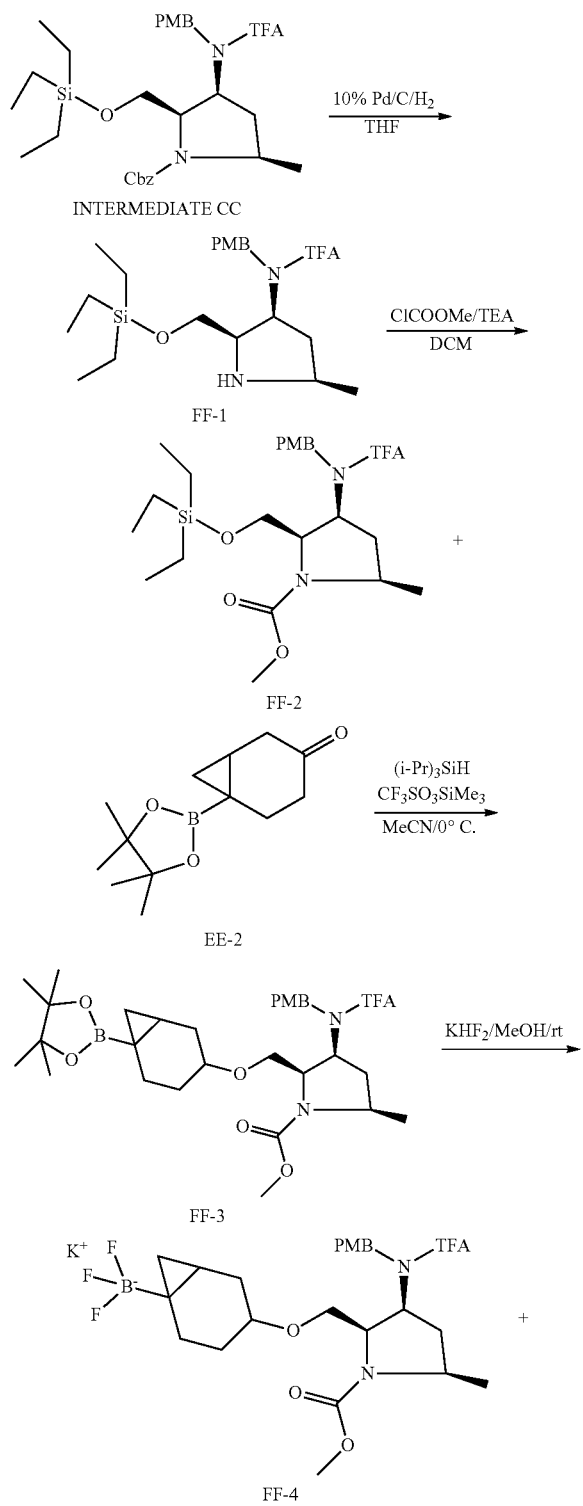

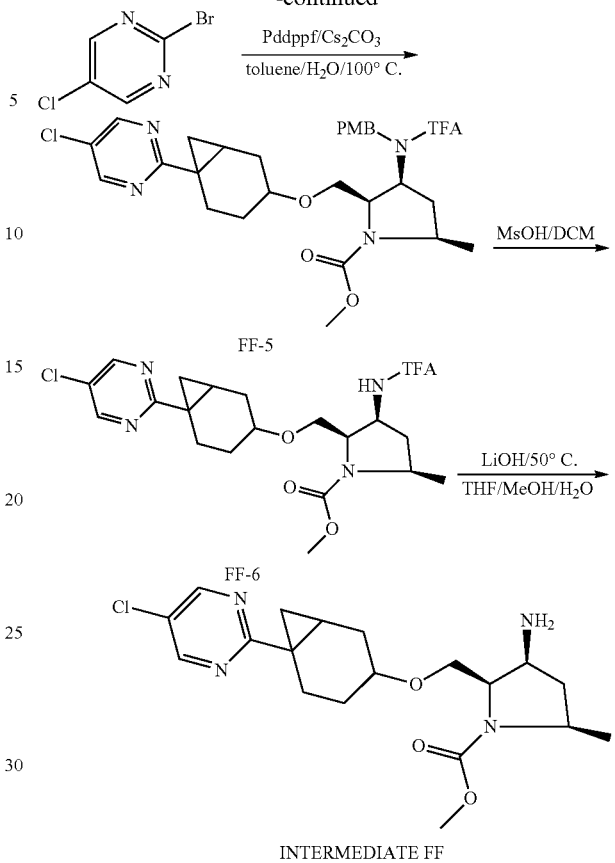

Step 1: 2,2,2-Trifluoro-N-(4-methoxybenzyl)-N-((2R,3S,5R)-5-methyl-2-(((triethylsilyl)oxy)methyl)pyrrolidin-3-yl)acetamide (FF-1)

To a solution of benzyl (2R,3S,5R)-5-methyl-2-(((triethylsilyl)oxy)methyl)-3-(2,2,2-trifluoro-N-(4-methoxybenzyl)acetamido)pyrrolidine-1-carboxylate (INTERMEDIATE CC, 5.5 g, 9.25 mmol) in THF (70 ml) was added 10% palladium on carbon (787 mg, 0.740 mmol). The reaction mixture was degassed and refilled with H2 from balloon for three times. The reaction mixture was stirred at rt under hydrogen balloon for 1.5 hrs. The reaction mixture was filtered through a celite pad. The filtrate was concentrated to afford the title compound. MS: 462.4 (M+1).

Step 2: Methyl (2R,3S,5R)-5-methyl-2-(((triethylsilyl)oxy)methyl)-3-(2,2,2-trifluoro-N-(4-methoxybenzyl)acetamido)pyrrolidine-1-carboxylate (FF-2)

To a solution of 2,2,2-trifluoro-N-(4-methoxybenzyl)-N-((2R,3S,5R)-5-methyl-2-(((triethylsilyl)oxy)methyl)pyrrolidin-3-yl)acetamide (FF-1, 2.4 g, 5.21 mmol) in CH2Cl2 (45 ml) at 0° C. was added Et3N (2.179 ml, 15.63 mmol) followed by methyl carbonochloridate (0.523 ml, 6.77 mmol) under N2. The reaction mixture was stirred at 0° C. for 20 mins and then warm up to rt and stirred at rt overnight. The reaction mixture was quenched with water. Separated the organic layer, dried with MgSO4, concentrated to leave colorless oil. The residue was purified by silica gel chromatography (0-25% EtOAc/hexane) to afford the title compound. MS: 519.3 (M+1).

Step 3: methyl (2R,3S,5R)-5-methyl-2-(((6-(4,4,5,5-tetramethyl-1,3,2-dioxaborolan-2-yl)bicyclo[4.1.0]heptan-3-yl)oxy)methyl)-3-(2,2,2-trifluoro-N-(4-methoxybenzyl)acetamido)pyrrolidine-1-carboxylate (FF-3)

To a solution of methyl (2R,3S,5R)-5-methyl-2-(((triethylsilyl)oxy)methyl)-3-(2,2,2-trifluoro-N-(4-methoxybenzyl)acetamido)pyrrolidine-1-carboxylate (FF-2, 1.76 g, 3.39 mmol) in Acetonitrile (40 ml) at 0° C. was added 6-(4,4,5,5-tetramethyl-1,3,2-dioxaborolan-2-yl)bicyclo[4.1.0]heptan-3-one (EE-2, 962 mg, 4.07 mmol) followed by triisopropylsilane (1.390 ml, 6.79 mmol) under N2. After stirring 5 mins at 0° C., trimethylsilyl trifluoromethanesulfonate (0.614 ml, 3.39 mmol) was added. The reaction mixture was continued to stir at 0° C. for 40 mins. The reaction mixture was quenched with sat. aq. NaHCO₃ in the ice bath. The reaction mixture was extracted by 2 portions of 30 ml of DCM. The combined organic phase was collected and concentrated. The residue was purified by silica gel chromatography (0-25% EtOAc/hexane) to afford the title compound. MS: 625.4 (M+1).

Step 4: potassium trifluoro(4-(((2R,3S,5R)-1-(methoxycarbonyl)-5-methyl-3-(2,2,2-trifluoro-N-(4-methoxybenzyl)acetamido)pyrrolidin-2-yl)methoxy)bicyclo[4.1.0]heptan-1-yl)borate (FF-4)

To a solution of methyl (2R,3S,5R)-5-methyl-2-(((6-(4,4,5,5-tetramethyl-1,3,2-dioxaborolan-2-yl)bicyclo[4.1.0]heptan-3-yl)oxy)methyl)-3-(2,2,2-trifluoro-N-(4-methoxybenzyl)acetamido)pyrrolidine-1-carboxylate (FF-3, 1.53 g, 2.45 mmol) in MeOH (26 mL) at rt was added potassium hydrogen fluoride (4.5 M in water, 4.36 ml, 19.60 mmol). The reaction mixture was stirred at rt overnight. The mixture was concentrated under vacuo to leave white solid. The solid was re-suspended in MTBE (60 mL) and filtered. The precipitate was collected and re-suspended in hot acetone, filtered. The filtrate was concentrated to afford the title compound. MS: 543.5 (M+1).

Step 5: methyl (2R,3S,5R)-2-(((6-(5-chloropyrimidin-2-yl)bicyclo[4.1.0]heptan-3-yl)oxy)methyl)-5-methyl-3-(2,2,2-trifluoro-N-(4-methoxybenzyl)acetamido)pyrrolidine-1-carboxylate (FF-5)

A suspension of potassium trifluoro(4-(((2R,3S,5R)-1-(methoxycarbonyl)-5-methyl-3-(2,2,2-trifluoro-N-(4-methoxybenzyl)acetamido)pyrrolidin-2-yl)methoxy)bicyclo[4.1.0]heptan-1-yl)borate (FF-4, 450 mg, 0.744 mmol), 2-bromo-5-chloropyrimidine (187 mg, 0.968 mmol), 1,1'-BIS(DIPHENYLPHOSPHINO)FERROCENE-PALLADIUM(II)DICHLORIDE DICHLOROMETHANE COMPLEX (182 mg, 223 µmol) and CESIUM CARBONATE (728 mg, 2.233 mmol) in toluene (6 ml) and Water (1.2 ml) was bubbled with nitrogen for 5 mins. The reaction mixture was sealed in the reaction vial and heated at 95° C. overnight. The reaction mixture was partitioned between EtOAc and water. The organic layer was washed with brine, dried over MgSO4, concentrated. The residue was purified by prep silica gel TLC (eluent with 3% MeOH/DCM) to afford the title compound. MS: 611.5 (M+1).

Step 6: methyl (2R,3S,5R)-2-(((6-(5-chloropyrimidin-2-yl)bicyclo[4.1.0]heptan-3-yl)oxy)methyl)-5-methyl-3-(2,2,2-trifluoroacetamido)pyrrolidine-1-carboxylate (FF-6)

To a solution of methyl (2R,3S,5R)-2-(((6-(5-chloropyrimidin-2-yl)bicyclo[4.1.0]heptan-3-yl)oxy)methyl)-5-methyl-3-(2,2,2-trifluoro-N-(4-methoxybenzyl)acetamido)pyrrolidine-1-carboxylate (FF-5, 410 mg, 0.671 mmol) in DCM (6 ml) was added MsOH (1.307 ml, 20.13 mmol). The reaction mixture was stirred at rt for 20 mins. The reaction was concentrated to leave red oil. The residue was purified by prep silica gel TLC (eluent with 5% MeOH/DCM) to afford the title compound. MS: 491.4 (M+1).

Step 7: methyl (2R,3S,5R)-3-amino-2-(((6-(5-chloropyrimidin-2-yl)bicyclo[4.1.0]heptan-3-yl)oxy)methyl)-5-methylpyrrolidine-1-carboxylate (Intermediate FF)

To a stirred solution of methyl (2R,3S,5R)-2-(((6-(5-chloropyrimidin-2-yl)bicyclo[4.1.0]heptan-3-yl)oxy)methyl)-5-methyl-3-(2,2,2-trifluoroacetamido)pyrrolidine-1-carboxylate (FF-6, 99 mg, 0.202 mmol) in THF (0.2 ml) and MeOH (1.6 ml) was added LITHIUM HYDROXIDE (48.43 mg, 2.017 mmol) followed by water (1.0 ml). The mixture was heated at 50° C. for 25 mins. Removed most of solvent under reduce pressure. The residue was purified by prep silica gel TLC (eluent with 5% 7N NH3 in MeOH/DCM) to afford the title compound. MS: 395.3 (M+1).

Intermediate GG, Intermediate HH, and Intermediate II 6-(5-chloropyrimidin-2-yl)bicyclo[4.1.0]heptan-3-one (Intermediate GG), 6-(5-methylpyrimidin-2-yl)bicyclo[4.1.0]heptan-3-one (Intermediate HH) and 6-(thiazol-2-yl)bicyclo[4.1.0]heptan-3-one (Intermediate II)

INTERMEDIATE GG

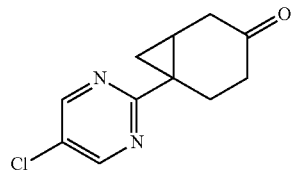

INTERMEDIATE HH

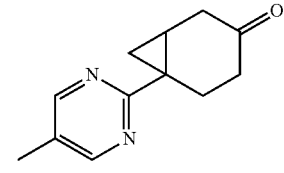

INTERMEDIATE II

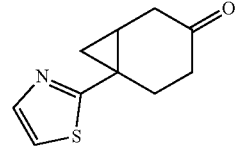

6-(5-chloropyrimidin-2-yl)bicyclo[4.1.0]heptan-3-one (INTERMEDIATE GG), 6-(5-methylpyrimidin-2-yl)bicyclo[4.1.0]heptan-3-one (INTERMEDIATE HH), and 6-(thiazol-2-yl)bicyclo[4.1.0]heptan-3-one (INTERMEDIATE II) were prepared in a similar matter to the previous described procedures starting with the appropriate aryl halide.

Intermediate JJ (+/−) tert-butyl (2R,3S,3aR,6aS)-2-(hydroxymethyl)-3-((4-methoxybenzyl)amino)hexahydro-1H-furo[3,4-b]pyrrole-1-carboxylate

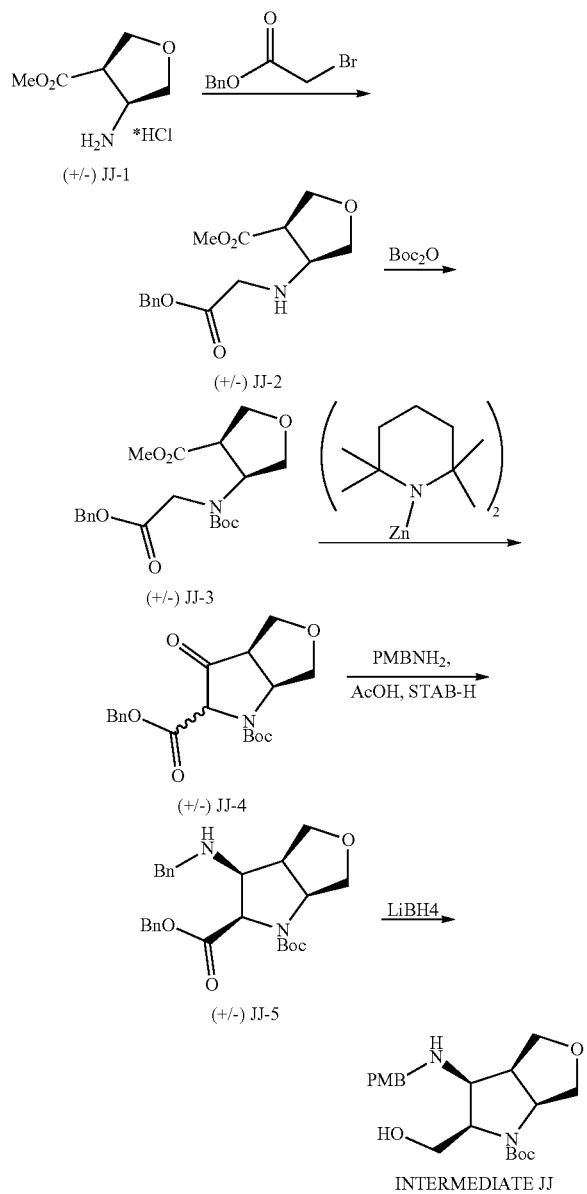

INTERMEDIATE JJ

Step 1: methyl (3R,4S)-4-((2-(benzyloxy)-2-oxoethyl)amino)tetrahydrofuran-3-carboxylate (JJ-2)

To a round-bottom-flask equipped with magnetic stirring and nitrogen inlet was charged with JJ-1 (0.795 g, 4.25 mmol, 1 eq) was charged DMA (8 mL) and DIPEA (2.2 mL, 12.7 mmol, 3 eq). The flask atm was evacuated and then filled with nitrogen. Benzyl bromo acetate was added in one portion at room temperature (0.7 mL, 4.46 mmol, 1.05 eq). The reaction was aged overnight at room temperature. Reaction was quenched by reverse addition into a flask with water (50 mL) and EtOAc (50 mL). Layers separated and the aques layer was extracted with 50 mL fresh EtOAc. Combined organics were washed with water (50 mL) twice. Organics were dried with brine then MgSO4 and filtered. The organics were concentrated and then loaded on silica gel column (0-100% Hex/3:1 EtOAc:EtOH) to obtain the title compound. LC/MS (M+1=294).

Step 2: methyl (3R,4S)-4-((2-(benzyloxy)-2-oxoethyl)(tert-butoxycarbonyl)amino)tetrahydrofuran-3-carboxylate (JJ-3)

To a round-bottom-flask equipped with magnetic stirring and nitrogen inlet was charged with JJ-2 (1.88 g, 6.41 mmol, 1 eq) was charged DCE (20 mL). Boc anhydride was added in one portion as a solid (2.80 g, 12.81 mmol, 2 eq) followed by catalytic amount of DMAP (0.078 g, 0.641 mmol, 0.1 eq) and the flask was heated to 50 C for 2 hr. The reaction was quenched by addition into a flask with water (50 mL) and EtOAc (50 mL). Layers separated and Organics were dried with brine then MgSO4 and filtered. The organics were concentrated and then loaded on silica gel column (0-100% Hex/3:1 EtOAc:EtOH) to give the title compound. LC/MS (M+1=394).

Step 3: 2-benzyl 1-(tert-butyl) (3aR,6aS)-3-oxo-hexahydro-1H-furo[3,4-b]pyrrole-1,2-dicarboxylate (JJ-4)

To a round bottom flask equipped with magnetic stirring and nitrogen inlet was charged JJ-3 (2.3 g, 5.85 mmol, 1 eq) and THF (42 mL). The reaction was cooled to −25° C. Bis(2,2,6,6-tetramethylpiperidinyl)zinc (0.5 M in toluene) was charged over 5 min (58.5 mL, 17.54 mmol, 3 eq). The reaction was aged at −25° C. for 20 min. Vessel was then warmed to −10° C. and aged for 30 min. Vessel was then warmed to 0° C. and held till the reaction was complete. Once the reaction was complete it was warmed to room temperature and reversed quench into a flask with pH7 buffered aq layer and EtOAc. The reaction was added in thirds and pH checked to make sure the pH was not rising above 7. The layers were separated and the organic layer was washed with brine and MgSO4 to dry and concentrated. The organics were concentrated and then loaded on silica gel column (0-100% Hex/3:1 EtOAc:EtOH) to give the title compound. LC/MS (M+1=362).

Step 4: 2-benzyl 1-(tert-butyl) (2R,3S,3aR,6aS)-3-(benzylamino)hexahydro-1H-furo[3,4-b]pyrrole-1,2-dicarboxylate (JJ-5)

To a round bottom flask equipped with magnetic stirring, internal temperature probe and nitrogen inlet was charged JJ-4 (0.95 g, 2.63 mmol, 1 eq) and THF (9 mL) followed by AcOH (150 uL, 2.63 mmol, 1 eq) and PMBNH2 (412 uL, 3.15 mmol, 1.2 eq) and aged at room temperature overnight. Sodium triacetoxyborohydride (1.11 g, 5.26 mmol, 2 eq) was then added in one portion as a solid and aged for 2 hr. The slurry was reverse quenched into a flask containing half saturated sodium bicarbonate (100 mL) and EtOAc (50 mL). The biphasic mixture was filtered through celite and transferred to a separation funnel. Layers separated and the organic was washed with brine and dried with MgSO4 and filtered. The organics were concentrated and then loaded on silica gel column (0-100% Hex/3:1 EtOAc:EtOH) to give the title compound. LC/MS (M+1=483).

Step 5: (+/−) tert-butyl (2R,3S,3aR,6aS)-2-(hydroxymethyl)-3-((4-methoxybenzyl)amino)hexahydro-1H-furo[3,4-b]pyrrole-1-carboxylate (Intermediate JJ)

To a round bottom flask equipped with magnetic stirring, and nitrogen inlet was charged JJ-5 (1.40 g, 2.90 mmol, 1 eq) and THF (14 mL). LiBH4 was added as a solid in one portion at room temperature (0.095 g, 4.35 mmol, 1.5 eq). The reaction was heated to 50 C for 5 hr. Reverse quench into half satd sodium bicarbate aq solution (30 mL) and EtOAc (50 mL). Layers were separated and the organic layer was washed with Brine, dried with MgSO4 and filtered. The organics were concentrated and then loaded on silica gel column (0-100% Hex/3:1 EtOAc:EtOH) to give the title compound. LC/MS (M+1=378).

Intermediate KK

Methyl (2R,3S,3aR,6aR)-3-amino-2-(((6-(5-fluoropyrimidin-2-yl)bicyclo[4.1.0]heptan-3-yl)oxy)methyl)hexahydrocyclopenta[b]pyrrole-1(2H)-carboxylate

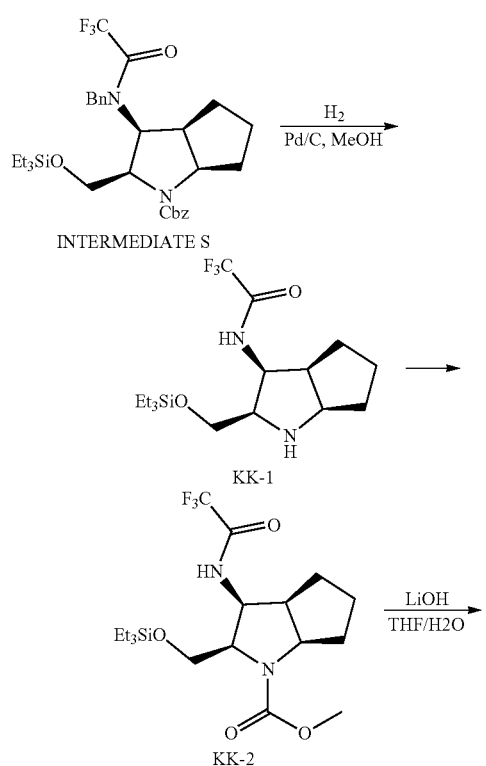

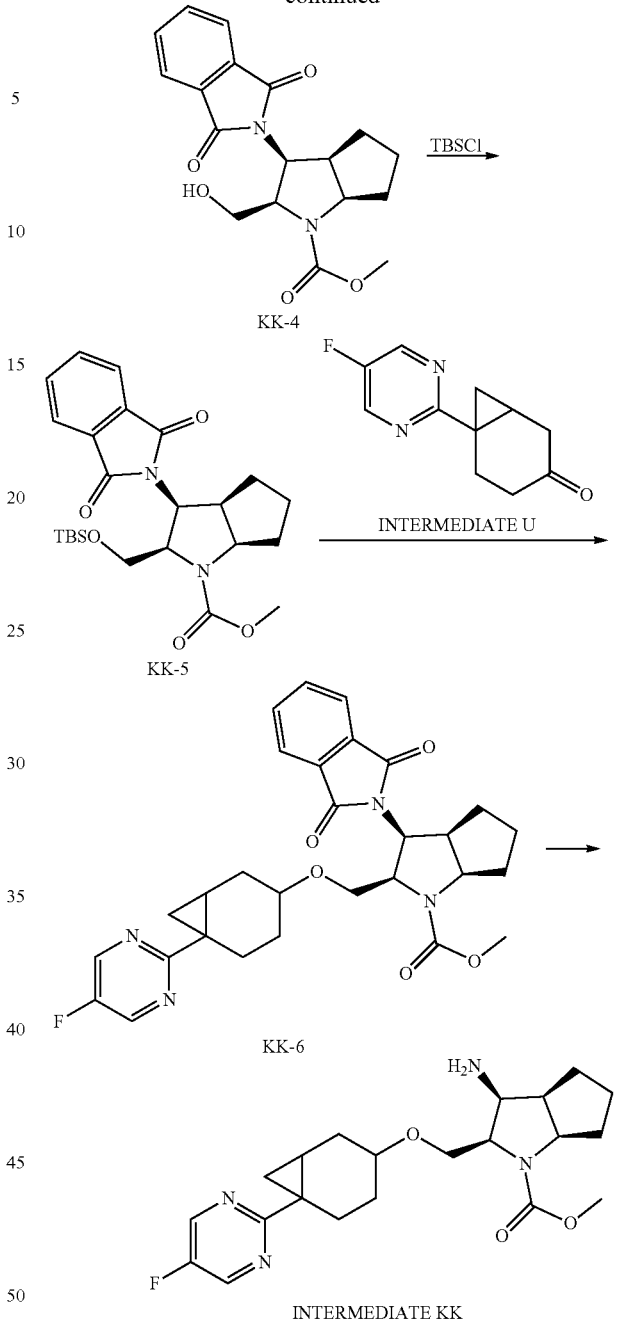

Step 1: 2,2,2-trifluoro-N-((2R,3S,3aS,6aR)-2-(((triethylsilyl)oxy)methyl)octahydrocyclopenta[b]pyrrol-3yl)acetamide (KK-1)

The mixture of benzyl (2R,3S,3aS,6aR)-3-(N-benzyl-2,2,2-trifluoroacetamido)-2-(((triethylsilyl)oxy)methyl)hexahydrocyclopenta[b]pyrrole-1(2H)-carboxylate (INTERMEDIATE S) (2.75 g, 4.66 mmol), Pd/C (0.991 g, 0.931 mmol) in MeOH (20 ml) was stirred under H2 at room temperature for 2 h. The mixture was filtered, washing with methanol, and concentrated to afford the title compound. MS: 368.4 (M+1)

Step 2: methyl (2R,3S,3aR,6aR)-2-(((triethylsilyl)oxy)methyl)-3-(2,2,2-trifluoroacetamido)hexahydrocyclopenta[b]pyrrole-1(2H)-carboxylate (KK-2) METHYL CHLORO- FORMATE (0.383 ml, 5.59 mmol) was added to a stirred, cooled 0° C. mixture of 2,2,2-trifluoro-N-((2R,3S,3aS,6aR)-2-(((triethylsilyl)oxy)methyl)octahydrocyclopenta[b]pyrrol-3-yl)acetamide (KK-1) (1.708 g, 4.66 mmol) in DCM (20 ml) and the mixture was moved to room temperature and stirred at room temperature for 15 min. The mixture was concentrated to afford the title compound. MS: 425.3 (M+1)

Step 3: methyl (2R,3S,3aR,6aR)-3-amino-2-(hydroxymethyl)hexahydrocyclopenta[b]pyrrole-1(2H)-carboxylate (KK-3)

LiOH (0.558 g, 23.30 mmol) was added to a stirred mixture of methyl (2R,3S,3aR,6aR)-2-(((triethylsilyl)oxy)methyl)-3-(2,2,2-trifluoroacetamido)hexahydrocyclopenta[b]pyrrole-1(2H)-carboxylate (KK-2) (1.978 g, 4.66 mmol) in THF (2.5 ml)/MeOH (20 ml)/Water (10 ml) and the mixture was stirred at 50° C. for 30 min. Concentrated, dried, and the residue was purified by column chromatography on silica gel (0-20% DCM: MeOH (10% NH3)) to afford the title compound. MS: 215.2 (M+1)

Step 4: methyl (2R,3S,3aR,6aR)-3-(1,3-dioxoisoindolin-2-yl)-2-(hydroxy methyl)hexahydrocyclopenta[b]pyrrole-1(2H)-carboxylate (KK-4)

PHTHALIC ANHYDRIDE (163 mg, 1.101 mmol) was added to a stirred mixture of methyl (2R,3S,3aR,6aR)-3-amino-2-(hydroxymethyl)hexahydrocyclopenta[b]pyrrole-1(2H)-carboxylate (KK-3) (118 mg, 0.551 mmol) and DIPEA (0.481 ml, 2.75 mmol) in Toluene (5 ml) and the mixture was stirred at 110° C. for Overnight. The mixture was cooled, aqueous ammonium chloride (saturated, 20 mL) was added and the mixture was extracted with ethyl acetate (3×30 mL). The combined organic fractions were washed with brine (saturated, 20 mL), dried (Na2SO4), filtered and the solvent was evaporated under reduced pressure. The residue was purified by column chromatography on silica gel (0-50% EtOAc/isohexane) to afford the title compound. MS: 345.3 (M+1)

Step 5: methyl (2R,3S,3aR,6aR)-2-(((tert-butyldimethylsilyl)oxy)methyl)-3-(1,3-dioxoisoindolin-2-yl)hexahydrocyclopenta[b]pyrrole-1(2H)-carboxylate (KK-5)

Imidazole (147 mg, 2.160 mmol) and TBS-Cl (119 mg, 0.792 mmol) were added to a stirred mixture of methyl (2R,3S,3aS,6aR)-3-(1,3-dioxoisoindolin-2-yl)-2-(hydroxymethyl)hexahydrocyclopenta[b]pyrrole-1(2H)-carboxylate (KK-4) (248 mg, 0.720 mmol) in DCM (5 ml) and the mixture was stirred at room temperature for 1 h. The solution was purified by column chromatography on silica gel (0-40% EtOAc/isohexane) to afford the title compound. MS: 460.4 (M+1)

Step 6: methyl (2R,3S,3aR,6aR)-3-(1,3-dioxoisoindolin-2-yl)-2-(((6-(5-fluoropyrimidin-2-yl)bicyclo[4.1.0]heptan-3-yl)oxy)methyl)hexahydrocyclopenta[b]pyrrole-1(2H)-carboxylate (KK-6)

TRIISOPROPYLSILANE (0.869 ml, 4.24 mmol) were added to a stirred, cooled 0° C. mixture of methyl (2R,3S,3aS,6aR)-2-(((tert-butyldimethylsilyl)oxy)methyl)-3-(1,3-dioxoisoindolin-2-yl)hexahydrocyclopenta[b]pyrrole-1(2H)-carboxylate (KK-5) (389 mg, 0.848 mmol) and 6-(5-fluoropyrimidin-2-yl)bicyclo[4.1.0]heptan-3-one (INTERMEDIATE U) (210 mg, 1.018 mmol) in Acetonitrile (10 ml). The reaction mixture was stirred at room temperature for 15 min. Then moved reaction to 0° C., Added trimethylsilyl trifluoromethanesulfonate (0.768 ml, 4.24 mmol). Open the reaction to air, the reaction mixture was stirred at 0° C. for 3 h. Aqueous sodium hydrogen carbonate (saturated, 30 mL) was added and the mixture was extracted with ethyl acetate (3×30 mL). The combined organic fractions were washed with brine (saturated, 20 mL), dried (Na2SO4), filtered and the solvent was evaporated under reduced pressure. The residue was purified by preparative TLC (eluting with EtOAc/isohexane (4:1)) to afford the title compound. MS: 536.4 (M+1)

Step 7: methyl (2R,3S,3aR,6aR)-3-amino-2-(((6-(5-fluoropyrimidin-2-yl)bicyclo[4.1.0]heptan-3-yl)oxy)methyl)hexahydrocyclopenta[b]pyrrole-1(2H)-carboxylate (Intermediate KK)

HYDRAZINE (0.021 ml, 0.670 mmol) was added to a stirred mixture of methyl (2R,3S,3aS,6aR)-3-(1,3-dioxoisoindolin-2-yl)-2-(((6-(5-fluoropyrimidin-2-yl)bicyclo[4.1.0]heptan-3-yl)oxy)methyl)hexahydrocyclopenta[b]pyrrole-1(2H)-carboxylate (KK-6) (71.6 mg, 0.134 mmol) in EtOH (3 ml) and the mixture was stirred at room temperature for 30 min. Then add TFA (0.103 ml, 1.339 mmol) and the reaction mixture was stirred at 50° C. for 2 h. Filtered, the solution was purified by preparative HPLC Reverse phase (C-18) (eluting with Acetonitrile/Water+0.1% TFA) to afford the title compound. MS: 405.4 (M+1)

Intermediate LL

Isopropyl 3-amino-2-(((6-(5-fluoropyrimidin-2-yl)bicyclo[4.1.0]heptan-3-yl)oxy)methyl)piperidine-1-carboxylate

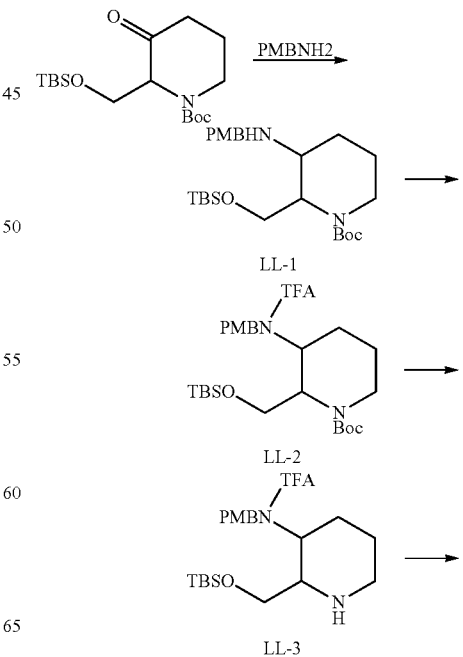

-continued

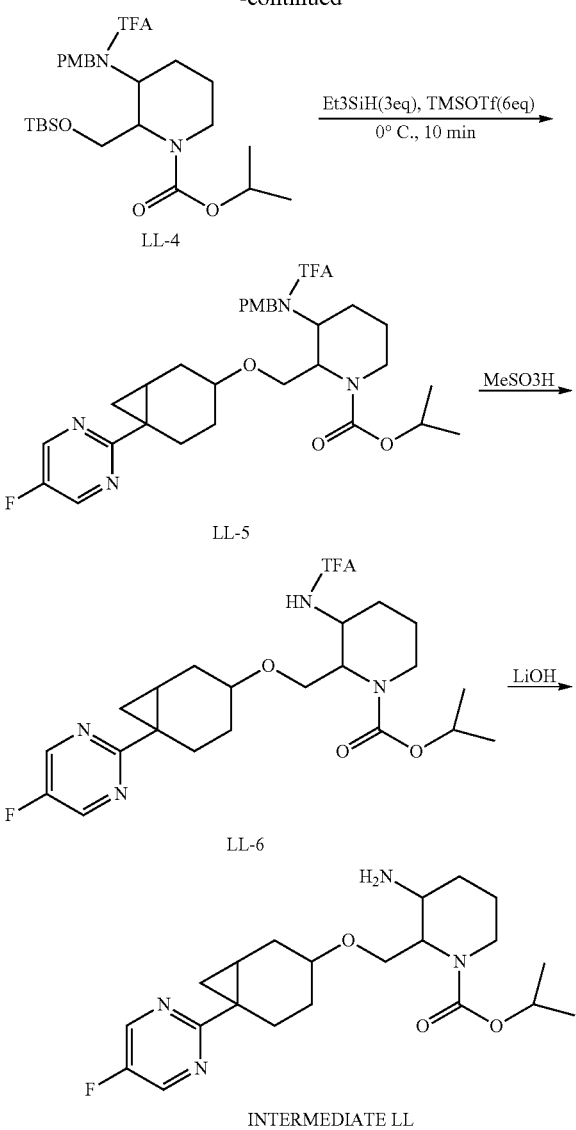

Step 1: tert-butyl 2-(((tert-butyldimethylsilyl)oxy)methyl)-3-((4-methoxybenzyl)amino)piperidine-1-carboxylate (LL-1)

4-METHOXYBENZYLAMINE (2.85 ml, 21.83 mmol), followed by SODIUM TRIACETOXYBOROHYDRIDE (9.25 g, 43.7 mmol) were added to a stirred mixture of tert-butyl 2-(((tert-butyldimethylsilyl)oxy)methyl)-3-oxopiperidine-1-carboxylate (5 g, 14.55 mmol) in 1,2-Dichloroethane (30 ml) and the mixture was stirred at room temperature for overnight. Aqueous sodium hydrogen carbonate (1M, 80 mL) was added and the mixture was extracted with ethyl acetate (3×80 mL). The combined organic fractions were washed with brine (saturated, 50 mL), dried ($Na_2SO_4$), filtered and the solvent was evaporated under reduced pressure. The residue was purified by column chromatography on silica (0-50% EtOAC/hexane, then 100% EtOAc:EtOH (3:1)) to afford the title compound. MS: 466.5 (M+1)

Step 2: tert-butyl 2-(((tert-butyldimethylsilyl)oxy)methyl)-3-(2,2,2-trifluoro-N-(4-methoxybenzyl)acetamido)piperidine-1-carboxylate (LL-2)

TFAA (0.543 ml, 3.91 mmol) was added to a stirred, cooled 0° C. mixture of tert-butyl 2-(((tert-butyldimethylsilyl)oxy)methyl)-3-((4-methoxybenzyl)amino)piperidine-1-carboxylate (LL-1) (1.21 g, 2.60 mmol), Et3N (1.089 ml, 7.81 mmol) in DCM (20 ml). The mixture was stirred at 0° C. for 30 min. Aqueous sodium hydrogen carbonate (saturated, 50 mL) was added and the mixture was extracted with ethyl acetate (3×50 mL). The combined organic fractions were washed with brine (saturated, 50 mL), dried ($Na_2SO_4$), filtered and the solvent was evaporated under reduced pressure. The residue was purified by column chromatography on silica gel (0-50% EtOAc/isohexane) to afford the title compound. MS: 562.5 (M+1)

Step 3: N-(2-(((tert-butyldimethylsilyl)oxy)methyl)piperidin-3-yl)-2,2,2-trifluoro-N-(4-methoxybenzyl)acetamide (LL-3)

Trimethylsilyl trifluoromethanesulfonate (1.152 ml, 6.37 mmol) was added slowly to a stirred, cooled 0° C. mixture of tert-butyl 2-(((tert-butyldimethylsilyl)oxy)methyl)-3-(2,2,2-trifluoro-N-(4-methoxybenzyl)acetamido)piperidine-1-carboxylate (LL-2) (1.19 g, 2.122 mmol) and 2,6-DIMETHYLPYRIDINE (1.977 ml, 16.98 mmol) in CH2Cl2 (10 ml) and the mixture was stirred at 0° C. for 15 min. Poured into aqueous sodium hydrogen carbonate (sat. 50 mL). The mixture was extracted with ethyl acetate (3×50 mL). The combined organic fractions were washed with brine (saturated, 50 mL), dried ($Na_2SO_4$), filtered and the solvent was evaporated under reduced pressure to afford the title compound. MS: 461.0 (M+1)

Step 4: isopropyl 2-(((tert-butyldimethylsilyl)oxy)methyl)-3-(2,2,2-trifluoro-N-(4-methoxybenzyl)acetamido)piperidine-1-carboxylate (LL-4)

ISOPROPYL CHLOROFORMATE (1M in toluene) (3.18 ml, 3.18 mmol) was added to a stirred mixture of N-(2-(((tert-butyldimethylsilyl)oxy)methyl)piperidin-3-yl)-2,2,2-trifluoro-N-(4-methoxybenzyl)acetamide (LL-3) (0.977 g, 2.12 mmol) and DIPEA (1.111 ml, 6.36 mmol) in DCM (10 ml) and the mixture was stirred at room temperature for 15 min before concentrating. The residue was purified by column chromatography on silica gel (0-50% EtOAc/isohexane) to afford the title compound. MS: 548.5 (M+1)

Step 5: isopropyl 2-(((6-(5-fluoropyrimidin-2-yl)bicyclo[4.1.0]heptan-3-yl)oxy)methyl)-3-(2,2,2-trifluoro-N-(4-methoxybenzyl)acetamido)piperidine-1-carboxylate (LL-5)

Triethylsilane (0.363 ml, 2.270 mmol) were added to a stirred, cooled 0° C. mixture of isopropyl 2-(((tert-butyldimethylsilyl)oxy)methyl)-3-(2,2,2-trifluoro-N-(4-methoxybenzyl)acetamido)piperidine-1-carboxylate (LL-4) (413.7 mg, 0.757 mmol) and 6-(5-fluoropyrimidin-2-yl)bicyclo[4.1.0]heptan-3-one (INTERMEDIATE U) (187 mg, 0.908 mmol) in Acetonitrile (10 ml). Then the reaction mixture was stirred at 0° C. for 10 min. Added trimethylsilyl trifluoromethanesulfonate (0.822 ml, 4.54 mmol). Then the reaction mixture was stirred at 0° C. for 15 min. Aqueous sodium hydrogen carbonate (saturated, 30 mL) was added and the mixture was extracted with ethyl acetate (3×30 mL). The combined organic fractions were washed with brine (saturated, 20 mL), dried (Na₂SO₄), filtered and the solvent was evaporated under reduced pressure. The residue was purified by preparative HPLC reverse phase (Acetonitrile/Water+0.1% TFA) to afford the title compound. MS: 623.5 (M+1)

Step 6: isopropyl 2-(((6-(5-fluoropyrimidin-2-yl)bicyclo[4.1.0]heptan-3-yl)oxy)methyl)-3-(2,2,2-trifluoroacetamido)piperidine-1-carboxylate (LL-6)

METHANESULFONIC ACID (0.069 ml, 1.065 mmol) was added to a stirred room temperature mixture of isopropyl 2-(((6-(5-fluoropyrimidin-2-yl)bicyclo[4.1.0]heptan-3-yl)oxy)methyl)-3-(2,2,2-trifluoro-N-(4-methoxybenzyl)acetamido)piperidine-1-carboxylate (LL-5) (221 mg, 0.355 mmol) in CH2Cl2 (5 ml) and the mixture was stirred at room temperature for 2 h. Aqueous sodium hydrogen carbonate (saturated, 20 mL) was added and the mixture was extracted with ethyl acetate (3×20 mL). The combined organic fractions were washed with brine (saturated, 20 mL), dried (Na₂SO₄), filtered and the solvent was evaporated under reduced pressure to afford the title compound. MS: 503.4 (M+1)

Step 7: isopropyl 3-amino-2-(((6-(5-fluoropyrimidin-2-yl)bicyclo[4.1.0]heptan-3yl)oxy)methyl)piperidine-1-carboxylate (Intermediate LL)

LiOH (41.7 mg, 1.741 mmol) was added to a stirred mixture of isopropyl 2-(((6-(5-fluoropyrimidin-2-yl)bicyclo[4.1.0]heptan-3-yl)oxy)methyl)-3-(2,2,2-trifluoroacetamido)piperidine-1-carboxylate (LL-6) (175 mg, 0.348 mmol) in THF (1 ml)/Methanol (4 ml)/Water (2 ml) and the mixture was stirred at 50° C. for 1 h. Concentrated, redissolved in MeOH (4 mL), filtered, the solution was purified by preparative HPLC Reverse phase (Acetonitrile/Water+ 0.1% TFA) to afford the title compound. MS: 407.4 (M+1)

Intermediate MM

Methyl (2R,3S,5S)-2-(((tert-butyldimethylsilyl)oxy)methyl)-5-(difluoromethyl)-3-(2,2,2-trifluoro-N-(4-methoxybenzyl)acetamido)pyrrolidine-1-carboxylate

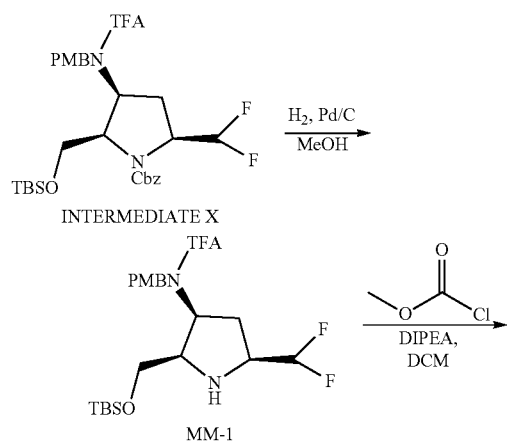

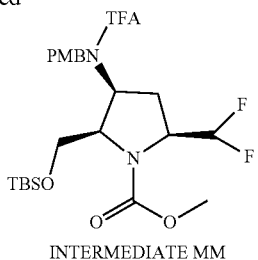

INTERMEDIATE MM

Step 1: (+/−) N-(2-(((tert-butyldimethylsilyl)oxy)methyl)-5-(difluoromethyl)pyrrolidin-3-yl)-2,2,2-trifluoro-N-(4-methoxybenzyl)acetamide (MM-1)

The mixture of benzyl 2-(((tert-butyldimethylsilyl)oxy)methyl)-5-(difluoromethyl)-3-(2,2,2-trifluoro-N-(4-methoxybenzyl)acetamido)pyrrolidine-1-carboxylate (INTERMEDIATE X) (1.62 g, 2.57 mmol) and Pd/C (0.547 g, 0.514 mmol) in MeOH (10 ml) was stirred under H2 at room temperature for 30 min. The mixture was filtered, washing with methanol, and the solution was concentrated to afford the title compound. MS: 497.4 (M+1)

Step 2: methyl (2R,3S,5S)-2-(((tert-butyldimethylsilyl)oxy)methyl)-5-(difluoromethyl)-3-(2,2,2-trifluoro-N-(4-methoxybenzyl)acetamido)pyrrolidine-1-carboxylate (Intermediate MM)

METHYL CHLOROFORMATE (0.210 ml, 3.07 mmol) was added to a stirred, cooled 0° C. mixture of (+/−) N-(2-(((tert-butyldimethylsilyl)oxy)methyl)-5-(difluoromethyl)pyrrolidin-3-yl)-2,2,2-trifluoro-N-(4-methoxybenzyl)acetamide (MM-1) (1.27 g, 2.56 mmol) in DCM (20 ml) and the mixture was moved to room temperature and stirred at room temperature for 15 min. The residue was purified by column chromatography on silica gel (0-50% EtOAc/isohexane) to mixture of enantiomers. SFC chiral separation to afford the title compound. MS: 556.5 (M+1)

Intermediate NN methyl (2R,3S,5R)-5-methyl-2-(((triethylsilyl)oxy)methyl)-3-(2,2,2-trifluoro-N-(4-methoxybenzyl)acetamido)pyrrolidine-1-carboxylate

INTERMEDIATE NN

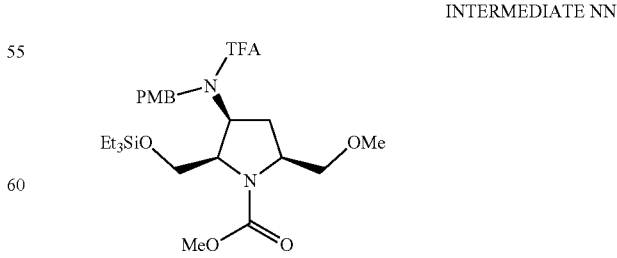

methyl (2R,3S,5R)-5-methyl-2-(((triethylsilyl)oxy)methyl)-3-(2,2,2-trifluoro-N-(4-methoxybenzyl)acetamido)pyrrolidine-1-carboxylate (INTERMEDIATE NN) was prepared according to the same procedure provided in INTERMEDIATE MM without SFC by starting with INTERMEDIATE T.

Intermediate OO

Methyl (2R,3S,5S)-3-amino-2-(((6-(5-fluoropyrimidin-2-yl)bicyclo[4.1.0]heptan-3-yl)oxy)methyl)-5-(trifluoromethyl)pyrrolidine-1-carboxylate

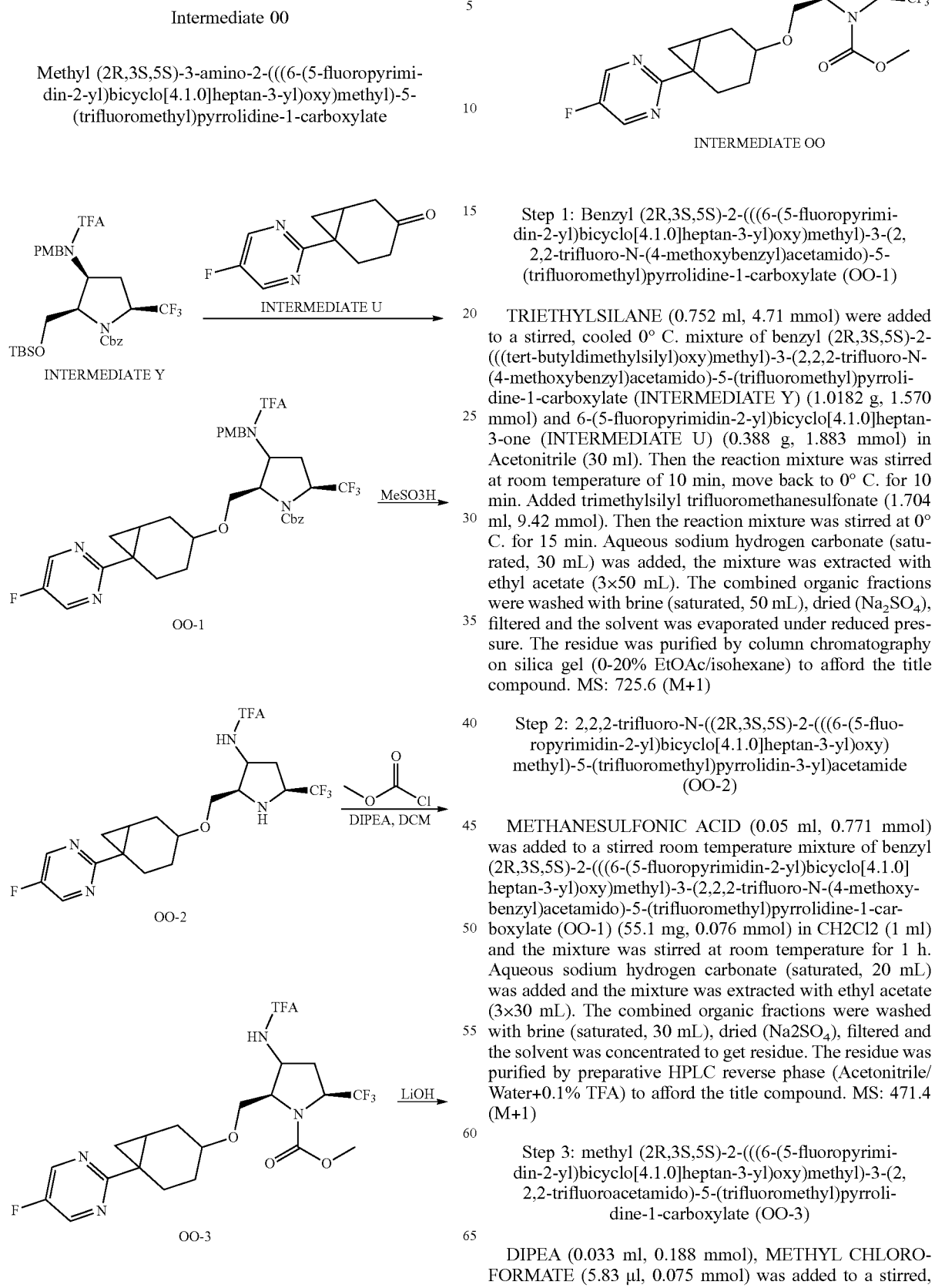

INTERMEDIATE OO

Step 1: Benzyl (2R,3S,5S)-2-(((6-(5-fluoropyrimidin-2-yl)bicyclo[4.1.0]heptan-3-yl)oxy)methyl)-3-(2,2,2-trifluoro-N-(4-methoxybenzyl)acetamido)-5-(trifluoromethyl)pyrrolidine-1-carboxylate (OO-1)

TRIETHYLSILANE (0.752 ml, 4.71 mmol) were added to a stirred, cooled 0° C. mixture of benzyl (2R,3S,5S)-2-(((tert-butyldimethylsilyl)oxy)methyl)-3-(2,2,2-trifluoro-N-(4-methoxybenzyl)acetamido)-5-(trifluoromethyl)pyrrolidine-1-carboxylate (INTERMEDIATE Y) (1.0182 g, 1.570 mmol) and 6-(5-fluoropyrimidin-2-yl)bicyclo[4.1.0]heptan-3-one (INTERMEDIATE U) (0.388 g, 1.883 mmol) in Acetonitrile (30 ml). Then the reaction mixture was stirred at room temperature of 10 min, move back to 0° C. for 10 min. Added trimethylsilyl trifluoromethanesulfonate (1.704 ml, 9.42 mmol). Then the reaction mixture was stirred at 0° C. for 15 min. Aqueous sodium hydrogen carbonate (saturated, 30 mL) was added, the mixture was extracted with ethyl acetate (3×50 mL). The combined organic fractions were washed with brine (saturated, 50 mL), dried (Na₂SO₄), filtered and the solvent was evaporated under reduced pressure. The residue was purified by column chromatography on silica gel (0-20% EtOAc/isohexane) to afford the title compound. MS: 725.6 (M+1)

Step 2: 2,2,2-trifluoro-N-((2R,3S,5S)-2-(((6-(5-fluoropyrimidin-2-yl)bicyclo[4.1.0]heptan-3-yl)oxy)methyl)-5-(trifluoromethyl)pyrrolidin-3-yl)acetamide (OO-2)

METHANESULFONIC ACID (0.05 ml, 0.771 mmol) was added to a stirred room temperature mixture of benzyl (2R,3S,5S)-2-(((6-(5-fluoropyrimidin-2-yl)bicyclo[4.1.0] heptan-3-yl)oxy)methyl)-3-(2,2,2-trifluoro-N-(4-methoxybenzyl)acetamido)-5-(trifluoromethyl)pyrrolidine-1-carboxylate (OO-1) (55.1 mg, 0.076 mmol) in CH2Cl2 (1 ml) and the mixture was stirred at room temperature for 1 h. Aqueous sodium hydrogen carbonate (saturated, 20 mL) was added and the mixture was extracted with ethyl acetate (3×30 mL). The combined organic fractions were washed with brine (saturated, 30 mL), dried (Na2SO4), filtered and the solvent was concentrated to get residue. The residue was purified by preparative HPLC reverse phase (Acetonitrile/Water+0.1% TFA) to afford the title compound. MS: 471.4 (M+1)

Step 3: methyl (2R,3S,5S)-2-(((6-(5-fluoropyrimidin-2-yl)bicyclo[4.1.0]heptan-3-yl)oxy)methyl)-3-(2,2,2-trifluoroacetamido)-5-(trifluoromethyl)pyrrolidine-1-carboxylate (OO-3)

DIPEA (0.033 ml, 0.188 mmol), METHYL CHLOROFORMATE (5.83 µl, 0.075 mmol) was added to a stirred, cooled room temperature mixture of 2,2,2-trifluoro-N-((2R,3S,5S)-2-(((6-(5-fluoropyrimidin-2-yl)bicyclo[4.1.0]heptan-3-yl)oxy)methyl)-5-(trifluoromethyl)pyrrolidin-3-yl)acetamide (OO-2) (29.5 mg, 0.063 mmol) in DCM (3 ml) and the mixture was stirred at room temperature for 15 min. Concentrated, redissolved in MeOH (2 mL), the solution was purified by preparative HPLC Reverse phase (Acetonitrile/Water+0.1% TFA) to afford the title compound. MS: 529.4 (M+1)

Step 4: methyl (2R,3S,5S)-3-amino-2-(((6-(5-fluoropyrimidin-2-yl)bicyclo[4.1.0]heptan-3-yl)oxy)methyl)-5-(trifluoromethyl)pyrrolidine-1-carboxylate (Intermediate OO)

LiOH (7.48 mg, 0.312 mmol) was added to a stirred mixture of methyl (2R,3S,5S)-2-(((6-(5-fluoropyrimidin-2-yl)bicyclo[4.1.0]heptan-3-yl)oxy)methyl)-3-(2,2,2-trifluoroacetamido)-5-(trifluoromethyl)pyrrolidine-1-carboxylate (OO-3) (33 mg, 0.062 mmol) in THF (1 ml)/Methanol (4 ml)/Water (2 ml) and the mixture was stirred at 60° C. for 1 h. Concentrated, the residue was purified by preparative HPLC Reverse phase (Acetonitrile/Water+0.1% TFA) to afford the title compound. MS: 433.4.4 (M+1)

Intermediate PP and Intermediate QQ

Methyl (2R,3S,5R)-3-amino-2-((((1S,3S,6R)-6-(5-fluoropyrimidin-2-yl)bicyclo[4.1.0]heptan-3-yl)oxy)methyl)-5-methylpyrrolidine-1-carboxylate (Intermediate PP) and methyl (2R,3S,5R)-3-amino-2-((((1R,3R,6S)-6-(5-fluoropyrimidin-2-yl)bicyclo[4.1.0]heptan-3-yl)oxy)methyl)-5-methylpyrrolidine-1-carboxylate (Intermediate QQ)

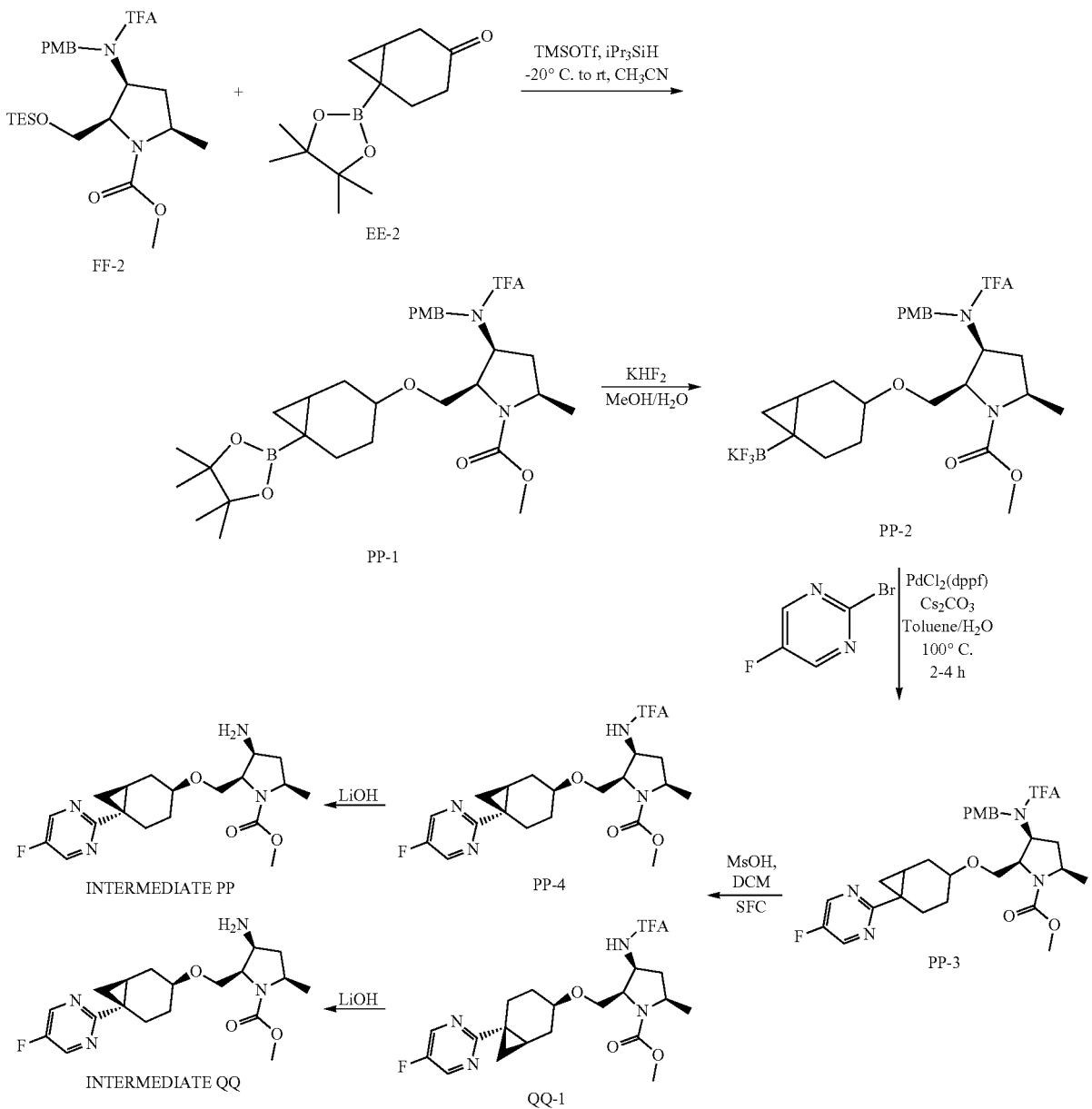

Step 1: methyl (2R,3S,5R)-5-methyl-2-(((6-(4,4,5,5-tetramethyl-1,3,2-dioxaborolan-2-yl)bicyclo[4.1.0]heptan-3-yl)oxy)methyl)-3-(2,2,2-trifluoro-N-(4-methoxybenzyl)acetamido)pyrrolidine-1-carboxylate (PP-1)

To a solution of 6-(4,4,5,5-tetramethyl-1,3,2-dioxaborolan-2-yl)bicyclo[4.1.0]heptan-3-one (EE-2) (800 mg, 3.39 mmol) and methyl (2R,3S,5R)-5-methyl-2-(((triethylsilyl)oxy)methyl)-3-(2,2,2-trifluoro-N-(4-methoxybenzyl)acetamido)pyrrolidine-1-carboxylate (FF-2) (1933 mg, 3.73 mmol) in acetonitrile (50 ml) was added triisopropylsilane (1073 mg, 6.78 mmol) at rt under N2. The reaction mixture was stirred for 5 min to make a homogeneous solution. The reaction mixture was cooled to −10° C., then was added trimethylsilyl trifluoromethanesulfonate (904 mg, 4.07 mmol). The mixture was allowed to raise to rt and stirred for 4 h. 2 ml of sat. aq. NaHCO3 was added, and the organic phase was taken up by 50 ml of EtOAc. The organic phase was collected, concentrated and the crude was chromatographed over silic gel (EtOAc in hexanes, 0-80%) to give the title compound. LC-MS 625.5 (M+1).

Step 2: methyl (2R,3S,5R)-5-methyl-2-(((6-(trifluoro-14-boraneyl)bicyclo[4.1.0]heptan-3-yl)oxy)methyl)-3-(2,2,2-trifluoro-N-(4-methoxybenzyl)acetamido)pyrrolidine-1-carboxylate, potassium salt (PP-2)

To a solution of methyl (2R,3S,5R)-5-methyl-2-(((6-(4,4,5,5-tetramethyl-1,3,2-dioxaborolan-2-yl)bicyclo[4.1.0]heptan-3-yl)oxy)methyl)-3-(2,2,2-trifluoro-N-(4-methoxybenzyl)acetamido)pyrrolidine-1-carboxylate (PP-1) (1900 mg, 3.04 mmol) in MeOH (20 ml) was added a solution of potassium hydrogen difluoride (713 mg, 9.13 mmol) dissolved in H2O (2.00 ml) at rt. The reaction mixture was stirred for 2 h. The reaction mixture was concentrated in vacuo, then was triturated with 10 ml of methyl t-butyl ether, dried in vacuo again. The white solid was dissolved in 10 ml of acetone, filtered, and the filtrate was concentrated in vacuo to give the title compound.

Step 3: methyl (2R,3S,5R)-2-(((6-(5-fluoropyrimidin-2-yl)bicyclo[4.1.0]heptan-3-yl)oxy)methyl)-5-methyl-3-(2,2,2-trifluoro-N-(4-methoxybenzyl)acetamido)pyrrolidine-1-carboxylate (PP-3)

To a 100 ml RBF was added cesium carbonate (1941 mg, 5.96 mmol), 2-bromo-5-fluoropyrimidine (527 mg, 2.98 mmol), methyl (2R,3S,5R)-5-methyl-2-(((6-(trifluoro-14-boraneyl)bicyclo[4.1.0]heptan-3-yl)oxy)methyl)-3-(2,2,2-trifluoro-N-(4-methoxybenzyl)acetamido)pyrrolidine-1-carboxylate, potassium salt (PP-2) (1200 mg, 1.985 mmol) and PdCl$_2$(dppf) (145 mg, 0.199 mmol), followed by Toluene (50 ml) and Water (10 ml). The reaction mixture was degassed for 15 min, then was heated at 95° C. for overnight. The reaction mixture was cooled to rt, then the organic phase was taken by 20 ml of EtOAc. The organic phase was collected, concentrated and the crude was chromatographed over silica gel (EtOAc in hexanes 0-60%) to give the title compound. LC-MS 595.5 (M+1).

Step 4: methyl (2R,3S,5R)-2-((((1S,3S,6R)-6-(5-fluoropyrimidin-2-yl)bicyclo[4.1.0]heptan-3-yl)oxy)methyl)-5-methyl-3-(2,2,2-trifluoroacetamido)pyrrolidine-1-carboxylate (PP-4) and methyl (2R,3S,5R)-2-((((1R,3R,6S)-6-(5-fluoropyrimidin-2-yl)bicyclo[4.1.0]heptan-3-yl)oxy)methyl)-5-methyl-3-(2,2,2-trifluoroacetamido)pyrrolidine-1-carboxylate (QQ-1)

To a solution of methyl (2R,3S,5R)-2-(((6-(5-fluoropyrimidin-2-yl)bicyclo[4.1.0]heptan-3-yl)oxy)methyl)-5-methyl-3-(2,2,2-trifluoro-N-(4-methoxybenzyl)acetamido)pyrrolidine-1-carboxylate (PP-3) (810 mg, 1.362 mmol) in CH2Cl2 (10 ml) was added methanesulfonic acid (393 mg, 4.09 mmol) at rt under N2. The reaction mixture was stirred at rt for 0.5 h. The crude was added to a stirred mixture of 20 ml of DCM and 2 ml of sat. aq. NaHOC$_3$. The organic phase was collected, concentrated and chromatographed over silica gel (EtOAc in Hexanes 0-80%) to give the desired racemic product. LC-MS 475.5 (M+1). The racemic methyl (2R,3S,5R)-2-((((1S,6R)-6-(5-fluoropyrimidin-2-yl)bicyclo[4.1.0]heptan-3-yl)oxy)methyl)-5-methyl-3-(2,2,2-trifluoroacetamido)pyrrolidine-1-carboxylate was purified using chiral resolution (Preparative Method: Column: OJ-H, 21×250 mm; Injection Volume: 0.5 ml; Co-Solvent: 35% MeOH; UV Wavelength: 210 nm; Concentration: 56 mg in 9 ml MeOH) to give the desired chiral intermediates.
PP-3: LC-MS 475.5 (M+1).
QQ-1: LC-MS 475.5 (M+1).

Step 5: methyl (2R,3S,5R)-3-amino-2-((((1S,3S,6R)-6-(5-fluoropyrimidin-2-yl)bicyclo[4.1.0]heptan-3-yl)oxy)methyl)-5-methylpyrrolidine-1-carboxylate (Intermediate PP) and methyl (2R,3S,5R)-3-amino-2-((((1R,3R,6S)-6-(5-fluoropyrimidin-2-yl)bicyclo[4.1.0]heptan-3-yl)oxy)methyl)-5-methylpyrrolidine-1-carboxylate (Intermediate QQ)

To a solution of methyl (2R,3S,5R)-2-((((1S,3S,6R)-6-(5-fluoropyrimidin-2-yl)bicyclo[4.1.0]heptan-3-yl)oxy)methyl)-5-methyl-3-(2,2,2-trifluoroacetamido)pyrrolidine-1-carboxylate (PP-3) (180 mg, 0.379 mmol) in THF (5 ml) was added aq. LiOH (2N) at rt under N2. The reaction mixture was stirred at rt for 2 h. The reaction mixture was filtered, then was concentrated, dissolved in 2 ml of MeOH, then the crude was purified using reverse phase HPLC (acetonitrile in H2O, 10-100%) to give the title compound. INTERMEDIATE PP: LC-MS 379.4 (M+1).

The same procedure was use to prepare methyl (2R,3S,5R)-3-amino-2-((((1S,3S,6R)-6-(5-fluoropyrimidin-2-yl)bicyclo[4.1.0]heptan-3-yl)oxy)methyl)-5-methylpyrrolidine-1-carboxylate (INTERMEDIATE QQ) LC-MS 379.4 (M+1).

Intermediate RR 1-((difluoromethyl)sulfonyl)-3-methyl-1H-imidazol-3-ium trifluoromethanesulfonate

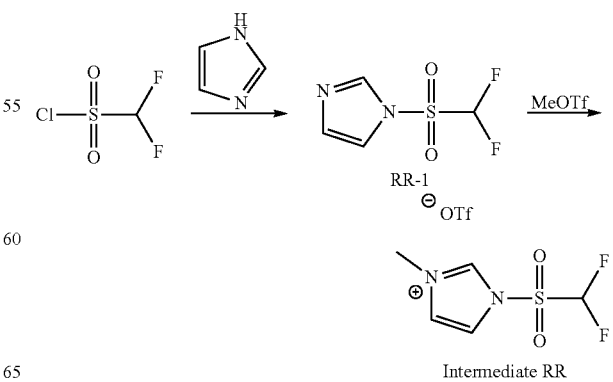

Intermediate RR

Step 1: methyl (R)-5-(((benzyloxy)carbonyl)amino)-3-oxohexanoate (RR-1)

To a mixture of 1H-imidazole (226 mg, 3.32 mmol) in DCM (10.100 ml) at ambient temperature was added triethylamine (0.509 ml, 3.65 mmol) followed by difluoromethanesulfonyl chloride (500 mg, 3.32 mmol) dropwise. The mixture stirred for 1 hour before quenching with H2O (25 mL). The mixture was extracted with DCM (3×@ 25 mL), dried over Na2SO4, and concentrated. The resulting residue was purified using silica column chromatography (5% to 80% EtOAc/hexanes) to obtain the title compound. LCMS: 182.9 (M+H).

Step 2: 1-((difluoromethyl)sulfonyl)-3-methyl-1H-imidazol-3-ium trifluoromethanesulfonate (Intermediate RR)

To a mixture of 1-((difluoromethyl)sulfonyl)-1H-imidazole (RR-1) (400 mg, 2.196 mmol) in DCM (6655 µl) at 0° C. was added METHYL TRIFLUOROMETHANESULFONATE (2660, 2.416 mmol) dropwise. The mixture was stirred for 1 hour before concentrating and placing under vacuum to obtain the title compound.

Example 1 and Example 2

Methyl (2R,3S,5R)-5-methyl-3-(methylsulfonamido)-2-(((6-phenylbicyclo[4.1.0]heptan-3-yl)oxy)methyl)pyrrolidine-1-carboxylate (1, PEAK 1) and Methyl (2R,3S,5R)-5-methyl-3-(methylsulfonamido)-2-(((6-phenylbicyclo[4.1.0]heptan-3-yl)oxy)methyl)pyrrolidine-1-carboxylate (2, Peak 2)

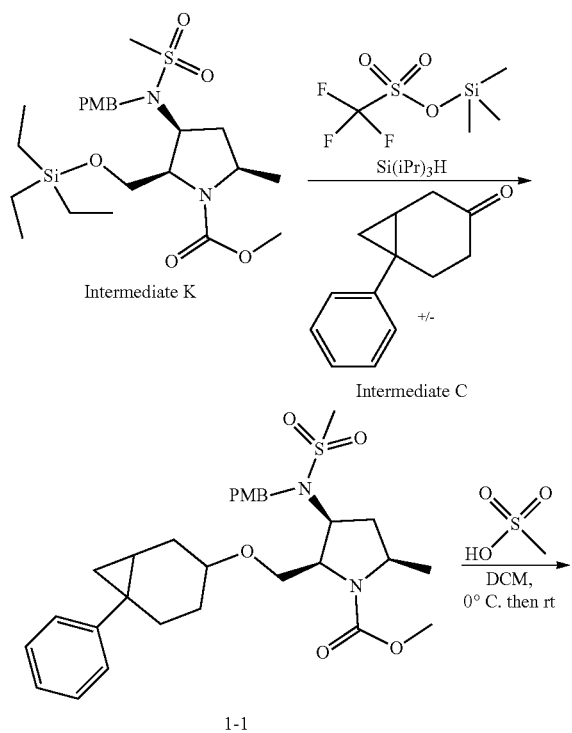

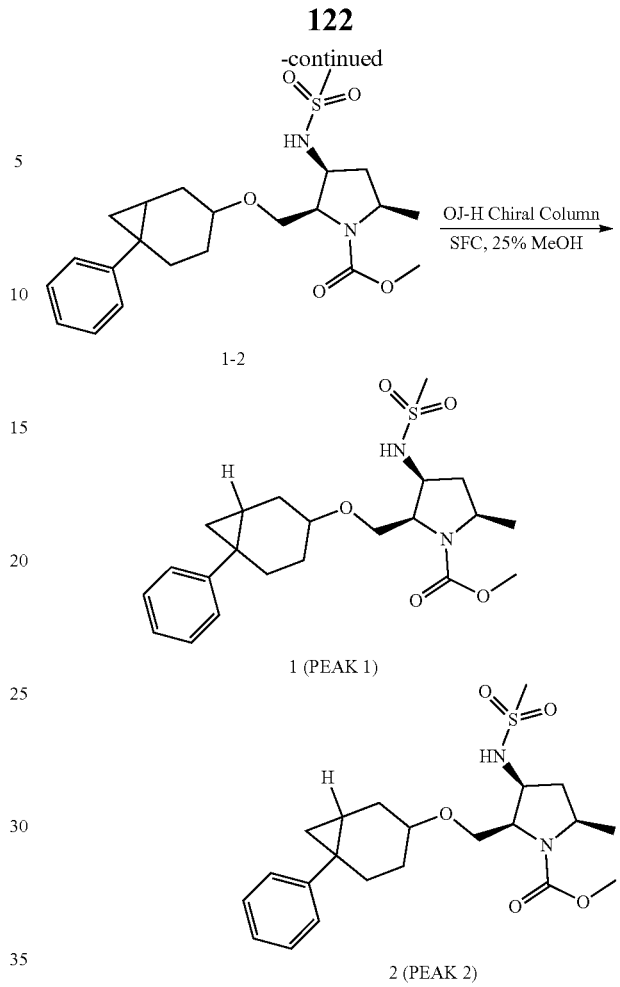

Step 1: methyl (2R,3S,5R)-3-(N-(4-methoxybenzyl)methylsulfonamido)-5-methyl-2-(((6-phenylbicyclo[4.1.0]heptan-3-yl)oxy)methyl)pyrrolidine-1-carboxylate (1-1)

A solution of methyl (2R,3S,5R)-3-(N-(4-methoxybenzyl)methylsulfonamido)-5-methyl-2-(((triethylsilyl)oxy)methyl)pyrrolidine-1-carboxylate (INTERMEDIATE K) (160 mg, 0.320 mmol), 6-phenylbicyclo[4.1.0]heptan-3-one, (INTERMEDIATE C) (89 mg, 0.479 mmol) and TRIISOPROPYLSILANE (131 µl, 0.639 mmol) at 25° C. was stirred for 5 min. then cool to −35° C. Trimethylsilyl trifluoromethanesulfonate (57.7 µl, 0.320 mmol) was then added dropwise and the mixture stirred at −35° C. (maintaining temp with dry ice) for 3 h. Allow to warm to 0° C. for 30 min and then quench with Sat. Aq. NaHCO₃ at −35° C. After warming to rt, the solvent was evaporated under reduced pressure and the residue diluted with EtOAc and washed with water. The organic layer was washed with brine, dried (MgSO4), filtered and concentrated under reduced pressure to afford the crude. The crude was purified on silica gel (ethyl acetate/hexane 0-60%) to give the title compound. LC-MS: m/z=557.2 (M+1).

Step 2: methyl (2R,3S,5R)-5-methyl-3-(methylsulfonamido)-2-(((6-phenylbicyclo[4.1.0]heptan-3-yl)oxy)methyl)pyrrolidine-1-carboxylate (1-2)

A solution of methyl (2R,3S,5R)-3-(N-(4-methoxybenzyl)methylsulfonamido)-5-methyl-2-(((6-phenylbicyclo

[4.1.0]heptan-3-yl)oxy)methyl)pyrrolidine-1-carboxylate, 1-1 (57 mg, 0.102 mmol) in DCM (512 μl) was treated with METHANESULFONIC ACID (66.5 μl, 1.024 mmol) and the mixture stirred at 25° C. for 3 h. At 0° C. the reaction was quenched with Sat. Aq. NaHCO3. The mixture was then extracted with DCM (×2) and the organic layer dried (MgSO4), filtered and concentrated under reduced pressure to afford the crude. The crude was purified on silica gel (ethyl acetate:ethanol (3:1)/hexane 0-40%) to give the title compound. LC-MS: m/z=437.3 (M+1).

Step 3: Methyl (2R,3S,5R)-5-methyl-3-(methyl-sulfonamido)-2-(((6-phenylbicyclo[4.1.0]heptan-3-yl)oxy)methyl)pyrrolidine-1-carboxylate (1, PEAK 1) and Methyl (2R,3S,5R)-5-methyl-3-(methylsulfonamido)-2-(((6-phenylbicyclo[4.1.0]heptan-3-yl)oxy)methyl)pyrrolidine-1-carboxylate (2, Peak 2)

The mixture of 1-2 was then resolved on the chiral OJ-H (21×250 mm) column with SFC coeluding with 25% MeOH to afford 1 (PEAK 1) and 2 (PEAK 2).

Example 3 methyl (2R,3S,5R)-3-((N,N-dimethylsulfamoyl) amino)-2-(((6-(3-fluorophenyl)bicyclo[4.1.0]heptan-3-yl)oxy)methyl)-5-methylpyrrolidine-1-carboxylate (Mixture)

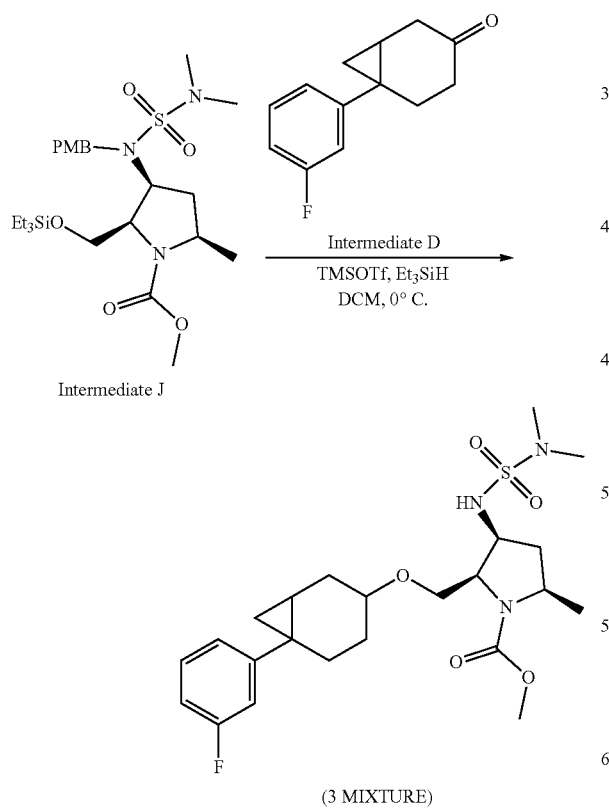

(3 MIXTURE)

To a solution of 6-(3-fluorophenyl)bicyclo[4.1.0]heptan-3-one (INTERMEDIATE D) (48.2 mg, 0.236 mmol) and INTERMEDIATE J (50 mg, 0.094 mmol) in DCM (2 mL) was added TMSOTf (84 mg, 0.378 mmol) at 0° C. and stirred at 0° C. for 1 h. Triethylsilane (43.9 mg, 0.378 mmol) was added and the mixture was stirred at 0° C. for 1 h. The mixture was quenched with water (2 mL), extracted with DCM (2 mL×3). The organic layers were combined and dried with Na2SO4, filtered. The filtrate was concentrated and purified by prep-HPLC (C18 H2O/MeCN with NH4HCO3 modifier) to give the title compound. LCMS m/z (M+H): 484.2 required, 484.2 found. $^1$H NMR (500 MHz, CD3OD) δ 7.27 (dt, J=6.2, 8.0 Hz, 1H), 7.08 (d, J=7.8 Hz, 1H), 6.99 (td, J=2.1, 10.6 Hz, 1H), 6.87 (dt, J=2.1, 8.4 Hz, 1H), 4.06 (br s, 1H), 3.91-3.67 (m, 7H), 3.49-3.38 (m, 1H), 2.80 (d, J=2.4 Hz, 6H), 2.67-2.51 (m, 1H), 2.43-2.21 (m, 2H), 2.12-1.75 (m, 3H), 1.60-1.48 (m, 1H), 1.38-1.20 (m, 5H), 0.99 (td, J=4.3, 9.2 Hz, 1H), 0.83 (t, J=5.1 Hz, 1H).

Example 4 methyl (2R,3S,5R)-2-(((6-(3,5-difluorophenyl)bicyclo[4.1.0]heptan-3-yl)oxy)methyl)-3-((N,N-dimethylsulfamoyl)amino)-5-methylpyrrolidine-1-carboxylate (Mixture)

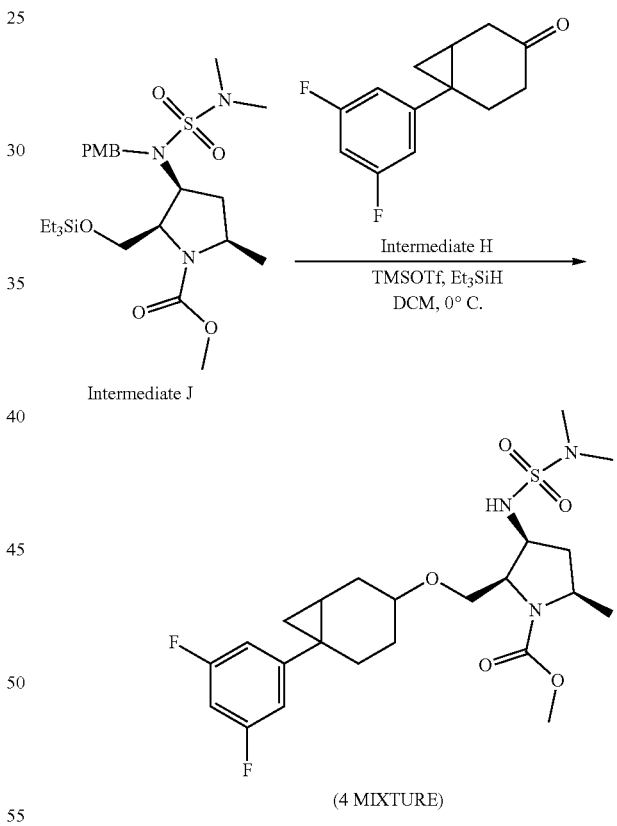

(4 MIXTURE)

To a solution of 6-(3,5-difluorophenyl)bicyclo[4.1.0]heptan-3-one (INTERMEDIATE H) (52.4 mg, 0.236 mmol) and INTERMEDIATE J (50 mg, 0.094 mmol) in DCM (2 mL) was added TMSOTf (84 mg, 0.378 mmol) at 0° C. and stirred at 0° C. for 60 minutes. Triethylsilane (43.9 mg, 0.378 mmol) was added and the mixture was stirred at 0° C. for 1 h. The mixture was quenched with water (2 mL), extracted with DCM (2 mL×3), separated. The organic layers were combined and dried with Na2SO4, filtered. The solution was concentrated and purified by prep-HPLC (C18 H2O/MeCN with NH4HCO3 modifier) to give the title compound. LCMS m/z (M+H): 502.2 required, 502.2 found. $^1$H NMR (500 MHz, CD$_3$OD) δ 6.83-6.74 (m, 2H), 6.62 (tt, J=2.3, 9.1 Hz, 1H), 3.96 (br s, 1H), 3.82-3.56 (m, 7H), 3.45-3.28 (m, 1H), 2.71 (d, J=2.3 Hz, 6H), 2.58-2.42 (m, 1H), 2.32-2.12 (m, 2H), 2.02-1.66 (m, 3H), 1.55-1.41 (m, 1H), 1.28-1.11 (m, 5H), 0.91 (td, J=4.4, 9.3 Hz, 1H), 0.78 (t, J=5.3 Hz, 1H).

Example 5 methyl (2R,3S,5R)-2-(((6-(4-cyanophenyl)bicyclo[4.1.0]heptan-3-yl)oxy)methyl)-3-((N,N-dimethylsulfamoyl)amino)-5-methylpyrrolidine-1-carboxylate (Mixture)

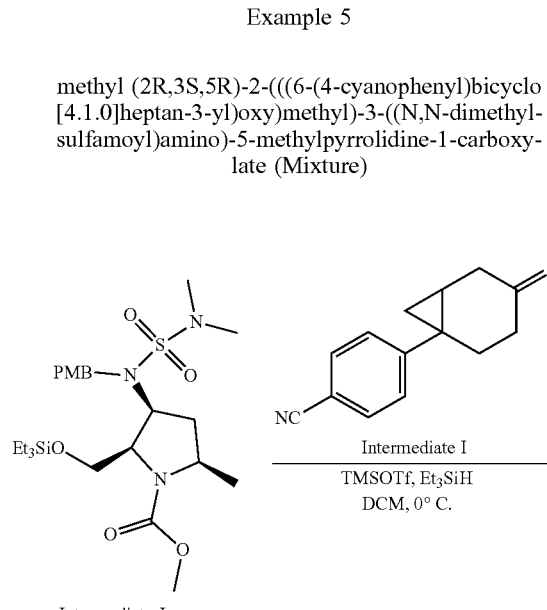

Example 6 methyl (2R,3S,5R)-3-((N,N-dimethylsulfamoyl)amino)-5-methyl-2-(((6-(pyrimidin-2-yl)bicyclo[4.1.0]heptan-3-yl)oxy)methyl)pyrrolidine-1-carboxylate (Mixture)

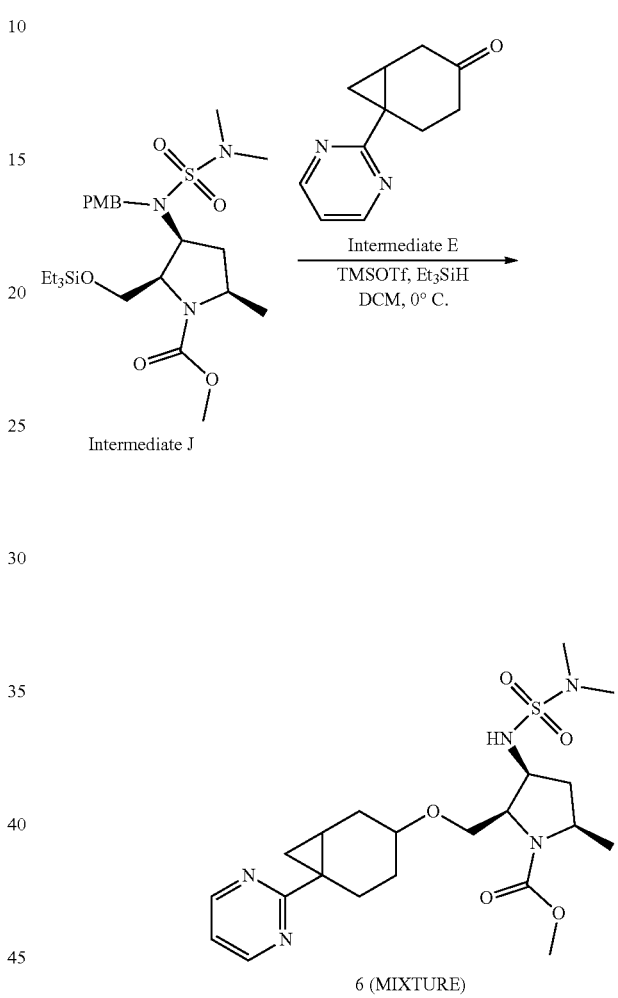

To a solution of 4-(4-oxobicyclo[4.1.0]heptan-1-yl)benzonitrile (INTERMEDIATE I) (29.9 mg, 0.142 mmol) and INTERMEDIATE J (30 mg, 0.057 mmol) in DCM (3 mL) was added TMSOTf (50.3 mg, 0.227 mmol) at 0° C. and stirred at 0° C. for 1 h. Triethylsilane (26.3 mg, 0.227 mmol) was added and the mixture was stirred at 0° C. for 1 h. LCMS showed desired compound was found. The mixture was quenched with water (2 mL), extracted with DCM (2 mL×3). The organic layers were combined and dried with Na$_2$SO$_4$, filtered. The solution was concentrated and purified by prep-HPLC (C18 H2O/MeCN with TFA modifier) to give the title compound. LCMS m/z (M+H): 491.2 required, 491.2 found.

$^1$H NMR (400 MHz, CD$_3$OD) δ 7.62 (d, J=8.6 Hz, 2H), 7.43 (d, J=8.2 Hz, 2H), 4.03 (br s, 1H), 3.87-3.61 (m, 7H), 3.42 (br s, 1H), 2.77 (d, J=2.0 Hz, 6H), 2.61 (br d, J=14.1 Hz, 1H), 2.37-2.26 (m, 2H), 2.04-1.79 (m, 3H), 1.57 (br d, J=13.3 Hz, 1H), 1.35-1.24 (m, 5H), 1.03 (br dd, J=4.1, 9.6 Hz, 1H), 0.91 (t, J=5.5 Hz, 1H).

To a solution of 6-(pyrimidin-2-yl)bicyclo[4.1.0]heptan-3-one (INTERMEDIATE E) (10.66 mg, 0.057 mmol) and INTERMEDIATE J (30 mg, 0.057 mmol) in DCM (2 mL) was added TMSOTf (50.3 mg, 0.227 mmol) at 0° C. and stirred at 0° C. for 1 h. Triethylsilane (26.3 mg, 0.227 mmol) was added and the mixture was stirred at 0° C. for 1 h. LCMS showed desired compound was found. The mixture was quenched with water (2 mL), extracted with DCM (2 mL×3). The organic layers were combined and dried with Na$_2$SO$_4$, filtered. The solution was concentrated and purified by prep-HPLC (C18, H2O/MeCN with TFA modifier) to give the title compound. LCMS m/z (M+H): 468.2 required, 468.2 found. $^1$H NMR (500 MHz, CD$_3$OD) δ 8.68-8.58 (m, 2H), 7.29-7.13 (m, 1H), 4.06 (br s, 1H), 3.91-3.63 (m, 7H), 3.42-3.34 (m, 1H), 2.82-2.67 (m, 7H), 2.60-2.43 (m, 1H), 2.41-2.24 (m, 2H), 2.02-1.60 (m, 4H), 1.52-1.44 (m, 1H), 1.38-1.30 (m, 4H), 1.05 (dd, J=4.0, 6.2 Hz, 1H).

Example 7 methyl (2R,3S,5R)-2-(((7,7-difluoro-6-(pyrimidin-2-yl)bicyclo[4.1.0]heptan-3-yl)oxy)methyl)-3-((N,N-dimethylsulfamoyl)amino)-5-methylpyrrolidine-1-carboxylate (Mixture)

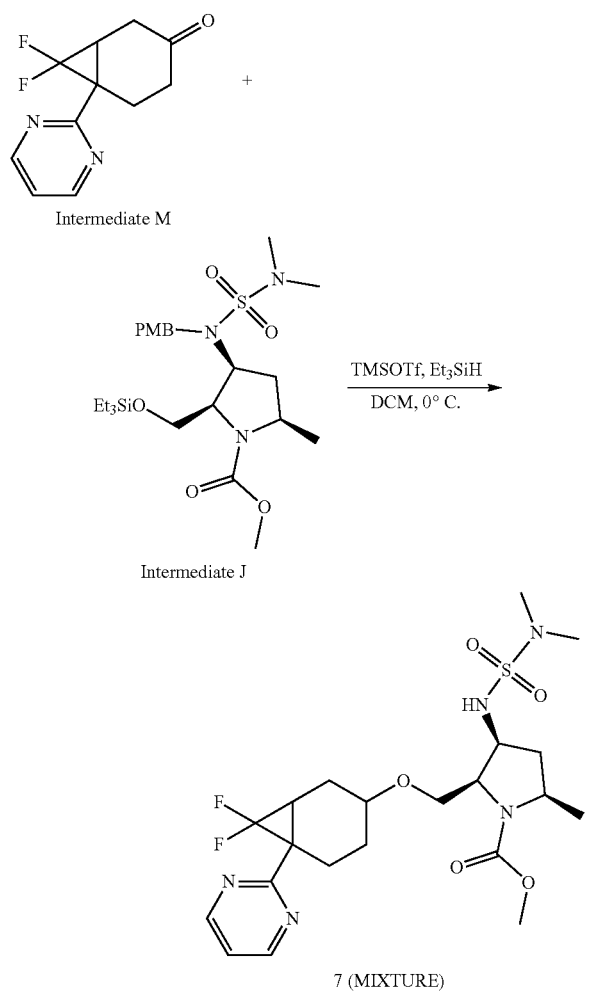

To a solution of INTERMEDIATE M (63.5 mg, 0.283 mmol) and INTERMEDIATE J (60 mg, 0.113 mmol) in DCM (5 mL) was added trimethylsilyl trifluoromethanesulfonate (101 mg, 0.453 mmol) at 0° C. and stirred at 0° C. for 2 h. triethylsilane (52.7 mg, 0.453 mmol) was added and the mixture was stirred at 0° C. for 2 h. LCMS showed desired compound was found. The mixture was quenched with water (2 mL), extracted with DCM (2 mL*3), separated. The organic layers were combined and dried with Na$_2$SO$_4$, filtered. The solution was concentrated and purified by prep-HPLC (C18, H2O/MeCN with TFA modifier) to give the title compound. LCMS m/z (M+H): 504.3 required, 504.3 found. $^1$H NMR (400 MHz, CD$_3$OD) δ 6.72 (br s, 1H), 6.27-6.13 (m, 2H), 4.11 (br d, J=18.0 Hz, 3H), 3.94-3.54 (m, 9H), 2.83-2.76 (m, 6H), 2.50-2.32 (m, 3H), 2.10-1.86 (m, 3H), 1.77 (br s, 1H), 1.31 (br dd, J=4.3, 14.9 Hz, 3H).

Example 8 isopropyl (2R,3S,5R)-3-((N,N-dimethylsulfamoyl)amino)-5-methyl-2-(((6-(pyrimidin-2-yl)bicyclo[4.1.0]heptan-3-yl)oxy)methyl)pyrrolidine-1-carboxylate (Mixture)

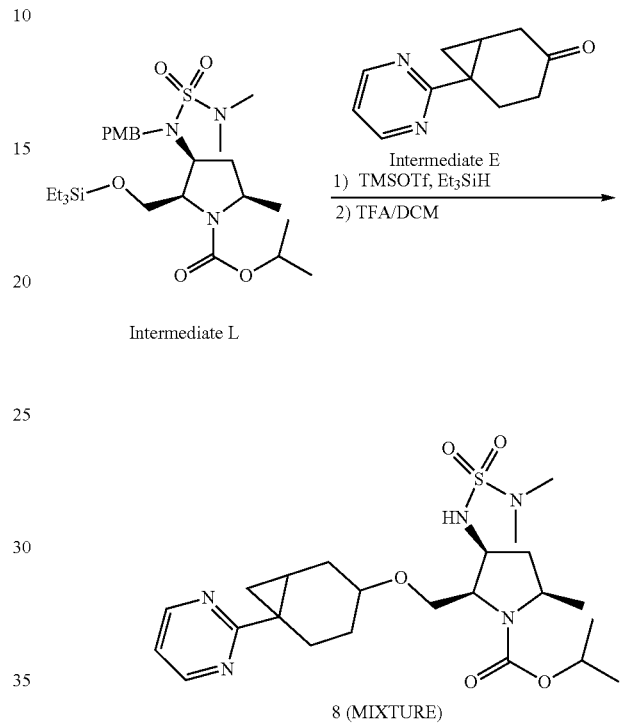

To a solution of INTERMEDIATE E (127 mg, 0.672 mmol) and INTERMEDIATE L (150 mg, 0.269 mmol) in DCM (10 mL) was added trimethylsilyl trifluoromethanesulfonate (239 mg, 1.076 mmol) at 0° C. and stirred at 0° C. for 2 h. Triethylsilane (125 mg, 1.076 mmol) was added and the mixture was stirred at 0° C. for 2 h. LCMS showed desired compound was found. The mixture was quenched with water (5 mL), extracted with DCM (5 mL*3), separated. The organic layers were combined and dried with Na$_2$SO$_4$, filtered. The solution was concentrated and purified by prep-HPLC (C18, H2O/MeCN with NH4HCO3 modifier) to give isopropyl (2R,3S,5R)-3-((N,N-dimethyl sulfamoyl)amino)-5-methyl-2-(((6-(pyrimidin-2-yl)bicyclo[4.1.0]heptan-3-yl)oxy)methyl)pyrrolidine-1-carboxylate. LCMS m/z (M+H): 616.2 required, 616.2 found.

A solution of isopropyl (2R,3S,5R)-3-((N,N-dimethylsulfamoyl)(4-methoxybenzyl)amino)-5-methyl-2-(((6-(pyrimidin-2-yl)bicyclo[4.1.0]heptan-3-yl)oxy)methyl)pyrrolidine-1-carboxylate (22 mg, 0.036 mmol) in DCM (1 mL) and TFA (1 mL) was stirred at 15° C. for 16 h. LCMS showed desired mass was found. The mixture was concentrated and purified by HPLC (C18, H2O/MeCN with TFA modifier) to give the title compound. LCMS m/z (M+H): 496.2 required, 496.2 found. $^1$H NMR (500 MHz, CD$_3$OD) δ 8.63 (d, J=4.9 Hz, 2H), 7.19 (t, J=5.0 Hz, 1H), 4.02 (br s, 1H), 3.91-3.62 (m, 4H), 2.84-2.67 (m, 7H), 2.57-2.43 (m, 1H), 2.40-2.23 (m, 2H), 2.02-1.57 (m, 5H), 1.45 (td, J=3.5, 9.5 Hz, 1H), 1.35-1.26 (m, 9H), 1.06-1.00 (m, 1H).

Example 9 methyl (2R,3S,5R)-3-((N,N-dimethylsulfamoyl)amino)-5-methyl-2-(((6-(pyridin-2-yl)bicyclo[4.1.0]heptan-3-yl)oxy)methyl)pyrrolidine-1-carboxylate (Mixture)

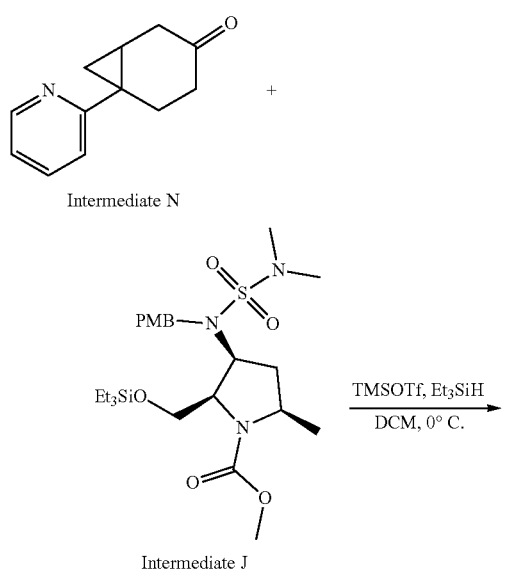

Example 10 methyl (2R,3S,5R)-3-((N,N-dimethylsulfamoyl)amino)-5-methyl-2-(((6-(pyrazin-2-yl)bicyclo[4.1.0]heptan-3-yl)oxy)methyl)pyrrolidine-1-carboxylate (Mixture)

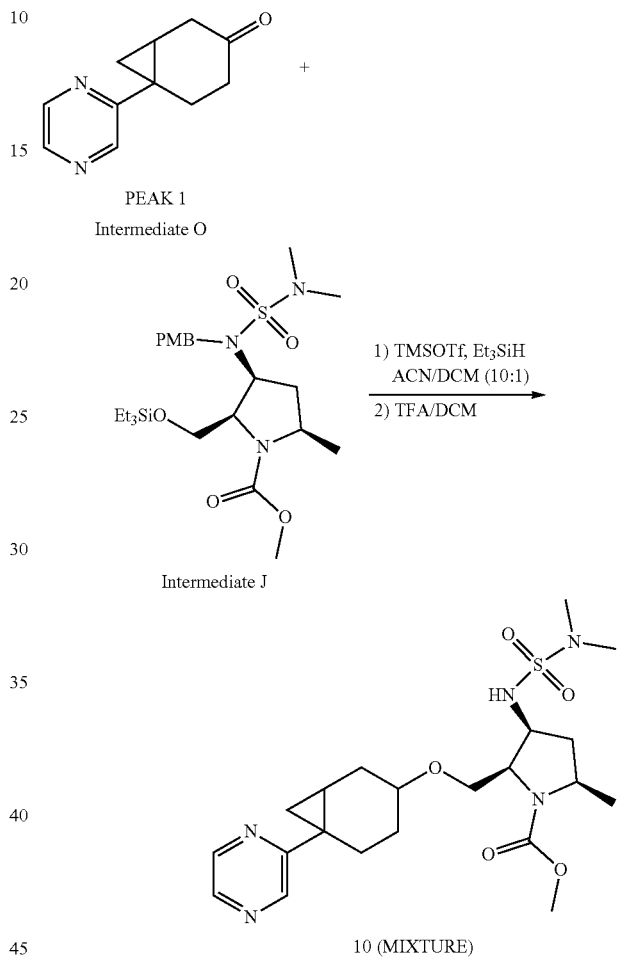

To a solution of INTERMEDIATE N (35.3 mg, 0.189 mmol) and INTERMEDIATE J (40 mg, 0.076 mmol) in DCM (5 mL) was added trimethylsilyl trifluoromethanesulfonate (67.1 mg, 0.302 mmol) at 0° C. and stirred at 0° C. for 2 h. Triethylsilane (35.1 mg, 0.302 mmol) was added and the mixture was stirred at 0° C. for 2 h. LCMS showed desired compound was found. The mixture was quenched with water (2 mL), extracted with DCM (2 mL*3). The organic layers were combined and dried with $Na_2SO_4$, filtered. The solution was concentrated and purified by prep-HPLC (C18, H2O/MeCN with $NH_4HCO_3$ modifier) to afford the title compound. LCMS m/z (M+H): 467.3 required, 467.3 found. $^1$H NMR (500 MHz, $CD_3OD$) δ 8.41 (br d, J=4.1 Hz, 1H), 7.73 (br t, J=7.0 Hz, 1H), 7.40 (d, J=8.1 Hz, 1H), 7.25-7.10 (m, 1H), 4.06 (br s, 1H), 3.94-3.60 (m, 8H), 3.43 (br d, J=10.1 Hz, 1H), 2.80 (s, 6H), 2.67-2.48 (m, 1H), 2.44-2.22 (m, 3H), 2.05-1.74 (m, 2H), 1.67-1.48 (m, 2H), 1.38-1.26 (m, 4H), 1.20 (br dd, J=4.0, 8.9 Hz, 1H), 0.91 (br t, J=5.0 Hz, 1H).

To a solution of INTERMEDIATE O (142 mg, 0.755 mmol) and INTERMEDIATE J (160 mg, 0.302 mmol) in ACN (5 mL) was added trimethylsilyl trifluoromethanesulfonate (268 mg, 1.208 mmol) in DCM (0.25 mL) at 0° C. and stirred at 0° C. for 1 h. Triethylsilane (140 mg, 1.208 mmol) in DCM (0.25 mL) was added and the mixture was stirred at 0° C. for 1 h. LCMS showed desired compound was found. The mixture was quenched with water (5 mL), extracted with DCM (5 mL*3), separated. The organic layers were combined and dried with $Na_2SO_4$, filtered. The solution was concentrated and purified by HPLC (C18, H2O/MeCN with $NH_4HCO_3$ modifier) to give methyl (2R,3S,5R)-3-((N,N-dimethylsulfamoyl)(4-methoxybenzyl)amino)-5-methyl-2-(((6-(pyrazin-2-yl)bicyclo[4.1.0]heptan-3-yl)oxy)methyl)pyrrolidine-1-carboxylate. LCMS m/z (M+H): 588.2 required, 588.2 found.

A solution of methyl (2R,3S,5R)-3-((N,N-dimethylsulfamoyl)(4-methoxybenzyl)amino)-5-methyl-2-(((6-(pyrazin-2-yl)bicyclo[4.1.0]heptan-3-yl)oxy)methyl)pyrrolidine-1-carboxylate (5 mg, 8.51 μmol) in DCM (0.5 ml) and TFA (0.5 ml) was stirred at 15° C. for 16 h. LCMS showed desired mass was found. The mixture was concentrated and purified by HPLC (C18 H2O/MeCN with TFA modifier) to give the title compound. LCMS m/z (M+H): 468.4 required, 468.4 found. ¹H NMR (500 MHz, CD₃OD) δ 8.61 (br s, 1H), 8.47 (br s, 1H), 8.34 (br s, 1H), 4.04 (br s, 1H), 3.85-3.65 (m, 7H), 3.43-3.38 (m, 1H), 2.85-2.71 (m, 6H), 2.61-2.47 (m, 1H), 2.46-2.29 (m, 3H), 2.06-1.90 (m, 1H), 1.80 (br d, J=9.8 Hz, 1H), 1.71-1.53 (m, 2H), 1.36-1.30 (m, 5H), 1.08-0.97 (m, 1H).

Example 11 and Example 12 methyl (2R,3S,5R)-3-((N,N-dimethylsulfamoyl) amino)-5-methyl-2-(((6-(pyrazin-2-yl)bicyclo[4.1.0] heptan-3-yl)oxy)methyl)pyrrolidine-1-carboxylate (11, Peak 1)

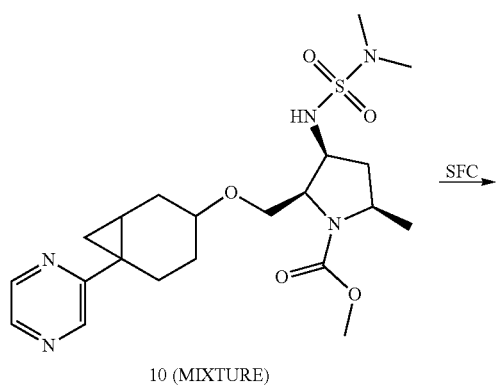

10 (MIXTURE)

10 (MIXTURE) was separated by SFC to give 11 (PEAK 1) and 12 (PEAK 2).
LCMS m/z (M+H): 468.4 required, 468.4 found.
SFC condition:
Column: Chiralpak IC-3 150*4.6 mm I.D., 3 um
Mobile phase: 40% of ethanol (0.05% DEA) in CO₂
Flow rate: 2.5 mL/min
Column temp.: 35° C.
ABPR: 1500 psi 11 (PEAK 1): ¹H NMR (500 MHz, CD₃OD) δ 8.60 (d, J=1.4 Hz, 1H), 8.47 (dd, J=1.5, 2.4 Hz, 1H), 8.33 (d, J=2.4 Hz, 1H), 4.12-3.98 (m, 1H), 3.91-3.61 (m, 7H), 3.43-3.35 (m, 1H), 2.84-2.74 (m, 6H), 2.64-2.54 (m, 1H), 2.44-2.32 (m, 3H), 2.00-1.88 (m, 1H), 1.80 (br d, J=9.9 Hz, 1H), 1.71-1.56 (m, 2H), 1.37-1.31 (m, 5H), 1.01 (dd, J=4.6, 6.0 Hz, 1H).

12 (PEAK 2): ¹H NMR (500 MHz, CD₃OD) δ 8.60 (d, J=1.5 Hz, 1H), 8.47 (dd, J=1.6, 2.4 Hz, 1H), 8.34 (d, J=2.6 Hz, 1H), 4.05 (br s, 1H), 3.88-3.58 (m, 7H), 3.38 (tdd, J=3.1, 6.5, 17.1 Hz, 1H), 2.84-2.69 (m, 6H), 2.56-2.30 (m, 4H), 2.02 (br dd, J=4.5, 8.9 Hz, 1H), 1.81 (br d, J=10.7 Hz, 1H), 1.70-1.56 (m, 2H), 1.34-1.29 (m, 5H), 1.02 (dd, J=4.4, 6.0 Hz, 1H).

Example 13 methyl (2R,3S,5R)-3-((N,N-dimethylsulfamoyl) amino)-5-methyl-2-(((6-(pyrazin-2-yl)bicyclo[4.1.0] heptan-3-yl)oxy)methyl)pyrrolidine-1-carboxylate (Mixture)

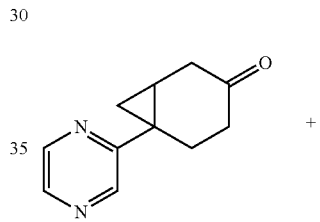

PEAK 2

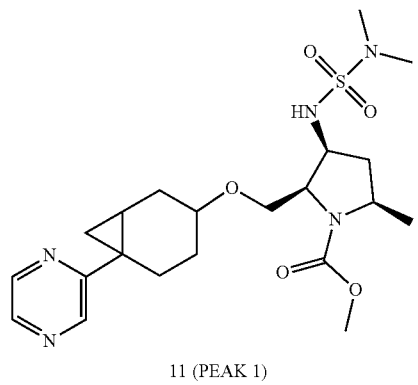

11 (PEAK 1)

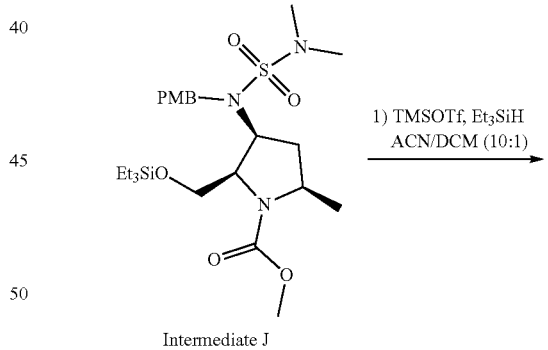

Intermediate J

1) TMSOTf, Et₃SiH
ACN/DCM (10:1)

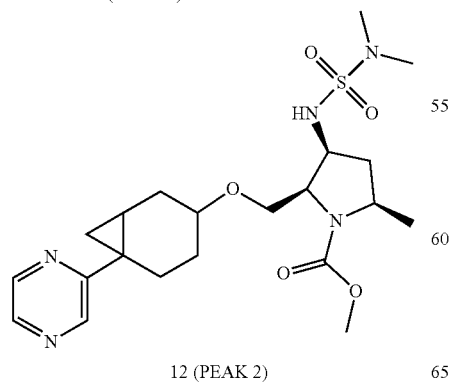

12 (PEAK 2)

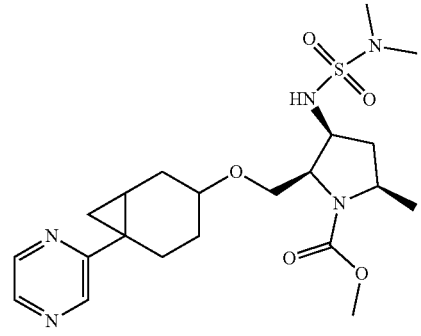

13 (MIXTURE)

To a solution of INTERMEDIATE P (107 mg, 0.566 mmol) and INTERMEDIATE J (120 mg, 0.227 mmol) in ACN (5 mL) was added trimethylsilyl trifluoromethanesulfonate (201 mg, 0.906 mmol) in DCM (0.25 mL) at 0° C. and stirred at 0° C. for 1 h. Triethylsilane (105 mg, 0.906 mmol) in DCM (0.25 mL) was added and the mixture was stirred at 0° C. for 1 h. LCMS showed desired compound was found. The mixture was quenched with water (5 mL), extracted with DCM (5 mL*3). The organic layers were combined and dried with Na$_2$SO$_4$, filtered. The solution was concentrated and purified by prep-HPLC (C18, H2O/MeCN with NH$_4$HCO3 modifier) to give the title compound. LCMS m/z (M+H): 468.4 required, 468.4 found. $^1$H NMR (500 MHz, CD$_3$OD) δ 8.59 (d, J=1.4 Hz, 1H), 8.52-8.41 (m, 1H), 8.33 (d, J=2.6 Hz, 1H), 4.04 (br s, 1H), 3.85-3.64 (m, 7H), 3.40-3.35 (m, 1H), 2.78 (s, 6H), 2.62-2.48 (m, 1H), 2.44-2.31 (m, 3H), 2.05-1.80 (m, 2H), 1.69-1.57 (m, 2H), 1.32 (br d, J=6.0 Hz, 5H), 1.07-0.96 (m, 1H).

Example 14 and Example 15 methyl (2R,3S,5R)-3-((N,N-dimethylsulfamoyl)amino)-5-methyl-2-(((6-(pyrazin-2-yl)bicyclo[4.1.0]heptan-3-yl)oxy)methyl)pyrrolidine-1-carboxylate (14, Peak 1)

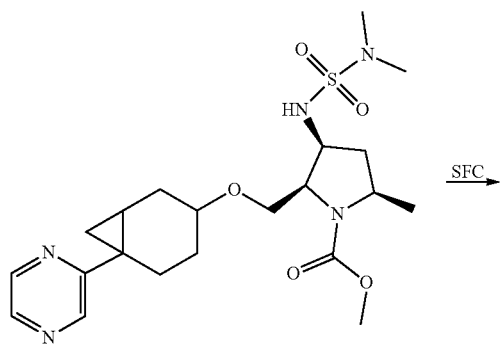

13 (MIXTURE)

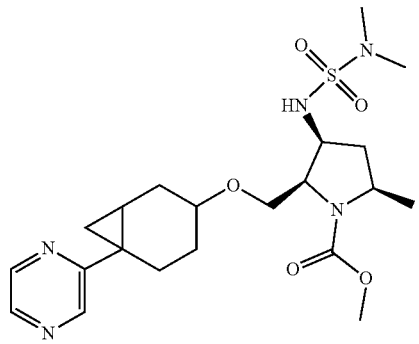

14 (PEAK 1)

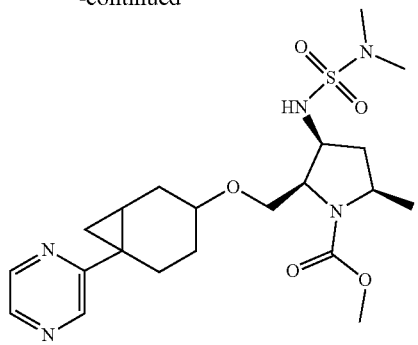

15 (PEAK 2)

13 (MIXTURE) was separated by SFC to give 14 (PEAK 1) and 15 (PEAK 2).
LCMS m/z (M+H): 468.4 required, 468.4 found.
SFC condition:
Column: Chiralpak IC-3 150*4.6 mm I.D., 3 um
Mobile phase: 40% of ethanol (0.05% DEA) in CO$_2$
Flow rate: 2.5 mL/min
Column temp.: 35° C.
ABPR: 1500 psi
14 (PEAK 1): $^1$H NMR (500 MHz, CD$_3$OD) δ 8.60 (d, J=1.1 Hz, 1H), 8.47 (dd, J=1.6, 2.4 Hz, 1H), 8.34 (d, J=2.6 Hz, 1H), 4.04 (br s, 1H), 3.89-3.64 (m, 7H), 3.45-3.36 (m, 1H), 2.85-2.72 (m, 6H), 2.64-2.53 (m, 1H), 2.45-2.29 (m, 3H), 1.99-1.91 (m, 1H), 1.80 (br d, J=10.2 Hz, 1H), 1.71-1.56 (m, 2H), 1.36-1.30 (m, 5H), 1.06-0.99 (m, 1H).
15 (PEAK 2): $^1$H NMR (500 MHz, CD$_3$OD) δ 8.60 (d, J=1.1 Hz, 1H), 8.47 (dd, J=1.5, 2.4 Hz, 1H), 8.33 (d, J=2.6 Hz, 1H), 4.05 (br s, 1H), 3.89-3.61 (m, 7H), 3.43-3.36 (m, 1H), 2.86-2.72 (m, 6H), 2.57-2.32 (m, 4H), 2.07-1.98 (m, 1H), 1.81 (br d, J=9.8 Hz, 1H), 1.70-1.59 (m, 2H), 1.35-1.31 (m, 5H), 1.07-0.98 (m, 1H).

Example 16, 17, 18, 19 and 20 methyl (2R,3S,5R)-5-methyl-3-(methylsulfonamido)-2-(((6-(pyrimidin-2-yl)bicyclo[4.1.0]heptan-3-yl)oxy)methyl)pyrrolidine-1-carboxylate (16, Mixture), methyl (2R,3S,5R)-5-methyl-3-(methylsulfonamido)-2-(((6-(pyrimidin-2-yl)bicyclo[4.1.0]heptan-3-yl)oxy)methyl)pyrrolidine-1-carboxylate (17, Peak 1), methyl (2R,3S,5R)-5-methyl-3-(methylsulfonamido)-2-((((1S,3S,6R)-6-(pyrimidin-2-yl)bicyclo[4.1.0]heptan-3-yl)oxy)methyl)pyrrolidine-1-carboxylate (19, Peak 3), and methyl (2R,3S,5R)-5-methyl-3-(methylsulfonamido)-2-((((1R,3R,6S)-6-(pyrimidin-2-yl)bicyclo[4.1.0]heptan-3-yl)oxy)methyl)pyrrolidine-1-carboxylate (20, Peak 4)

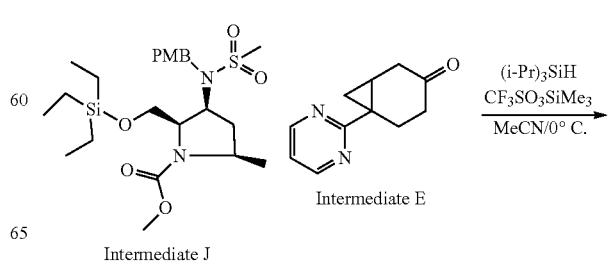

Intermediate J    Intermediate E

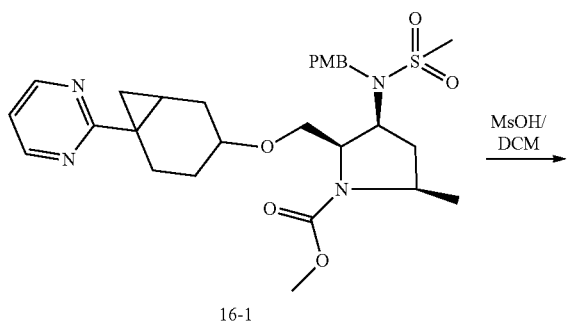

16-1

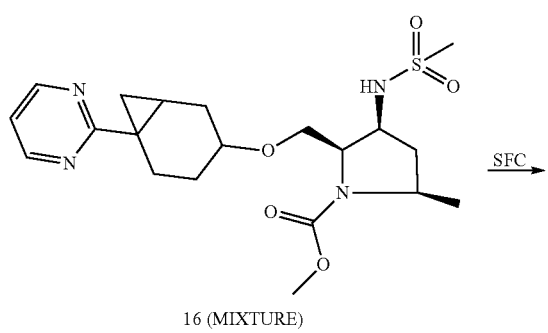

16 (MIXTURE)

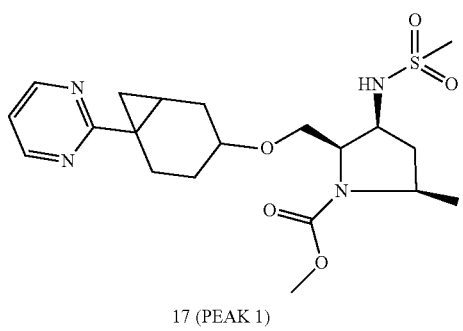

17 (PEAK 1)

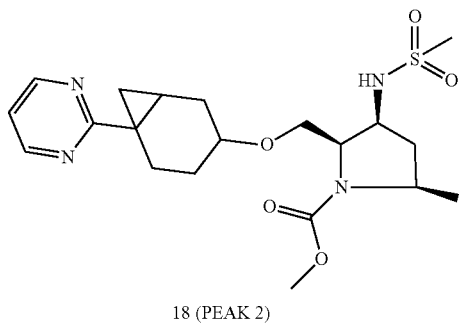

18 (PEAK 2)

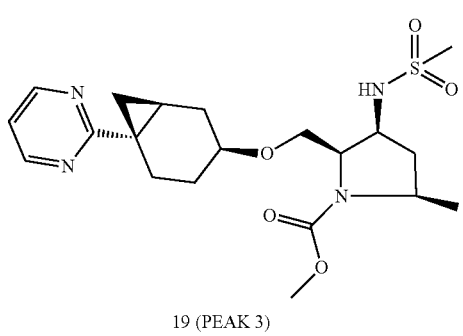

19 (PEAK 3)

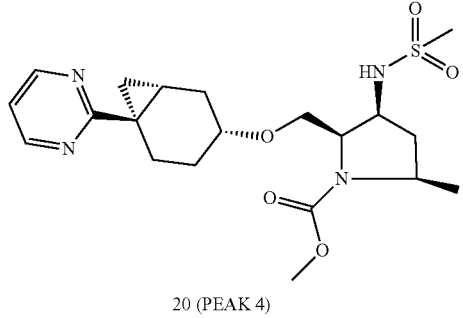

20 (PEAK 4)

Step 1: methyl (2R,3S,5R)-3-(N-(4-methoxybenzyl)methylsulfonamido)-5-methyl-2-(((6-(pyrimidin-2-yl)bicyclo[4.1.0]heptan-3-yl)oxy)methyl)pyrrolidine-1-carboxylate (16-1)

To a solution of methyl (2R,3S,5R)-3-(N-(4-methoxybenzyl)methylsulfonamido)-5-methyl-2-(((triethylsilyl)oxy)methyl)pyrrolidine-1-carboxylate (INTERMEDIATE J) (280 mg, 0.559 mmol) in Acetonitrile (5.0 ml) at 0° C. was added 6-(pyrimidin-2-yl)bicyclo[4.1.0]heptan-3-one (INTERMEDIATE E) (137 mg, 0.727 mmol) followed by triisopropylsilane (0.229 ml, 1.118 mmol) under N2. After stirring 5 mins at 0° C., trimethylsilyl trifluoromethanesulfonate (0.101 ml, 0.559 mmol) was added. The reaction mixture was continued to stir at 0° C. for 45 mins. More triisopropylsilane (0.229 ml, 1.118 mmol, 2 eq) was added at 0° C. After stirring 5 mins at 0° C., trimethylsilyl trifluoromethanesulfonate (0.101 ml, 0.559 mmol, 1 eq) was added. Kept stirring at 0° C. for another 3 hrs and then let it warm up to rt slowly and stirred at rt overnight. The reaction mixture was quenched with sat. aq. NaHCO$_3$ and then extracted by 2 portions of 10 ml of DCM. The combined organic phase was collected and concentrated. The residue was purified by prep silica gel TLC with 4% MeOH/DCM to afford the title compound. MS: 559.0.

Step 2: methyl (2R,3S,5R)-5-methyl-3-(methylsulfonamido)-2-(((6-(pyrimidin-2-yl)bicyclo[4.1.0]heptan-3-yl)oxy)methyl)pyrrolidine-1-carboxylate (16, Mixture), methyl (2R,3S,5R)-5-methyl-3-(methylsulfonamido)-2-(((6-(pyrimidin-2-yl)bicyclo[4.1.0]heptan-3-yl)oxy)methyl)pyrrolidine-1-carboxylate (17, Peak 1), methyl (2R,3S,5R)-5-methyl-3-(methylsulfonamido)-2-((((1S,3S,6R)-6-(pyrimidin-2-yl)bicyclo[4.1.0]heptan-3-yl)oxy)methyl)pyrrolidine-1-carboxylate (19, Peak 3), and methyl (2R,3S,5R)-5-methyl-3-(methylsulfonamido)-2-((((1R,3R,6S)-6-(pyrimidin-2-yl)bicyclo[4.1.0]heptan-3-yl)oxy)methyl)pyrrolidine-1-carboxylate (20, Peak 4)

To a solution of methyl (2R,3S,5R)-3-(N-(4-methoxybenzyl)methylsulfonamido)-5-methyl-2-(((6-(pyrimidin-2-yl)bicyclo[4.1.0]heptan-3-yl)oxy)methyl)pyrrolidine-1-carboxylate (16-1, 137 mg, 0.245 mmol) in CH2Cl2 (3 ml) was added MsOH (24 μl, 0.368 mmol) at rt under N2. The reaction mixture was stirred at rt for 30 mins. And then the reaction mixture was concentrated. The residue was purified by column chromatography on C18 (5-95% MeCN/water with 0.05% TFA modifier) to afford racemic product.

16 (MIXTURE): MS: 439.2 (M+1). 1H NMR (500 MHz, Methanol-d4) δ 8.69 (s, 2H), 7.27 (s, 1H), 4.05 (s, 1H), 3.99-3.89 (m, 1H), 3.87-3.55 (m, 7H), 3.52-3.28 (m, 3H), 3.00 (s, 3H), 2.92 (s, 1H), 2.63-2.12 (m, 3H), 1.90 (ddd, J=61.3, 43.2, 30.0 Hz, 4H), 1.63 (s, 1H), 1.58-1.44 (m, 1H), 1.34 (s, 2H), 1.12 (dd, J=17.7, 8.5 Hz, 2H), 0.92 (s, 1H).

16 (MIXTURE) was purified using chiral resolution (Preparative Method: AD-H (2×25 cm); 20% ethanol/CO2; 100 bar; 60 mL/min, 220 nm; inj vol.: 0.3 mL; 10 mg/mL ethanol).

17 (PEAK 1): MS: 439.2 (M+1). 1H NMR (500 MHz, Methanol-d4) δ 8.62 (s, 2H), 7.24-7.11 (m, 1H), 4.04 (s, 1H), 4.00-3.89 (m, 1H), 3.88-3.77 (m, 1H), 3.69 (d, J=18.4 Hz, 5H), 3.32 (s, 6H), 3.00 (s, 3H), 2.72 (t, J=13.0 Hz, 1H), 2.62-2.49 (m, 1H), 2.44-2.33 (m, 1H), 2.27 (d, J=14.5 Hz, 1H), 1.86 (dd, J=34.4, 11.1 Hz, 2H), 1.76-1.59 (m, 2H), 1.46 (d, J=8.8 Hz, 1H), 1.32 (d, J=16.0 Hz, 3H), 1.02 (s, 1H).

18 (PEAK 2): MS: 439.2 (M+1). 1H NMR (500 MHz, Methanol-d4) δ 8.62 (s, 2H), 7.26-7.11 (m, 1H), 4.05 (s, 1H), 4.00-3.89 (m, 1H), 3.87-3.78 (m, 1H), 3.67 (d, J=31.5 Hz, 5H), 3.32 (s, 5H), 3.00 (s, 3H), 2.74 (t, J=11.9 Hz, 1H), 2.55-2.23 (m, 3H), 1.96 (d, J=10.8 Hz, 1H), 1.91-1.57 (m, 3H), 1.40 (d, J=61.1 Hz, 5H), 1.02 (s, 1H).

19 (PEAK 3): MS: 439.2 (M+1). 1H NMR (500 MHz, Methanol-d4) δ 8.64 (s, 2H), 7.29-7.12 (m, 1H), 4.12-3.88 (m, 2H), 3.70 (s, 5H), 3.47 (s, 1H), 3.32 (s, 5H), 2.92 (s, 4H), 2.44-2.24 (m, 2H), 1.95 (d, J=12.2 Hz, 1H), 1.76 (dd, J=53.3, 9.0 Hz, 4H), 1.49 (d, J=20.6 Hz, 2H), 1.11 (s, 3H), 0.87 (s, 1H).

20 (PEAK 4): MS: 439.2 (M+1). 1H NMR (500 MHz, Methanol-d4) δ 8.62 (s, 2H), 7.24-7.11 (m, 1H), 4.04 (s, 1H), 4.00-3.89 (m, 1H), 3.88-3.77 (m, 1H), 3.69 (d, J=18.4 Hz, 5H), 3.32 (s, 5H), 3.00 (s, 3H), 2.72 (t, J=13.0 Hz, 1H), 2.62-2.49 (m, 1H), 2.44-2.33 (m, 1H), 2.27 (d, J=14.5 Hz, 1H), 1.86 (dd, J=34.4, 11.1 Hz, 2H), 1.76-1.59 (m, 2H), 1.46 (d, J=8.8 Hz, 1H), 1.32 (d, J=16.0 Hz, 4H), 1.02 (s, 1H).

Example 21, 22, 23, 24, and 25 methyl (2R,3S)-3-(methylsulfonamido)-2-(((6-(pyrimidin-2-yl)bicyclo[4.1.0]heptan-3-yl)oxy)methyl)pyrrolidine-1-carboxylate (21, Mixture), methyl (2R,3S)-3-(methylsulfonamido)-2-((((1S,3S,6R)-6-(pyrimidin-2-yl)bicyclo[4.1.0]heptan-3-yl)oxy)methyl)pyrrolidine-1-carboxylate (24, Peak 3), and methyl (2R,3S)-3-(methylsulfonamido)-2-((((1R,3R,6S)-6-(pyrimidin-2-yl)bicyclo[4.1.0]heptan-3-yl)oxy)methyl)pyrrolidine-1-carboxylate (25, Peak 4)

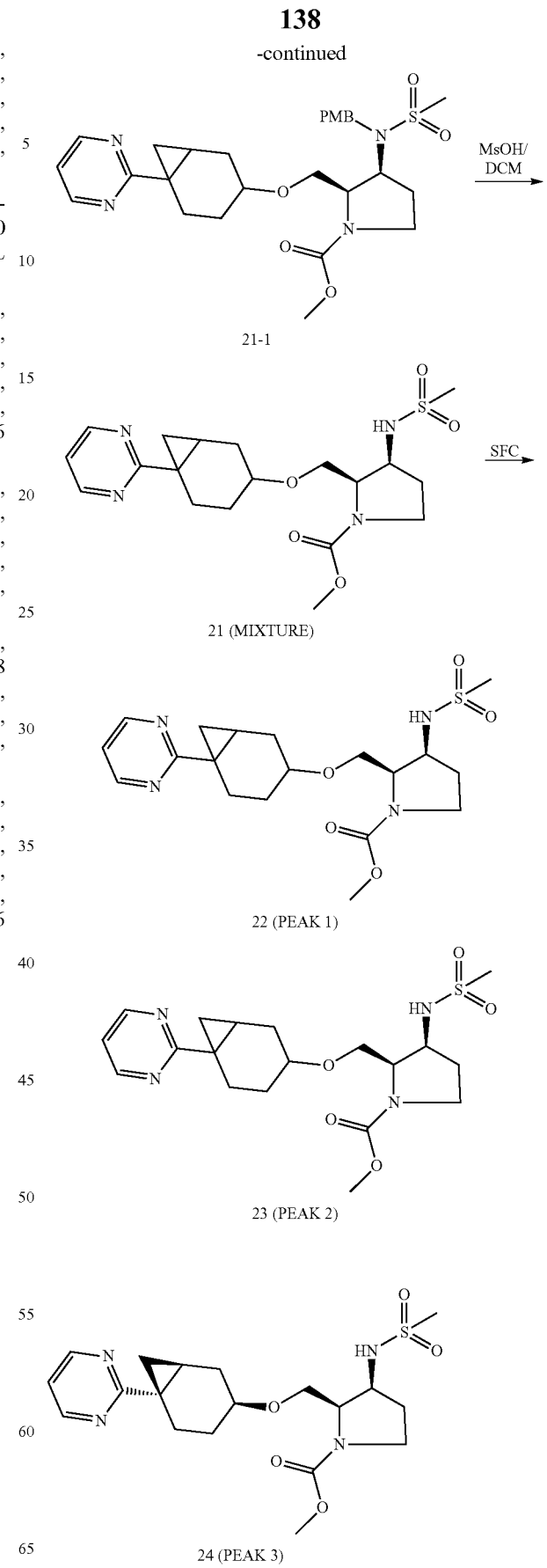

-continued

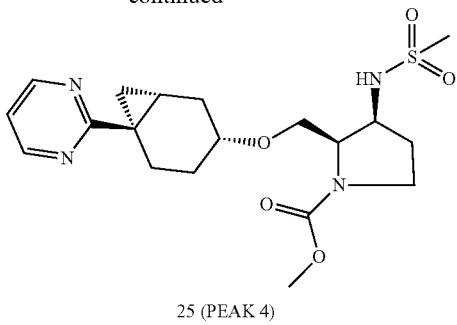

25 (PEAK 4)

Step 1: methyl (2R,3S)-3-(N-(4-methoxybenzyl)
methylsulfonamido)-2-(((6-(pyrimidin-2-yl)bicyclo
[4.1.0]heptan-3-yl)oxy)methyl)pyrrolidine-1-carboxylate (21-1)

To a solution of methyl (2R,3S)-2-(((tert-butyldimethylsilyl)oxy)methyl)-3-(N-(4-methoxybenzyl)methylsulfonamido)pyrrolidine-1-carboxylate (INTERMEDIATE R, 190 mg, 0.390 mmol) in Acetonitrile (4.0 ml) at 0° C. was added 6-(pyrimidin-2-yl)bicyclo[4.1.0]heptan-3-one (INTERMEDIATE E) (85 mg, 0.449 mmol) followed by triisopropylsilane (0.160 ml, 0.781 mmol) under N2. After stirring 5 mins at 0° C., trimethylsilyl trifluoromethanesulfonate (0.071 ml, 0.390 mmol) was added. The reaction mixture was continued to stir at 0° C. for 20 mins. More triisopropylsilane (0.160 ml, 0.781 mmol, 2 eq) was added at 0° C. After stirring 5 mins at 0° C., trimethylsilyl trifluoromethanesulfonate (0.071 ml, 0.390 mmol, 1 eq) was added. Kept stirring at 0° C. for another 3 hrs. The reaction mixture was quenched with sat. aq. NaHCO$_3$. The reaction mixture was extracted by 2 portions of 10 ml of DCM. The combined organic phase was collected and concentrated to leave yellow oil. The residue was purified by prep silica gel TLC with 3% MeOH/DCM to afford the title compound. MS: 545.3 (M+1).

Step 2: methyl (2R,3S)-3-(methylsulfonamido)-2-
(((6-(pyrimidin-2-yl)bicyclo[4.1.0]heptan-3-yl)oxy)
methyl)pyrrolidine-1-carboxylate (21, Mixture),
methyl (2R,3S)-3-(methylsulfonamido)-2-((((1S,3S,
6R)-6-(pyrimidin-2-yl)bicyclo[4.1.0]heptan-3-yl)
oxy)methyl)pyrrolidine-1-carboxylate (24, Peak 3),
and methyl (2R,3S)-3-(methylsulfonamido)-2-
((((1R,3R,6S)-6-(pyrimidin-2-yl)bicyclo[4.1.0]heptan-3-yl)oxy)methyl)pyrrolidine-1-carboxylate (25, Peak 4)

To a solution of methyl (2R,3S)-3-(N-(4-methoxybenzyl) methylsulfonamido)-2-(((6-(pyrimidin-2-yl)bicyclo[4.1.0] heptan-3-yl)oxy)methyl)pyrrolidine-1-carboxylate (21-1, 99 mg, 0.182 mmol) in CH2Cl2 (2 ml) was added MsOH (118 μl, 1.818 mmol) at rt under N2. The reaction mixture was stirred at rt for 30 mins. The reaction mixture was concentrated to leave brown film. The residue was purified by column chromatography on C18 (5-95% MeCN/water with 0.05% TFA modifier) to afford racemic product.

21 (MIXTURE): MS: 425.2 (M+1). 1H NMR (500 MHz, Methanol-d4) δ 8.71 (d, J=14.7 Hz, 2H), 7.30 (d, J=13.6 Hz, 1H), 4.11-3.90 (m, 2H), 3.67 (d, J=42.8 Hz, 5H), 3.53-3.13 (m, 4H), 3.09-2.65 (m, 4H), 2.58-1.26 (m, 9H), 1.22-0.82 (m, 1H).

21 (MIXTURE) was purified using chiral resolution (Preparative Method: Column: OJ-H, 21×250 mm; Injection Volume: 0.5 ml; Co-Solvent: 35% MeOH; UV Wavelength: 210 nm; Concentration: 56 mg in 9 ml MeoH).

22 (PEAK 1): MS: 425.2 (M+1). 1H NMR (500 MHz, Methanol-d4) δ 8.62 (s, 2H), 7.26-7.10 (m, 1H), 4.10-3.91 (m, 2H), 3.71 (s, 4H), 3.34 (d, J=18.2 Hz, 3H), 3.02 (s, 3H), 2.76 (t, J=12.2 Hz, 1H), 2.47 (s, 1H), 2.13 (dd, J=51.9, 10.5 Hz, 3H), 1.86-1.61 (m, 3H), 1.46 (d, J=8.5 Hz, 1H), 1.33 (d, J=22.6 Hz, 3H), 1.01 (s, 1H).

23 (PEAK 2): MS: 425.2 (M+1). 1H NMR (500 MHz, Methanol-d4) δ 8.71 (s, 2H), 7.30 (s, 1H), 4.08-3.91 (m, 2H), 3.74 (d, J=30.6 Hz, 5H), 3.44 (s, 1H), 3.34 (d, J=19.4 Hz, 3H), 2.94 (s, 4H), 2.33 (s, 1H), 2.08 (s, 2H), 1.95 (d, J=11.7 Hz, 1H), 1.89-1.70 (m, 3H), 1.56-1.42 (m, 2H), 1.31 (s, 1H), 0.92 (s, 1H).

24 (PEAK 3): MS: 425.2 (M+1). 1H NMR (500 MHz, Methanol-d4) δ 8.68 (s, 2H), 7.26 (s, 1H), 4.12-3.92 (m, 2H), 3.72 (s, 5H), 3.34 (d, J=18.7 Hz, 3H), 3.02 (s, 3H), 2.73 (t, J=12.0 Hz, 1H), 2.40 (s, 1H), 2.20 (dd, J=46.5, 18.4 Hz, 3H), 1.99-1.86 (m, 1H), 1.80-1.59 (m, 2H), 1.55-1.26 (m, 3H), 1.07 (s, 1H).

25 (PEAK 4): MS: 425.2 (M+1). 1H NMR (500 MHz, Methanol-d4) δ 8.70 (s, 2H), 7.27 (s, 1H), 4.08-3.88 (m, 2H), 3.84-3.59 (m, 5H), 3.42 (s, 1H), 3.19 (s, 2H), 3.00 (s, 4H), 2.40-1.71 (m, 5H), 1.60 (s, 2H), 1.50 (s, 1H), 1.31 (s, 1H), 0.91 (s, 2H).

Example 26, 27, 28, 29, and 30 isopropyl (2R,3S,5R)-2-(((6-(5-fluoropyrimidin-2-
yl)bicyclo[4.1.0]heptan-3-yl)oxy)methyl)-5-methyl-
3-(methylsulfonamido)pyrrolidine-1-carboxylate
(26, Mixture), isopropyl (2R,3S,5R)-2-((((1S,3S,
6R)-6-(5-fluoropyrimidin-2-yl)bicyclo[4.1.0]heptan-3-yl)oxy)methyl)-5-methyl-3-(methylsulfonamido)
pyrrolidine-1-carboxylate (28, Peak 3), and
isopropyl (2R,3S,5R)-2-((((1R,3R,6S)-6-(5-fluoropyrimidin-2-yl)bicyclo[4.1.0]heptan-3-yl)oxy)
methyl)-5-methyl-3-(methylsulfonamido)pyrrolidine-1-carboxylate (29, Peak 4)

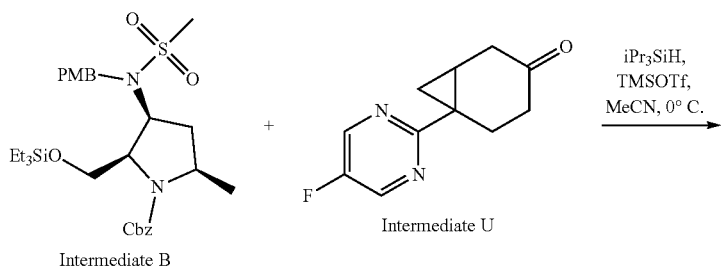

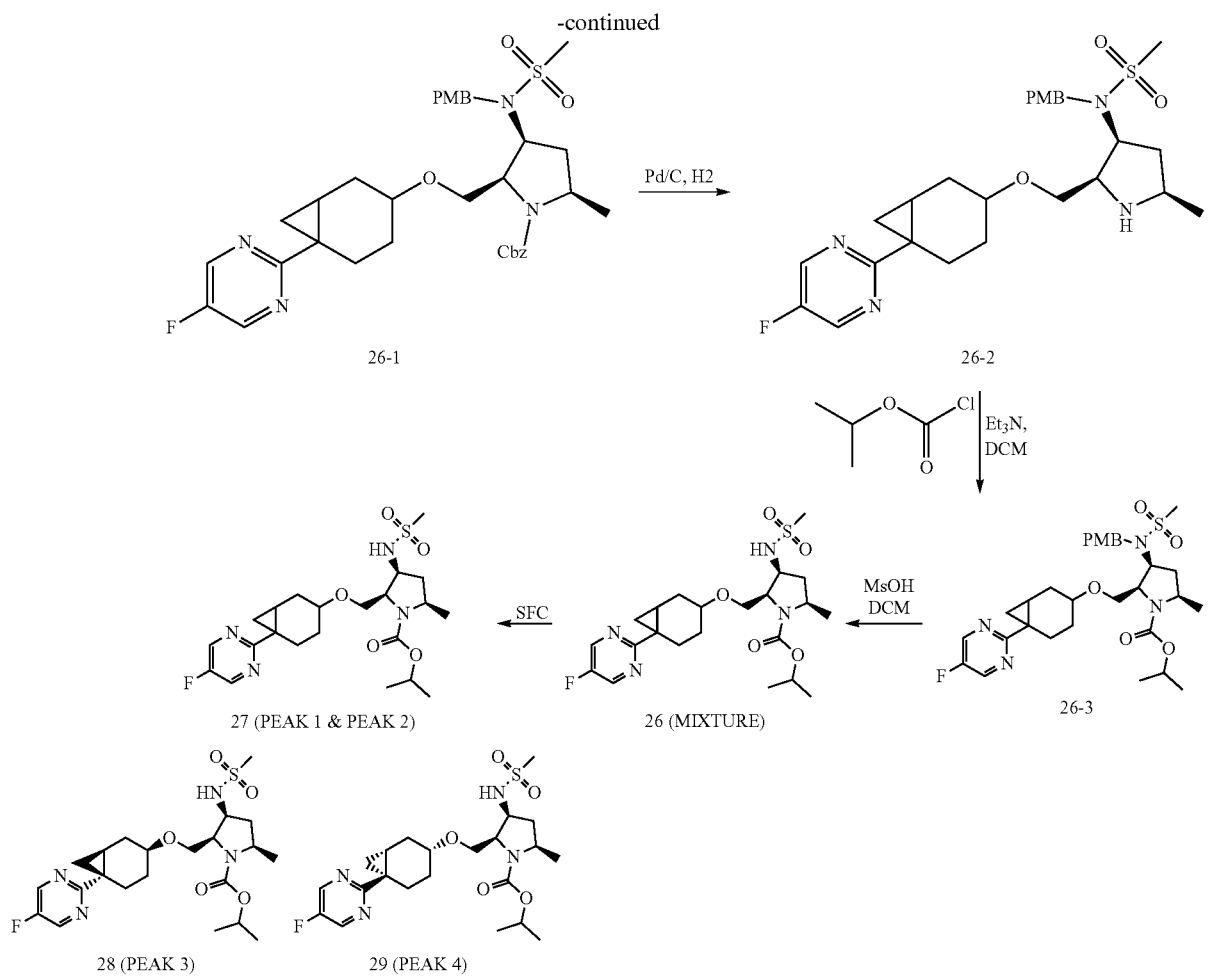

Step 1: Isopropyl (2R,3S,5R)-2-(((6-(5-fluoropyrimidin-2-yl)bicyclo[4.1.0]heptan-3-yl)oxy)methyl)-3-(N-(4-methoxybenzyl)methylsulfonamido)-5-methyl pyrrolidine-1-carboxylate (26-1)

To a solution of benzyl (2R,3S,5R)-3-(N-(4-methoxybenzyl)methylsulfonamido)-5-methyl-2-(((triethylsilyl)oxy)methyl)pyrrolidine-1-carboxylate (INTERMEDIATE B) (400 mg, 0.693 mmol), 6-(5-fluoropyrimidin-2-yl)bicyclo[4.1.0]heptan-3-one (INTERMEDIATE U) (172 mg, 0.832 mmol) in acetonitrile (10 ml) was added triisopropylsilane (220 mg, 1.387 mmol), followed by addition of trimethylsilyl trifluoromethanesulfonate (185 mg, 0.832 mmol) at −20° C. under N2. The reaction mixture was raised to 0° C. and stirred for 2 h, then raised to rt and stirred for overnight. The reaction was worked up by addition of 1 ml of sat. aq. NaHCO$_3$. The organic phase was collected, concentrated and chromatographed over silica gel (EtOAc in hexanes 0-100%) to give the title compound. LC-MS 653.5 (M+1).

Step 2: N-((2R,3S,5R)-2-(((6-(5-fluoropyrimidin-2-yl)bicyclo[4.1.0]heptan-3-yl)oxy)methyl)-5-methylpyrrolidin-3-yl)-N-(4-methoxybenzyl)methanesulfonamide (26-2)

To a solution of benzyl (2R,3S,5R)-2-(((6-(5-fluoropyrimidin-2-yl)bicyclo[4.1.0]heptan-3-yl)oxy)methyl)-3-(N-(4-methoxybenzyl)methylsulfonamido)-5-methylpyrrolidine-1-carboxylate (26-1) (102 mg, 0.156 mmol) in tetrahydrofuran (10 ml) was added Palladium on carbon (1.663 mg, 0.016 mmol), degassed, then refilled with H2 (3.15 mg, 1.563 mmol) from balloon. The reaction was stirred for 0.5 h. The crude was filtered through a celite pad. The filtrate was concentrated, and the crude was chromatographed using reverse phase HPLC (acetonitrile in H2O 10-100%) to give the title compound. LC-MS 519.3.

Step 3: isopropyl (2R,3S,5R)-2-(((6-(5-fluoropyrimidin-2-yl)bicyclo[4.1.0]heptan-3-yl)oxy)methyl)-3-(N-(4-methoxybenzyl)methylsulfonamido)-5-methylpyrrolidine-1-carboxylate (26-3)

To a solution of N-((2R,3S,5R)-2-(((6-(5-fluoropyrimidin-2-yl)bicyclo[4.1.0]heptan-3-yl)oxy)methyl)-5-methylpyrrolidin-3-yl)-N-(4-methoxybenzyl)methanesulfonamide (26-2) (52 mg, 0.100 mmol) in CH2Cl2 (2 ml) was added TEA (0.028 ml, 0.201 mmol) and isopropyl carbonochloridate (14.74 mg, 0.120 mmol) at 0° C. under N2. The reaction mixture was stirred for 1 h. To the reaction mixture was added a few drops of methanol. The crude was concentrated and chromatographed over silica gel (0-100% EtOAc in hexanexs) to give the title compound. LC-MS 605.3.

Step 4: isopropyl (2R,3S,5R)-2-(((6-(5-fluoropyrimidin-2-yl)bicyclo[4.1.0]heptan-3-yl)oxy)methyl)-5-methyl-3-(methylsulfonamido)pyrrolidine-1-carboxylate (26, Mixture), isopropyl (2R,3S,5R)-2-(((6-(5-fluoropyrimidin-2-yl)bicyclo[4.1.0]heptan-3-yl)oxy)methyl)-5-methyl-3-(methylsulfonamido)pyrrolidine-1-carboxylate (27, Peak 1 and Peak 2), isopropyl (2R,3S,5R)-2-((((1S,3S,6R)-6-(5-fluoropyrimidin-2-yl)bicyclo[4.1.0]heptan-3-yl)oxy)methyl)-5-methyl-3-(methylsulfonamido)pyrrolidine-1-carboxylate (28, Peak 3), and isopropyl (2R,3S,5R)-2-((((1R,3R,6S)-6-(5-fluoropyrimidin-2-yl)bicyclo[4.1.0]heptan-3-yl)oxy)methyl)-5-methyl-3-(methylsulfonamido)pyrrolidine-1-carboxylate (29, Peak 4)

To a solution of isopropyl (2R,3S,5R)-2-(((6-(5-fluoropyrimidin-2-yl)bicyclo[4.1.0]heptan-3-yl)oxy)methyl)-3-(N-(4-methoxybenzyl)methylsulfonamido)-5-methylpyrrolidine-1-carboxylate (26-3) (32 mg, 0.053 mmol) in CH2Cl2 (2 ml) was added methanesulfonic acid (0.034 ml, 0.529 mmol) at 0° C. under N2. The reaction mixture was stirred at rt for 1 h. The reaction mixture was diluted with 10 ml of DCM, then added a few drops of sat. aq. NaHCO3. The organic phase was collected, dried (MgSO4), filtered and concentrated. The crude was chromatographed over silica gel (EtOAc in Hexanes 0-100%) to give the desired product isopropyl (2R,3S,5R)-2-(((6-(5-fluoropyrimidin-2-yl)bicyclo[4.1.0]heptan-3-yl)oxy)methyl)-5-methyl-3-(methylsulfonamido)pyrrolidine-1-carboxylate (26, MIXTURE). It is a mixture of 4 diastereomers. LC-MS 485.3.

26 (MIXTURE) was purified using chiral resolution (Preparative Method: Column: OJ-H, 21×250 mm; Injection Volume: 0.5 ml; Co-Solvent: 35% MeOH; UV Wavelength: 210 nm; Concentration: 56 mg in 9 ml MeOH).

27 (PEAK 1+PEAK 2): MS: 485.3 (M+1). 1H NMR (500 MHz, Methanol-d4) δ 8.56 (d, J=5.5 Hz, 2H), 4.89 (dt, J=15.0, 6.2 Hz, 1H), 4.03 (s, 1H), 3.94 (tt, J=11.6, 7.8 Hz, 1H), 3.81-3.56 (m, 3H), 3.52-3.41 (m, 1H), 3.00 (s, 1H), 2.93 (s, 2H), 2.30 (ddd, J=19.3, 10.7, 5.9 Hz, 2H), 2.24-2.09 (m, 1H), 1.92 (dtd, J=15.3, 10.3, 9.5, 3.8 Hz, 1H), 1.83 (d, J=14.2 Hz, 2H), 1.56 (td, J=8.5, 5.3 Hz, 2H), 1.51-1.41 (m, 1H), 1.38-1.22 (m, 6H), 1.23-1.02 (m, 3H), 0.85 (dd, J=6.3, 4.2 Hz, 1H).

28 (PEAK 3): MS: 485.3 (M+1). 1H NMR (500 MHz, Methanol-d4) δ 8.55 (s, 2H), 4.97-4.86 (m, 1H), 4.03 (s, 1H), 3.94 (dt, J=12.0, 7.7 Hz, 1H), 3.81 (dt, J=9.3, 6.8 Hz, 1H), 3.69 (d, J=2.5 Hz, 2H), 3.37 (dd, J=6.9, 3.1 Hz, 1H), 3.01 (s, 3H), 2.75 (td, J=13.9, 5.1 Hz, 1H), 2.53 (dd, J=13.6, 6.9 Hz, 1H), 2.38 (dt, J=12.0, 7.4 Hz, 1H), 2.26 (dt, J=14.2, 4.4 Hz, 1H), 1.95-1.74 (m, 2H), 1.74-1.59 (m, 2H), 1.45 (dd, J=9.4, 3.8 Hz, 1H), 1.41-1.23 (m, 10H), 1.01 (dd, J=6.0, 4.0 Hz, 1H).

29 (PEAK 4): MS: 485.3 (M+1). 1H NMR (500 MHz, Methanol-d4) δ 8.55 (s, 2H), 4.90 (dq, J=12.5, 6.2 Hz, 1H), 4.04 (s, 1H), 3.94 (dt, J=12.0, 7.7 Hz, 1H), 3.88-3.76 (m, 1H), 3.71 (dd, J=10.0, 2.4 Hz, 1H), 3.68-3.60 (m, 1H), 3.43-3.36 (m, 1H), 3.33 (s, 6H), 2.77 (ddd, J=14.1, 12.0, 5.2 Hz, 1H), 2.47 (dt, J=13.8, 7.1 Hz, 1H), 2.44-2.33 (m, 1H), 2.27 (dt, J=14.2, 4.5 Hz, 1H), 2.03-1.91 (m, 1H), 1.82 (d, J=9.7 Hz, 1H), 1.77-1.57 (m, 2H), 1.45 (dd, J=9.5, 3.8 Hz, 1H), 1.40-1.18 (m, 10H), 1.01 (dd, J=6.0, 4.0 Hz, 1H).

Example 30 methyl (2R,3S,5R)-3-((fluoromethyl)sulfonamido)-2-((((1S,3S,6R)-6-(5-fluoropyrimidin-2-yl)bicyclo[4.1.0]heptan-3-yl)oxy)methyl)-5-methylpyrrolidine-1-carboxylate

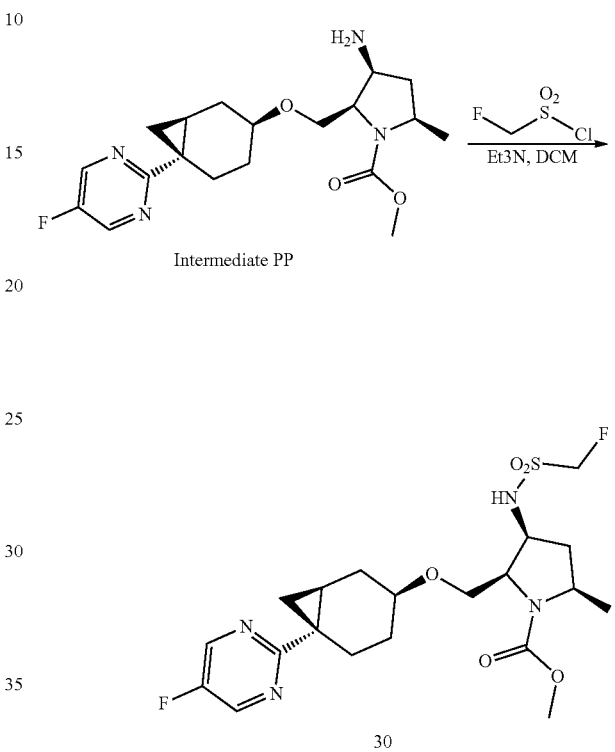

Intermediate PP

30

To a solution of methyl (2R,3S,5R)-3-amino-2-((((1S,6R)-6-(5-fluoropyrimidin-2-yl)bicyclo[4.1.0]heptan-3-yl)oxy)methyl)-5-methylpyrrolidine-1-carboxylate (INTERMEDIATE PP) (180 mg, 0.476 mmol) in CH2Cl2 (10 ml) was added triethylamine (0.133 ml, 0.951 mmol) and fluoromethanesulfonyl chloride (95 mg, 0.713 mmol). The reaction mixture was stirred for 2 h. To the reaction mixture was added a few drops of methanol, then the crude was concentrated and chromatographed using reverse phase HPLC (acetonitrile in H2O 10-100%) to give the title compound. LC-MS 475.9 (M+1). 1H NMR (500 MHz, Methanol-d4) δ 8.55 (s, 2H), 7.19 (s, 1H), 5.26 (ddd, J=46.9, 37.1, 10.0 Hz, 2H), 4.03 (s, 2H), 3.88-3.75 (m, 1H), 3.70 (d, J=9.2 Hz, 4H), 2.82-2.68 (m, 1H), 2.55 (dt, J=14.0, 7.4 Hz, 1H), 2.43-2.32 (m, 1H), 2.27 (d, J=14.3 Hz, 1H), 1.86 (d, J=12.6 Hz, 2H), 1.75-1.58 (m, 2H), 1.46 (d, J=9.0 Hz, 1H), 1.34 (d, J=5.9 Hz, 3H), 1.01 (s, 1H).

The following compounds were prepared from INTERMEDIATE PP according to the general procedure provided in EXAMPLE 30, and procedures herein, by substituting the appropriate methylsulfamoyl chloride. The starting materials are either prepared as described in the intermediates section, commercially available, or may be prepared from commercially available reagents using conventional reactions well known in the art.

| Example Number | Structure | Name | Exact Mass [M + H]+ |
|---|---|---|---|
| 31 | 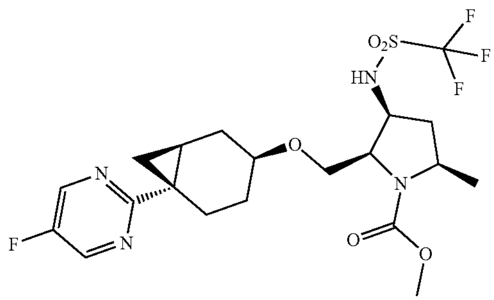 [SMILES: COC(=O)N1[C@H](C)C[C@H](NS(=O)(=O)C(F)(F)F)[C@@H]1CO[C@H]1CC[C@@]2(c3ncc(F)cn3)C[C@H]2C1] | methyl (2R,3S,5R)-2-((((1S,3S,6R)-6-(5-fluoropyrimidin-2-yl)bicyclo[4.1.0]heptan-3-yl)oxy)methyl)-5-methyl-3-((trifluoromethyl)sulfonamido)pyrrolidine-1-carboxylate | 511.7 |
| 32 | 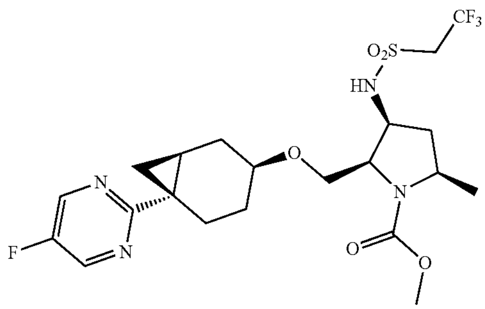 [SMILES: COC(=O)N1[C@H](C)C[C@H](NS(=O)(=O)CC(F)(F)F)[C@@H]1CO[C@H]1CC[C@@]2(c3ncc(F)cn3)C[C@H]2C1] | methyl (2R,3S,5R)-2-((((1S,3S,6R)-6-(5-fluoropyrimidin-2-yl)bicyclo[4.1.0]heptan-3-yl)oxy)methyl)-5-methyl-3-((2,2,2-trifluoroethyl)sulfonamido)pyrrolidine-1-carboxylate | 475.6 |
| 33 | 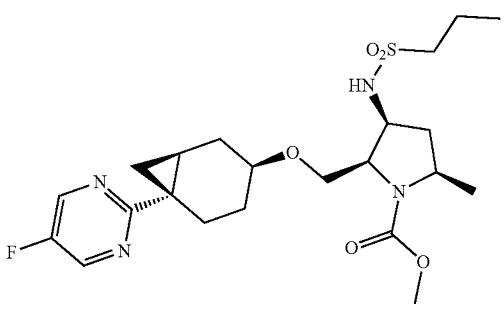 [SMILES: CCCS(=O)(=O)N[C@H]1C[C@@H](C)N(C(=O)OC)[C@H]1CO[C@H]1CC[C@@]2(c3ncc(F)cn3)C[C@H]2C1] | methyl (2R,3S,5R)-2-((((1S,3S,6R)-6-(5-fluoropyrimidin-2-yl)bicyclo[4.1.0]heptan-3-yl)oxy)methyl)-5-methyl-3-(propylsulfonamido)pyrrolidine-1-carboxylate | 485.6 |
| 34 | 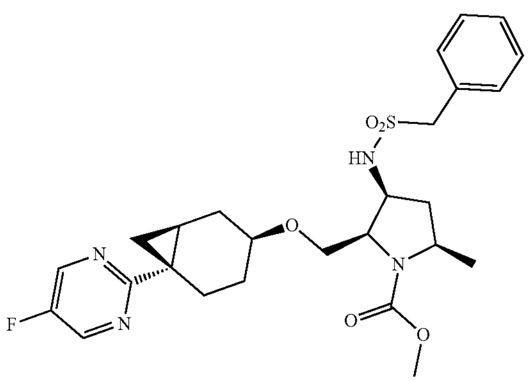 [SMILES: COC(=O)N1[C@H](C)C[C@H](NS(=O)(=O)Cc2ccccc2)[C@@H]1CO[C@H]1CC[C@@]2(c3ncc(F)cn3)C[C@H]2C1] | methyl (2R,3S,5R)-2-((((1S,3S,6R)-6-(5-fluoropyrimidin-2-yl)bicyclo[4.1.0]heptan-3-yl)oxy)methyl)-5-methyl-3-((phenylmethyl)sulfonamido)pyrrolidine-1-carboxylate | 533.8 |

-continued

| Example Number | Structure | Name | Exact Mass [M + H]+ |
|---|---|---|---|
| 35 | 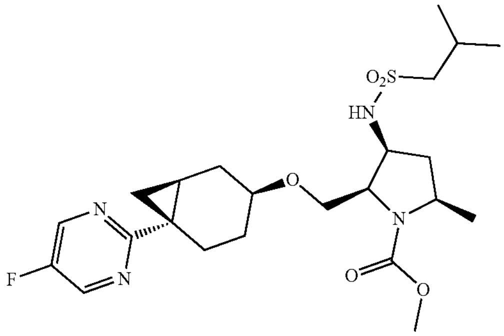 [SMILES: COC(=O)N1[C@H](C)C[C@H](NS(=O)(=O)CC(C)C)[C@@H]1CO[C@H]1CC[C@@]2(c3ncc(F)cn3)C[C@H]2C1] | methyl (2R,3S,5R)-2-((((1S,3S,6R)-6-(5-fluoropyrimidin-2-yl)bicyclo[4.1.0]heptan-3-yl)oxy)methyl)-5-methyl-3-((2-methylpropyl)sulfonamido)pyrrolidine-1-carboxylate | 499.7 |
| 36 | 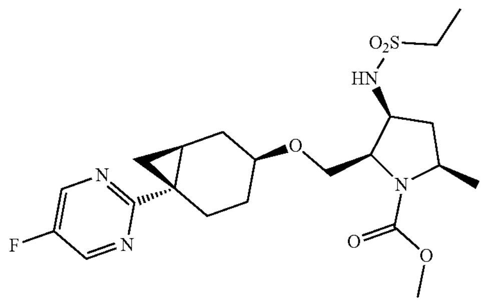 [SMILES: CCS(=O)(=O)N[C@H]1C[C@@H](C)N(C(=O)OC)[C@H]1CO[C@H]1CC[C@@]2(c3ncc(F)cn3)C[C@H]2C1] | methyl (2R,3S,5R)-3-(ethylsulfonamido)-2-((((1S,3S,6R)-6-(5-fluoropyrimidin-2-yl)bicyclo[4.1.0]heptan-3-yl)oxy)methyl)-5-methylpyrrolidine-1-carboxylate | 471.7 |
| 37 | 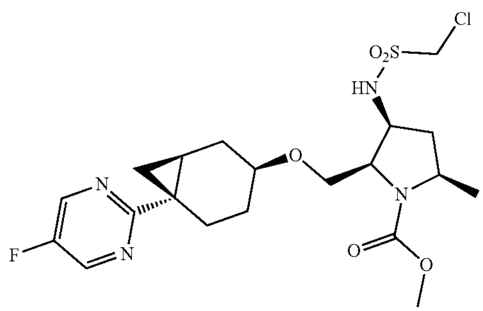 [SMILES: COC(=O)N1[C@H](C)C[C@H](NS(=O)(=O)CCl)[C@@H]1CO[C@H]1CC[C@@]2(c3ncc(F)cn3)C[C@H]2C1] | methyl (2R,3S,5R)-3-((chloromethyl)sulfonamido)-2-((((1S,3S,6R)-6-(5-fluoropyrimidin-2-yl)bicyclo[4.1.0]heptan-3-yl)oxy)methyl)-5-methylpyrrolidine-1-carboxylate | 491.3 |

Example 38 methyl (2R,3S,5R)-2-((((1S,3S,6R)-6-(5-fluoropyrimidin-2-yl)bicyclo[4.1.0]heptan-3-yl)oxy)methyl)-5-methyl-3-((1-methylethyl)sulfonamido)pyrrolidine-1-carboxylate

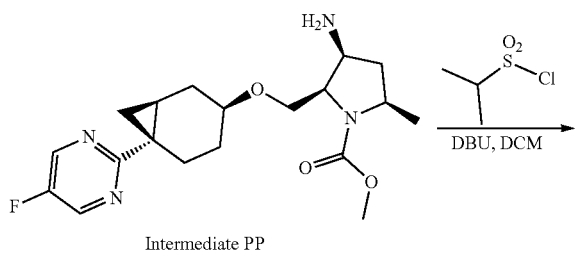

Intermediate PP

-continued

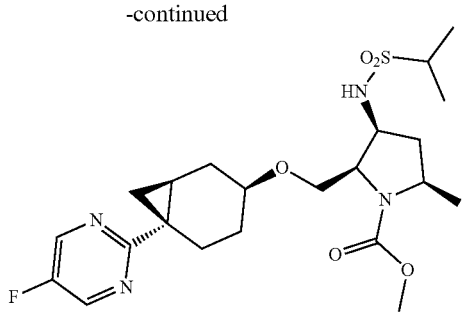

38

To a solution of methyl (2R,3S,5R)-3-amino-2-((((1S,6R)-6-(5-fluoropyrimidin-2-yl)bicyclo[4.1.0]heptan-3-yl)oxy)methyl)-5-methylpyrrolidine-1-carboxylate (INTERMEDIATE PP) (5 mg, 0.013 mmol) in CH2Cl2 (2 ml) was added 2,3,4,6,7,8,9,10-octahydropyrimido[1,2-a]azepine (4.02 mg, 0.026 mmol) and propane-2-sulfonyl chloride (2.83 mg, 0.020 mmol). The reaction mixture was stirred for 2 h. To the reaction was stopped and the crude was concentrated and chromatographed using reverse phase HPLC (acetonitrile in H2O 10-100%) to give the title compound. LC-MS 485.4 (M+1).

The following compounds were prepared from INTERMEDIATE PP according to the general procedure provided in EXAMPLE 38, and procedures herein, by substituting the appropriate methylsulfamoyl chloride. The starting materials are either prepared as described in the intermediates section, commercially available, or may be prepared from commercially available reagents using conventional reactions well known in the art.

| Example Number | Structure | Name | Exact Mass [M + H]+ |
|---|---|---|---|
| 39 | 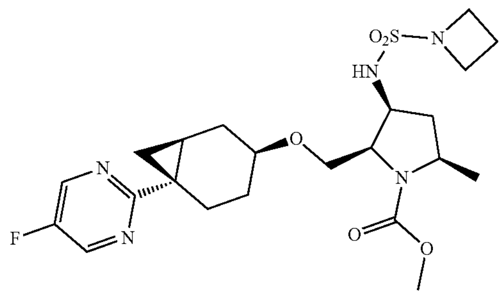 [SMILES: COC(=O)N1[C@H](C)C[C@H](NS(=O)(=O)N2CCC2)[C@@H]1CO[C@H]1CC[C@@]2(c3ncc(F)cn3)C[C@H]2C1] | methyl (2R,3S,5R)-3-(azetidine-1-sulfonamido)-2-((((1S,3S,6R)-6-(5-fluoropyrimidin-2-yl)bicyclo[4.1.0]heptan-3-yl)oxy)methyl)-5-methylpyrrolidine-1-carboxylate | 498.7 |
| 40 | 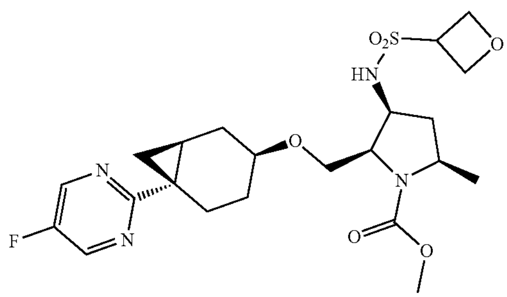 [SMILES: COC(=O)N1[C@H](C)C[C@H](NS(=O)(=O)C2COC2)[C@@H]1CO[C@H]1CC[C@@]2(c3ncc(F)cn3)C[C@H]2C1] | methyl(2R,3S,5R)-2-((((1S,3S,6R)-6-(5-fluoropyrimidin-2-yl)bicyclo[4.1.0]heptan-3-yl)oxy)methyl)-5-methyl-3-(oxetane-3-sulfonamido)pyrrolidine-1-carboxylate | 499.4 |
| 41 | 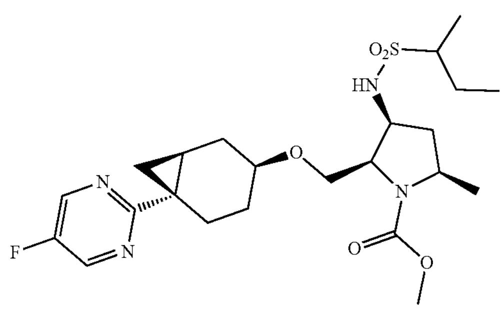 [SMILES: CCC(C)S(=O)(=O)N[C@H]1C[C@@H](C)N(C(=O)OC)[C@H]1CO[C@H]1CC[C@@]2(c3ncc(F)cn3)C[C@H]2C1] | methyl (2R,3S,5R)-2-((((1S,3S,6R)-6-(5-fluoropyrimidin-2-yl)bicyclo[4.1.0]heptan-3-yl)oxy)methyl)-5-methyl-3-((1-methylpropyl)sulfonamido)pyrrolidine-1-carboxylate | 499.7 |
| 42 | 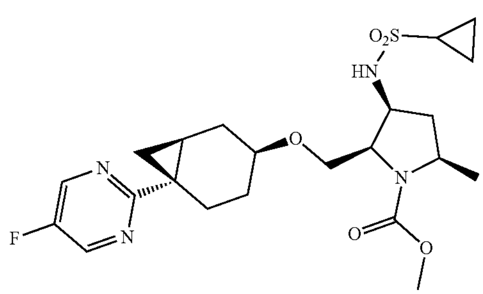 [SMILES: COC(=O)N1[C@H](C)C[C@H](NS(=O)(=O)C2CC2)[C@@H]1CO[C@H]1CC[C@@]2(c3ncc(F)cn3)C[C@H]2C1] | methyl (2R,3S,5R)-3-(cyclopropanesulfonamido)-2-((((1S,3S,6R)-6-(5-fluoropyrimidin-2-yl)bicyclo[4.1.0]heptan-3-yl)oxy)methyl)-5-methylpyrrolidine-1-carboxylate | 483.2 |

The following compounds were prepared from INTERMEDIATE QQ according to the general procedure provided in EXAMPLE 30 or EXAMPLE 38, and procedures herein, by substituting the appropriate methylsulfamoyl chloride.

The starting materials are either prepared as described in the intermediates section, commercially available, or may be prepared from commercially available reagents using conventional reactions well known in the art.

| Example Number | Structure | Name | Exact Mass [M + H]+ |
|---|---|---|---|
| 43 | 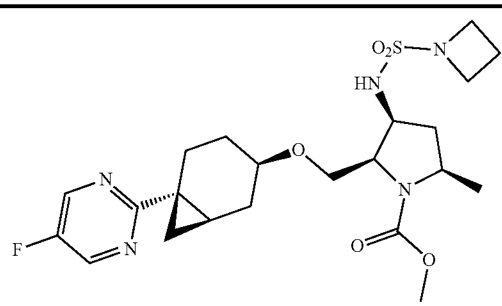 | methyl (2R,3S,5R)-3-(azetidine-1-sulfonamido)-2-((((1R,3R,6S)-6-(5-fluoropyrimidin-2-yl)bicyclo[4.1.0]heptan-3-yl)oxy)methyl)-5-methylpyrrolidine-1-carboxylate | 498.8 |
| 44 | 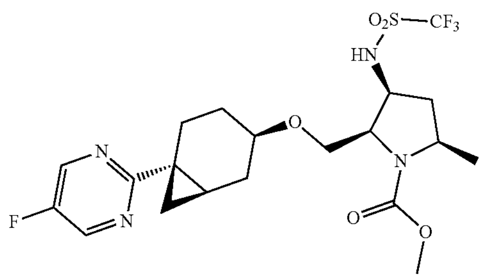 [SMILES: COC(=O)N1[C@H](C)C[C@H](NS(=O)(=O)C(F)(F)F)[C@@H]1CO[C@@H]1CC[C@]2(c3ncc(F)cn3)C[C@@H]2C1] | methyl (2R,3S,5R)-2-((((1R,3R,6S)-6-(5-fluoropyrimidin-2-yl)bicyclo[4.1.0]heptan-3-yl)oxy)methyl)-5-methyl-3-((trifluoromethyl)sulfonamido)pyrrolidine-1-carboxylate | 511.6 |
| 45 | 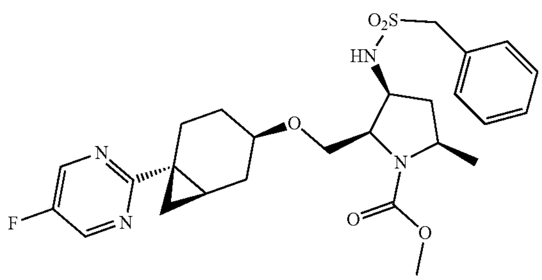 [SMILES: COC(=O)N1[C@H](C)C[C@H](NS(=O)(=O)Cc2ccccc2)[C@@H]1CO[C@@H]1CC[C@]2(c3ncc(F)cn3)C[C@@H]2C1] | methyl (2R,3S,5R)-2-((((1R,3R,6S)-6-(5-fluoropyrimidin-2-yl)bicyclo[4.1.0]heptan-3-yl)oxy)methyl)-5-methyl-3-((phenylmethyl)sulfonamido)pyrrolidine-1-carboxylate | 533.8 |
| 46 | 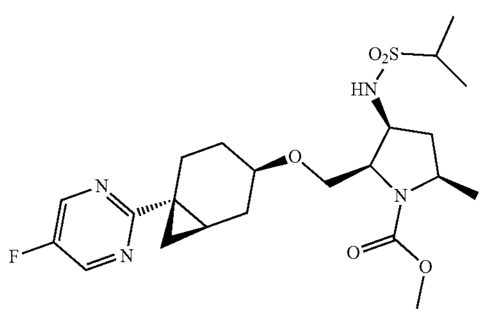 [SMILES: COC(=O)N1[C@H](C)C[C@H](NS(=O)(=O)C(C)C)[C@@H]1CO[C@@H]1CC[C@]2(c3ncc(F)cn3)C[C@@H]2C1] | methyl (2R,3S,5R)-2-((((1R,3R,6S)-6-(5-fluoropyrimidin-2-yl)bicyclo[4.1.0]heptan-3-yl)oxy)methyl)-5-methyl-3-((1-methylethyl)sulfonamido)pyrrolidine-1-carboxylate | 485.5 |
| 47 | 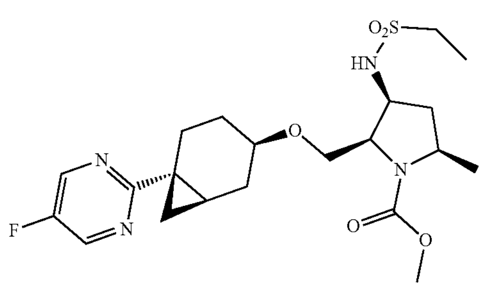 [SMILES: CCS(=O)(=O)N[C@H]1C[C@@H](C)N(C(=O)OC)[C@H]1CO[C@@H]1CC[C@]2(c3ncc(F)cn3)C[C@@H]2C1] | methyl (2R,3S,5R)-3-(ethylsulfonamido)-2-((((1R,3R,6S)-6-(5-fluoropyrimidin-2-yl)bicyclo[4.1.0]heptan-3-yl)oxy)methyl)-5-methylpyrrolidine-1-carboxylate | 471.6 |

Example 48 methyl (2R,3S,5R)-3-((difluoromethyl)sulfonamido)-2-((((1S,3S,6R)-6-(5-fluoropyrimidin-2-yl)bicyclo[4.1.0]heptan-3-yl)oxy)methyl)-5-methylpyrrolidine-1-carboxylate

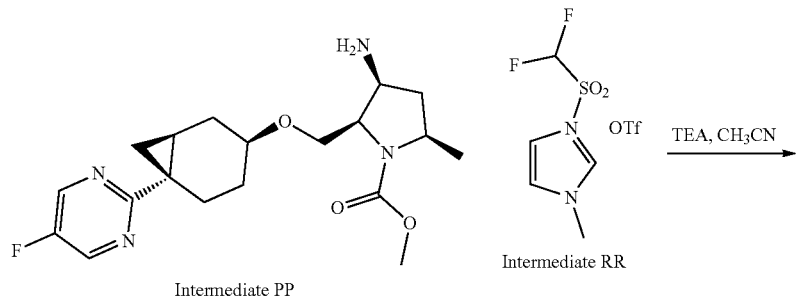

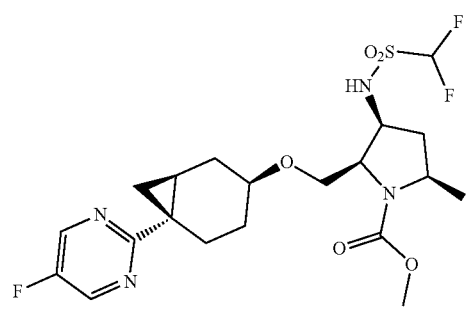

To a solution of methyl (2R,3S,5R)-3-amino-2-((((1S,3S,6R)-6-(5-fluoropyrimidin-2-yl)bicyclo[4.1.0]heptan-3-yl)oxy)methyl)-5-methylpyrrolidine-1-carboxylate (INTERMEDIATE PP) (36 mg, 0.095 mmol) in acetonitrile (5 ml) was added TEA (0.066 ml, 0.476 mmol), followed by 3-((difluoromethyl)sulfonyl)-1-methyl-1H-314-imidazole trifluoromethanesulfonate (INTERMEDIATE RR) (99 mg, 0.285 mmol) under N2 at rt. After stirring for 0.5 h, the reaction mixture was concentrated and chromatographed by reverse phase HPLC (acetonitrile in water, 0-100% with 0.05% of TFA) to give the title compound. LC-MS 493.6 (M+1). 1H NMR (500 MHz, Methanol-d4) δ 8.55 (s, 2H), 6.58 (t, J=53.3 Hz, 2H), 4.05 (d, J=19.1 Hz, 2H), 3.82 (d, J=7.7 Hz, 1H), 3.71 (s, 2H), 3.68 (s, 1H), 2.74 (s, 1H), 2.55 (s, 1H), 2.46-2.33 (m, 1H), 2.27 (d, J=14.1 Hz, 1H), 1.90 (d, J=11.1 Hz, 1H), 1.76-1.58 (m, 2H), 1.45 (d, J=5.9 Hz, 1H), 1.43-1.29 (m, 3H), 1.01 (s, 1H).

Example 49

(3-fluorocyclobutyl)methyl (2R,3S,5R)-2-((((1S,3S,6R)-6-(5-fluoropyrimidin-2-yl)bicyclo[4.1.0]heptan-3-yl)oxy)methyl)-5-methyl-3-(methylsulfonamido)pyrrolidine-1-carboxylate

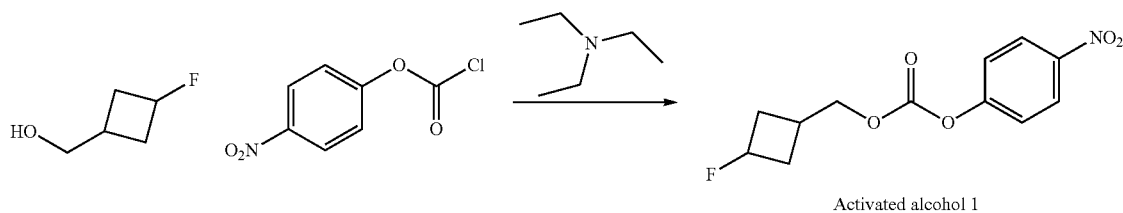

Activated alcohol 1

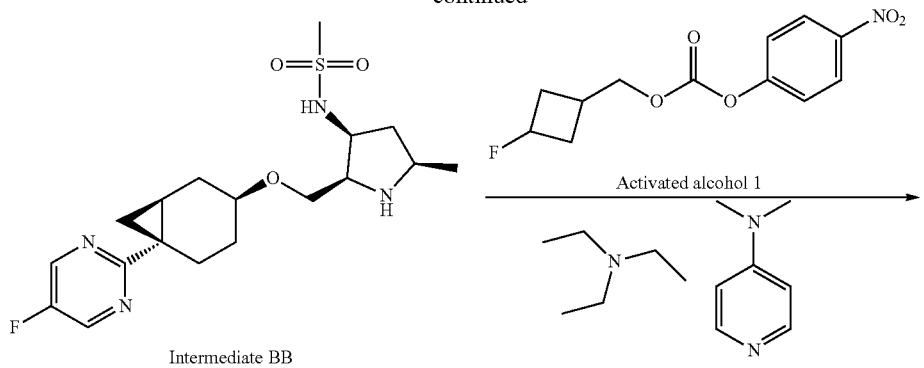

Intermediate BB

Activated alcohol 1

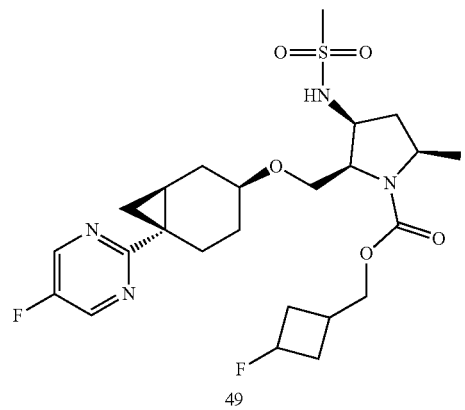

49

Step 1: In-Situ Activation of Alcohol Building Blocks (Activated Alcohol 1)

To a 4 mL vial containing (3-fluorocyclobutyl)methanol (52 mg, 0.5 mmol) was added CH2Cl2 (0.5 mL), 4-nitrophenyl carbonchloridate (50 mg, 0.25 mmol) and triethylamine (0.105 mL, 76 mg, 0.75 mmol). The mixture was stirred at 25 degrees for 16 hours and used directly in without further purification.

Step 2: (3-fluorocyclobutyl)methyl (2R,3S,5R)-2-((((1S,3S,6R)-6-(5-fluoropyrimidin-2-yl)bicyclo[4.1.0]heptan-3-yl)oxy)methyl)-5-methyl-3-(methylsulfonamido)pyrrolidine-1-carboxylate (49)

To a 4 mL vial containing a stir bar was added activated alcohol 1 (201 μl of 0.5M CH2Cl2 solution, 0.0075 mmol). A stock solution of INTERMEDIATE BB (420 mg, 1.054 mmol), triethylamine (320 mg, 441 uL, 3.162 mmol), 4-dimethylaminopyridine (6.4 mg, 0.053 mmol) in CH2Cl2 (2.798 mL) was prepared. 133 uL of this solution (containing 20 mg, 0.05 mmol INTERMEDIATE BB) was added into the vial containing activated alcohol 1 above. The reaction mixture was stirred at 25° C. for 16 h. The reaction mixture was diluted with 800 uL DMSO containing 4% AcOH by volume. The mixture was chromatographed using preparative HPLC reverse phase C18 (Acetonitrile/Water) to afford the title compound. MS: 529.46 (M+1). 1H NMR (500 MHz, DMSO-d6) δ 8.74 (s, 2H), 5.14 (dt, J=55.5, 6.1 Hz, 1H), 3.99 (d, J=6.6 Hz, 2H), 3.89 (m, 1H), 3.84 (m, 1H), 3.70 (s, 1H), 3.51 (s, 1H), 2.95 (s, 3H), 2.70-2.62 (m, 1H), 2.55 (s, 3H), 2.48-2.39 (m, 1H), 2.30-2.13 (m, 7H), 1.76 (d, J=12.7 Hz, 1H), 1.68 (m, 1H), 1.60-1.51 (m, 2H), 1.35 (dd, J=9.4, 3.5 Hz, 1H), 1.22 (d, J=5.9 Hz, 3H).

The following examples shown in the table were prepared in an analogous manner of that described above using appropriate starting materials described previously or commercially available.

| Example Number | Structure | IUPAC Name | Observed Mass [M + H]+ |
|---|---|---|---|
| 50 | 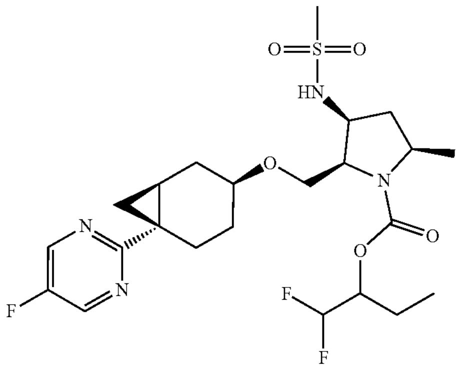 [SMILES: CCC(OC(=O)N1[C@H](C)C[C@H](NS(C)(=O)=O)[C@@H]1CO[C@H]1CC[C@@]2(c3ncc(F)cn3)C[C@H]2C1)C(F)F] | 1,1-difluorobutan-2-yl (2R,3S,5R)-2-(((((1S,3S,6R)-6-(5-fluoropyrimidin-2-yl)bicyclo[4.1.0]heptan-3-yl)oxy)methyl)-5-methyl-3-(methylsulfonamido)pyrrolidine-1-carboxylate | 536.56 |
| 51 | 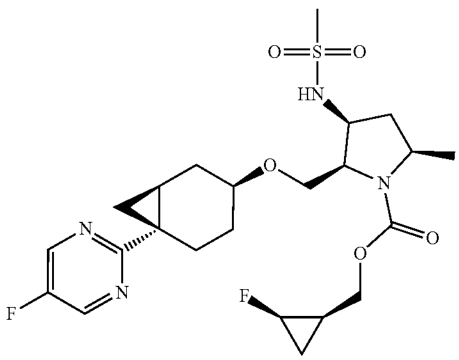 [SMILES: C[C@@H]1C[C@H](NS(C)(=O)=O)[C@H](CO[C@H]2CC[C@@]3(c4ncc(F)cn4)C[C@H]3C2)N1C(=O)OC[C@H]1C[C@H]1F] | ((1R,2R)-2-fluorocyclopropyl)methyl (2R,3S,5R)-2-(((((1S,3S,6R)-6-(5-fluoropyrimidin-2-yl)bicyclo[4.1.0]heptan-3-yl)oxy)methyl)-5-methyl-3-(methylsulfonamido)pyrrolidine-1-carboxylate | 515.49 |
| 52 | 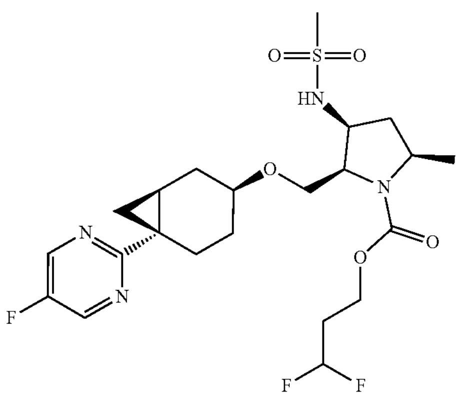 [SMILES: C[C@@H]1C[C@H](NS(C)(=O)=O)[C@H](CO[C@H]2CC[C@@]3(c4ncc(F)cn4)C[C@H]3C2)N1C(=O)OCCC(F)F] | 3,3-difluoropropyl (2R,3S,5R)-2-(((((1S,3S,6R)-6-(5-fluoropyrimidin-2-yl)bicyclo[4.1.0]heptan-3-yl)oxy)methyl)-5-methyl-3-(methylsulfonamido)pyrrolidine-1-carboxylate | 521.45 |
| 53 | 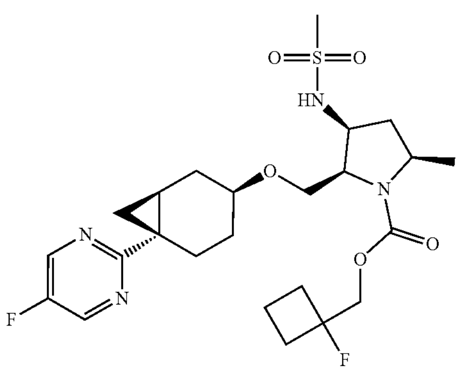 [SMILES: C[C@@H]1C[C@H](NS(C)(=O)=O)[C@H](CO[C@H]2CC[C@@]3(c4ncc(F)cn4)C[C@H]3C2)N1C(=O)OCC1(F)CCC1] | (1-fluorocyclobutyl)methyl (2R,3S,5R)-2-(((((1S,3S,6R)-6-(5-fluoropyrimidin-2-yl)bicyclo[4.1.0]heptan-3-yl)oxy)methyl)-5-methyl-3-(methylsulfonamido)pyrrolidine-1-carboxylate | 529.46 |

| Example Number | Structure | IUPAC Name | Observed Mass [M + H]+ |
|---|---|---|---|
| 54 | 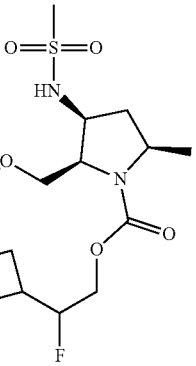 | 2-cyclobutyl-2-fluoroethyl (2R,3S,5R)-2-((((1S,3S,6R)-6-(5-fluoropyrimidin-2-yl)bicyclo[4.1.0]heptan-3-yl)oxy)methyl)-5-methyl-3-(methylsulfonamido)pyrrolidine-1-carboxylate | 543.58 |
| 55 | 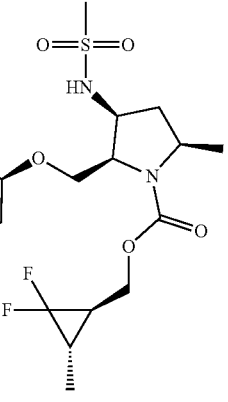 | ((1R,3S)-2,2-difluoro-3-methylcyclopropyl)methyl (2R,3S,5R)-2-((((1S,3S,6R)-6-(5-fluoropyrimidin-2-yl)bicyclo[4.1.0]heptan-3-yl)oxy)methyl)-5-methyl-3-(methylsulfonamido)pyrrolidine-1-carboxylate | 547.47 |
| 56 | 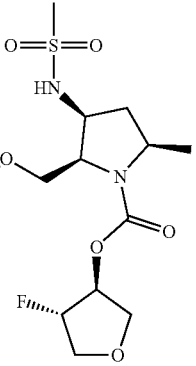 | (3S,4S)-4-fluorotetrahydrofuran-3-yl (2R,3S,5R)-2-((((1S,3S,6R)-6-(5-fluoropyrimidin-2-yl)bicyclo[4.1.0]heptan-3-yl)oxy)methyl)-5-methyl-3-(methylsulfonamido)pyrrolidine-1-carboxylate | 531.2 |
| 57 | 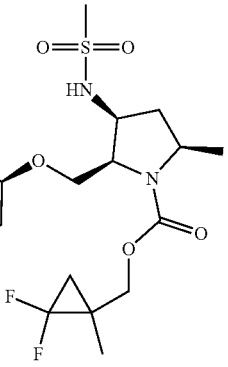 | (2,2-difluoro-1-methylcyclopropyl)methyl (2R,3S,5R)-2-((((1S,3S,6R)-6-(5-fluoropyrimidin-2-yl)bicyclo[4.1.0]heptan-3-yl)oxy)methyl)-5-methyl-3-(methylsulfonamido)pyrrolidine-1-carboxylate | 547.47 |

-continued

| Example Number | Structure | IUPAC Name | Observed Mass [M + H]+ |
|---|---|---|---|
| 58 | 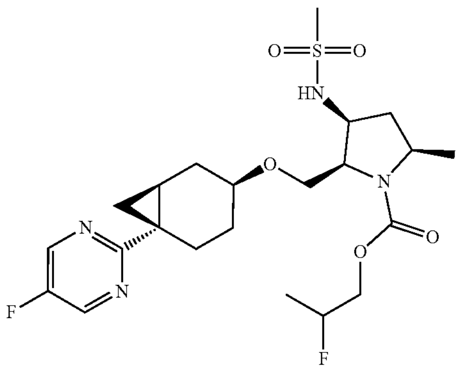 [SMILES: CC(F)COC(=O)N1[C@H](C)C[C@H](NS(C)(=O)=O)[C@@H]1CO[C@H]1CC[C@@]2(c3ncc(F)cn3)C[C@H]2C1] | 2-fluoropropyl (2R,3S,5R)-2-((((1S,3S,6R)-6-(5-fluoropyrimidin-2-yl)bicyclo[4.1.0]heptan-3-yl)oxy)methyl)-5-methyl-3-(methylsulfonamido)pyrrolidine-1-carboxylate | 503.39 |
| 59 | 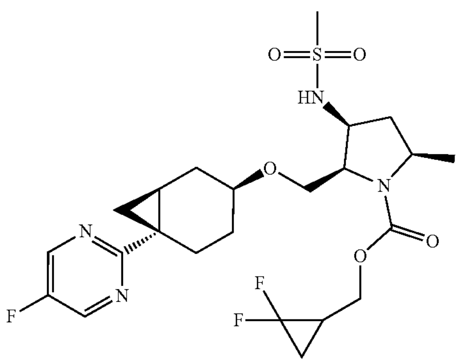 [SMILES: C[C@@H]1C[C@H](NS(C)(=O)=O)[C@H](CO[C@H]2CC[C@@]3(c4ncc(F)cn4)C[C@H]3C2)N1C(=O)OCC1CC1(F)F] | (2,2-difluorocyclopropyl)methyl (2R,3S,5R)-2-((((1S,3S,6R)-6-(5-fluoropyrimidin-2-yl)bicyclo[4.1.0]heptan-3-yl)oxy)methyl)-5-methyl-3-(methylsulfonamido)pyrrolidine-1-carboxylate | 533.45 |
| 60 | 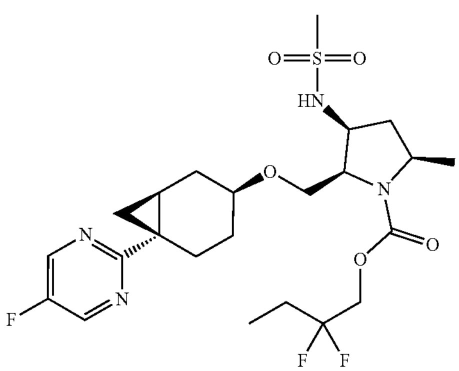 [SMILES: CCC(F)(F)COC(=O)N1[C@H](C)C[C@H](NS(C)(=O)=O)[C@@H]1CO[C@H]1CC[C@@]2(c3ncc(F)cn3)C[C@H]2C1] | 2,2-difluorobutyl (2R,3S,5R)-2-((((1S,3S,6R)-6-(5-fluoropyrimidin-2-yl)bicyclo[4.1.0]heptan-3-yl)oxy)methyl)-5-methyl-3-(methylsulfonamido)pyrrolidine-1-carboxylate | 535.51 |
| 61 | 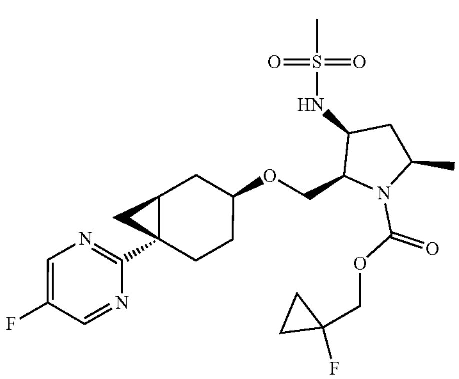 [SMILES: C[C@@H]1C[C@H](NS(C)(=O)=O)[C@H](CO[C@H]2CC[C@@]3(c4ncc(F)cn4)C[C@H]3C2)N1C(=O)OCC1(F)CC1] | (1-fluorocyclopropyl)methyl (2R,3S,5R)-2-((((1S,3S,6R)-6-(5-fluoropyrimidin-2-yl)bicyclo[4.1.0]heptan-3-yl)oxy)methyl)-5-methyl-3-(methylsulfonamido)pyrrolidine-1-carboxylate | 515.44 |

Example 62

2-Fluoroethyl (2R,3S,5R)-2-((((1S,3S,6R)-6-(5-fluoropyrimidin-2-yl)bicyclo[4.1.0]heptan-3-yl)oxy)methyl)-5-methyl-3-(methylsulfonamido)pyrrolidine-1-carboxylate

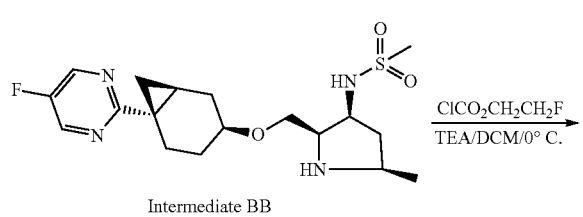

Intermediate BB

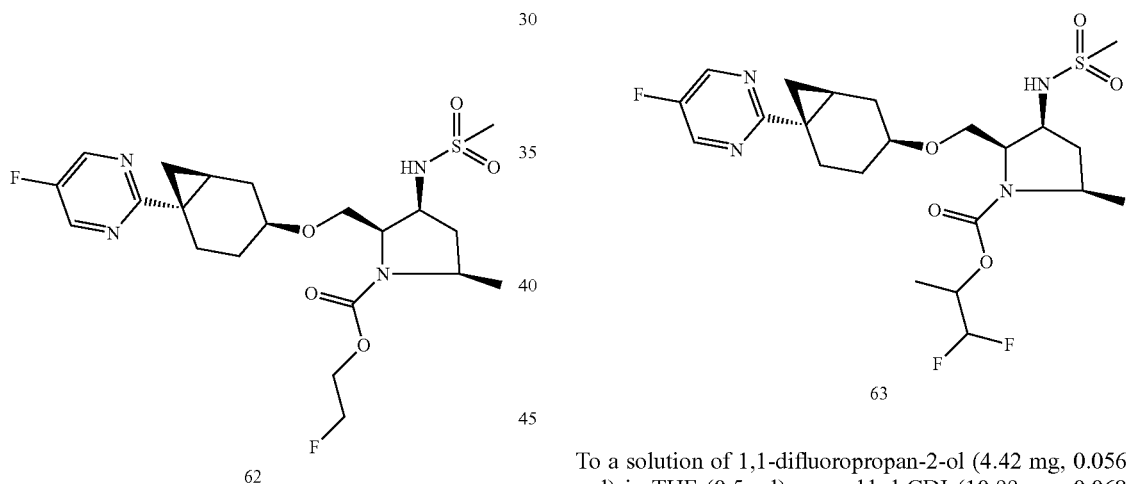

To a solution of N-((2R,3S,5R)-2-((((1S,3S,6R)-6-(5-fluoropyrimidin-2-yl)bicyclo[4.1.0]heptan-3-yl)oxy)methyl)-5-methylpyrrolidin-3-yl)methanesulfonamide (INTERMEDIATE BB, 15 mg, 0.038 mmol) in DCM (0.6 ml) at 0° C. was added TEA (16 µl, 0.113 mmol) followed by 2-fluoroethyl carbonochloridate (4.62 µl, 0.049 mmol). The reaction was stirred at 0° C. for 10 mins. The reaction mixture was quenched with MeOH, concentrated in vacuum. The residue was purified by reverse phase HPLC (5-95% MeCN/water with 0.05% TFA modifier) to afford the title compounds. MS: 489.4 (M+1). 1H NMR (500 MHz, Methanol-d4) δ 8.55 (s, 2H), 4.61 (d, J=47.8 Hz, 2H), 4.33 (d, J=26.7 Hz, 2H), 4.08 (d, J=7.4 Hz, 1H), 4.03-3.79 (m, 2H), 3.71 (s, 2H), 3.01 (s, 3H), 2.74 (td, J=13.3, 5.0 Hz, 1H), 2.54 (dt, J=14.1, 7.8 Hz, 1H), 2.47-2.34 (m, 1H), 2.26 (d, J=14.2 Hz, 1H), 2.11-1.76 (m, 3H), 1.75-1.58 (m, 2H), 1.53-1.24 (m, 5H), 1.07-0.95 (m, 1H).

Example 63

1,1-Difluoropropan-2-yl (2R,3S,5R)-2-((((1S,3S,6R)-6-(5-fluoropyrimidin-2-yl)bicyclo[4.1.0]heptan-3-yl)oxy)methyl)-5-methyl-3-(methylsulfonamido)pyrrolidine-1-carboxylate

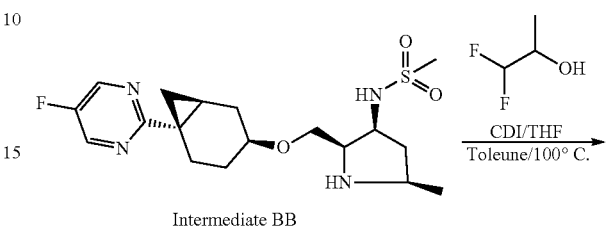

Intermediate BB

To a solution of 1,1-difluoropropan-2-ol (4.42 mg, 0.056 mmol) in THF (0.5 ml) was added CDI (10.99 mg, 0.068 mmol). The reaction mixture was stirred at rt overnight. The reaction was concentrated to remove THF solvent. N-((2R,3S,5R)-2-((((1S,3S,6R)-6-(5-fluoropyrimidin-2-yl)bicyclo[4.1.0]heptan-3-yl)oxy)methyl)-5-methylpyrrolidin-3-yl)methanesulfonamide (INTERMEDIATE BB, 15 mg, 0.038 mmol) was added followed by toluene (1.0 ml) and heated at 100° C. for 2 hrs. The reaction mixture was concentrated in vacuum. The residue was purified by reverse phase HPLC (5-95% MeCN/water with 0.05% TFA modifier) to afford the title compounds. MS: 521.3 (M+1). 1H NMR (500 MHz, Methanol-d4) δ 8.55 (s, 2H), 6.10-5.72 (m, 1H), 4.97 (s, 1H), 4.19-3.60 (m, 5H), 3.01 (s, 3H), 2.75 (t, J=14.9 Hz, 1H), 2.54 (dt, J=14.0, 7.5 Hz, 1H), 2.46-2.35 (m, 1H), 2.27 (d, J=14.2 Hz, 1H), 2.00-1.77 (m, 3H), 1.75-1.59 (m, 2H), 1.52-1.23 (m, 8H), 1.01 (s, 1H).

The following examples shown in the table were prepared in an analogous manner of that described above using appropriate starting materials described previously or commercially available.

| Example Number | Structure | IUPAC Name | Observed Mass [M + H]+ |
|---|---|---|---|
| 64 | 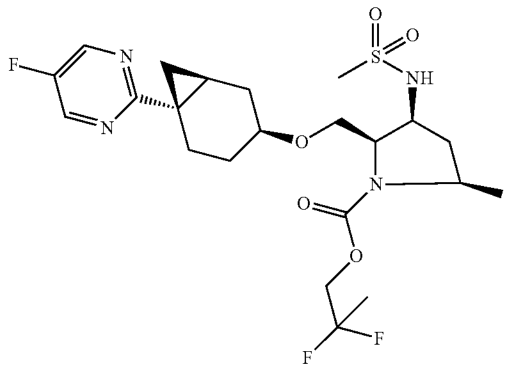 [SMILES: C[C@@H]1C[C@H](NS(C)(=O)=O)[C@H](CO[C@H]2CC[C@@]3(c4ncc(F)cn4)C[C@H]3C2)N1C(=O)OCC(C)(F)F] | 2,2-difluoropropyl (2R,3S,5R)-2-((((1S,3S,6R)-6-(5-fluoropyrimidin-2-yl)bicyclo[4.1.0]heptan-3-yl)oxy)methyl)-5-methyl-3-(methylsulfonamido)pyrrolidine-1-carboxylate | 521.3 |
| 65 | 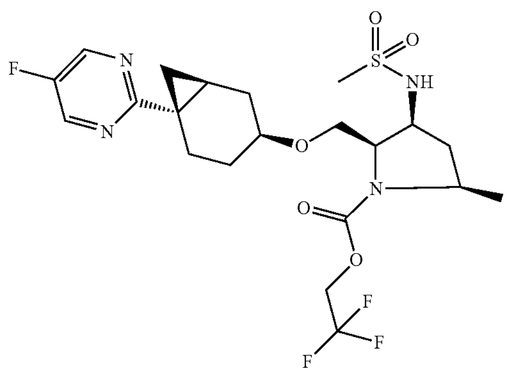 [SMILES: C[C@@H]1C[C@H](NS(C)(=O)=O)[C@H](CO[C@H]2CC[C@@]3(c4ncc(F)cn4)C[C@H]3C2)N1C(=O)OCC(F)(F)F] | 2,2,2-trifluoroethyl-(2R,3S,5R)-2-((((1S,3S,6R)-6-(5-fluoropyrimidin-2-yl)bicyclo[4.1.0]heptan-3-yl)oxy)methyl)-5-methyl-3-methylsulfonamido)pyrrolidine-1-carboxylate | 525.4 |
| 66 | 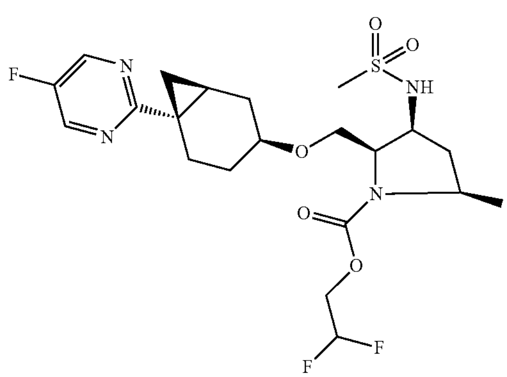 [SMILES: C[C@@H]1C[C@H](NS(C)(=O)=O)[C@H](CO[C@H]2CC[C@@]3(c4ncc(F)cn4)C[C@H]3C2)N1C(=O)OCC(F)F] | 2,2-difluoroethyl-(2R,3S,5R)-2-((((1S,3S,6R)-6-(5-fluoropyrimidin-2-yl)bicyclo[4.1.0]heptan-3-yl)oxy)methyl)-5-methyl-3-(methylsulfonamido)pyrrolidine-1-carboxylate | 507.4 |

Example 67, 68, & 69 methyl (2R,3S,5R)-3-((difluoromethyl)sulfonamido)-5-methyl-2-(((6-(pyrimidin-2-yl)bicyclo[4.1.0]heptan-3-yl)oxy)methyl)pyrrolidine-1-carboxylate (67, Mixture), methyl (2R,3S,5R)-3-((difluoromethyl)sulfonamido)-5-methyl-2-((((1S,3S,6R)-6-(pyrimidin-2-yl)bicyclo[4.1.0]heptan-3-yl)oxy)methyl)pyrrolidine-1-carboxylate (68, Peak 1), and methyl (2R,3S,5R)-3-((difluoromethyl)sulfonamido)-5-methyl-2-((((1R,3R,6S)-6-(pyrimidin-2-yl)bicyclo[4.1.0]heptan-3-yl)oxy)methyl)pyrrolidine-1-carboxylate (69, Peak 2)

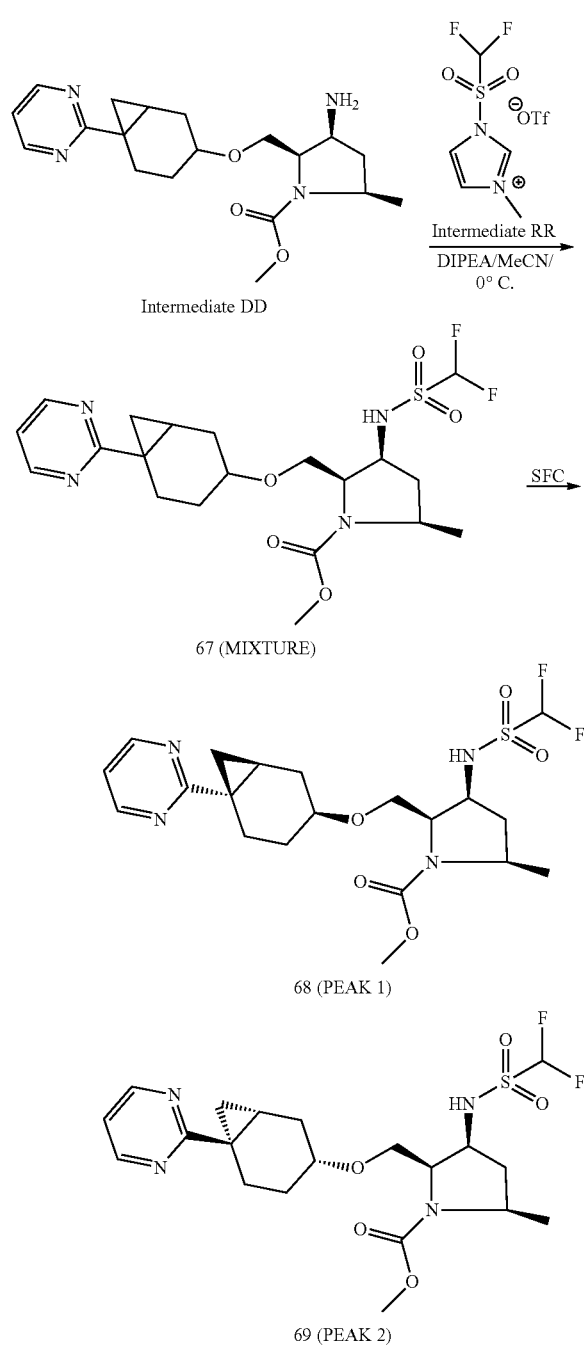

To a solution of methyl (2R,3S,5R)-3-amino-5-methyl-2-(((6-(pyrimidin-2-yl)bicyclo[4.1.0]heptan-3-yl)oxy)methyl)pyrrolidine-1-carboxylate (INTERMEDIATE DD, 45 mg, 0.125 mmol) in Acetonitrile (2.0 ml) at 0° C. was added 3-((difluoromethyl)sulfonyl)-1-methyl-1H-314-imidazole trifluoromethanesulfonate (INTERMEDIATE RR, 130 mg, 0.375 mmol). After stirring 5 mins at 0° C., DIPEA (109 μl, 0.624 mmol) was added. It was continued to stir for 5 mins at 0° C., The reaction mixture was concentrated and the residue was purified by reverse phase HPLC (5-95% MeCN/water with 0.05% TFA modifier) to afford the title compound (67, MIXTURE).

67 (MIXTURE): MS: 475.4 (M+1). 1H NMR (500 MHz, Methanol-d4) δ 8.69 (d, J=4.9 Hz, 2H), 7.28 (t, J=4.8 Hz, 1H), 6.58 (t, J=53.5 Hz, 1H), 4.05 (d, J=17.5 Hz, 2H), 3.92-3.61 (m, 6H), 2.69 (td, J=12.5, 5.7 Hz, 1H), 2.52 (ddt, J=32.2, 14.3, 7.7 Hz, 1H), 2.43-2.20 (m, 2H), 2.12-1.60 (m, 5H), 1.57-1.45 (m, 1H), 1.34 (d, J=5.9 Hz, 4H), 1.17-1.05 (m, 1H).

67 (MIXTURE), was separated by SFC to give 68 (PEAK 1) & 69 (PEAK 2).

LCMS m/z (M+H): 475.4 required, 475.4 found.

SFC condition:
Column: OJ-H (3×25 cm)
Mobile phase: 30% methanol/CO2
Flow rate: 60 mL/min, 220 nm
ABPR: 100 bar 68 (PEAK 1). MS: 475.2 (M+1). 1H NMR (500 MHz, Methanol-d4) δ 8.79-8.53 (m, 2H), 7.18 (s, 1H), 6.58 (t, J=53.5 Hz, 1H), 4.05 (d, J=18.5 Hz, 2H), 3.82 (d, J=6.5 Hz, 1H), 3.70 (d, J=16.9 Hz, 5H), 2.73 (t, J=12.9 Hz, 1H), 2.55 (dt, J=14.0, 7.7 Hz, 1H), 2.45-2.23 (m, 2H), 1.90 (t, J=10.6 Hz, 2H), 1.68 (dt, J=36.1, 9.6 Hz, 2H), 1.46 (d, J=9.4 Hz, 1H), 1.34 (d, J=5.4 Hz, 4H), 1.02 (s, 1H).

69 (PEAK 2). MS: 475.2 (M+1). 1H NMR (500 MHz, Methanol-d4) δ 8.75-8.40 (m, 2H), 7.18 (s, 1H), 6.58 (t, J=53.5 Hz, 1H), 4.06 (d, J=16.9 Hz, 2H), 3.82 (d, J=6.8 Hz, 1H), 3.77-3.62 (m, 5H), 2.74 (t, J=12.5 Hz, 1H), 2.49 (dt, J=13.9, 7.5 Hz, 1H), 2.43-2.23 (m, 2H), 2.06-1.82 (m, 2H), 1.67 (dt, J=37.0, 9.5 Hz, 2H), 1.46 (d, J=9.3 Hz, 1H), 1.34 (d, J=5.6 Hz, 4H), 1.03 (s, 1H).

Example 70 methyl (2R,3S,5R)-2-(((6-(5-chloro-4-methoxypyrimidin-2-yl)bicyclo[4.1.0]heptan-3-yl)oxy)methyl)-5-methyl-3-(methylsulfonamido)pyrrolidine-1-carboxylate (Mixture)

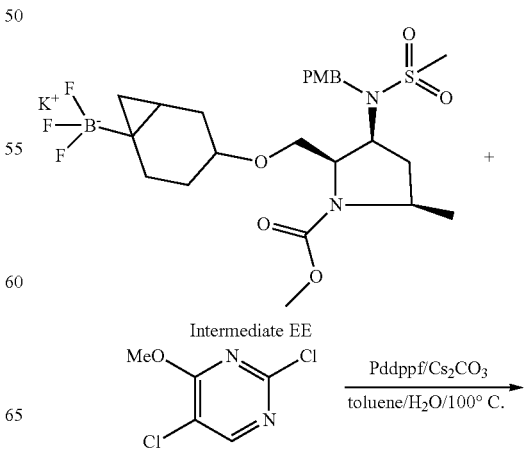

-continued

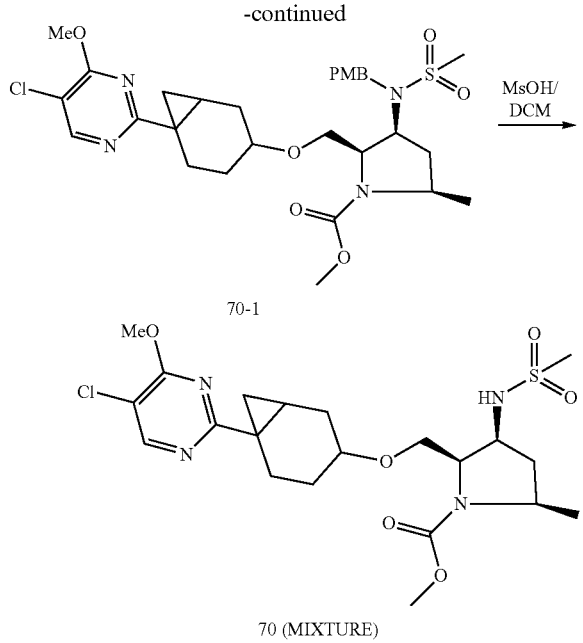

Step 1: methyl (2R,3S,5R)-2-(((6-(5-chloro-4-methoxypyrimidin-2-yl)bicyclo[4.1.0]heptan-3-yl)oxy)methyl)-3-(N-(4-methoxybenzyl)methylsulfonamido)-5-methylpyrrolidine-1-carboxylate (70-1)

A suspension of potassium trifluoro(4-(((2R,3S,5R)-3-(N-(4-methoxybenzyl)methylsulfonamido)-1-(methoxycarbonyl)-5-methylpyrrolidin-2-yl)methoxy)bicyclo[4.1.0]heptan-1-yl)borate (INTERMEDIATE EE, 15 mg, 0.026 mmol), 2,5-dichloro-4-methoxypyrimidine (6.87 mg, 0.038 mmol), 1,1'-BIS(DIPHENYLPHOSPHINO)FERROCENE-PALLADIUM(II)DICHLORIDE DICHLOROMETHANE COMPLEX (4.18 mg, 5.11 µmol) and CESIUM CARBONATE (25.0 mg, 0.077 mmol) in toluene (0.5 ml) and Water (0.1 ml) was bubbled with nitrogen for 5 mins. The reaction mixture was sealed in the reaction vial and heated at 90° C. overnight. The reaction mixture was partitioned between EtOAc and water. The organic layer was washed with brine, dried over MgSO4, concentrated. The residue was purified by reverse phase HPLC (5-95% MeCN/water with 0.05% TFA modifier) to afford the title compound. MS: 623.5 (M+1).

Step 2: methyl (2R,3S,5R)-2-(((6-(5-chloro-4-methoxypyrimidin-2-yl)bicyclo[4.1.0]heptan-3-yl)oxy)methyl)-5-methyl-3-(methylsulfonamido)pyrrolidine-1-carboxylate (70, Mixture)

To a solution of methyl (2R,3S,5R)-2-(((6-(5-chloro-4-methoxypyrimidin-2-yl)bicyclo[4.1.0]heptan-3-yl)oxy)methyl)-3-(N-(4-methoxybenzyl)methylsulfonamido)-5-methylpyrrolidine-1-carboxylate (70-1, 9 mg, 14 µmol) in DCM (0.6 ml) was added MsOH (11 µl, 0.173 mmol). The reaction mixture was stirred at rt for 15 mins. The reaction mixture was concentrated. The residue was purified reverse phase HPLC (5-95% MeCN/water with 0.05% TFA modifier) to afford the title compound. MS: 503.3 (M+1). 1H NMR (400 MHz, Methanol-d4) δ 8.35 (d, J=7.7 Hz, 1H), 4.14-3.54 (m, 3H), 3.10-2.82 (m, 4H), 2.80-2.63 (m, 1H), 2.62-2.09 (m, 4H), 2.07-1.45 (m, 7H), 1.31 (t, J=6.0 Hz, 3H), 1.12 (t, J=5.4 Hz, 2H), 1.08-1.00 (m, 1H), 0.90 (d, J=3.0 Hz, 1H).

The following examples shown in the table were prepared in an analogous manner of EXAMPLE 70 using the appropriate aryl halide described previously or commercially available.

| Example Number | Structure | IUPAC Name | Observed Mass [M + H]+ |
|---|---|---|---|
| 71 (MIXTURE) | 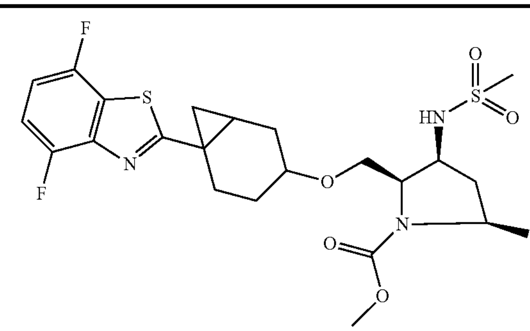 | methyl (2R,3S,5R)-2-(((6-(4,7-difluorobenzo[d]thiazol-2-yl)bicyclo[4.1.0]heptan-3-yl)oxy)methyl)-5-methyl-3-(methylsulfonamido)pyrrolidine-1-carboxylate | 530.3 |
| 72 (MIXTURE) | 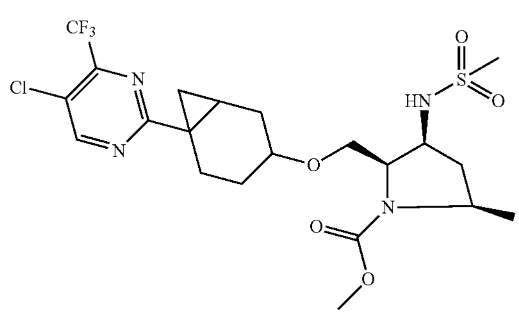 [SMILES: COC(=O)N1[C@H](C)C[C@H](NS(C)(=O)=O)[C@@H]1COC1CCC2(c3ncc(Cl)c(C(F)(F)F)n3)CC2C1] | methyl (2R,3S,5R)-2-(((6-(5-chloro-4-(trifluoromethyl)pyrimidin-2-yl)bicyclo[4.1.0]heptan-3-yl)oxy)methyl)-5-methyl-3-(methylsulfonamido)pyrrolidine-1-carboxylate | 541.3 |

-continued

| Example Number | Structure | IUPAC Name | Observed Mass [M + H]+ |
|---|---|---|---|
| 73 (MIXTURE) | 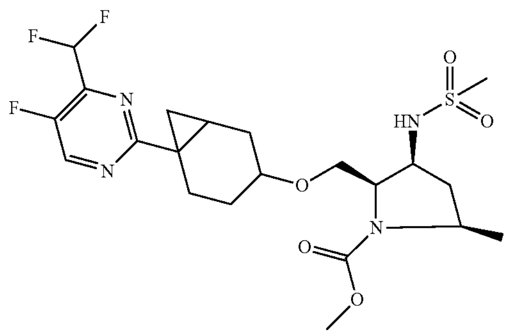 [SMILES: COC(=O)N1[C@H](C)C[C@H](NS(C)(=O)=O)[C@@H]1COC1CCC2(c3ncc(F)c(C(F)F)n3)CC2C1] | methyl (2R,3S,5R)-2-(((6-(4-(difluoromethyl)-5-fluoropyrimidin-2-yl)bicyclo[4.1.0]heptan-3-yl)oxy)methyl)-5-methyl-3-(methylsulfonamido)pyrrolidine-1-carboxylate | 507.3 |
| 74 (MIXTURE) | 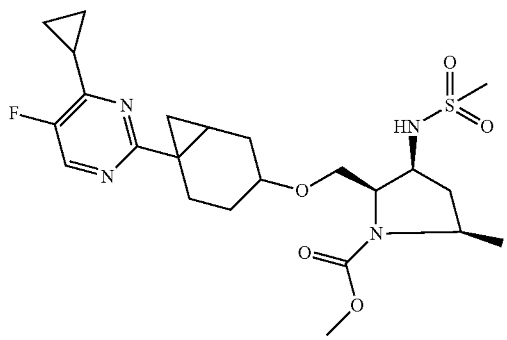 [SMILES: COC(=O)N1[C@H](C)C[C@H](NS(C)(=O)=O)[C@@H]1COC1CCC2(c3ncc(F)c(C4CC4)n3)CC2C1] | methyl (2R,3S,5R)-2-(((6-(4-cyclopropyl-5-fluoropyrimidin-2-yl)bicyclo[4.1.0]heptan-3-yl)oxy)methyl)-5-methyl-3-(methylsulfonamido)pyrrolidine-1-carboxylate | 497.4 |
| 75 (MIXTURE) | 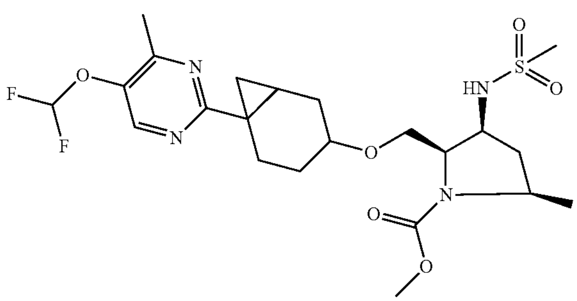 [SMILES: COC(=O)N1[C@H](C)C[C@H](NS(C)(=O)=O)[C@@H]1COC1CCC2(c3ncc(OC(F)F)c(C)n3)CC2C1] | methyl (2R,3S,5R)-2-(((6-(5-(difluoromethoxy)-4-methylpyrimidin-2-yl)bicyclo[4.1.0]heptan-3-yl)oxy)methyl)-5-methyl-3-(methylsulfonamido)pyrrolidine-1-carboxylate | 519.4 |
| 76 (MIXTURE) | 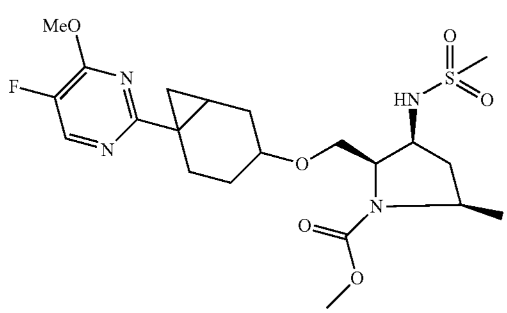 [SMILES: COC(=O)N1[C@H](C)C[C@H](NS(C)(=O)=O)[C@@H]1COC1CCC2(c3ncc(F)c(OC)n3)CC2C1] | methyl (2R,3S,5R)-2-(((6-(5-fluoro-4-methoxypyrimidin-2-yl)bicyclo[4.1.0]heptan-3-yl)oxy)methyl)-5-methyl-3-(methylsulfonamido)pyrrolidine-1-carboxylate | 487.3 |

| Example Number | Structure | IUPAC Name | Observed Mass [M + H]+ |
|---|---|---|---|
| 77 (MIXTURE) | 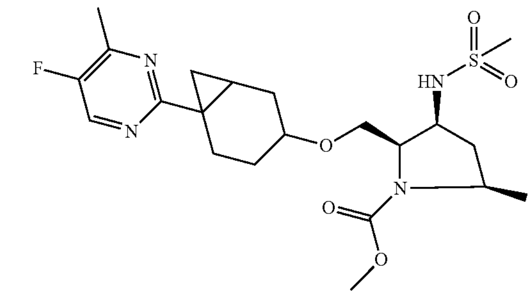 [SMILES: COC(=O)N1[C@H](C)C[C@H](NS(C)(=O)=O)[C@@H]1COC1CCC2(c3ncc(F)c(C)n3)CC2C1] | methyl (2R,3S,5R)-2-(((6-(5-fluoro-4-methylpyrimidin-2-yl)bicyclo[4.1.0]heptan-3-yl)oxy)methyl)-5-methyl-3-(methylsulfonamido)pyrrolidine-1-carboxylate | 471.2 |

Example 78 methyl (2R,3S,5R)-2-((((1S,3S,6R)-6-(5-chloropyrimidin-2-yl)bicyclo[4.1.0]heptan-3-yl)oxy)methyl)-3-((difluoromethyl)sulfonamido)-5-methylpyrrolidine-1-carboxylate (Peak 2)

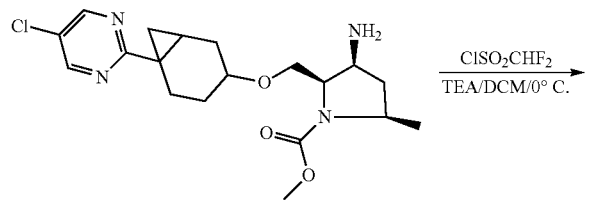

Intermediate FF

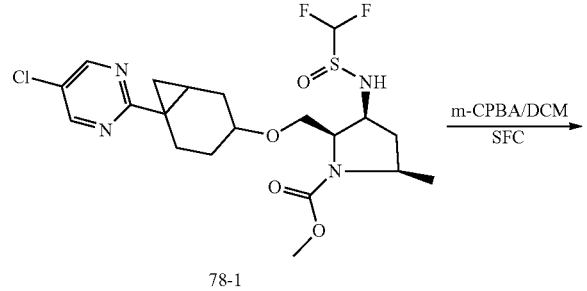

78-1

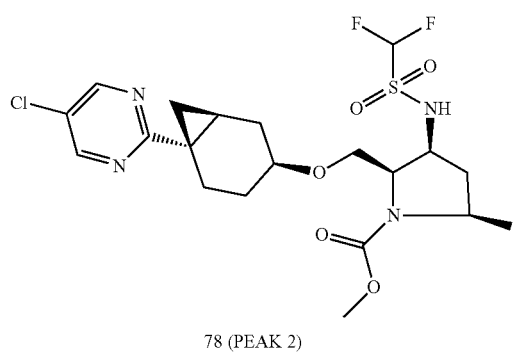

78 (PEAK 2)

Step 1: methyl (2R,3S,5R)-2-(((6-(5-chloropyrimidin-2-yl)bicyclo[4.1.0]heptan-3-yl)oxy)methyl)-3-(((difluoromethyl)sulfinyl)amino)-5-methylpyrrolidine-1-carboxylate (78-1)

To a solution of methyl (2R,3S,5R)-3-amino-2-(((6-(5-chloropyrimidin-2-yl)bicyclo[4.1.0]heptan-3-yl)oxy)methyl)-5-methylpyrrolidine-1-carboxylate (INTERMEDIATE FF, 59 mg, 0.149 mmol) in CH2Cl2 (1.5 ml) was added TEA (521 μl, 3.74 mmol) followed by addition of difluoromethanesulfonyl chloride (225 mg, 1.494 mmol) at rt under N2. The reaction mixture was continued to stir at rt for 5 mins. The reaction mixture was quenched with MeOH, concentrated in vacuum. The residue was purified by reverse phase HPLC (5-95% MeCN/water with 0.05% TFA modifier) to afford the title compound. MS: 493.4 (M+1).

Step 2: methyl (2R,3S,5R)-2-((((1S,3S,6R)-6-(5-chloropyrimidin-2-yl)bicyclo[4.1.0]heptan-3-yl)oxy)methyl)-3-((difluoromethyl)sulfonamido)-5-methylpyrrolidine-1-carboxylate (78, Peak To a solution of methyl (2R,3S,5R)-2-(((6-(5-chloropyrimidin-2-yl)bicyclo[4.1.0]heptan-3-yl)oxy)methyl)-3-(((difluoromethyl)sulfinyl)amino)-5-methylpyrrolidine-1-carboxylate (78-1, 44 mg, 0.089 mmol) in DCM (1.5 ml) at rt was added mCPBA (70%, 33.0 mg, 0.134 mmol). The reaction mixture was stirred at rt overnight. The reaction mixture was concentrated in vacuum. The residue was purified by reverse phase HPLC (5-95% MeCN/water with 0.05% TFA modifier) to afford a mixture of compounds.

This mixture compound was separated by SFC to give PEAK 1 and title compound 78 (PEAK 2).

LCMS m/z (M+H): 509.3 required, 509.3 found.

SFC condition:

Column: AD-H (3×25 cm)

Mobile phase: 35% methanol/CO2

Flow rate: 80 mL/min, 220 nm

ABPR: 100 bar 78 (PEAK 2): MS: 509.3 (M+1). 1H NMR (500 MHz, Methanol-d4) δ 8.62 (s, 2H), 6.58 (t, J=53.4 Hz, 1H), 4.15-3.97 (m, 2H), 3.91-3.61 (m, 6H), 2.74 (td, J=13.1, 4.9 Hz, 1H), 2.54 (dt, J=14.1, 7.7 Hz, 1H), 2.37 (dt, J=13.9, 7.1 Hz, 1H), 2.25 (d, J=14.2 Hz, 1H), 1.88 (q, J=12.8, 11.0 Hz, 2H), 1.68 (dq, J=31.3, 11.4, 10.0 Hz, 2H), 1.48 (dd, J=9.4, 3.0 Hz, 1H), 1.42-1.25 (m, 5H), 1.13-1.01 (m, 1H).

Example 79 & 80 methyl (2R,3S,5R)-2-((((1S,3S,6R)-6-(5-chloropyrimidin-2-yl)bicyclo[4.1.0]heptan-3-yl)oxy)methyl)-3-((fluoromethyl)sulfonamido)-5-methylpyrrolidine-1-carboxylate (79, Peak 2)

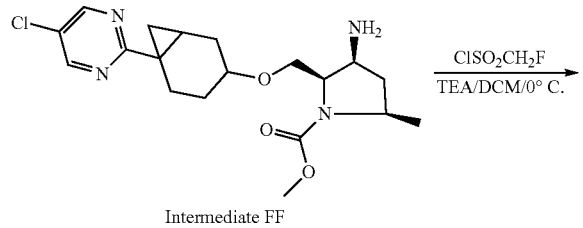

Intermediate FF

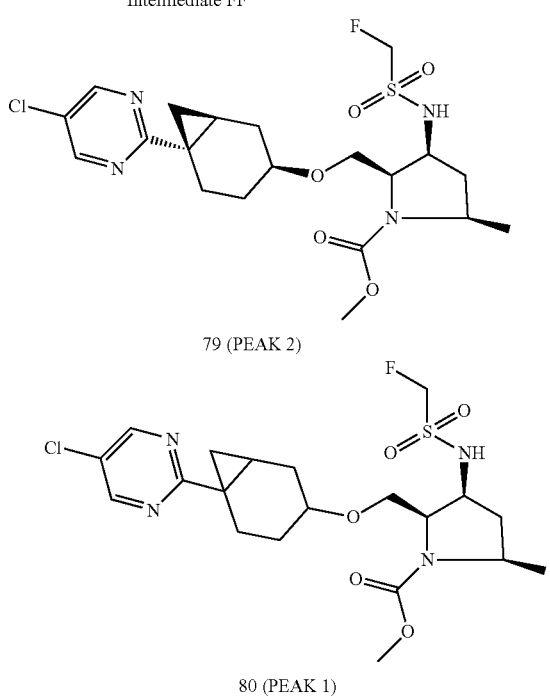

79 (PEAK 2)

80 (PEAK 1)

To a solution of methyl (2R,3S,5R)-3-amino-2-(((6-(5-chloropyrimidin-2-yl)bicyclo[4.1.0]heptan-3-yl)oxy)methyl)-5-methylpyrrolidine-1-carboxylate (INTERMEDIATE FF, 25 mg, 0.063 mmol) in CH2Cl2 (1.2 ml) was added TEA (44 µl, 0.317 mmol) followed by addition of fluoromethanesulfonyl chloride (11.48 mg, 0.082 mmol) at 0° C. under N2. After stirring for 20 mins at 0° C., the reaction mixture was concentrated in vacuum. The residue was purified reverse phase HPLC (5-95% MeCN/water with 0.05% TFA modifier) to afford a mixture compounds.

This mixture compound was separated by SFC to give 80 (PEAK 1) and 79 (PEAK 2).

LCMS m/z (M+H): 491.3 required, 491.3 found.

SFC condition:

Column: OJ-H (2×25 cm)

Mobile phase: 25% methanol/CO2

Flow rate: 60 mL/min, 220 nm

ABPR: 100 bar 79 (PEAK 2): MS: 491.3 (M+1). 1H NMR (500 MHz, Methanol-d4) δ 8.63 (s, 2H), 5.27 (ddd, J=46.8, 40.2, 10.1 Hz, 2H), 4.01 (d, J=16.3 Hz, 2H), 3.82 (dq, J=13.4, 6.6 Hz, 1H), 3.70 (d, J=8.7 Hz, 5H), 2.75 (td, J=13.2, 5.0 Hz, 1H), 2.55 (dt, J=14.2, 7.6 Hz, 1H), 2.43-2.32 (m, 1H), 2.25 (dt, J=14.2, 4.1 Hz, 1H), 1.87 (t, J=11.1 Hz, 2H), 1.68 (ddd, J=33.6, 14.6, 9.7 Hz, 2H), 1.48 (dd, J=9.5, 3.4 Hz, 1H), 1.33 (t, J=7.1 Hz, 5H), 1.10-1.01 (m, 1H).

80 (PEAK 1): MS: 491.3 (M+1). 1H NMR (500 MHz, Methanol-d4) δ 8.65 (s, 2H), 5.62-5.10 (m, 2H), 4.02 (d, J=15.0 Hz, 2H), 3.87-3.55 (m, 5H), 3.45 (d, J=4.5 Hz, 1H), 3.09 (dd, J=16.8, 7.6 Hz, 1H), 2.36-2.12 (m, 2H), 1.97-1.73 (m, 4H), 1.67 (dd, J=9.4, 3.7 Hz, 1H), 1.52 (t, J=8.3 Hz, 2H), 1.32 (d, J=7.2 Hz, 1H), 1.16 (d, J=5.2 Hz, 3H), 0.95-0.81 (m, 1H).

The following examples shown in the table were prepared in an analogous manner of that described above using appropriate starting materials described previously or commercially available.

| Example Number | Structure | IUPAC Name | Observed Mass [M + H]+ |
|---|---|---|---|
| 81 (PEAK 2 from SFC) | 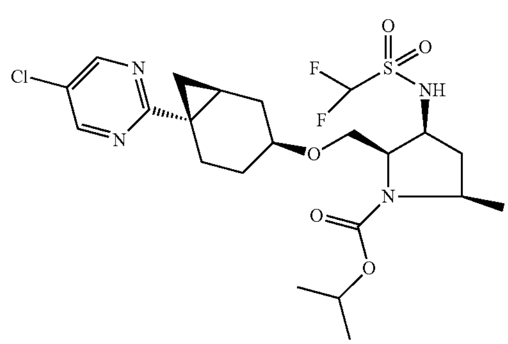 [SMILES: CC(C)OC(=O)N1[C@H](C)C[C@H](NS(=O)(=O)C(F)F)[C@@H]1CO[C@H]1CC[C@@]2(c3ncc(Cl)cn3)C[C@H]2C1] | isopropyl (2R,3S,5R)-2-((((1S,3S,6R)-6-(5-chloropyrimidin-2-yl)bicyclo[4.1.0]heptan-3-yl)oxy)methyl)-3-((difluoromethyl)sulfonamido)-5-methylpyrrolidine-1-carboxylate | 537.4 |

-continued

| Example Number | Structure | IUPAC Name | Observed Mass [M + H]+ |
|---|---|---|---|
| 82 (MIXTURE) | 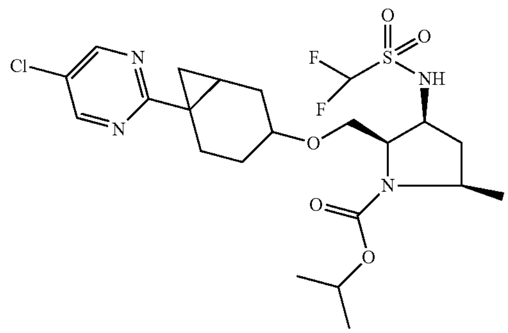 [SMILES: CC(C)OC(=O)N1[C@H](C)C[C@H](NS(=O)(=O)C(F)F)[C@@H]1COC1CCC2(c3ncc(Cl)cn3)CC2C1] | isopropyl (2R,3S,5R)-2-(((6-(5-chloropyrimidin-2-yl)bicyclo[4.1.0]heptan-3-yl)oxy)methyl)-3-((difluoromethyl)sulfonamido)-5-methylpyrrolidine-1-carboxylate | 537.4 |
| 83 (PEAK 2 from SFC) | 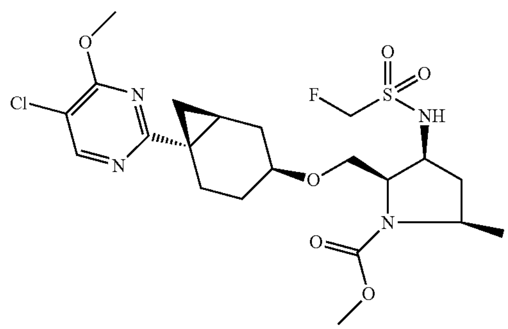 [SMILES: COC(=O)N1[C@H](C)C[C@H](NS(=O)(=O)CF)[C@@H]1CO[C@H]1CC[C@@]2(c3ncc(Cl)c(OC)n3)C[C@H]2C1] | methyl (2R,3S,5R)-2-(((((1S,3S,6R)-6-(5-fluoro-4-methoxypyrimidin-2-yl)bicyclo[4.1.0]heptan-3-yl)oxy)methyl)-3-((fluoromethyl)sulfonamido)-5-methylpyrrolidine-1-carboxylate | 505.4 |
| 84 (PEAK 2 from SFC) | 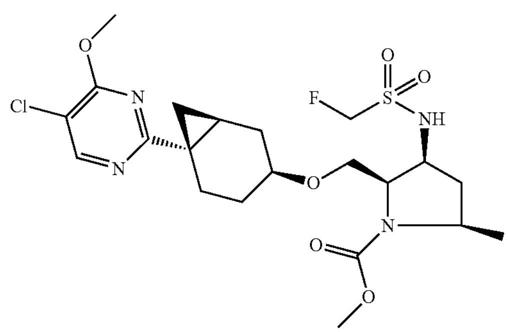 [SMILES: COC(=O)N1[C@H](C)C[C@H](NS(=O)(=O)CF)[C@@H]1CO[C@H]1CC[C@@]2(c3ncc(Cl)c(OC)n3)C[C@H]2C1] | methyl (2R,3S,5R)-2-(((((1S,3S,6R)-6-(5-chloro-4-methoxypyrimidin-2-yl)bicyclo[4.1.0]heptan-3-yl)oxy)methyl)-3-((fluoromethyl)sulfonamido)-5-methylpyrrolidine-1-carboxylate | 521.1 |
| 85 (MIXTURE) | 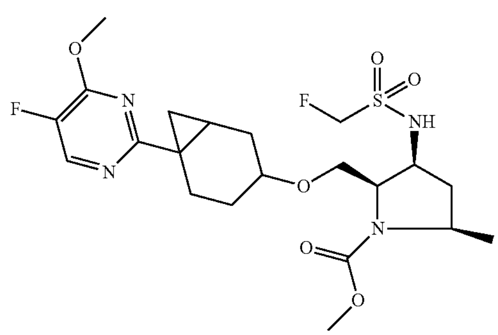 [SMILES: COC(=O)N1[C@H](C)C[C@H](NS(=O)(=O)CF)[C@@H]1COC1CCC2(c3ncc(F)c(OC)n3)CC2C1] | methyl (2R,3S,5R)-2-(((6-(5-fluoro-4-methoxypyrimidin-2-yl)bicyclo[4.1.0]heptan-3-yl)oxy)methyl)-3-((fluoromethyl)sulfonamido)-5-methylpyrrolidine-1-carboxylate | 505.2 |

| Example Number | Structure | IUPAC Name | Observed Mass [M + H]+ |
|---|---|---|---|
| 86 (MIXTURE) | 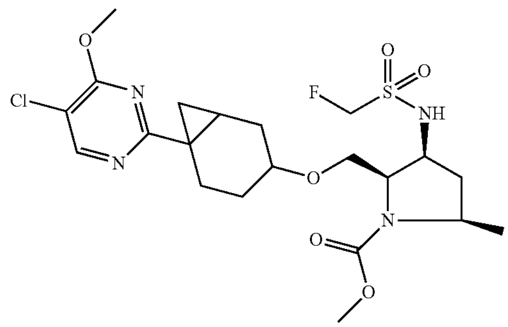 [SMILES: COC(=O)N1[C@H](C)C[C@H](NS(=O)(=O)CF)[C@@H]1COC1CCC2(c3ncc(Cl)c(OC)n3)CC2C1] | methyl (2R,3S,5R)-2-(((6-(5-chloro-4-methoxypyrimidin-2-yl)bicyclo[4.1.0]heptan-3-yl)oxy)methyl)-3-((fluoromethyl)sulfonamido)-5-methylpyrrolidine-1-carboxylate | 521.1 |
| 87 (PEAK 2 from SFC) | 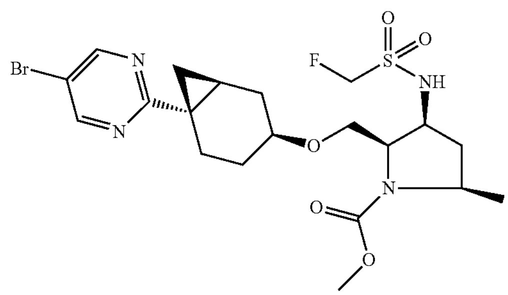 [SMILES: COC(=O)N1[C@H](C)C[C@H](NS(=O)(=O)CF)[C@@H]1CO[C@H]1CC[C@@]2(c3ncc(Br)cn3)C[C@H]2C1] | methyl (2R,3S,5R)-2-((((1S,3S,6R)-6-(5-bromopyrimidin-2-yl)bicyclo[4.1.0]heptan-3-yl)oxy)methyl)-3-((fluoromethyl)sulfonamido)-5-methylpyrrolidine-1-carboxylate | 537.0 |
| 89 (MIXTURE) | 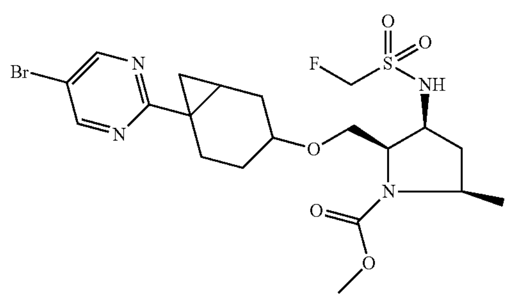 [SMILES: COC(=O)N1[C@H](C)C[C@H](NS(=O)(=O)CF)[C@@H]1COC1CCC2(c3ncc(Br)cn3)CC2C1] | methyl (2R,3S,5R)-2-(((6-(5-bromopyrimidin-2-yl)bicyclo[4.1.0]heptan-3-yl)oxy)methyl)-3-((fluoromethyl)sulfonamido)-5-methylpyrrolidine-1-carboxylate | 537.0 |
| 90 (PEAK 4 from SFC) | 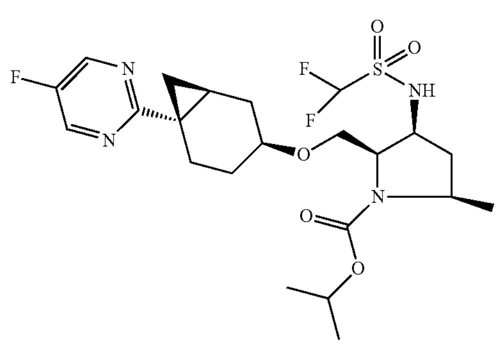 [SMILES: CC(C)OC(=O)N1[C@H](C)C[C@H](NS(=O)(=O)C(F)F)[C@@H]1CO[C@H]1CC[C@@]2(c3ncc(F)cn3)C[C@H]2C1] | isopropyl (2R,3S,5R)-3-((difluoromethyl)sulfonamido)-2-((((1S,3S,6R)-6-(5-fluoropyrimidin-2-yl)bicyclo[4.1.0]heptan-3-yl)oxy)methyl)-5-methylpyrrolidine-1-carboxylate | 521.3 |

| Example Number | Structure | IUPAC Name | Observed Mass [M + H]+ |
|---|---|---|---|
| 91 (PEAK 3 from SFC) | 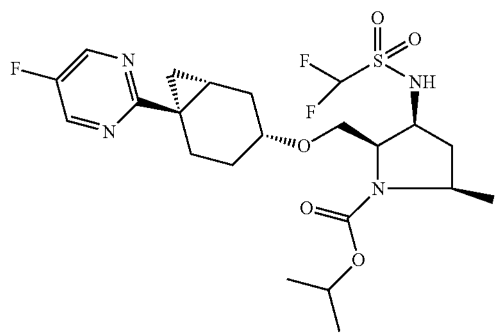 [SMILES: CC(C)OC(=O)N1[C@H](C)C[C@H](NS(=O)(=O)C(F)F)[C@@H]1CO[C@@H]1CC[C@]2(c3ncc(F)cn3)C[C@@H]2C1] | isopropyl (2R,3S,5R)-3-((difluoromethyl)sulfonamido)-2-((((1R,3R,6S)-6-(5-fluoropyrimidin-2-yl)bicyclo[4.1.0]heptan-3-yl)oxy)methyl)-5-methylpyrrolidine-1-carboxylate | 521.4 |
| 92 (PEAK 2 from SFC) | 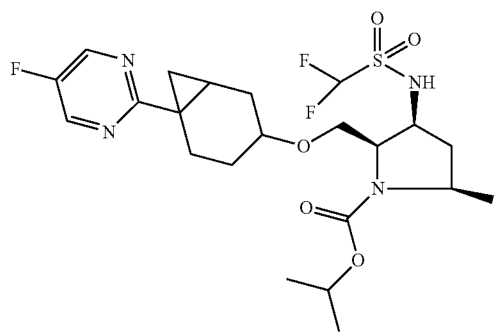 [SMILES: CC(C)OC(=O)N1[C@H](C)C[C@H](NS(=O)(=O)C(F)F)[C@@H]1COC1CCC2(c3ncc(F)cn3)CC2C1] | isopropyl (2R,3S,5R)-3-((difluoromethyl)sulfonamido)-2-(((6-(5-fluoropyrimidin-2-yl)bicyclo[4.1.0]heptan-3-yl)oxy)methyl)-5-methylpyrrolidine-1-carboxylate | 521.4 |
| 93 (PEAK 1 from SFC) | 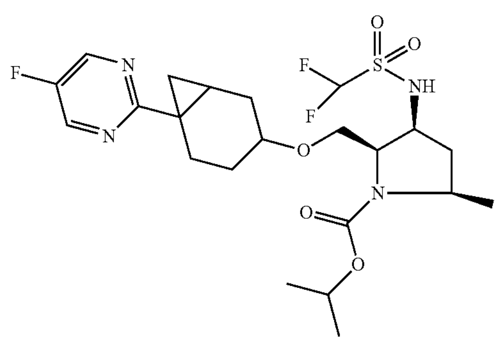 [SMILES: CC(C)OC(=O)N1[C@H](C)C[C@H](NS(=O)(=O)C(F)F)[C@@H]1COC1CCC2(c3ncc(F)cn3)CC2C1] | isopropyl (2R,3S,5R)-3-((difluoromethyl)sulfonamido)-2-(((6-(5-fluoropyrimidin-2-yl)bicyclo[4.1.0]heptan-3-yl)oxy)methyl)-5-methylpyrrolidine-1-carboxylate | 521.4 |
| 94 (MIXTURE) | 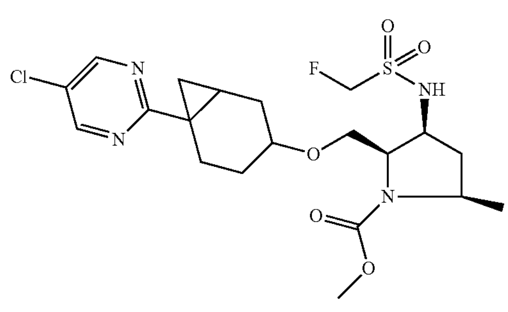 [SMILES: COC(=O)N1[C@H](C)C[C@H](NS(=O)(=O)CF)[C@@H]1COC1CCC2(c3ncc(Cl)cn3)CC2C1] | methyl (2R,3S,5R)-2-(((6-(5-chloropyrimidin-2-yl)bicyclo[4.1.0]heptan-3-yl)oxy)methyl)-3-((fluoromethyl)sulfonamido)-5-methylpyrrolidine-1-carboxylate | 491.3 |

| Example Number | Structure | IUPAC Name | Observed Mass [M + H]+ |
|---|---|---|---|
| 95 (PEAK 4 from SFC) | 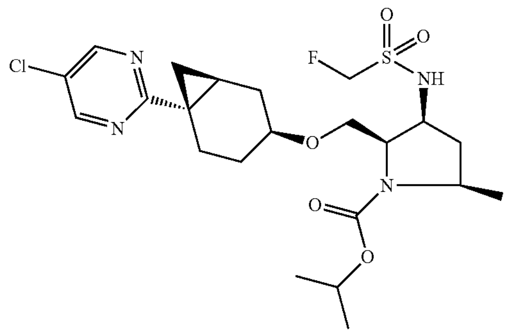 [SMILES: CC(C)OC(=O)N1[C@H](C)C[C@H](NS(=O)(=O)CF)[C@@H]1CO[C@H]1CC[C@@]2(c3ncc(Cl)cn3)C[C@H]2C1] | isopropyl (2R,3S,5R)-2-((((1S,3S,6R)-6-(5-chloropyrimidin-2-yl)bicyclo[4.1.0]heptan-3-yl)oxy)methyl)-3-((fluoromethyl)sulfonamido)-5-methylpyrrolidine-1-carboxylate | 519.3 |
| 96 (PEAK 3 from SFC) | 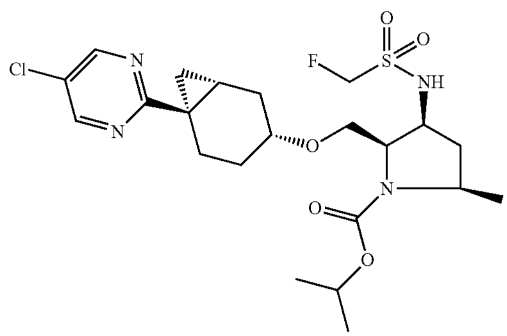 [SMILES: CC(C)OC(=O)N1[C@H](C)C[C@H](NS(=O)(=O)CF)[C@@H]1CO[C@@H]1CC[C@]2(c3ncc(Cl)cn3)C[C@@H]2C1] | isopropyl (2R,3S,5R)-2-((((1R,3R,6S)-6-(5-chloropyrimidin-2-yl)bicyclo[4.1.0]heptan-3-yl)oxy)methyl)-3-((fluoromethyl)sulfonamido)-5-methylpyrrolidine-1-carboxylate | 519.3 |
| 99 (PEAK 4 from SFC) | 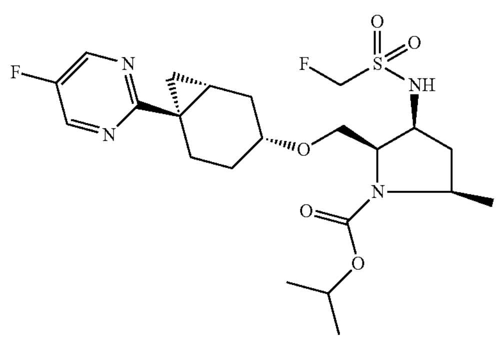 [SMILES: CC(C)OC(=O)N1[C@H](C)C[C@H](NS(=O)(=O)CF)[C@@H]1CO[C@@H]1CC[C@]2(c3ncc(F)cn3)C[C@@H]2C1] | isopropyl (2R,3S,5R)-3-((fluoromethyl)sulfonamido)-2-((((1R,3R,6S)-6-(5-fluoropyrimidin-2-yl)bicyclo[4.1.0]heptan-3-yl)oxy)methyl)-5-methylpyrrolidine-1-carboxylate | 503.4 |
| 100 (PEAK 3 from SFC) | 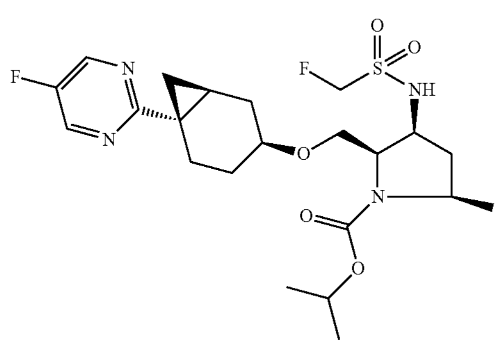 [SMILES: CC(C)OC(=O)N1[C@H](C)C[C@H](NS(=O)(=O)CF)[C@@H]1CO[C@H]1CC[C@@]2(c3ncc(F)cn3)C[C@H]2C1] | isopropyl (2R,3S,5R)-3-((fluoromethyl)sulfonamido)-2-((((1S,3S,6R)-6-(5-fluoropyrimidin-2-yl)bicyclo[4.1.0]heptan-3-yl)oxy)methyl)-5-methylpyrrolidine-1-carboxylate | 503.4 |

| Example Number | Structure | IUPAC Name | Observed Mass [M + H]+ |
|---|---|---|---|
| 103 (PEAK 4 from SFC) | 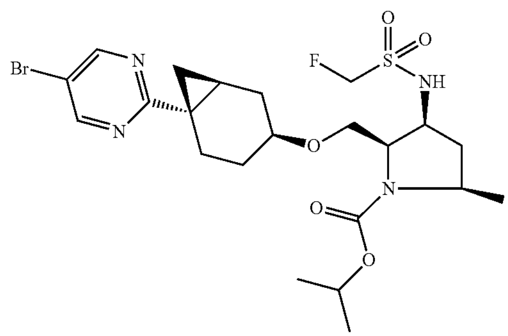 | isopropyl (2R,3S,5R)-2-((((1S,3S,6R)-6-(5-bromopyrimidin-2-yl)bicyclo[4.1.0]heptan-3-yl)oxy)methyl)-3-((fluoromethyl)sulfonamido)-5-methylpyrrolidine-1-carboxylate | 565.4 |
| 104 (PEAK 3 from SFC) | 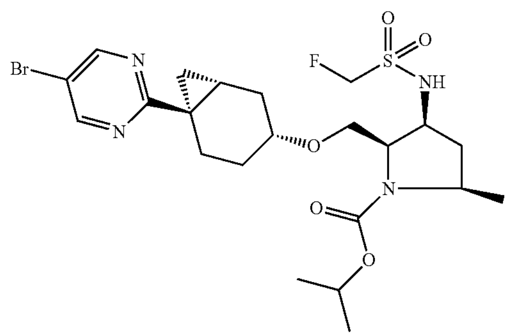 | isopropyl (2R,3S,5R)-2-((((1R,3R,6S)-6-(5-bromopyrimidin-2-yl)bicyclo[4.1.0]heptan-3-yl)oxy)methyl)-3-((fluoromethyl)sulfonamido)-5-methylpyrrolidine-1-carboxylate | 565.4 |
| 105 (PEAK 2 from SFC) | 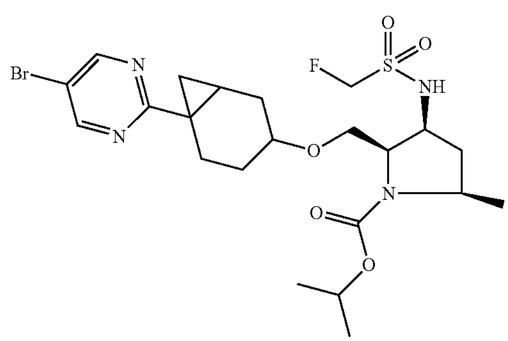 | isopropyl (2R,3S,5R)-2-(((6-(5-bromopyrimidin-2-yl)bicyclo[4.1.0]heptan-3-yl)oxy)methyl)-3-((fluoromethyl)sulfonamido)-5-methylpyrrolidine-1-carboxylate | 565.4 |
| 107 (MIXTURE) | 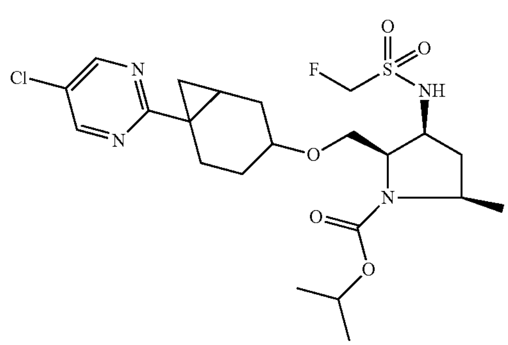 | isopropyl (2R,3S,5R)-2-(((6-(5-chloropyrimidin-2-yl)bicyclo[4.1.0]heptan-3-yl)oxy)methyl)-3-((fluoromethyl)sulfonamido)-5-methylpyrrolidine-1-carboxylate | 521.3 |

| Example Number | Structure | IUPAC Name | Observed Mass [M + H]+ |
|---|---|---|---|
| 108 (MIXTURE) | 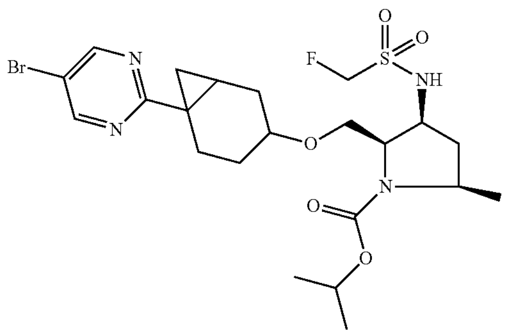 [SMILES: CC(C)OC(=O)N1[C@H](C)C[C@H](NS(=O)(=O)CF)[C@@H]1COC1CCC2(c3ncc(Cl)cn3)CC2C1] | isopropyl (2R,3S,5R)-2-(((6-(5-bromopyrimidin-2-yl)bicyclo[4.1.0]heptan-3-yl)oxy)methyl)-3-((fluoromethyl)sulfonamido)-5-methylpyrrolidine-1-carboxylate | 563.3 |
| 109 (MIXTURE) | 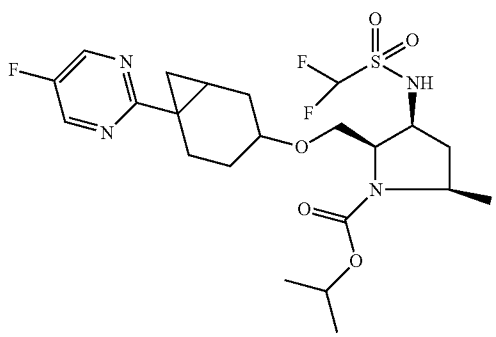 [SMILES: CC(C)OC(=O)N1[C@H](C)C[C@H](NS(=O)(=O)C(F)F)[C@@H]1COC1CCC2(c3ncc(F)cn3)CC2C1] | isopropyl (2R,3S,5R)-3-((difluoromethyl)sulfonamido)-2-(((6-(5-fluoropyrimidin-2-yl)bicyclo[4.1.0]heptan-3-yl)oxy)methyl)-5-methylpyrrolidine-1-carboxylate | 521.4 |
| 111 (MIXTURE) | 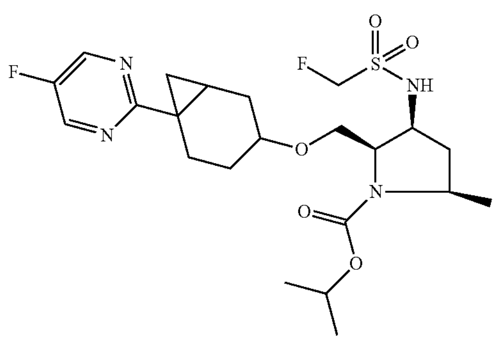 [SMILES: CC(C)OC(=O)N1[C@H](C)C[C@H](NS(=O)(=O)CF)[C@@H]1COC1CCC2(c3ncc(F)cn3)CC2C1] | isopropyl (2R,3S,5R)-3-((fluoromethyl)sulfonamido)-2-(((6-(5-fluoropyrimidin-2-yl)bicyclo[4.1.0]heptan-3-yl)oxy)methyl)-5-methylpyrrolidine-1-carboxylate | 503.2 |
| 112 (PEAK 1 from SFC) | 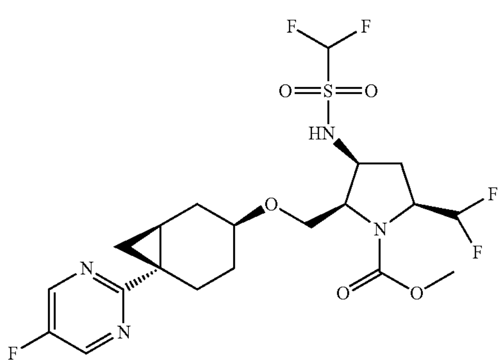 [SMILES: COC(=O)N1[C@H](C(F)F)C[C@H](NS(=O)(=O)C(F)F)[C@@H]1CO[C@H]1CC[C@@]2(c3ncc(F)cn3)C[C@H]2C1] | methyl (2R,3S,5S)-5-(difluoromethyl)-3-((difluoromethyl)sulfonamido)-2-((((1S,3S,6R)-6-(5-fluoropyrimidin-2-yl)bicyclo[4.1.0]heptan-3-yl)oxy)methyl)pyrrolidine-1-carboxylate | 529.4 |

| Example Number | Structure | IUPAC Name | Observed Mass [M + H]+ |
|---|---|---|---|
| 113 (PEAK 1 from SFC) | 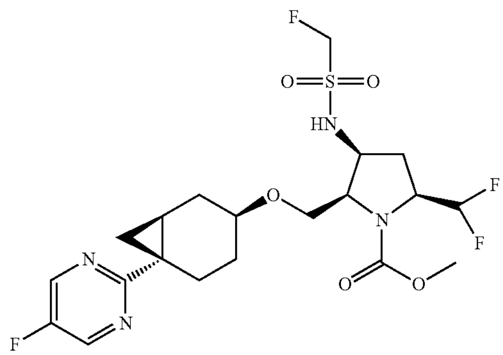 [SMILES: COC(=O)N1[C@H](C(F)F)C[C@H](NS(=O)(=O)CF)[C@@H]1CO[C@H]1CC[C@@]2(c3ncc(F)cn3)C[C@H]2C1] | methyl (2R,3S,5S)-5-(difluoromethyl)-3-((fluoromethyl)sulfonamido)-2-((((1S,3S,6R)-6-(5-fluoropyrimidin-2-yl)bicyclo[4.1.0]heptan-3-yl)oxy)methyl)pyrrolidine-1-carboxylate | 511.4 |
| 114 (PART B PEAK 2 from SFC) | 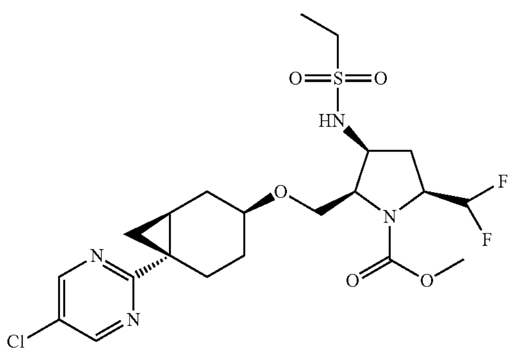 [SMILES: CCS(=O)(=O)N[C@H]1C[C@@H](C(F)F)N(C(=O)OC)[C@H]1CO[C@H]1CC[C@@]2(c3ncc(Cl)cn3)C[C@H]2C1] | methyl (2R,3S,5S)-2-((((1S,3S,6R)-6-(5-chloropyrimidin-2-yl)bicyclo[4.1.0]heptan-3-yl)oxy)methyl)-5-(difluoromethyl)-3-(ethylsulfonamido)pyrrolidine-1-carboxylate | 523.4 |
| 115 (PART C PEAK 1 from SFC) | 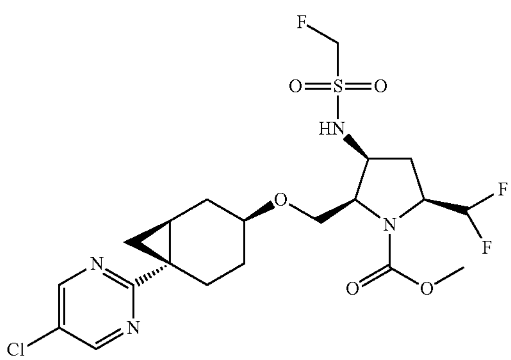 [SMILES: COC(=O)N1[C@H](C(F)F)C[C@H](NS(=O)(=O)CF)[C@@H]1CO[C@H]1CC[C@@]2(c3ncc(Cl)cn3)C[C@H]2C1] | methyl (2R,3S,5S)-2-((((1S,3S,6R)-6-(5-chloropyrimidin-2-yl)bicyclo[4.1.0]heptan-3-yl)oxy)methyl)-5-(difluoromethyl)-3-((fluoromethyl)sulfonamido)pyrrolidine-1-carboxylate | 527.4 |
| 116 (MIXTURE) | 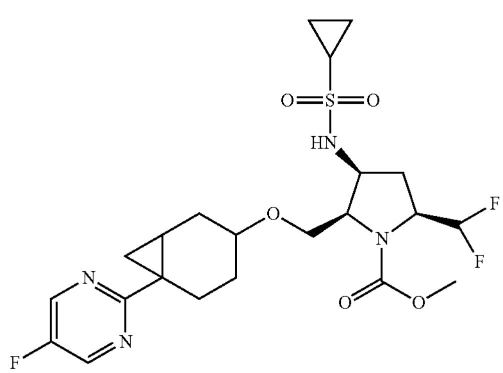 [SMILES: COC(=O)N1[C@H](C(F)F)C[C@H](NS(=O)(=O)C2CC2)[C@@H]1COC1CCC2(c3ncc(F)cn3)CC2C1] | methyl (2R,3S,5S)-3-(cyclopropanesulfonamido)-5-(difluoromethyl)-2-(((6-(5-fluoropyrimidin-2-yl)bicyclo[4.1.0]heptan-3-yl)oxy)methyl)pyrrolidine-1-carboxylate | 519.4 |

| Example Number | Structure | IUPAC Name | Observed Mass [M + H]+ |
|---|---|---|---|
| 117 (MIXTURE) | 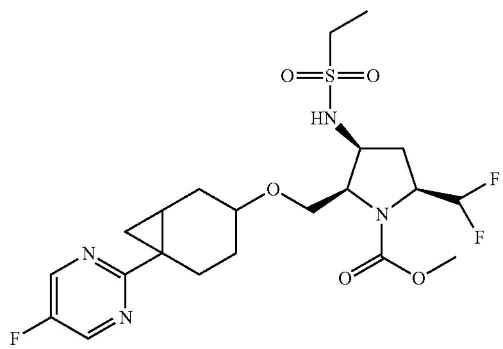 [SMILES: CCS(=O)(=O)N[C@H]1C[C@@H](C(F)F)N(C(=O)OC)[C@H]1COC1CCC2(c3ncc(F)cn3)CC2C1] | methyl (2R,3S,5S)-5-(difluoromethyl)-3-(ethylsulfonamido)-2-(((6-(5-fluoropyrimidin-2-yl)bicyclo[4.1.0]heptan-3-yl)oxy)methyl)pyrrolidine-1-carboxylate | 507.4 |
| 118 (PEAK 2 from SFC) | 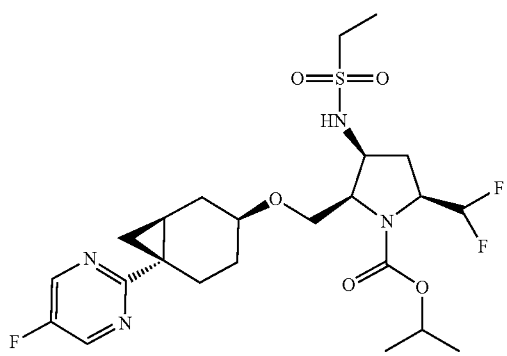 [SMILES: CCS(=O)(=O)N[C@H]1C[C@@H](C(F)F)N(C(=O)OC(C)C)[C@H]1CO[C@H]1CC[C@@]2(c3ncc(F)cn3)C[C@H]2C1] | isopropyl (2R,3S,5S)-5-(difluoromethyl)-3-(ethylsulfonamido)-2-((((1S,3S,6R)-6-(5-fluoropyrimidin-2-yl)bicyclo[4.1.0]heptan-3-yl)oxy)methyl)pyrrolidine-1-carboxylate | 535.5 |
| 119 (PEAK 1B from SFC) | 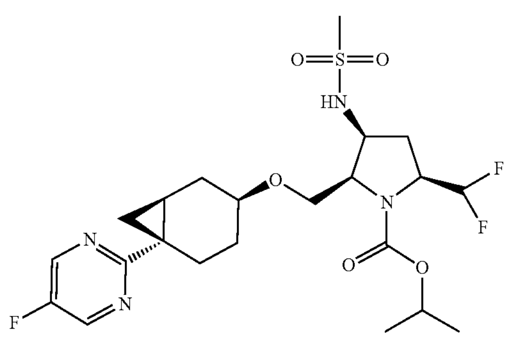 [SMILES: CC(C)OC(=O)N1[C@H](C(F)F)C[C@H](NS(C)(=O)=O)[C@@H]1CO[C@H]1CC[C@@]2(c3ncc(F)cn3)C[C@H]2C1] | isopropyl (2R,3S,5S)-5-(difluoromethyl)-2-((((1S,3S,6R)-6-(5-fluoropyrimidin-2-yl)bicyclo[4.1.0]heptan-3-yl)oxy)methyl)-3-(methylsulfonamido)pyrrolidine-1-carboxylate | 521.5 |
| 120 (MIXTURE) | 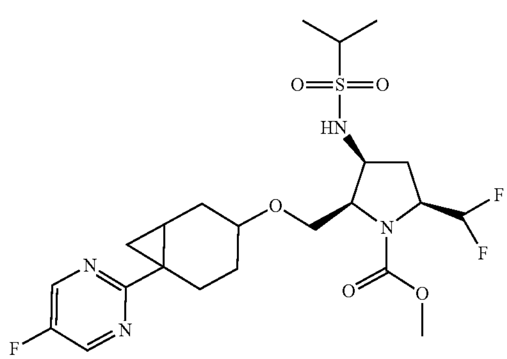 [SMILES: COC(=O)N1[C@H](C(F)F)C[C@H](NS(=O)(=O)C(C)C)[C@@H]1COC1CCC2(c3ncc(F)cn3)CC2C1] | methyl (2R,3S,5S)-5-(difluoromethyl)-2-(((6-(5-fluoropyrimidin-2-yl)bicyclo[4.1.0]heptan-3-yl)oxy)methyl)-3-((1-methylethyl)sulfonamide)pyrrolidine-1-carboxylate | 521.4 |

| Example Number | Structure | IUPAC Name | Observed Mass [M + H]+ |
|---|---|---|---|
| 121 (PEAK 2B from SFC) | 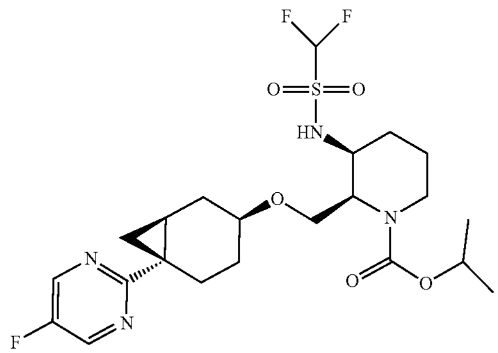 [SMILES: CC(C)OC(=O)N1CCC[C@H](NS(=O)(=O)C(F)F)[C@@H]1CO[C@H]1CC[C@@]2(c3ncc(F)cn3)C[C@H]2C1] | isopropyl (2R,3S)-3-((difluoromethyl)sulfonamido)-2-((((1S,3S,6R)-6-(5-fluoropyrimidin-2-yl)bicyclo[4.1.0]heptan-3-yl)oxy)methyl)piperidine-1-carboxylate | 521.5 |
| 122 (MIXTURE) | 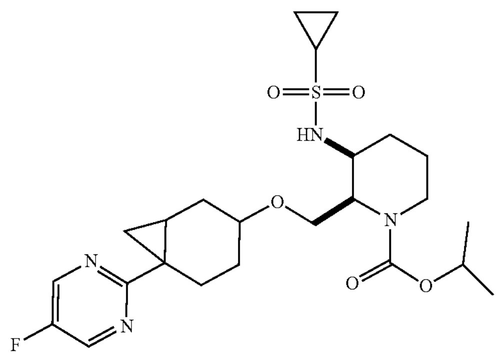 [SMILES: CC(C)OC(=O)N1CCC[C@H](NS(=O)(=O)C2CC2)[C@@H]1COC1CCC2(c3ncc(F)cn3)CC2C1] | isopropyl (2R,3S)-3-(cyclopropanesulfonamido)-2-(((6-(5-fluoropyrimidin-2-yl)bicyclo[4.1.0]heptan-3-yl)oxy)methyl)piperidine-1-carboxylate | 511.4 |
| 123 (MIXTURE) | 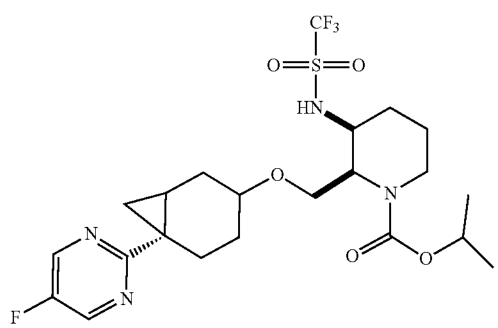 [SMILES: CC(C)OC(=O)N1CCC[C@H](NS(=O)(=O)C(F)(F)F)[C@@H]1COC1CC[C@@]2(c3ncc(F)cn3)CC2C1] | isopropyl (2R,3S)-2-(((6-(5-fluoropyrimidin-2-yl)bicyclo[4.1.0]heptan-3-yl)oxy)methyl)-3-((trifluoromethyl)sulfonamido)piperidine-1-carboxylate | 539.4 |
| 124 (PEAK 2 from SFC) | 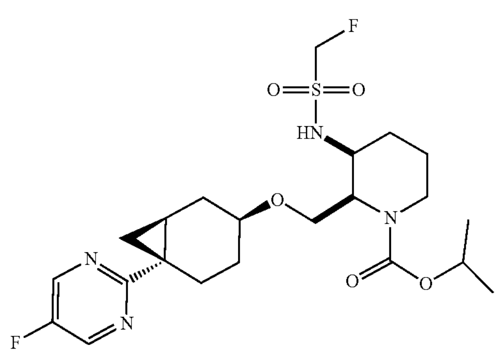 [SMILES: CC(C)OC(=O)N1CCC[C@H](NS(=O)(=O)CF)[C@@H]1CO[C@H]1CC[C@@]2(c3ncc(F)cn3)C[C@H]2C1] | isopropyl (2R,3S)-3-((fluoromethyl)sulfonamido)-2-((((1S,3S,6R)-6-(5-fluoropyrimidin-2-yl)bicyclo[4.1.0]heptan-3-yl)oxy)methyl)piperidine-1-carboxylate | 503.4 |

-continued

| Example Number | Structure | IUPAC Name | Observed Mass [M + H]+ |
|---|---|---|---|
| 125 (PEAK 3 from SFC) | 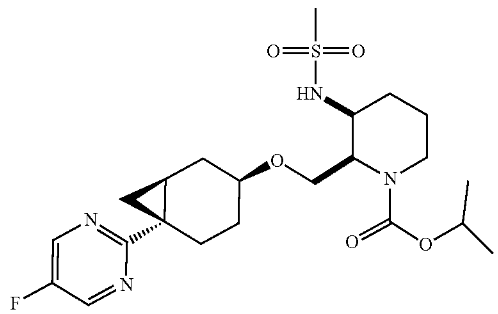 [SMILES: CC(C)OC(=O)N1CCC[C@H](NS(C)(=O)=O)[C@@H]1CO[C@H]1CC[C@@]2(c3ncc(F)cn3)C[C@H]2C1] | isopropyl (2R,3S)-2-((((1S,3S,6R)-6-(5-fluoropyrimidin-2-yl)bicyclo[4.1.0]heptan-3-yl)oxy)methyl)-3-(methylsulfonamido)piperidine-1-carboxylate | 485.4 |
| 126 (MIXTURE) | 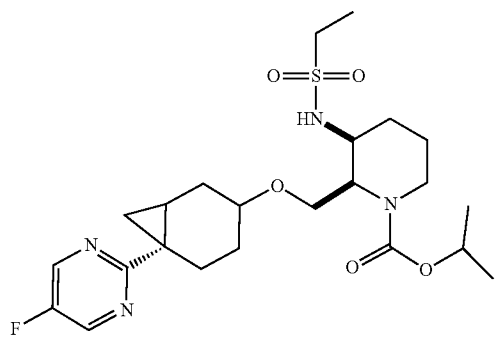 [SMILES: CCS(=O)(=O)N[C@H]1CCCN(C(=O)OC(C)C)[C@H]1COC1CC[C@@]2(c3ncc(F)cn3)CC2C1] | isopropyl (2R,3S)-3-(ethylsulfonamido)-2-(((6-(5-fluoropyrimidin-2-yl)bicyclo[4.1.0]heptan-3-yl)oxy)methyl)piperidine-1-carboxylate | 499.4 |
| 127 (PEAK 2 from SFC) | 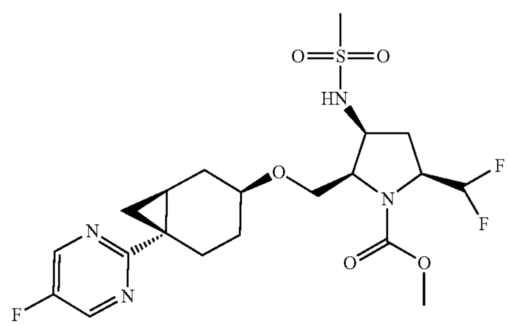 [SMILES: COC(=O)N1[C@H](C(F)F)C[C@H](NS(C)(=O)=O)[C@@H]1CO[C@H]1CC[C@@]2(c3ncc(F)cn3)C[C@H]2C1] | methyl (2R,3S,5S)-5-(difluoromethyl)-2-((((1S,3S,6R)-6-(5-fluoropyrimidin-2-yl)bicyclo[4.1.0]heptan-3-yl)oxy)methyl)-3-(methylsulfonamido)pyrrolidine-1-carboxylate | 493.4 |
| 128 (MIXTURE) | 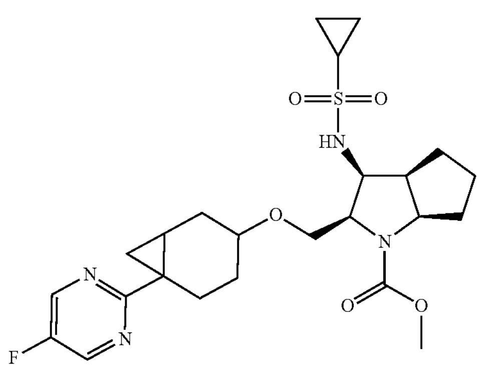 [SMILES: COC(=O)N1[C@@H]2CCC[C@@H]2[C@H](NS(=O)(=O)C2CC2)[C@@H]1COC1CCC2(c3ncc(F)cn3)CC2C1] | methyl (2R,3S,3aS,6aR)-3-(cyclopropanesulfonamido)-2-(((6-(5-fluoropyrimidin-2-yl)bicyclo[4.1.0]heptan-3-yl)oxy)methyl)hexahydrocyclopenta[b]pyrrole-1(2H)-carboxylate | 509.4 |

-continued

| Example Number | Structure | IUPAC Name | Observed Mass [M + H]+ |
|---|---|---|---|
| 129 (MIXTURE) | 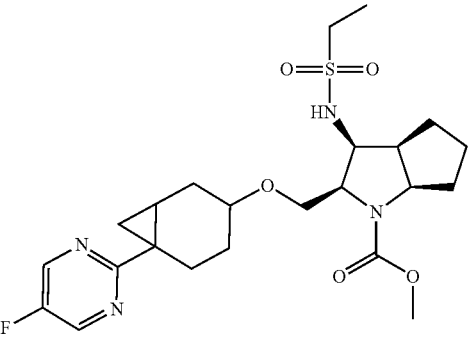 [SMILES: CCS(=O)(=O)N[C@H]1[C@H]2CCC[C@H]2N(C(=O)OC)[C@H]1COC1CCC2(c3ncc(F)cn3)CC2C1] | methyl (2R,3S,3aS,6aR)-3-(ethylsulfonamido)-2-(((6-(5-fluoropyrimidin-2-yl)bicyclo[4.1.0]heptan-3-yl)oxy)methyl)hexahydrocyclopenta[b]pyrrole-1(2H)-carboxylate | 497.4 |
| 130 (MIXTURE) | 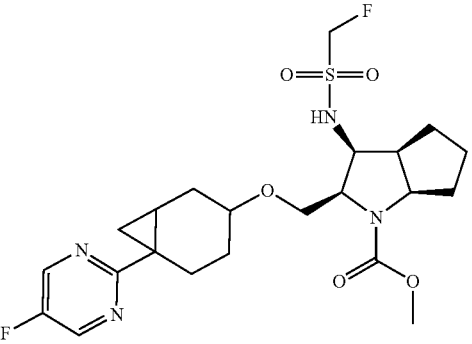 [SMILES: COC(=O)N1[C@@H]2CCC[C@@H]2[C@H](NS(=O)(=O)CF)[C@@H]1COC1CCC2(c3ncc(F)cn3)CC2C1] | methyl (2R,3S,3aS,6aR)-3-((fluoromethyl)sulfonamido)-2-(((6-(5-fluoropyrimidin-2-yl)bicyclo[4.1.0]heptan-3-yl)oxy)methyl)hexahydrocyclopenta[b]pyrrole-1(2H)-carboxylate | 501.4 |
| 131 (PEAK 4 from SFC) | 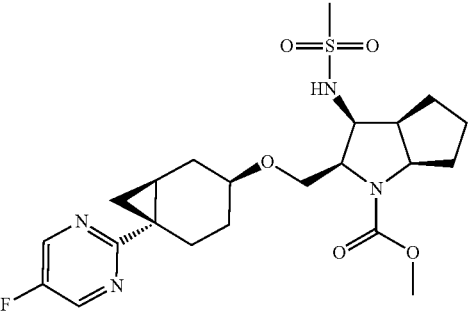 [SMILES: COC(=O)N1[C@@H]2CCC[C@@H]2[C@H](NS(C)(=O)=O)[C@@H]1CO[C@H]1CC[C@@]2(c3ncc(F)cn3)C[C@H]2C1] | methyl (2R,3S,3aS,6aR)-2-((((1S,3S,6R)-6-(5-fluoropyrimidin-2-yl)bicyclo[4.1.0]heptan-3-yl)oxy)methyl)-3-(methylsulfonamido)hexahydrocyclopenta[b]pyrrole-1(2H)-carboxylate | 483.3 |
| 132 (PEAK 2A from SFC) | 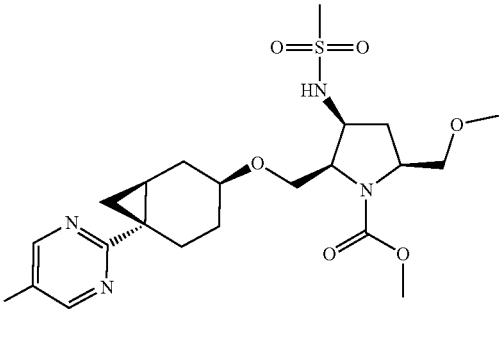 | methyl (2R,3S,5S)-2-((((1S,3S,6R)-6-(5-fluoropyrimidin-2-yl)bicyclo[4.1.0]heptan-3-yl)oxy)methyl)-5-(methoxymethyl)-3-(methylsulfonamido)pyrrolidine-1-carboxylate | 487.3 |

| Example Number | Structure | IUPAC Name | Observed Mass [M + H]+ |
|---|---|---|---|
| 133 (PEAK 2 from SFC) | 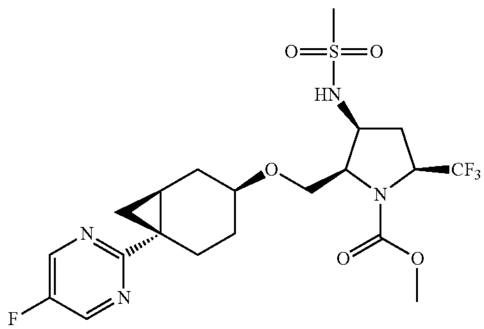 [SMILES: COC(=O)N1[C@H](C(F)(F)F)C[C@H](NS(C)(=O)=O)[C@@H]1CO[C@H]1CC[C@@]2(c3ncc(F)cn3)C[C@H]2C1] | methyl (2R,3S,5S)-2-((((1S,3S,6R)-6-(5-fluoropyrimidin-2-yl)bicyclo[4.1.0]heptan-3-yl)oxy)methyl)-3-(methylsulfonamido)-5-(trifluoromethyl)pyrrolidine-1-carboxylate | 511.3 |

Example 134

Methyl (2R,3aS,6aS)-2-((((6-(5-fluoropyrimidin-2-yl)bicyclo[4.1.0]heptan-3-yl)oxy)methyl)-3-(methylsulfonamido)hexahydro-1H-furo[3,4-b]pyrrole-1-carboxylate (Mixture)

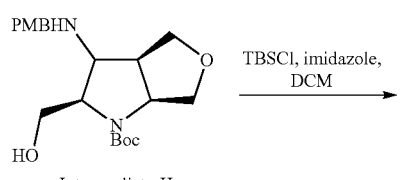

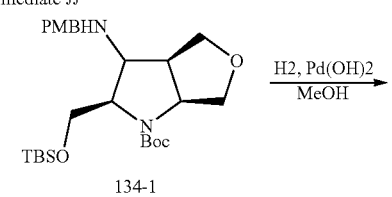

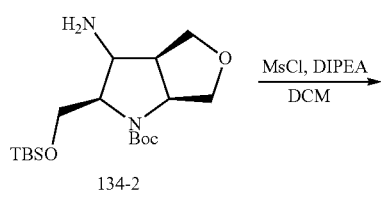

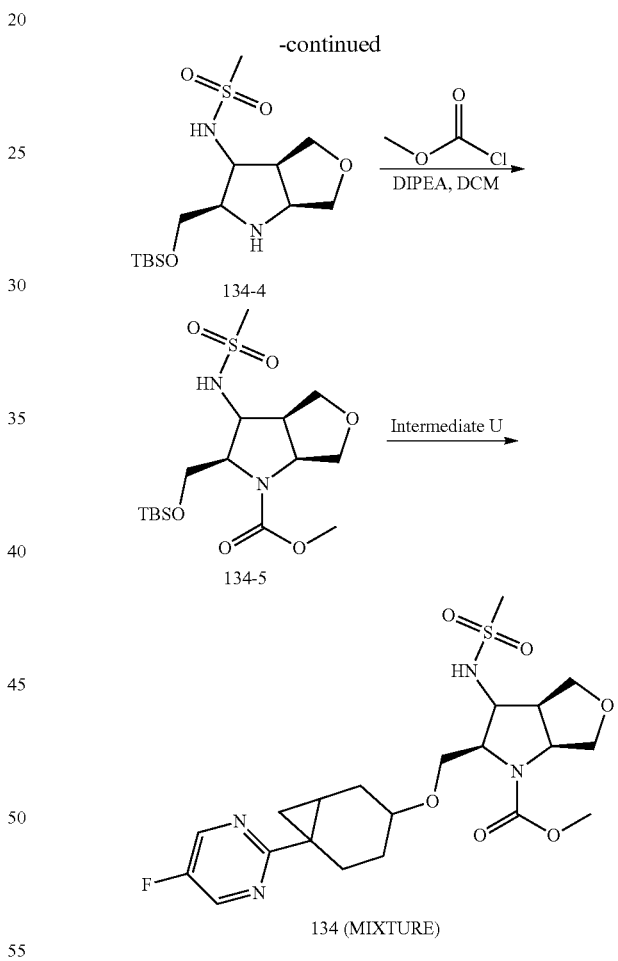

Step 1: tert-butyl (2R,3aR,6aS)-2-(((tert-butyldimethylsilyl)oxy)methyl)-3-((4-methoxybenzyl)amino)hexahydro-1H-furo[3,4-b]pyrrole-1-carboxylate (134-1)

Imidazole (56.5 mg, 0.830 mmol) and TBS-Cl (45.9 mg, 0.304 mmol) were added to a stirred mixture of tert-butyl (2R,3aR,6aS)-2-(hydroxymethyl)-3-((4-methoxybenzyl)amino)hexahydro-1H-furo[3,4-b]pyrrole-1-carboxylate (INTERMEDIATE JJ) (104.7 mg, 0.277 mmol) in DCM (3 ml)

and the mixture was stirred at room temperature for 1 h. The solution was purified by column chromatography on silica gel (EtOAc/isohexane 0-50%) to afford the title compound. MS: 494.5 (M+1).

Step 2: tert-butyl (2R,3aR,6aS)-3-amino-2-(((tert-butyldimethylsilyl)oxy)methyl)hexahydro-1H-furo[3,4-b]pyrrole-1-carboxylate (134-2)

Palladium hydroxide on carbon (27.9 mg, 0.040 mmol) was added to a stirred mixture of tert-butyl (2R,3aR,6aS)-2-(((tert-butyldimethylsilyl)oxy)methyl)-3-((4-methoxybenzyl)amino)hexahydro-1H-furo[3,4-b]pyrrole-1-carboxylate (134-1) (98 mg, 0.199 mmol) in MeOH (5 ml) and the mixture was stirred at room temperature for 90 min.

The mixture was filtered, washing with methanol, the solution was concentrated, dried to afford the title compound. MS: 373.8 (M+1).

Step 3: tert-butyl (2R,3aS,6aS)-2-(((tert-butyldimethylsilyl)oxy)methyl)-3-(methylsulfonamido)hexahydro-1H-furo[3,4-b]pyrrole-1-carboxylate (134-3)

methanesulfonyl chloride (0.024 ml, 0.299 mmol) was added to a stirred mixture of tert-butyl (2R,3aR,6aS)-3-amino-2-(((tert-butyldimethylsilyl)oxy)methyl)hexahydro-1H-furo[3,4-b]pyrrole-1-carboxylate (134-2) (74.1 mg, 0.199 mmol) and DIEA (0.104 ml, 0.597 mmol) in DCM (3 ml) and the mixture was stirred at room temperature for 15 min. Hydrochloric acid (1M, 80 mL) was added and the mixture was extracted with ethyl acetate (3×80 mL). The combined organic fractions were washed with brine (saturated, 50 mL), dried ($Na_2SO_4$), filtered and the solvent was evaporated under reduced pressure. The residue was purified by column chromatography on silica gel (EtOAc:hexane 0-50%) to afford the title compound. MS: 451.4 (M+1).

Step 4: N-((2R,3aS,6aS)-2-(((tert-butyldimethylsilyl)oxy)methyl)hexahydro-1H-furo[3,4-b]pyrrol-3-yl)methanesulfonamide (134-4)

Trimethylsilyl trifluoromethanesulfonate (0.070 ml, 0.386 mmol) was added slowly to a stirred, cooled 0° C. mixture of tert-butyl (2R,3aS,6aS)-2-(((tert-butyldimethylsilyl)oxy)methyl)-3-(methylsulfonamido)hexahydro-1H-furo[3,4-b]pyrrole-1-carboxylate (134-3) (58 mg, 0.129 mmol) and 2,6-DIMETHYLPYRIDINE (0.120 ml, 1.030 mmol) in CH2Cl2 (5 ml) and the mixture was stirred at 0° C. for 90 min., Poured into aqueous sodium hydrogen carbonate (sat. 50 mL), The mixture was extracted with ethyl acetate (3×80 mL). The combined organic fractions were washed with brine (saturated, 60 mL), dried ($Na_2SO_4$), filtered and the solvent was evaporated under reduced pressure to afford the title compound. MS: 351.3 (M+1).

Step 5: methyl (2R,3aS,6aS)-2-(((tert-butyldimethylsilyl)oxy)methyl)-3-(methylsulfonamido)hexahydro-1H-furo[3,4-b]pyrrole-1-carboxylate (135-5)

METHYL CHLOROFORMATE (10.55 µl, 0.154 mmol) was added to a stirred, cooled mixture of N-((2R,3aS,6aS)-2-(((tert-butyldimethylsilyl)oxy)methyl)hexahydro-1H-furo[3,4-b]pyrrol-3-yl)methanesulfonamide (134-4) (45 mg, 0.128 mmol) and DIPEA (0.067 ml, 0.385 mmol) in DCM (3 ml) and the mixture was moved to room temperature and stirred at room temperature for 15 min. The residue was purified by column chromatography on silica gel (EtOAc/isohexane 0-70%-100%) to afford the title compound. MS: 409.3 (M+1).

Step 6: methyl (2R,3aS,6aS)-2-(((6-(5-fluoropyrimidin-2-yl)bicyclo[4.1.0]heptan-3-yl)oxy)methyl)-3-(methylsulfonamido)hexahydro-1H-furo[3,4-b]pyrrole-1-carboxylate (134, Mixture)

Triisopropylsilane (0.045 ml, 0.220 mmol) were added to a stirred, cooled 0° C. mixture of methyl (2R,3aS,6aS)-2-(((tert-butyldimethylsilyl)oxy)methyl)-3-(methylsulfonamido)hexahydro-1H-furo[3,4-b]pyrrole-1-carboxylate (134-5) (18 mg, 0.044 mmol) and 6-(5-fluoropyrimidin-2-yl)bicyclo[4.1.0]heptan-3-one (INTERMEDIATE U)(10.90 mg, 0.053 mmol) in Acetonitrile (2 ml). The reaction mixture was stirred at room temperature for 30 min. Then moved reaction to 0° C., Added trimethylsilyl trifluoromethanesulfonate (0.048 ml, 0.264 mmol). Then the reaction mixture was stirred at 0° C. for 30 min. Aqueous sodium hydrogen carbonate (saturated, 30 mL) was added and the mixture was extracted with ethyl acetate (3×30 mL). The combined organic fractions were washed with brine (saturated, 20 mL), dried ($Na_2SO_4$), filtered and the solvent was evaporated under reduced pressure. The residue was purified by preparative TLC (EtOAc/isohexane 4:1), to afford the title compound (mixture of 8 isomers). MS: 485.4 (M+1).

Example 135, 136, 137, 138, and 139 methyl (2R,3S,5R)-2-(((6-(5-fluoropyrimidin-2-yl)bicyclo[4.1.0]heptan-3-yl)oxy)methyl)-5-methyl-3-(methylsulfonamido)pyrrolidine-1-carboxylate (135, Mixture), methyl (2R,3S,5R)-2-((((1R,3R,6S)-6-(5-fluoropyrimidin-2-yl)bicyclo[4.1.0]heptan-3-yl)oxy)methyl)-5-methyl-3-(methylsulfonamido)pyrrolidine-1-carboxylate (136, Peak 4), methyl (2R,3S,5R)-2-((((1S,3S,6R)-6-(5-fluoropyrimidin-2-yl)bicyclo[4.1.0]heptan-3-yl)oxy)methyl)-5-methyl-3-(methylsulfonamido)pyrrolidine-1-carboxylate (137, Peak 3)

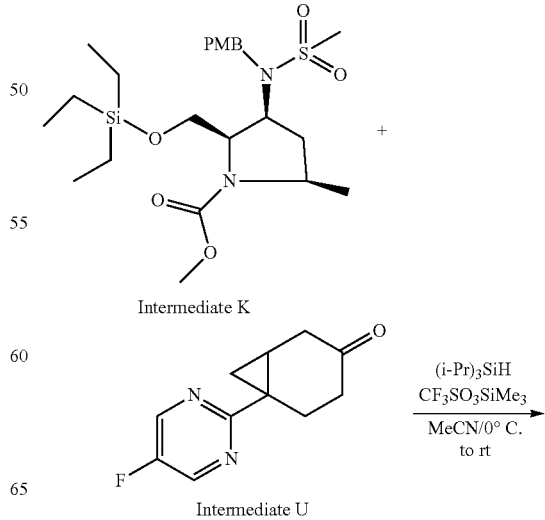

Intermediate K

Intermediate U

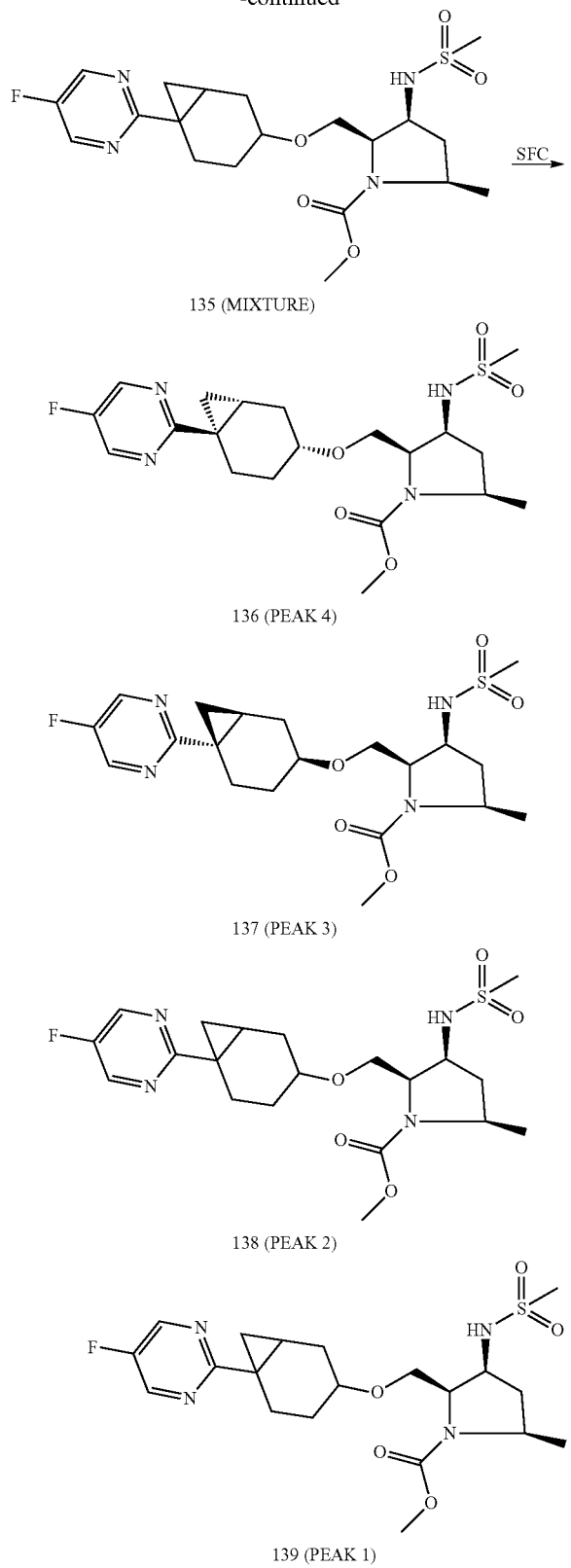

135 (MIXTURE)

136 (PEAK 4)

137 (PEAK 3)

138 (PEAK 2)

139 (PEAK 1)

To a solution of methyl (2R,3S,5R)-3-(N-(4-methoxybenzyl)methylsulfonamido)-5-methyl-2-(((triethylsilyl)oxy)methyl)pyrrolidine-1-carboxylate (INTERMEDIATE K) (369 mg, 0.737 mmol) in Acetonitrile (8.0 ml) at 0° C. was added 6-(5-fluoropyrimidin-2-yl)bicyclo[4.1.0]heptan-3-one (INTERMEDIATE U) (182 mg, 0.884 mmol) followed by triisopropylsilane (0.302 ml, 1.474 mmol) under N2. After stirring 5 mins at 0° C., trimethylsilyl trifluoromethanesulfonate (0.133 ml, 0.737 mmol) was added. The reaction mixture was continued to stir at 0° C. for 30 mins. More triisopropylsilane (0.302 ml, 1.474 mmol) was added. After stirring 5 mins at 0° C., more trimethylsilyl trifluoromethanesulfonate (0.133 ml, 0.737 mmol) was added at 0° C. The reaction mixture was continued to stir at 0° C. for another hour. More triisopropylsilane (0.302 ml, 1.474 mmol) was added at 0° C. After stirring 5 mins at 0° C., more trimethylsilyl trifluoromethanesulfonate (0.133 ml, 0.737 mmol) was added. Kept stirring at 0° C. for 10 mins. Removed ice bath and let it warm up to ambient temperature slowly and stirred at rt overnight. The reaction mixture was quenched with sat. aq. NaHCO$_3$. The reaction mixture was extracted by 2 portions of 10 ml of DCM. The combined organic phase was collected and concentrated to leave yellow oil. The residue was purified by reverse phase HPLC (MeCN/H2O with TFA modifier) to afford the mixture title compound 135 (MIXTURE). MS: 457.1 (M+1). 1H NMR (500 MHz, Methanol-d4) δ 8.56 (s, 4H), 4.18-3.89 (m, 4H), 3.69 (q, J=20.5, 19.7 Hz, 12H), 3.50-3.27 (m, 6H), 2.97 (d, J=36.5 Hz, 7H), 2.74 (s, 1H), 2.61-2.22 (m, 4H), 2.15 (d, J=14.8 Hz, 1H), 2.04-1.39 (m, 12H), 1.33 (s, 4H), 1.12 (d, J=18.3 Hz, 3H), 1.00 (s, 1H), 0.84 (s, 1H).

135 (MIXTURE) was separated by SFC to give 136 (PEAK 4), 137 (PEAK 3), 138 (PEAK 2), and 139 (PEAK 1).

LCMS m/z (M+H): 457.1 required, 457.1 found.
SFC condition:
Step 1:
Column: SFC-B (2×25 cm)
Mobile phase: 12% methanol/CO2
Flow rate: 60 mL/min, 220 nm
ABPR: 100 bar
Step 2:
Column: AD-H (2×15 cm)
Mobile phase: 15% isopropanol/CO2
Flow rate: 65 mL/min, 220 nm
ABPR: 100 bar 136 (PEAK 4): MS: 457.3 (M+1). 1H NMR (500 MHz, Methanol-d4) δ 8.54 (s, 2H), 4.05 (s, 1H), 4.00-3.89 (m, 1H), 3.82 (s, 1H), 3.67 (d, J=29.0 Hz, 5H), 3.00 (s, 3H), 2.76 (t, J=12.8 Hz, 1H), 2.54-2.19 (m, 3H), 1.88 (dd, J=62.7, 10.1 Hz, 2H), 1.73-1.54 (m, 2H), 1.44 (d, J=8.4 Hz, 1H), 1.33 (s, 5H), 1.08-0.94 (m, 1H).

137 (PEAK 3): MS: 457.3 (M+1). 1H NMR (500 MHz, Methanol-d4) δ 8.54 (s, 2H), 4.04 (s, 1H), 3.99-3.89 (m, 1H), 3.82 (s, 1H), 3.70 (s, 5H), 3.00 (s, 3H), 2.74 (t, J=12.8 Hz, 1H), 2.53 (s, 1H), 2.42-2.33 (m, 1H), 2.26 (d, J=11.6 Hz, 1H), 1.85 (dd, J=31.8, 11.2 Hz, 2H), 1.74-1.54 (m, 2H), 1.45 (d, J=8.4 Hz, 1H), 1.31 (d, J=20.4 Hz, 5H), 1.00 (s, 1H).

138 (PEAK 2): MS: 457.2 (M+1). 1H NMR (500 MHz, Methanol-d4) δ 8.54 (s, 2H), 4.04 (s, 1H), 3.99-3.89 (m, 1H), 3.82 (s, 1H), 3.70 (s, 5H), 3.00 (s, 3H), 2.74 (t, J=12.8 Hz, 1H), 2.53 (s, 1H), 2.42-2.33 (m, 1H), 2.26 (d, J=11.6 Hz, 1H), 1.85 (dd, J=31.8, 11.2 Hz, 2H), 1.74-1.54 (m, 2H), 1.45 (d, J=8.4 Hz, 1H), 1.31 (d, J=20.4 Hz, 5H), 1.00 (s, 1H).

139 (PEAK 1): MS: 457.4 (M+1). 1H NMR (500 MHz, Methanol-d4) δ 8.56 (s, 2H), 4.12-3.90 (m, 2H), 3.71 (d, J=33.2 Hz, 6H), 3.00 (s, 4H), 2.38-2.23 (m, 1H), 2.15 (d, J=13.0 Hz, 1H), 1.98-1.67 (m, 4H), 1.55 (d, J=15.8 Hz, 3H), 1.14 (s, 4H), 0.83 (s, 1H).

Example 140, 141, 142, 143 & 144 methyl (2R,3S,5R)-2-(((6-(5-chloropyrimidin-2-yl)bicyclo[4.1.0]heptan-3-yl)oxy)methyl)-5-methyl-3-(methylsulfonamido)pyrrolidine-1-carboxylate (140, Mixture), methyl (2R,3S,5R)-2-((((1R,3R,6S)-6-(5-chloropyrimidin-2-yl)bicyclo[4.1.0]heptan-3-yl)oxy)methyl)-5-methyl-3-(methylsulfonamido)pyrrolidine-1-carboxylate (141, Peak 4), methyl (2R,3S,5R)-2-((((1S,3S,6R)-6-(5-chloropyrimidin-2-yl)bicyclo[4.1.0]heptan-3-yl)oxy)methyl)-5-methyl-3-(methylsulfonamido)pyrrolidine-1-carboxylate (142, Peak 3)

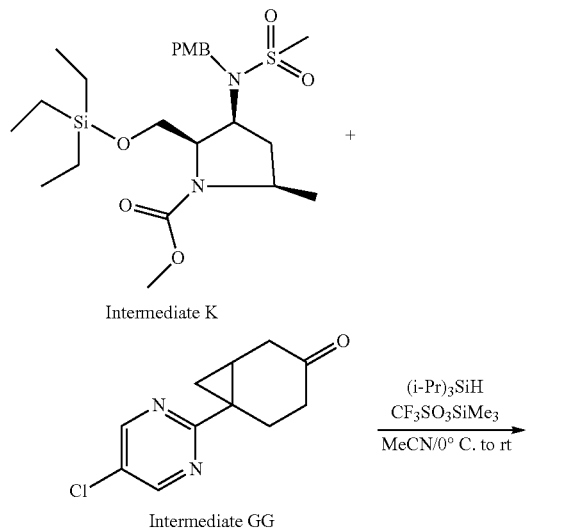

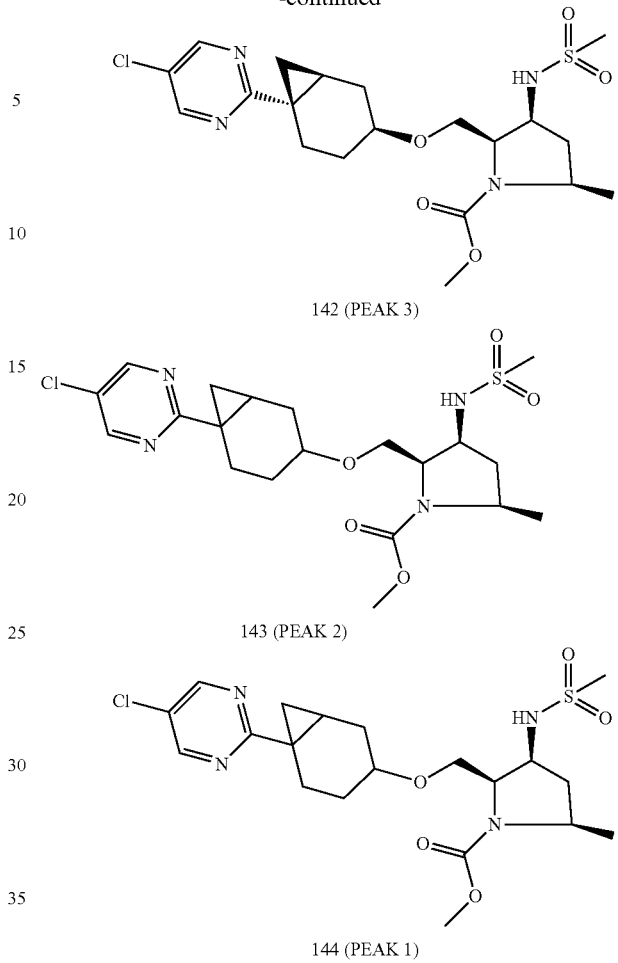

142 (PEAK 3)

143 (PEAK 2)

144 (PEAK 1)

To a solution of methyl (2R,3S,5R)-3-(N-(4-methoxybenzyl)methylsulfonamido)-5-methyl-2-(((triethylsilyl)oxy)methyl)pyrrolidine-1-carboxylate (INTERMEDIATE K) (369 mg, 0.737 mmol) in Acetonitrile (8.0 ml) at 0° C. was added 6-(5-chloropyrimidin-2-yl)bicyclo[4.1.0]heptan-3-one (INTERMEDIATE GG) (189 mg, 0.847 mmol) followed by triisopropylsilane (0.302 ml, 1.474 mmol). After stirring 5 mins at 0° C., trimethylsilyl trifluoromethanesulfonate (0.133 ml, 0.737 mmol) was added. The reaction mixture was continued to stir at 0° C. for 30 mins. More triisopropylsilane (0.302 ml, 1.474 mmol, 2 eq) was added followed by trimethylsilyl trifluoromethanesulfonate (0.133 ml, 0.737 mmol, 1 eq). Kept stirring at 0° C. for another 50 mins. More triisopropylsilane (0.302 ml, 1.474 mmol, 2 eq) was added followed by trimethylsilyl trifluoromethanesulfonate (0.133 ml, 0.737 mmol, 1 eq). Kept stirring at 0° C. for 5 mins and then removed ice bath and let it warm up to rt slowly and stirred at rt overnight. The reaction mixture was quenched with sat. aq. NaHCO$_3$. The reaction mixture was extracted by 2 portions of 20 ml of DCM. The combined organic phase was collected and concentrated. The residue was purified by reverse phase HPLC (MeCN/H2O with TFA modifier) to afford the mixture title compound 140 (MIXTURE). MS: 473.2 (M+1). 1H NMR (500 MHz, Methanol-d4) δ 8.66-8.59 (m, 2H), 4.05 (s, 1H), 4.00-3.89 (m, 1H), 3.88-3.57 (m, 6H), 3.52-3.27 (m, 13H), 3.00 (s, 4H), 2.62-2.10 (m, 3H), 2.00-1.42 (m, 7H), 1.34 (d, J=6.0 Hz, 2H), 1.13 (dd, J=15.8, 5.9 Hz, 2H), 0.96-0.81 (m, 1H).

140 (MIXTURE) was separated by SFC to give 141 (PEAK 4), 142 (PEAK 3), 143 (PEAK 2), and 144 (PEAK 1).
LCMS m/z (M+H): 473.2 required, 473.2 found.
SFC condition:
Step 1:
Column: OJ-H (2×25 cm)
Mobile phase: 20% methanol/CO2
Flow rate: 60 mL/min, 220 nm
ABPR: 100 bar
Step 2:
Column: OD-H (2×15 cm)
Mobile phase: 15% isopropanol/CO2
Flow rate: 60 mL/min, 220 nm
ABPR: 100 bar 141 (PEAK 4): MS: 473.2 (M+1). 1H NMR (500 MHz, Methanol-d4) δ 8.62 (s, 2H), 4.05 (s, 1H), 3.95 (dt, J=12.0, 7.7 Hz, 1H), 3.88-3.77 (m, 1H), 3.76-3.59 (m, 5H), 3.47-3.27 (m, 1H), 3.00 (s, 3H), 2.77 (ddd, J=14.2, 11.8, 5.2 Hz, 1H), 2.53-2.34 (m, 2H), 2.25 (dt, J=14.2, 4.6 Hz, 1H), 2.00-1.90 (m, 1H), 1.82 (q, J=11.5 Hz, 1H), 1.75-1.58 (m, 2H), 1.47 (dd, J=9.5, 3.8 Hz, 1H), 1.40-1.25 (m, 4H), 1.05 (dd, J=6.2, 3.9 Hz, 1H)

142 (PEAK 3): MS: 473.2 (M+1). 1H NMR (500 MHz, Methanol-d4) δ 8.62 (s, 2H), 4.12-4.01 (m, 1H), 3.94 (dt, J=12.0, 7.7 Hz, 1H), 3.88-3.77 (m, 1H), 3.76-3.62 (m, 5H), 3.45-3.28 (m, 1H), 3.00 (s, 3H), 2.75 (ddd, J=14.1, 12.1, 5.2 Hz, 1H), 2.53 (dt, J=14.9, 7.5 Hz, 1H), 2.38 (dt, J=12.0, 7.4 Hz, 1H), 2.24 (dt, J=14.2, 4.5 Hz, 1H), 1.96-1.76 (m, 2H), 1.75-1.59 (m, 2H), 1.48 (dd, J=9.5, 3.8 Hz, 1H), 1.42-1.26 (m, 4H), 1.05 (dd, J=6.2, 3.9 Hz, 1H).

143 (PEAK 2): MS: 473.2 (M+1). 1H NMR (500 MHz, Methanol-d4) δ 8.62 (s, 2H), 4.04 (s, 1H), 3.93 (dt, J=11.8, 7.9 Hz, 1H), 3.82-3.58 (m, 6H), 3.47 (dtd, J=5.9, 4.1, 2.1 Hz, 1H), 3.01-2.87 (m, 4H), 2.32 (dt, J=12.7, 7.7 Hz, 2H), 2.00-1.63 (m, 5H), 1.57-1.43 (m, 2H), 1.11 (d, J=6.0 Hz, 3H), 0.89 (dd, J=6.3, 4.0 Hz, 1H).

144 (PEAK 1): MS: 473.2 (M+1). 1H NMR (500 MHz, Methanol-d4) δ 8.63 (s, 2H), 4.05 (d, J=7.3 Hz, 1H), 3.96 (dt, J=12.0, 7.7 Hz, 1H), 3.82-3.56 (m, 6H), 3.44 (dtd, J=6.6, 4.6, 2.2 Hz, 1H), 3.09 (ddd, J=15.3, 10.1, 5.6 Hz, 1H), 3.00 (s, 3H), 2.29 (dt, J=11.9, 7.4 Hz, 1H), 2.21-2.10 (m, 1H), 1.98-1.68 (m, 4H), 1.67-1.49 (m, 3H), 1.14 (d, J=5.9 Hz, 3H), 0.91-0.84 (m, 1H).

The following examples shown in the table were prepared in an analogous manner of that described above using appropriate starting materials described previously or commercially available.

| Example Number | Structure | IUPAC Name | Observed Mass [M + H]+ |
|---|---|---|---|
| 145 (PEAK 4 from SFC) | 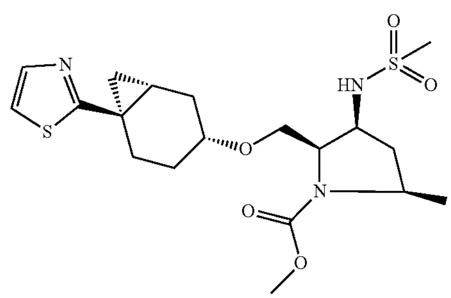 [SMILES: COC(=O)N1[C@H](C)C[C@H](NS(C)(=O)=O)[C@@H]1CO[C@@H]1CC[C@]2(c3nccs3)C[C@@H]2C1] | methyl (2R,3S,5R)-5-methyl-3-(methylsulfonamido)-2-((((1R,3R,6S)-6-(thiazol-2-yl)bicyclo[4.1.0]heptan-3-yl)oxy)methyl)pyrrolidine-1-carboxylate | 444.2 |
| 146 (PEAK 3 from SFC) | 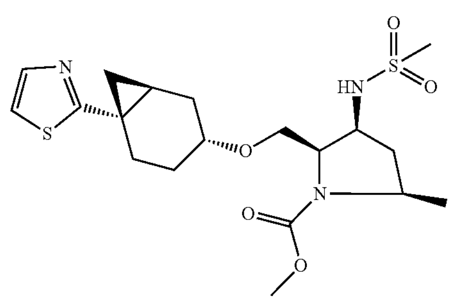 [SMILES: COC(=O)N1[C@H](C)C[C@H](NS(C)(=O)=O)[C@@H]1CO[C@@H]1CC[C@@]2(c3nccs3)C[C@H]2C1] | methyl (2R,3S,5R)-5-methyl-3-(methylsulfonamido)-2-((((1S,3S,6R)-6-(thiazol-2-yl)bicyclo[4.1.0]heptan-3-yl)oxy)methyl)pyrrolidine-1-carboxylate | 444.2 |
| 149 (MIXTURE) | 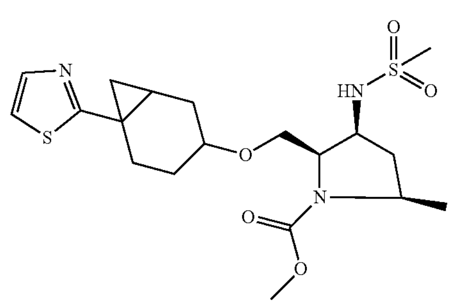 [SMILES: COC(=O)N1[C@H](C)C[C@H](NS(C)(=O)=O)[C@@H]1COC1CCC2(c3nccs3)CC2C1] | methyl (2R,3S,5R)-5-methyl-3-(methylsulfonamido)-2-(((6-(thiazol-2-yl)bicyclo[4.1.0]heptan-3-yl)oxy)methyl)pyrrolidine-1-carboxylate | 444.0 |

-continued

| Example Number | Structure | IUPAC Name | Observed Mass [M + H]⁺ |
|---|---|---|---|
| 150 (PEAK 4 from SFC) | 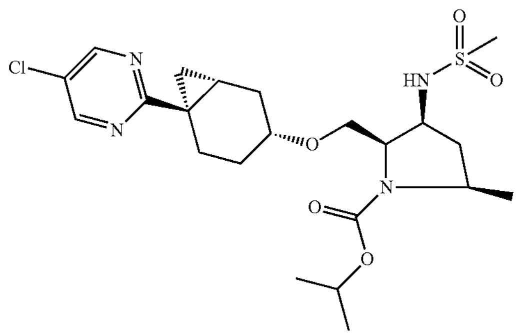 [SMILES: CC(C)OC(=O)N1[C@H](C)C[C@H](NS(C)(=O)=O)[C@@H]1CO[C@@H]1CC[C@]2(c3ncc(Cl)cn3)C[C@@H]2C1] | isopropyl (2R,3S,5R)-2-((((1R,3R,6S)-6-(5-chloropyrimidin-2-yl)bicyclo[4.1.0]heptan-3-yl)oxy)methyl)-5-methyl-3-(methylsulfonamido)pyrrolidine-1-carboxylate | 501.3 |
| 151 (PEAK 3 from SFC) | 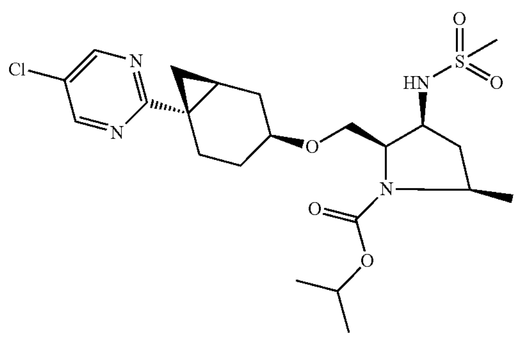 [SMILES: CC(C)OC(=O)N1[C@H](C)C[C@H](NS(C)(=O)=O)[C@@H]1CO[C@H]1CC[C@@]2(c3ncc(Cl)cn3)C[C@H]2C1] | isopropyl (2R,3S,5R)-2-((((1S,3S,6R)-6-(5-chloropyrimidin-2-yl)bicyclo[4.1.0]heptan-3-yl)oxy)methyl)-5-methyl-3-(methylsulfonamido)pyrrolidine-1-carboxylate | 501.3 |
| 154 (MIXTURE) | 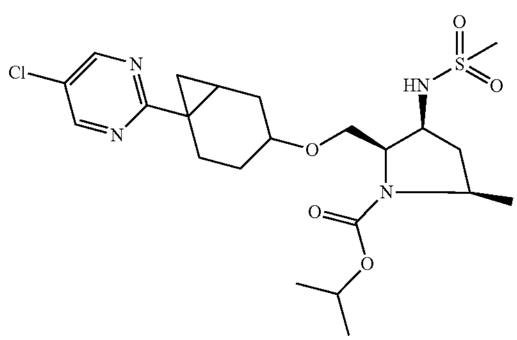 [SMILES: CC(C)OC(=O)N1[C@H](C)C[C@H](NS(C)(=O)=O)[C@@H]1COC1CCC2(c3ncc(Cl)cn3)CC2C1] | isopropyl (2R,3S,5R)-2-(((6-(5-chloropyrimidin-2-yl)bicyclo[4.1.0]heptan-3-yl)oxy)methyl)-5-methyl-3-(methylsulfonamido)pyrrolidine-1-carboxylate | 501.3 |
| 155 (PEAK 4 from SFC) | 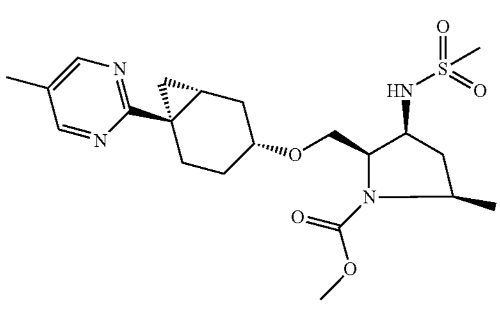 | methyl (2R,3S,5R)-5-methyl-2-(((1R,3R,6S)-6-(5-methylpyrimidin-2-yl)bicyclo[4.1.0]heptan-3-yl)oxy)methyl)-3-(methylsulfonamido)pyrrolidine-1-carboxylate | 453.2 |

-continued

| Example Number | Structure | IUPAC Name | Observed Mass [M + H]+ |
|---|---|---|---|
| 156 (PEAK 3 from SFC) | 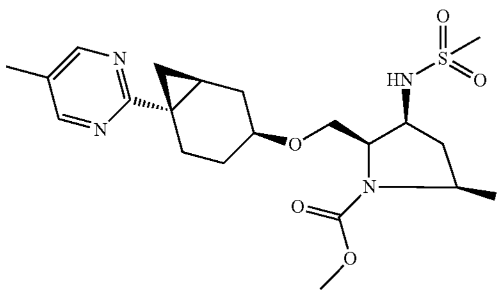 | methyl (2R,3S,5R)-5-methyl-2-((((1S,3S,6R)-6-(5-methylpyrimidin-2-yl)bicyclo[4.1.0]heptan-3-yl)oxy)methyl)-3-(methylsulfonamido)pyrrolidine-1-carboxylate | 453.3 |
| 159 (MIXTURE) | 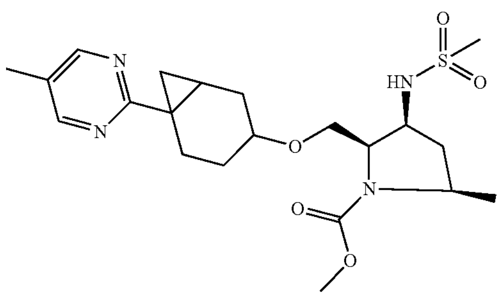 | methyl (2R,3S,5R)-5-methyl-2-(((6-(5-methylpyrimidin-2-yl)bicyclo[4.1.0]heptan-3-yl)oxy)methyl)-3-(methylsulfonamido)pyrrolidine-1-carboxylate | 453.2 |
| 160 (PEAK 4 from SFC) | 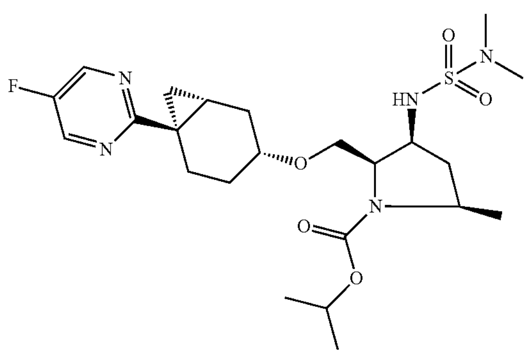 [SMILES: CC(C)OC(=O)N1[C@H](C)C[C@H](NS(=O)(=O)N(C)C)[C@@H]1CO[C@@H]1CC[C@]2(c3ncc(F)cn3)C[C@@H]2C1] | isopropyl (2R,3S,5R)-3-((N,N-dimethylsulfamoyl)amino)-2-((((1R,3R,6S)-6-(5-fluoropyrimidin-2-yl)bicyclo[4.1.0]heptan-3-yl)oxy)methyl)-5-methylpyrrolidine-1-carboxylate | 514.3 |
| 161 (PEAK 3 from SFC) | 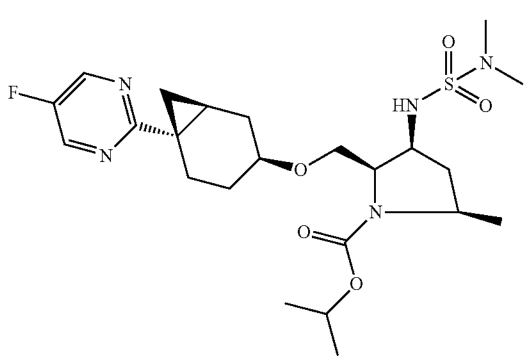 [SMILES: CC(C)OC(=O)N1[C@H](C)C[C@H](NS(=O)(=O)N(C)C)[C@@H]1CO[C@H]1CC[C@@]2(c3ncc(F)cn3)C[C@H]2C1] | isopropyl (2R,3S,5R)-3-((N,N-dimethylsulfamoyl)amino)-2-((((1S,3S,6R)-6-(5-fluoropyrimidin-2-yl)bicyclo[4.1.0]heptan-3-yl)oxy)methyl)-5-methylpyrrolidine-1-carboxylate | 514.4 |

| Example Number | Structure | IUPAC Name | Observed Mass [M + H]+ |
|---|---|---|---|
| 164 (MIXTURE) | 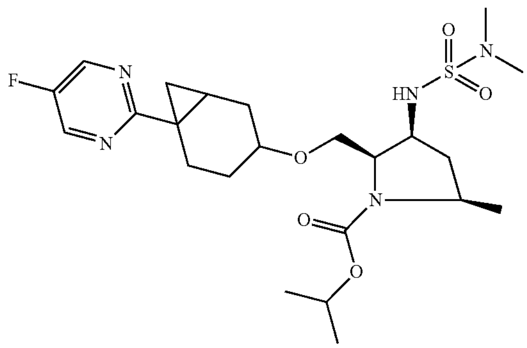 [SMILES: CC(C)OC(=O)N1[C@H](C)C[C@H](NS(=O)(=O)N(C)C)[C@@H]1COC1CCC2(c3ncc(F)cn3)CC2C1] | isopropyl (2R,3S,5R)-3-((N,N-dimethylsulfamoyl)amino)-2-(((6-(5-fluoropyrimidin-2-yl)bicyclo[4.1.0]heptan-3-yl)oxy)methyl)-5-methylpyrrolidine-1-carboxylate | 514.2 |
| 165 (PEAK 4 from SFC) | 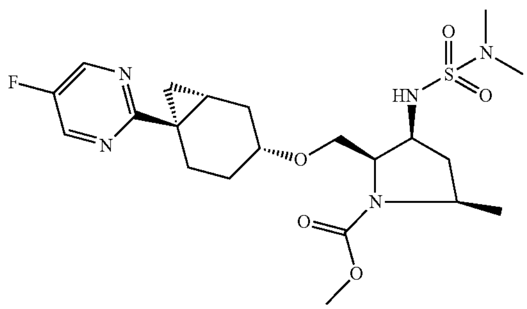 [SMILES: COC(=O)N1[C@H](C)C[C@H](NS(=O)(=O)N(C)C)[C@@H]1CO[C@@H]1CC[C@]2(c3ncc(F)cn3)C[C@@H]2C1] | methyl (2R,3S,5R)-3-((N,N-dimethylsulfamoyl)amino)-2-((((1R,3R,6S)-6-(5-fluoropyrimidin-2-yl)bicyclo[4.1.0]heptan-3-yl)oxy)methyl)-5-methylpyrrolidine-1-carboxylate | 486.3 |
| 166 (PEAK 3 from SFC) | 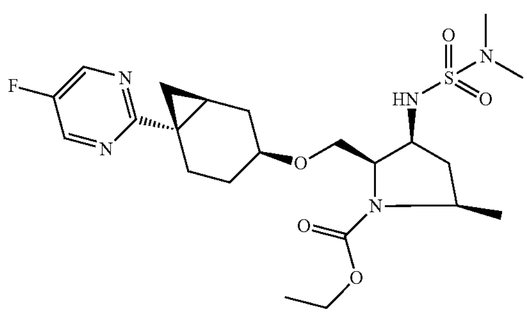 [SMILES: CCOC(=O)N1[C@H](C)C[C@H](NS(=O)(=O)N(C)C)[C@@H]1CO[C@H]1CC[C@@]2(c3ncc(F)cn3)C[C@H]2C1] | methyl (2R,3S,5R)-3-((N,N-dimethylsulfamoyl)amino)-2-((((1S,3S,6R)-6-(5-fluoropyrimidin-2-yl)bicyclo[4.1.0]heptan-3-yl)oxy)methyl)-5-methylpyrrolidine-1-carboxylate | 486.3 |
| 167 (PEAK 2 from SFC) | 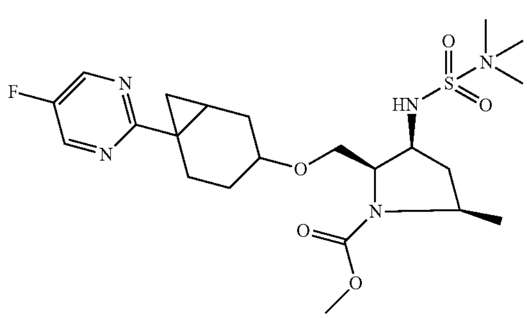 | methyl (2R,3S,5R)-3-((N,N-dimethylsulfamoyl)amino)-2-(((6-(5-fluoropyrimidin-2-yl)bicyclo[4.1.0]heptan-3-yl)oxy)methyl)-5-methylpyrrolidine-1-carboxylate | 486.4 |

-continued

| Example Number | Structure | IUPAC Name | Observed Mass [M + H]+ |
|---|---|---|---|
| 169 (MIXTURE) | 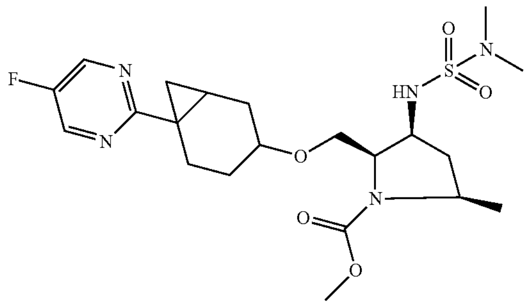 [SMILES: COC(=O)N1[C@H](C)C[C@H](NS(=O)(=O)N(C)C)[C@@H]1COC1CCC2(c3ncc(F)cn3)CC2C1] | methyl (2R,3S,5R)-3-((N,N-dimethylsulfamoyl)amino)-2-(((6-(5-fluoropyrimidin-2-yl)bicyclo[4.1.0]heptan-3-yl)oxy)methyl)-5-methylpyrrolidine-1-carboxylate | 486.3 |
| 170 (PEAK 4 from SFC) | 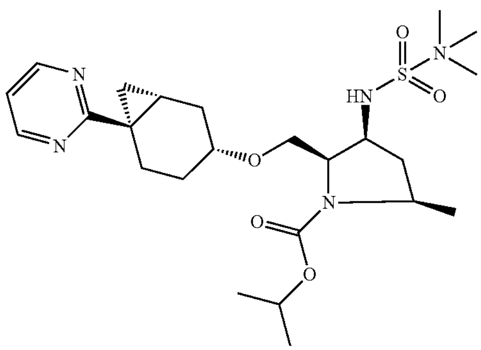 | isopropyl (2R,3S,5R)-3-((N,N-dimethylsulfamoyl)amino)-5-methyl-2-((((1R,3R,6S)-6-(pyrimidin-2-yl)bicyclo[4.1.0]heptan-3-yl)oxy)methyl)pyrrolidine-1-carboxylate | 496.3 |
| 171 (PEAK 3 from SFC) | 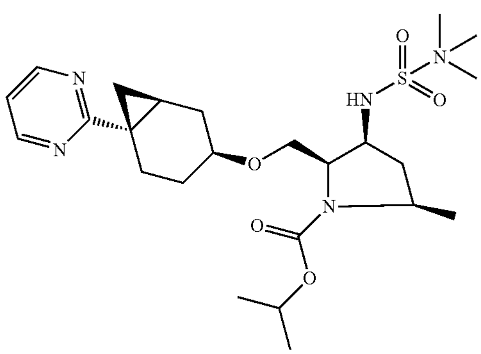 | isopropyl (2R,3S,5R)-3-((N,N-dimethylsulfamoyl)amino)-5-methyl-2-((((1S,3S,6R)-6-(pyrimidin-2-yl)bicyclo[4.1.0]heptan-3-yl)oxy)methyl)pyrrolidine-1-carboxylate | 496.3 |
| 174 (MIXTURE) | 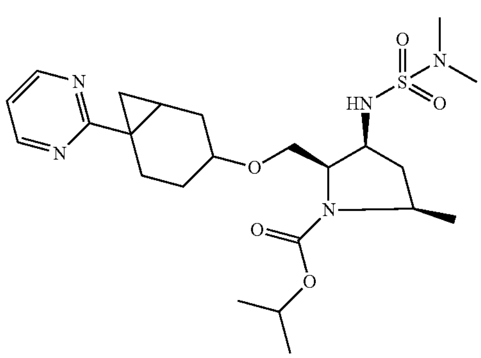 [SMILES: CC(C)OC(=O)N1[C@H](C)C[C@H](NS(=O)(=O)N(C)C)[C@@H]1COC1CCC2(c3ncccn3)CC2C1] | isopropyl (2R,3S,5R)-3-((N,N-dimethylsulfamoyl)amino)-5-methyl-2-(((6-(pyrimidin-2-yl)bicyclo[4.1.0]heptan-3-yl)oxy)methyl)pyrrolidine-1-carboxylate | 496.3 |

-continued

| Example Number | Structure | IUPAC Name | Observed Mass [M + H]+ |
|---|---|---|---|
| 175 (MIXTURE) | 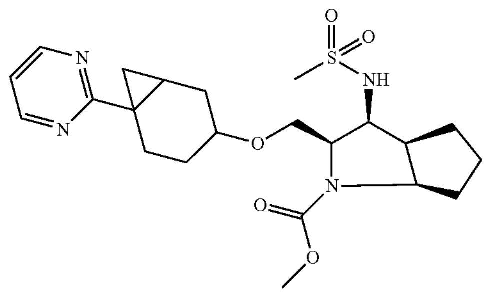 [SMILES: COC(=O)N1[C@@H]2CCC[C@@H]2[C@H](NS(C)(=O)=O)[C@@H]1COC1CCC2(c3ncccn3)CC2C1] | methyl (2R,3S,3aS,6aR)-3-(methylsulfonamide)-2-(((6-(pyrimidin-2-yl)bicyclo[4.1.0]heptan-3-yl)oxy)methyl)hexahydro-cyclopenta[b]pyrrole-1(2H)-carboxylate | 465.3 |
| 176 (PEAK 4 from SFC) | 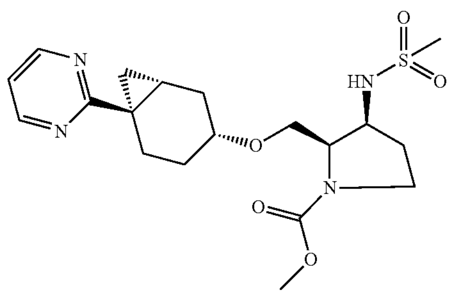 [SMILES: COC(=O)N1CC[C@H](NS(C)(=O)=O)[C@@H]1CO[C@@H]1CC[C@]2(c3ncccn3)C[C@@H]2C1] | methyl (2R,3S)-3-(methylsulfonamido)-2-((((1R,3R,6S)-6-(pyrimidin-2-yl)bicyclo[4.1.0]heptan-3-yl)oxy)methyl)pyrrolidine-1-carboxylate | 425.3 |
| 177 (PEAK 3 from SFC) | 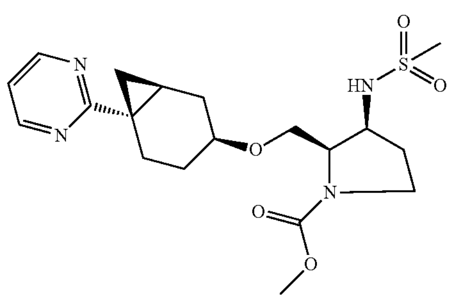 [SMILES: COC(=O)N1CC[C@H](NS(C)(=O)=O)[C@@H]1CO[C@H]1CC[C@@]2(c3ncccn3)C[C@H]2C1] | methyl (2R,3S)-3-(methylsulfonamido)-2-((((1S,3S,6R)-6-(pyrimidin-2-yl)bicyclo[4.1.0]heptan-3-yl)oxy)methyl)pyrrolidine-1-carboxylate | 425.3 |
| 180 (PEAK 4 from SFC) | 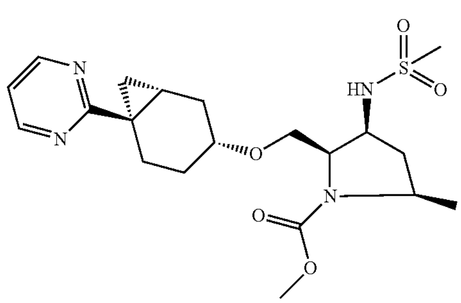 [SMILES: COC(=O)N1[C@H](C)C[C@H](NS(C)(=O)=O)[C@@H]1CO[C@@H]1CC[C@]2(c3ncccn3)C[C@@H]2C1] | methyl (2R,3S,5R)-5-methyl-3-(methylsulfonamido)-2-((((1R,3R,6S)-6-(pyrimidin-2-yl)bicyclo[4.1.0]heptan-3-yl)oxy)methyl)pyrrolidine-1-carboxylate | 439.3 |
| 181 (PEAK 3 from SFC) | 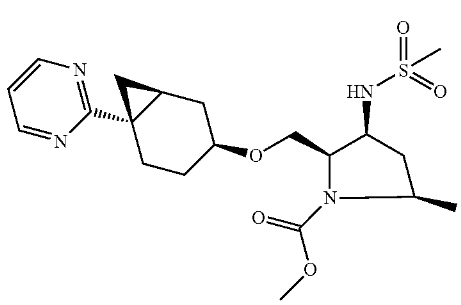 [SMILES: COC(=O)N1[C@H](C)C[C@H](NS(C)(=O)=O)[C@@H]1CO[C@H]1CC[C@@]2(c3ncccn3)C[C@H]2C1] | methyl (2R,3S,5R)-5-methyl-3-(methylsulfonamido)-2-((((1S,3S,6R)-6-(pyrimidin-2-yl)bicyclo[4.1.0]heptan-3-yl)oxy)methyl)pyrrolidine-1-carboxylate | 439.3 |

-continued

| Example Number | Structure | IUPAC Name | Observed Mass [M + H]+ |
|---|---|---|---|
| 183 (PEAK 1 from SFC) | 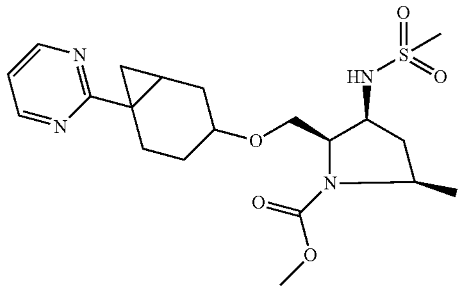 [SMILES: COC(=O)N1[C@H](C)C[C@H](NS(C)(=O)=O)[C@@H]1COC1CCC2(c3ncccn3)CC2C1] | methyl (2R,3S,5R)-5-methyl-3-(methylsulfonamido)-2-(((6-(pyrimidin-2-yl)bicyclo[4.1.0]heptan-3-yl)oxy)methyl)pyrrolidine-1-carboxylate | 439.2 |
| 184 (MIXTURE) | 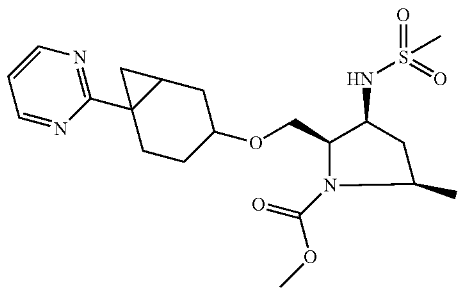 [SMILES: COC(=O)N1[C@H](C)C[C@H](NS(C)(=O)=O)[C@@H]1COC1CCC2(c3ncccn3)CC2C1] | methyl (2R,3S,5R)-5-methyl-3-(methylsulfonamido)-2-(((6-(pyrimidin-2-yl)bicyclo[4.1.0]heptan-3-yl)oxy)methyl)pyrrolidine-1-carboxylate | 439.2 |
| 185 (MIXTURE) | 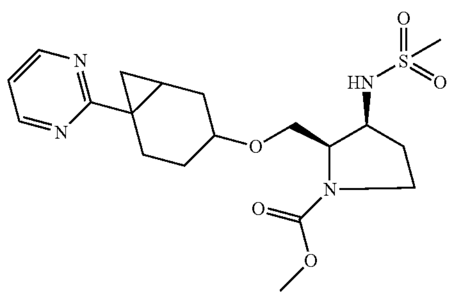 [SMILES: COC(=O)N1CC[C@H](NS(C)(=O)=O)[C@@H]1COC1CCC2(c3ncccn3)CC2C1] | methyl (2R,3S)-3-(methylsulfonamido)-2-(((6-(pyrimidin-2-yl)bicyclo[4.1.0]heptan-3-yl)oxy)methyl)pyrrolidine-1-carboxylate | 425.2 |
| 186 (MIXTURE, PEAK 2 from HPLC) | 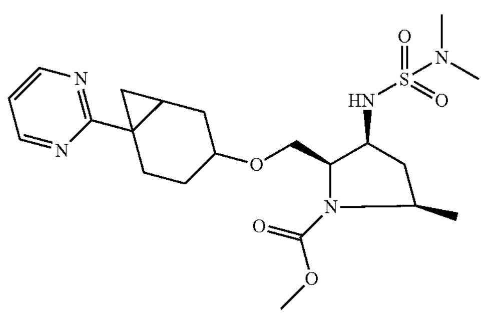 [SMILES: COC(=O)N1[C@H](C)C[C@H](NS(=O)(=O)N(C)C)[C@@H]1COC1CCC2(c3ncccn3)CC2C1] | methyl (2R,3S,5R)-3-((N,N-dimethylsulfamoyl)amino)-5-methyl-2-(((6-(pyrimidin-2-yl)bicyclo[4.1.0]heptan-3-yl)oxy)methyl)pyrrolidine-1-carboxylate | 468.2 |
| 187 (MIXTURE, PEAK 1 from HPLC) | 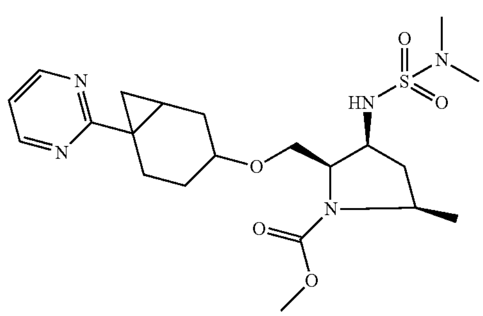 [SMILES: COC(=O)N1[C@H](C)C[C@H](NS(=O)(=O)N(C)C)[C@@H]1COC1CCC2(c3ncccn3)CC2C1] | methyl (2R,3S,5R)-3-((N,N-dimethylsulfamoyl)amino)-5-methyl-2-(((6-(pyrimidin-2-yl)bicyclo[4.1.0]heptan-3-yl)oxy)methyl)pyrrolidine-1-carboxylate | 468.2 |

Example 188, 189, 190, 191, and 192 methyl (2R,3S,5R)-2-(((6-(5-cyanopyrimidin-2-yl)
bicyclo[4.1.0]heptan-3-yl)oxy)methyl)-5-methyl-3-
(methylsulfonamido)pyrrolidine-1-carboxylate (188,
Mixture), methyl (2R,3S,5R)-2-((((1S,3S,6R)-6-(5-
cyanopyrimidin-2-yl)bicyclo[4.1.0]heptan-3-yl)oxy)
methyl)-5-methyl-3-(methylsulfonamido)pyrrolidine-1-carboxylate (190, Peak 3)

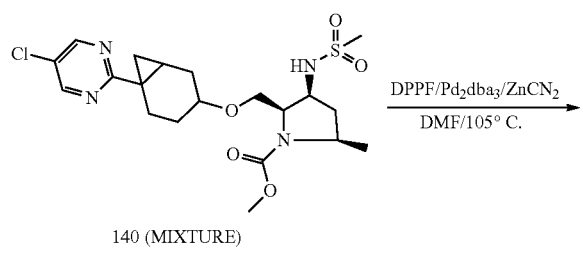

140 (MIXTURE)

DPPF/Pd₂dba₃/ZnCN₂
DMF/105° C.

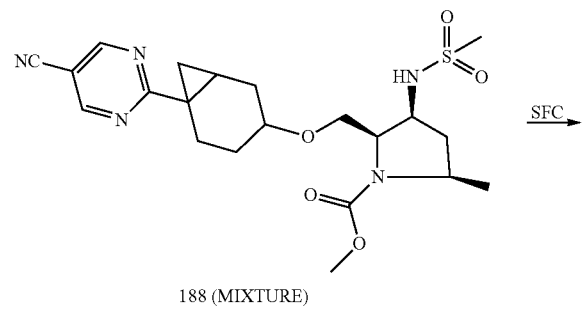

188 (MIXTURE)

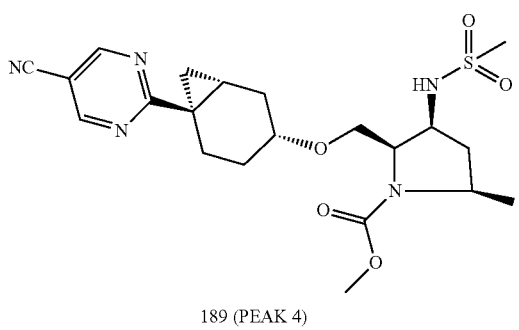 [SMILES: COC(=O)N1[C@H](C)C[C@H](NS(C)(=O)=O)[C@@H]1COC1CCC2(c3ncc(C#N)cn3)CC2C1]

189 (PEAK 4)

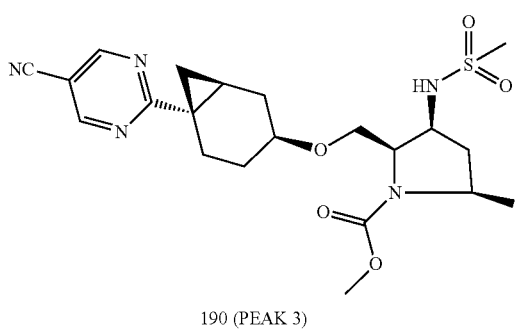

190 (PEAK 3)

-continued

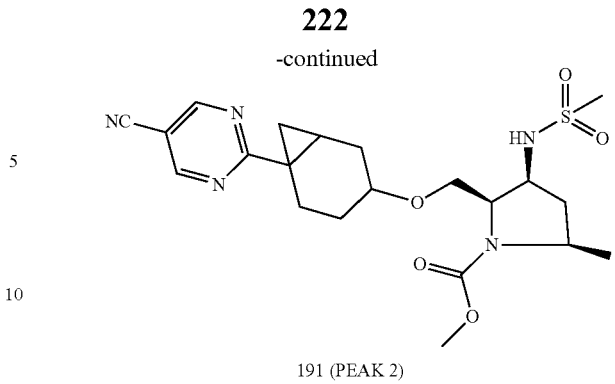

191 (PEAK 2)

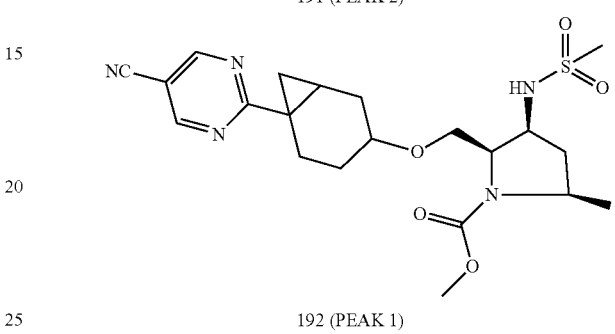

192 (PEAK 1)

To a solution of methyl (2R,3S,5R)-2-((((3S)-6-(5-chloropyrimidin-2-yl)bicyclo[4.1.0]heptan-3-yl)oxy)methyl)-5-methyl-3-(methylsulfonamido)pyrrolidine-1-carboxylate (140, MIXTURE) (194 mg, 0.410 mmol) in DMF (4.5 ml) in the reaction vial was added DPPF (46.9 mg, 0.082 mmol) followed by TRIS(DIBENZYLIDENEACETONE)DIPALLADIUM(0) (37.6 mg, 0.041 mmol) and ZINC CYANIDE (144 mg, 1.230 mmol). Let nitrogen was bubbled through for 5 mins. The reaction mixture was sealed in the reaction vial and heated at 105° C. for 5 days. The reaction mixture was partitioned between water and EtOAc. The aqueous layer was extracted with EtOAc twice. The combined organic phase was collected and concentrated. The residue was purified by prep silica gel TLC (60% EtOAc/hexanes twice) to afford mixture 188 (MIXTURE).

LCMS m/z (M+H): 464.3 required, 464.3 found.

188 (MIXTURE) was separated by SFC to give 189 (PEAK 4), 190 (PEAK 3), 191 (PEAK 2), and 192 (PEAK 1).

LCMS m/z (M+H): 464.3 required, 464.3 found.

SFC condition:
Column: OJ-H (2×25 cm)
Mobile phase: 15% isopropanol/CO2
Flow rate: 60 mL/min, 220 nm
ABPR: 100 bar 189 (PEAK 4): MS: 464.3 (M+1). 1H NMR (500 MHz, Methanol-d4) δ 8.96 (s, 2H), 4.12-4.01 (m, 1H), 3.94 (dt, J=13.3, 7.5 Hz, 1H), 3.81-3.58 (m, 4H), 3.46 (qd, J=5.8, 4.8, 3.5 Hz, 1H), 3.17 (ddd, J=14.8, 9.6, 5.7 Hz, 1H), 3.00 (s, 3H), 2.30 (dt, J=11.9, 7.4 Hz, 1H), 2.15 (dt, J=13.1, 6.2 Hz, 1H), 2.06-1.85 (m, 2H), 1.83-1.53 (m, 4H), 1.44-1.28 (m, 1H), 1.16 (dd, J=13.6, 6.0 Hz, 4H), 1.03 (dd, J=6.5, 3.8 Hz, 1H), 0.99-0.78 (m, 1H).

190 (PEAK 3): MS: 464.3 (M+1). 1H NMR (500 MHz, Methanol-d4) δ 8.95 (s, 2H), 4.04 (s, 1H), 3.98-3.87 (m, 1H), 3.82-3.61 (m, 6H), 3.54-3.46 (m, 1H), 3.05 (ddd, J=14.2, 10.9, 5.7 Hz, 1H), 2.93 (s, 3H), 2.31 (ddd, J=12.9, 7.1, 3.8 Hz, 2H), 1.98-1.73 (m, 4H), 1.66 (dd, J=9.6, 3.8 Hz, 1H), 1.56-1.45 (m, 1H), 1.17 (d, J=6.2 Hz, 2H), 1.13-0.99 (m, 3H).

191 (PEAK 2): MS: 464.3 (M+1). 1H NMR (500 MHz, Methanol-d4) δ 8.95 (s, 2H), 4.10-4.01 (m, 1H), 3.94 (dt, J=12.8, 7.4 Hz, 1H), 3.88-3.77 (m, 1H), 3.75-3.63 (m, 3H), 3.45-3.29 (m, 1H), 3.00 (s, 3H), 2.84 (ddd, J=14.3, 11.6, 5.3 Hz, 1H), 2.52 (dt, J=14.6, 7.8 Hz, 1H), 2.38 (dt, J=12.0, 7.4 Hz, 1H), 2.23 (dt, J=14.3, 4.7 Hz, 1H), 1.94-1.77 (m, 3H), 1.74-1.66 (m, 1H), 1.62 (dd, J=9.6, 3.7 Hz, 1H), 1.45-1.29 (m, 4H), 1.23-1.13 (m, 3H).

192 (PEAK 1): MS: 464.3 (M+1). 1H NMR (500 MHz, Methanol-d4) δ 8.94 (s, 2H), 4.13-4.02 (m, 1H), 3.94 (dt, J=12.7, 7.6 Hz, 1H), 3.88-3.78 (m, 1H), 3.72 (d, J=2.7 Hz, 4H), 3.68-3.60 (m, 1H), 3.44-3.35 (m, 1H), 3.00 (s, 3H), 2.86 (ddd, J=14.5, 11.3, 5.3 Hz, 1H), 2.52-2.33 (m, 2H), 2.23 (dt, J=14.3, 4.8 Hz, 1H), 1.99-1.89 (m, 1H), 1.82 (dt, J=17.3, 9.3 Hz, 2H), 1.69 (ddd, J=13.7, 8.8, 1.8 Hz, 1H), 1.61 (dd, J=9.6, 3.7 Hz, 1H), 1.44-1.26 (m, 4H), 1.25-1.13 (m, 1H).

The following table shows data for representative compounds of the Examples as orexin receptor agonists as determine by assays described herein.

| Example | hOX2R_IP_IC$_{50}$ (nM) | Emax (%) |
|---|---|---|
| 1 | 20.6 | 99.6% |
| 2 | 176 | 100.5% |
| 3 | 186.7 | 99.9% |
| 4 | 604.2 | 97.3% |
| 5 | 278 | 99.8% |
| 6 | 0.94 | 100.7% |
| 7 | 9389 | 39.4% |
| 8 | 7.5 | 95.4% |
| 9 | 28.8 | 99.0% |
| 10 | 323.2 | 85.6% |
| 11 | 146.2 | 96.1% |
| 13 | 461.4 | 82.0% |
| 14 | 160.5 | 93.5% |
| 16 | 16.4 | 102.2% |
| 17 | 2258 | 89.7% |
| 19 | 4.5 | 100.9% |
| 20 | 100.4 | 99.7% |
| 21 | 1625 | 94.6% |
| 24 | 238.2 | 99.8% |
| 25 | 2033 | 94.7% |
| 26 | 11.4 | 100.6% |
| 28 | 3.4 | 102.7% |
| 29 | 8.0 | 102.4% |
| 30 | 0.57 | 99.2% |
| 31 | 3.0 | 101.2% |
| 32 | 8.9 | 102.7% |
| 33 | 5.4 | 105.2% |
| 34 | 34.4 | 96.5% |
| 35 | 46.5 | 100.8% |
| 36 | 0.93 | 102% |
| 37 | 2.1 | 102.6% |
| 38 | 0.90 | 100.5% |
| 39 | 2.0 | 103.3% |
| 40 | 4.4 | 101.8% |
| 41 | 8.0 | 103.7% |
| 42 | 3.0 | 102.8% |
| 43 | 49.3 | 97.82% |
| 44 | 17.4 | 102.6% |
| 45 | 172.8 | 92.66% |
| 46 | 13.4 | 100.5% |
| 47 | 13.8 | 98.4% |
| 48 | 1.4 | 100.8% |
| 49 | 1.1 | 103% |
| 50 | 1.2 | 104.5% |
| 51 | 1.3 | 101.9% |
| 52 | 1.4 | 101.9% |
| 53 | 6.1 | 104.4% |
| 54 | 6.0 | 103.9% |
| 55 | 1.0 | 105.1% |
| 56 | 9.2 | 103.6% |
| 57 | 1.4 | 102.3% |
| 58 | 2.0 | 103% |
| 59 | 0.71 | 103.7% |
| 60 | 1.4 | 103.8% |
| 61 | 2.3 | 103.5% |
| 62 | 1.7 | 100% |
| 63 | 0.77 | 103.7% |
| 64 | 2.1 | 100.9% |
| 65 | 1.6 | 102.4% |
| 66 | 0.60 | 101.4% |
| 67 | 3.4 | 101.2% |
| 68 | 1.5 | 99.7% |
| 69 | 20.4 | 101.2% |
| 70 | 33.5 | 101.3% |
| 71 | 832 | 57.9% |
| 72 | 187 | 91.7% |
| 73 | 220 | 90.7% |
| 74 | 299 | 84.0% |
| 75 | 257 | 89.5% |
| 76 | 51.2 | 101.4% |
| 77 | 736 | 74.5% |
| 78 | 1.2 | 100.8% |
| 79 | 0.86 | 102.8% |
| 81 | 4.5 | 100% |
| 82 | 10.8 | 102.2% |
| 83 | 7.6 | 100.5% |
| 84 | 4.6 | 100.7% |
| 85 | 25.2 | 97.1% |
| 86 | 9.9 | 101.3% |
| 87 | 2.0 | 102.3% |
| 89 | 1.0 | 103.6% |
| 90 | 1.2 | 101% |
| 91 | 3.3 | 101.6% |
| 92 | 775 | 73.2% |
| 93 | 458 | 40.6% |
| 94 | 1.7 | 102.1% |
| 95 | 1.8 | 100.6% |
| 96 | 6.5 | 103% |
| 99 | 2.5 | 102.8% |
| 100 | 1.0 | 100.4% |
| 103 | 4.3 | 101.2% |
| 104 | 34.5 | 101.5% |
| 105 | 233 | 91.7% |
| 107 | 4.5 | 103.7% |
| 108 | 7.4 | 104.6% |
| 109 | 3.5 | 104.8% |
| 110 | 80.9 | 100.9% |
| 111 | 1.0 | 98.5% |
| 112 | 0.78 | 100.4% |
| 113 | 0.60 | 103.4% |
| 114 | 1.4 | 98.6% |
| 115 | 1.1 | 103.1% |
| 116 | 2.3 | 102% |
| 117 | 1.2 | 100.6% |
| 118 | 0.99 | 100.2% |
| 119 | 1.4 | 100% |
| 120 | 2.4 | 101.7% |
| 121 | 0.86 | 108.1% |
| 122 | 6.1 | 104.3% |
| 123 | 4.1 | 102.2% |
| 124 | 0.37 | 99.3% |
| 125 | 0.95 | 103.1% |
| 126 | 3.3 | 104% |
| 127 | 1.7 | 100.7% |
| 128 | 1.8 | 100.4% |
| 129 | 0.90 | 100.8% |
| 130 | 1.4 | 101.1% |
| 131 | 1.8 | 101.4% |
| 132 | 9.7 | 102.8% |
| 133 | 2.6 | 100.7% |
| 134 | 83.7 | 99.7% |
| 135 | 6.3 | 99.5% |
| 136 | 24.5 | 100.9% |
| 137 | 1.4 | 101.1% |
| 140 | 11.1 | 103.1% |
| 141 | 86.4 | 98.7% |
| 142 | 2.8 | 102% |
| 146 | 50.7 | 101.2% |
| 149 | 179 | 96.8% |
| 150 | 19.6 | 101.6% |
| 151 | 4.4 | 101.2% |

225
-continued

| Example | hOX2R_IP_IC$_{50}$ (nM) | Emax (%) |
|---|---|---|
| 154 | 16.9 | 100.6% |
| 155 | 717 | 54.3% |
| 156 | 19.2 | 102.4% |
| 159 | 79.4 | 98.1% |
| 160 | 1.6 | 102.5% |
| 161 | 0.80 | 102.3% |
| 164 | 2.6 | 100% |
| 165 | 3.9 | 100.7% |
| 166 | 0.41 | 99.4% |
| 167 | 575.1 | 74.4% |
| 169 | 1.5 | 100.2% |
| 170 | 5.2 | 99.5% |
| 171 | 2.3 | 101.3% |
| 174 | 7.5 | 95.4% |
| 175 | 22.6 | 99.9% |
| 176 | 2033 | 94.7% |
| 177 | 238 | 99.8% |
| 180 | 100.4 | 99.7% |
| 181 | 4.5 | 100.9% |
| 183 | 2258 | 89.7% |
| 184 | 16.4 | 102.2% |
| 185 | 1625 | 94.6% |
| 186 | 141.7 | 99.5% |
| 187 | 2.1 | 100.0% |
| 188 | 195 | 96.9% |
| 190 | 49.5 | 103% |

With respect to other compounds such as those disclosed in US 2017/0226137, WO 2017/135306, WO 2018/164191, WO 2018/164192, WO 2019/027003, WO 2019/027058, WO2020/122092, WO2020/122093, WO 2020/158958, U.S. Pat. Nos. 9,527,807, 10,287,305, 10,428,023, or 10,508,083, it would be desirable that the present compounds exhibit unexpected properties, such as better drug-like properties and better physical and pharmacokinetic properties. For example, in contrast to compounds of US 2017/0226137, WO 2017/135306, WO 2018/164191, WO 2018/164192, WO 2019/027003, WO 2019/027058, WO2020/122092, WO2020/122093, WO 2020/158958, U.S. Pat. Nos. 9,527,807, 10,287,305, 10,428,023, or 10,508,083, the compounds of the present examples may possess improved potency and/or better metabolic stability and solubility.

As indicated by the data herein, the compounds of the present examples provide unexpected potency as orexin receptor agonists. The distinction in potency as orexin receptor agonists provides greater functional activity and potential for enhanced in vivo efficacy and may provide benefits over other orexin receptor agonists that are known in the art.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:
1. A compound of the formula I:

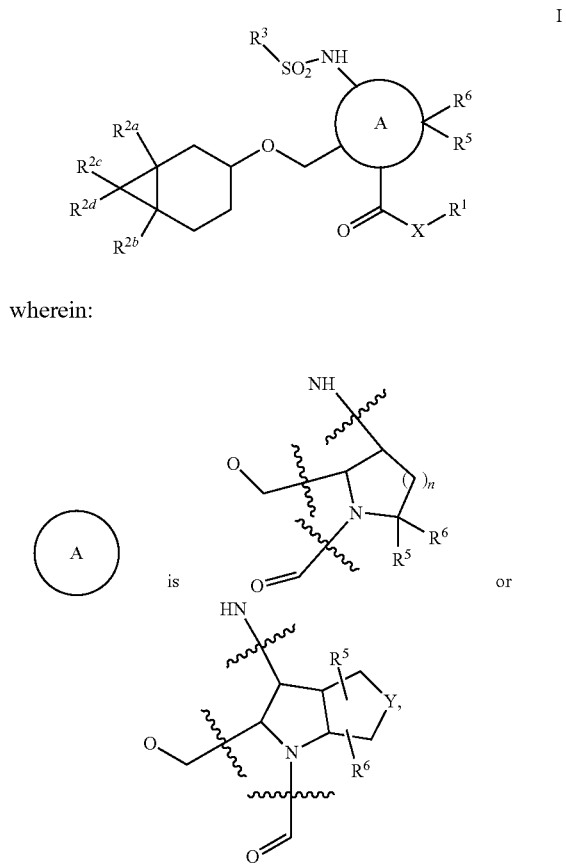

wherein:

wherein n is 0 or 1;
X is —O— or —NH—, or X may be a direct bond to $R^1$;
Y is O or $CH_2$;
$R^1$ is selected from:
(1) —$C_{1-6}$alkyl, where the alkyl is unsubstituted or substituted with one to six substituents independently selected from $R^4$,
(2) —$C_{3-6}$cycloalkyl, where the cycloalkyl is unsubstituted or substituted with one to six substituents independently selected from $R^4$; and
(3) -heterocyclyl, where the heterocyclyl is unsubstituted or substituted with one to three substituents independently selected from $R^4$;
$R^{2a}$ and $R^{2b}$ are selected from:
(1) hydrogen,
(2) —$C_{1-6}$alkyl, where the alkyl is unsubstituted or substituted with one to six substituents independently selected from $R^4$,
(3) —$C_{3-6}$cycloalkyl, where the cycloalkyl is unsubstituted or substituted with one to six substituents independently selected from $R^4$,
(4) -phenyl, where the phenyl is unsubstituted or substituted with one to three substituents independently selected from $R^4$, and
(5) -heteroaryl, where the heteroaryl is selected from: pyridyl, pyrimidinyl, benzothiazolyl, thiazolyl and pyrazinyl, and the heteroaryl is unsubstituted or substituted with one to three substituents independently selected from $R^4$, Provided that at least one of $R^{2a}$ and $R^{2b}$ is hydrogen;
$R^{2c}$ and $R^{2d}$ are independently selected from:
(1) hydrogen, and
(2) fluoro;
$R^3$ is selected from:
(1) —$C_{1-6}$alkyl, where the alkyl is unsubstituted or substituted with one to six substituents independently selected from $R^4$,
(2) —$C_{3-6}$cycloalkyl, where the cycloalkyl is unsubstituted or substituted with one to six substituents independently selected from $R^4$,
(3) -phenyl, where the phenyl is unsubstituted or substituted with one to three substituents independently selected from $R^4$,
(4) —$NR^{10}R^{11}$, wherein $R^{10}$ and $R^{11}$ are independently selected from:
  (a) hydrogen, and
  (b) $C_{1-6}$alkyl, which is unsubstituted or substituted with one to six $R^4$,
(5) -heterocyclyl, where the heterocyclyl is unsubstituted or substituted with one to three substituents independently selected from $R^4$,
(6) —$CHF_2$, and
(7) —$CF_3$;
$R^4$ is independently selected from:
(1) hydroxyl,
(2) halogen,
(3) $C_{1-6}$alkyl, which is unsubstituted or substituted with one to six substituents independently selected from $R^7$,
(4) $C_{2-4}$alkenyl,
(5) $C_{2-4}$alkynyl,
(6) —$C_{3-6}$cycloalkyl, which is unsubstituted or substituted with one to six substituents independently selected from $R^7$,
(7) —O—$C_{1-6}$alkyl, where the alkyl is unsubstituted or substituted with one to six substituents independently selected from $R^7$,
(8) —O(C=O)—$C_{1-6}$alkyl,
(9) —$NH_2$,
(10) —NH—$C_{1-6}$alkyl,
(11) —$NO_2$,
(12) phenyl,
(13) —$CO_2H$,
(14) —$SO_2$—$C_{1-6}$alkyl,
(15) —$C_{3-5}$cycloalkyl($SO_2$),
(16) —CN,
(17) -heterocyclyl, where the heterocyclyl is unsubstituted or substituted with one to three substituents independently selected from $R^7$,
(18) —$CHF_2$, and
(19) —$CF_3$;
$R^5$ and $R^6$ are independently selected from:
(1) hydrogen,
(2) $C_{1-6}$alkyl, where the alkyl is unsubstituted or substituted with one to six substituents independently selected from $R^4$, and
(3) —$C_{3-6}$cycloalkyl, where the cycloalkyl is unsubstituted or substituted with one to six substituents independently selected from $R^4$,
or $R^5$ and $R^6$ are joined together with the carbon atoms to which they are attached to form a —$C_{3-6}$cycloalkyl ring, where the cycloalkyl is unsubstituted or substituted with one to six substituents independently selected from $R^4$;

$R^7$ is independently selected from:
(1) halogen,
(2) $C_{1-6}$alkyl, which is unsubstituted or substituted with one to six substituents independently selected from halo, phenyl or cycloalkyl,
(3) —$CHF_2$, and
(4) —$CF_3$;
or a pharmaceutically acceptable salt thereof.

2. The compound of claim 1, or a pharmaceutically acceptable salt thereof, wherein\

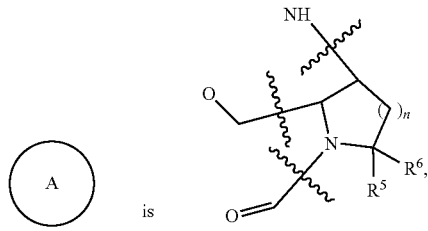

wherein n is 0 or 1.

3. The compound of claim 1, according to formula IA:

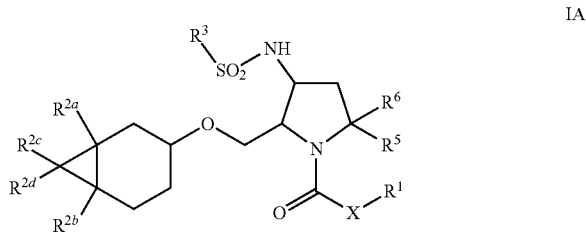

IA wherein:
X is —O— or —NH—, or X may be a direct bond to $R^1$;
$R^1$ is selected from:
(1) —$C_{1-6}$alkyl, where the alkyl is unsubstituted or substituted with one to six substituents independently selected from $R^4$, and
(2) —$C_{3-6}$cycloalkyl, where the cycloalkyl is unsubstituted or substituted with one to six substituents independently selected from $R^4$;
$R^{2a}$ and $R^{2b}$ are selected from:
(1) hydrogen,
(2) —$C_{1-6}$alkyl, where the alkyl is unsubstituted or substituted with one to six substituents independently selected from $R^4$,
(3) —$C_{3-6}$cycloalkyl, where the cycloalkyl is unsubstituted or substituted with one to six substituents independently selected from $R^4$,
(4) -phenyl, where the phenyl is unsubstituted or substituted with one to three substituents independently selected from $R^4$, and
(5) -heteroaryl, where the heteroaryl is selected from: pyridyl, pyrimidinyl, and pyrazinyl, and the heteroaryl is unsubstituted or substituted with one to three substituents independently selected from $R^4$;
Provided that at least one of $R^{2a}$ and $R^{2b}$ is hydrogen;
$R^{2c}$ and $R^{2d}$ are independently selected from:
(1) hydrogen, and
(2) fluoro;

$R^3$ is selected from:
(1) —$C_{1-6}$alkyl, where the alkyl is unsubstituted or substituted with one to six substituents independently selected from $R^4$,
(2) —$C_{3-6}$cycloalkyl, where the cycloalkyl is unsubstituted or substituted with one to six substituents independently selected from $R^4$,
(3) -phenyl, where the phenyl is unsubstituted or substituted with one to three substituents independently selected from $R^4$, and
(4) —$NR^{10}R^{11}$, wherein $R^{10}$ and $R^{11}$ are independently selected from:
  (a) hydrogen, and
  (b) $C_{1-6}$alkyl, which is unsubstituted or substituted with one to six $R^4$;
$R^4$ is independently selected from:
(1) hydroxyl,
(2) halogen,
(3) $C_{1-6}$alkyl, which is unsubstituted or substituted with one to six substituents independently selected from $R^7$,
(4) $C_{2-4}$alkenyl,
(5) $C_{2-4}$alkynyl,
(6) —$C_{3-6}$cycloalkyl, which is unsubstituted or substituted with one to six substituents independently selected from $R^7$,
(7) —O—$C_{1-6}$alkyl, where the alkyl is unsubstituted or substituted with one to six substituents independently selected from $R^7$,
(8) —O(C=O)—$C_{1-6}$alkyl,
(9) —$NH_2$,
(10) —NH—$C_{1-6}$alkyl,
(11) —$NO_2$,
(12) phenyl,
(13) —$CO_2H$,
(14) —$SO_2$—$C_{1-6}$alkyl,
(15) —$C_{3-5}$cycloalkyl($SO_2$),
(16) —CN,
(17) -heterocyclyl, where the heterocyclyl is unsubstituted or substituted with one to three substituents independently selected from $R^7$,
(18) —$CHF_2$, and
(19) —$CF_3$;
$R^5$ and $R^6$ are independently selected from:
(1) hydrogen,
(2) $C_{1-6}$alkyl, where the alkyl is unsubstituted or substituted with one to six substituents independently selected from $R^4$, and
(3) —$C_{3-6}$cycloalkyl, where the cycloalkyl is unsubstituted or substituted with one to six substituents independently selected from $R^4$,
or $R^5$ and $R^6$ are joined together with the carbon atoms to which they are attached to form a —$C_{3-6}$cycloalkyl ring, where the cycloalkyl is unsubstituted or substituted with one to six substituents independently selected from $R^4$;
$R^7$ is independently selected from:
(1) halogen,
(2) $C_{1-6}$alkyl, which is unsubstituted or substituted with one to six substituents independently selected from halo, phenyl or cycloalkyl,
(3) —$CHF_2$, and
(4) —$CF_3$;
or a pharmaceutically acceptable salt thereof.

4. The compound of claim 1 or a pharmaceutically acceptable salt thereof wherein $R^1$ is selected from:
(1) —$C_{1-6}$alkyl, where the alkyl is unsubstituted or substituted with one to three substituents independently selected from hydroxyl, halo, —$C_{3-6}$cycloalkyl, —O—$C_{1-6}$alkyl, —O(C=O)—$C_{1-6}$alkyl, and
(2) —$C_{3-6}$cycloalkyl, where the cycloalkyl is unsubstituted or substituted with one to three substituents independently selected from $R^4$.

5. The compound of claim 1 or a pharmaceutically acceptable salt thereof wherein $R^{2a}$ and $R^{2b}$ are selected from:
(1) hydrogen,
(2) —$C_{1-6}$alkyl, where the alkyl is unsubstituted or substituted with one to three fluoro,
(3) phenyl, which is unsubstituted or substituted with one to three fluoro, —CN, or —$C_{1-6}$ alkyl, where the alkyl is unsubstituted or substituted with one to three fluoro, and
(4) heteroaryl, where the heteroaryl is selected from: pyridyl, pyrimidinyl, benzothiazolyl, thiazolyl and pyrazinyl, and the heteroaryl is unsubstituted or substituted with one to three substituents selected from halo, —$C_{3-6}$cycloalkyl, —O—$C_{1-6}$ alkyl, CN, or —$C_{1-6}$ alkyl, where the alkyl is unsubstituted or substituted with one to three fluoro;
Provided that at least one of $R^{2a}$ and $R^{2b}$ is hydrogen.

6. The compound of claim 1 or a pharmaceutically acceptable salt thereof wherein $R^{2a}$ and $R^{2b}$ are selected from:
(1) hydrogen,
(2) —$CH_2(CH_3)_2$,
(3) —$CF_3$,
(4) —$CH_2CHF_2$,
(5) —$CH_2CF_3$,
(6) pyridyl,
(7) pyrimidinyl,
(8) pyrazinyl,
(9) phenyl,
(10) benzothiazolyl, and
(11) thiazolyl;
Wherein said pyridyl, pyrimidinyl, pyrazinyl, phenyl, benzothiazolyl or thiazolyl is unsubstituted or substituted with halo, —$C_{3-6}$cycloalkyl, —O—$C_{1-6}$alkyl, CN, or —$C_{1-6}$alkyl, where the alkyl is unsubstituted or substituted with one to three fluoro;
Provided that at least one of $R^{2a}$ and $R^{2b}$ is hydrogen.

7. The compound of claim 1 or a pharmaceutically acceptable salt thereof wherein $R^3$ is selected from:
(1) —$C_{1-6}$alkyl, where the alkyl is unsubstituted or substituted with one to four substituents independently selected from $R^4$,
(2) —$C_{3-6}$cycloalkyl, where the cycloalkyl is unsubstituted or substituted with one to four substituents independently selected from $R^4$,
(3) -phenyl, where the phenyl is unsubstituted or substituted with one to three substituents independently selected from $R^4$,
(4) —$NR^{10}R^{11}$, wherein $R^{10}$ and $R^{11}$ are independently selected from:
  (a) hydrogen, and
  (b) $C_{1-6}$alkyl, which is unsubstituted or substituted with one to four $R^4$,
(5) -heterocyclyl, where the heterocyclyl is azetidinyl or oxetanyl and is unsubstituted or substituted with one to three substituents independently selected from $R^4$,
(6) —$CHF_2$, and
(7) —$CF_3$.

8. The compound of claim 1 or a pharmaceutically acceptable salt thereof wherein $R^3$ is —$C_{1-6}$alkyl, where the alkyl is unsubstituted or substituted with one to three fluoro.

9. The compound of claim 1 or a pharmaceutically acceptable salt thereof wherein $R^5$ and $R^6$ are independently selected from:
(1) hydrogen,
(2) methyl,
(3) ethyl,
(4) —CHF$_2$,
(5) —CF$_3$,
(6) —CH$_2$OH,
(7) —CH$_2$OCH$_3$, and
(8) cyclopropyl.

10. The compound of claim 1 or a pharmaceutically acceptable salt thereof wherein $R^5$ is $C_{1-6}$alkyl, where the alkyl is unsubstituted or substituted with one to six substituents independently selected from $R^4$, and $R^6$ is hydrogen.

11. A pharmaceutical composition which comprises an inert carrier and a compound of claim 1 or a pharmaceutically acceptable salt thereof.

12. A method for treating a sleep disorder in a mammalian subject which comprises administering to the patient an effective amount of the compound of claim 1 or a pharmaceutically acceptable salt thereof.

13. A method for treating narcolepsy in a mammalian subject which comprises administering to the patient an effective amount of the compound of claim 1 or a pharmaceutically acceptable salt thereof.

14. A method for treating hypersomnia in a mammalian subject which comprises administering to the patient an effective amount of the compound of claim 1 or a pharmaceutically acceptable salt thereof.

15. A compound which is selected from
methyl (2R,3S,5R)-3-((fluoromethyl)sulfonamido)-2-((((1S,3S,6R)-6-(5-fluoropyrimidin-2-yl)bicyclo[4.1.0]heptan-3-yl)oxy)methyl)-5-methylpyrrolidine-1-carboxylate;
methyl (2R,3S,5R)-2-((((1S,3S,6R)-6-(5-fluoropyrimidin-2-yl)bicyclo[4.1.0]heptan-3-yl)oxy)methyl)-5-methyl-3-((trifluoromethyl)sulfonamido)pyrrolidine-1-carboxylate;
methyl (2R,3S,5R)-3-(ethylsulfonamido)-2-((((1S,3S,6R)-6-(5-fluoropyrimidin-2-yl)bicyclo[4.1.0]heptan-3-yl)oxy)methyl)-5-methylpyrrolidine-1-carboxylate;
methyl (2R,3S,5R)-3-((difluoromethyl)sulfonamido)-2-((((1S,3S,6R)-6-(5-fluoropyrimidin-2-yl)bicyclo[4.1.0]heptan-3-yl)oxy)methyl)-5-methylpyrrolidine-1-carboxylate;
2,2-difluoroethyl (2R,3S,5R)-2-((((1S,3S,6R)-6-(5-fluoropyrimidin-2-yl)bicyclo[4.1.0]heptan-3-yl)oxy)methyl)-5-methyl-3-(methylsulfonamido)pyrrolidine-1-carboxylate;
methyl (2R,3S,5R)-3-((difluoromethyl)sulfonamido)-5-methyl-2-(((6-(pyrimidin-2-yl)bicyclo[4.1.0]heptan-3-yl)oxy)methyl)pyrrolidine-1-carboxylate;
methyl (2R,3S,5R)-3-((difluoromethyl)sulfonamido)-5-methyl-2-((((1S,3S,6R)-6-(pyrimidin-2-yl)bicyclo[4.1.0]heptan-3-yl)oxy)methyl)pyrrolidine-1-carboxylate;
methyl (2R,3S,5R)-3-((difluoromethyl)sulfonamido)-5-methyl-2-((((1R,3R,6S)-6-(pyrimidin-2-yl)bicyclo[4.1.0]heptan-3-yl)oxy)methyl)pyrrolidine-1-carboxylate;
methyl (2R,3S,5 S)-2-((((1S,3S,6R)-6-(5-fluoropyrimidin-yl)bicyclo[4.1.0]heptan-3-yl)oxy)methyl)-5-(methoxymethyl)-3-(methylsulfonamido) pyrrolidine-1-carboxylate;
methyl (2R,3S,5R)-2-(((6-(5-fluoropyrimidin-2-yl)bicyclo[4.1.0]heptan yl)oxy)methyl)-5-methyl-3-(methylsulfonamido)pyrrolidine-1-carboxylate;
methyl (2R,3S,5R)-2-((((1R,3R,6S)-6-(5-fluoropyrimidin yl)bicyclo[4.1.0]heptan-3-yl)oxy)methyl)-5-methyl-3-(methylsulfonamido)pyrrolidine-1-carboxylate;
methyl (2R,3S,5R)-2-((((1S,3S,6R)-6-(5-fluoropyrimidin-2-yl)bicyclo[4.1.0]heptan-3-yl)oxy)methyl)-5-methyl-3-(methylsulfonamido)pyrrolidine-1-carboxylate;
methyl (2R,3S,5R)-2-(((6-(5-chloropyrimidin-2-yl)bicyclo[4.1.0]heptan-3-yl)oxy)methyl)-5-methyl-3-(methylsulfonamido)pyrrolidine-1-carboxylate;
methyl (2R,3S,5R)-2-((((1R,3R,6S)-6-(5-chloropyrimidin-2-yl)bicyclo[4.1.0]heptan-3-yl)oxy)methyl)-5-methyl-3-(methylsulfonamido)pyrrolidine-1-carboxylate;
methyl (2R,3S,5R)-2-((((1S,3S,6R)-6-(5-chloropyrimidin-2-yl)bicyclo[4.1.0]heptan-3-yl)oxy)methyl)-5-methyl-3-(methylsulfonamido)pyrrolidine-1-carboxylate;
methyl (2R,3S,5R)-5-methyl-3-(methylsulfonamido)-2-(((((1R,3R,6S)-6-(thiazol-2-yl)bicyclo[4.1.0]heptan-3-yl)oxy)methyl)pyrrolidine-1-carboxylate;
methyl (2R,3S,5R)-5-methyl-3-(methylsulfonamido)-2-((((1S,3S,6R)-6-(thiazol-2-yl)bicyclo[4.1.0]heptan-3-yl)oxy)methyl)pyrrolidine-1-carboxylate;
methyl (2R,3S,5R)-5-methyl-3-(methylsulfonamido)-2-(((6-(thiazol-2-yl)bicyclo[4.1.0]heptan-3-yl)oxy)methyl)pyrrolidine-1-carboxylate;
methyl (2R,3S,5R)-3-((N,N-dimethylsulfamoyl)amino)-2-((((1R,3R,6S)-6-(5-fluoropyrimidin-2-yl)bicyclo[4.1.0]heptan-3-yl)oxy)methyl)-5-methylpyrrolidine-1-carboxylate;
methyl (2R,3S,5R)-3-((N,N-dimethylsulfamoyl)amino)-2-((((1S,3S,6R)-6-(5-fluoropyrimidin-2-yl)bicyclo[4.1.0]heptan-3-yl)oxy)methyl)-5-methylpyrrolidine-1-carboxylate; and
methyl (2R,3S,5R)-3-((N,N-dimethylsulfamoyl)amino)-2-(((6-(5-fluoropyrimidin-2-yl)bicyclo[4.1.0]heptan-3-yl)oxy)methyl)-5-methylpyrrolidine-1-carboxylate;
or a pharmaceutically acceptable salt thereof.

16. A pharmaceutical composition which comprises an inert carrier and a compound of claim 15 or a pharmaceutically acceptable salt thereof.

17. A method for treating a sleep disorder in a mammalian subject in need which comprises administering to the patient an effective amount of the compound of claim 15 or a pharmaceutically acceptable salt thereof.

18. A method for treating narcolepsy in a mammalian subject in need which comprises administering to the patient an effective amount of the compound of claim 15 or a pharmaceutically acceptable salt thereof.

19. A method for treating hypersomnia in a mammalian subject in need which comprises administering to the patient an effective amount of the compound of claim 15 or a pharmaceutically acceptable salt thereof.

20. A compound having the structure

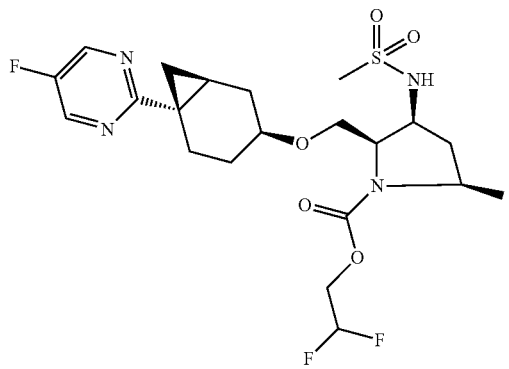 [SMILES: C[C@@H]1C[C@H](NS(C)(=O)=O)[C@H](CO[C@H]2CC[C@@]3(c4ncc(F)cn4)C[C@H]3C2)N1C(=O)OCC(F)F]

2,2-difluoroethyl (2R,3S,5R)-2-((((1S,3S,6R)-6-(5-fluoropyrimidin-2-yl)bicyclo[4.1.0]heptan-3-yl)oxy)methyl)-5-methyl-3-(methylsulfonamido)pyrrolidine-1-carboxylate or a pharmaceutically acceptable salt thereof.

21. The compound of claim 20 with the structure

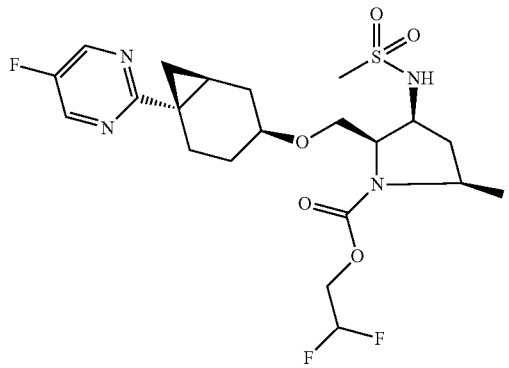 [SMILES: C[C@@H]1C[C@H](NS(C)(=O)=O)[C@H](CO[C@H]2CC[C@@]3(c4ncc(F)cn4)C[C@H]3C2)N1C(=O)OCC(F)F]

2,2-difluoroethyl (2R,3S,5R)-2-((((1S,3S,6R)-6-(5-fluoropyrimidin-2-yl)bicyclo[4.1.0]heptan-3-yl)oxy)methyl)-5-methyl-3-(methylsulfonamido)pyrrolidine-1-carboxylate.

22. A pharmaceutical composition which comprises an inert carrier and a compound of claim 20 or a pharmaceutically acceptable salt thereof.

23. A compound having the structure

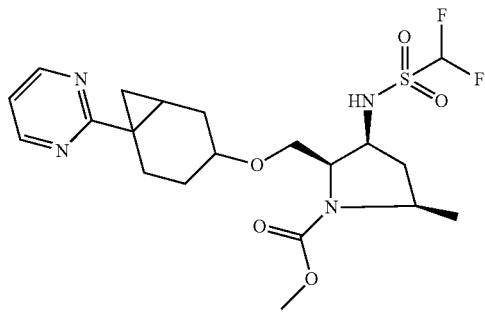 [SMILES: COC(=O)N1[C@H](C)C[C@H](NS(=O)(=O)C(F)F)[C@@H]1COC1CCC2(c3ncccn3)CC2C1]

methyl (2R,3S,5R)-3-((difluoromethyl)sulfonamido)-5-methyl-2-(((6-(pyrimidin-2-yl)bicyclo[4.1.0]heptan-3-yl)oxy)methyl)pyrrolidine-1-carboxylate or a pharmaceutically acceptable salt thereof.

24. The compound of claim 23 having the structure:

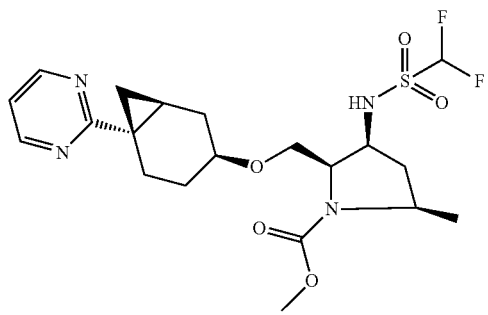 [SMILES: COC(=O)N1[C@H](C)C[C@H](NS(=O)(=O)C(F)F)[C@@H]1CO[C@H]1CC[C@@]2(c3ncccn3)C[C@H]2C1]

methyl (2R,3S,5R)-3-((difluoromethyl)sulfonamido)-5-methyl-2-((((1S,3S,6R)-6-(pyrimidin-2-yl)bicyclo[4.1.0]heptan-3-yl)oxy)methyl)pyrrolidine-1-carboxylate or a pharmaceutically acceptable salt thereof.

25. The compound of claim 23 having the structure:

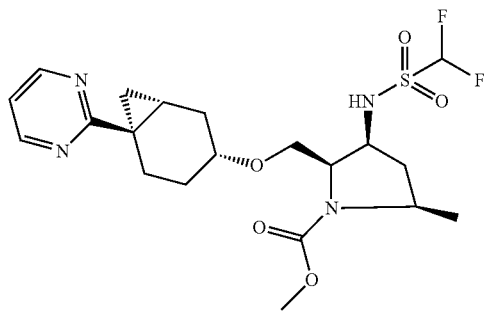 [SMILES: COC(=O)N1[C@H](C)C[C@H](NS(=O)(=O)C(F)F)[C@@H]1CO[C@@H]1CC[C@]2(c3ncccn3)C[C@@H]2C1]

methyl (2R,3S,5R)-3-((difluoromethyl)sulfonamido)-5-methyl-2-((((1R,3R,6S)-6-(pyrimidin-2-yl)bicyclo[4.1.0]heptan-3-yl)oxy)methyl)pyrrolidine-1-carboxylate or a pharmaceutically acceptable salt thereof.

26. The compound of claim 23 having the structure

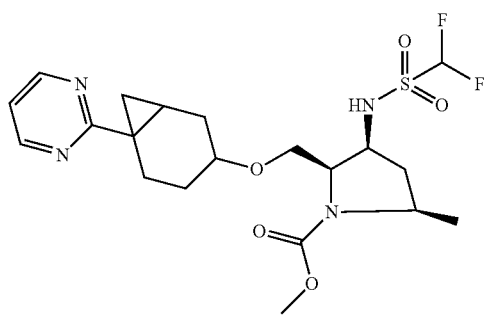 [SMILES: COC(=O)N1[C@H](C)C[C@H](NS(=O)(=O)C(F)F)[C@@H]1COC1CCC2(c3ncccn3)CC2C1]

methyl (2R,3S,5R)-3-((difluoromethyl)sulfonamido)-5-methyl-2-(((6-(pyrimidin-2-yl)bicyclo[4.1.0]heptan-3-yl)oxy)methyl)pyrrolidine-1-carboxylate.

27. A pharmaceutical composition which comprises an inert carrier and a compound of claim 23 or a pharmaceutically acceptable salt thereof.

28. A pharmaceutical composition which comprises an inert carrier and a compound of claim 24 or a pharmaceutically acceptable salt thereof.

29. A pharmaceutical composition which comprises an inert carrier and a compound of claim 25 or a pharmaceutically acceptable salt thereof.

30. A compound having the structure

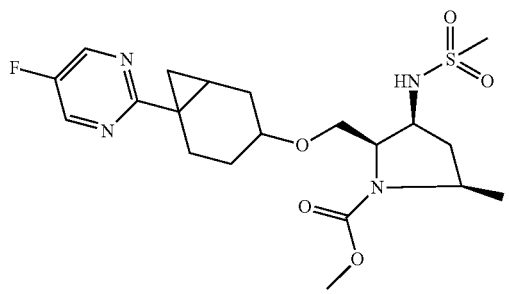 [SMILES: COC(=O)N1[C@H](C)C[C@H](NS(C)(=O)=O)[C@@H]1COC1CCC2(c3ncc(F)cn3)CC2C1]

methyl (2R,3S,5R)-2-((((6-(5-fluoropyrimidin-2-yl)bicyclo[4.1.0]heptan-3-yl)oxy)methyl) methyl-3-(methylsulfonamido)pyrrolidine-1-carboxylate or a pharmaceutically acceptable salt thereof.

31. The compound of claim 30, having the structure

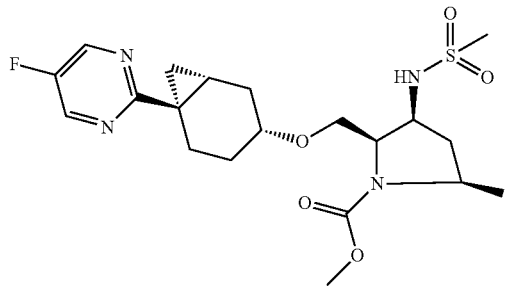 [SMILES: COC(=O)N1[C@H](C)C[C@H](NS(C)(=O)=O)[C@@H]1CO[C@@H]1CC[C@]2(c3ncc(F)cn3)C[C@@H]2C1]

methyl (2R,3S,5R)-2-((((1R,3R,6S)-6-(5-fluoropyrimidin-2-yl)bicyclo[4.1.0]heptan-3-yl)oxy)methyl)-5-methyl-3-(methylsulfonamido)pyrrolidine-1-carboxylate or a pharmaceutically acceptable salt thereof.

32. The compound of claim 30, having the structure

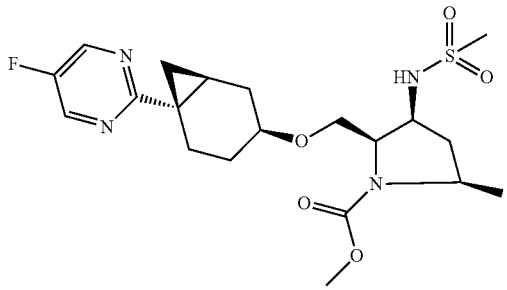 [SMILES: COC(=O)N1[C@H](C)C[C@H](NS(C)(=O)=O)[C@@H]1CO[C@H]1CC[C@@]2(c3ncc(F)cn3)C[C@H]2C1]

methyl (2R,3S,5R)-2-((((1S,3S,6R)-6-(5-fluoropyrimidin-2-yl)bicyclo[4.1.0]heptan-3-yl)oxy)methyl)-5-methyl-3-(methylsulfonamido)pyrrolidine-1-carboxylate or a pharmaceutically acceptable salt thereof.

33. The compound of claim 30, having the structure

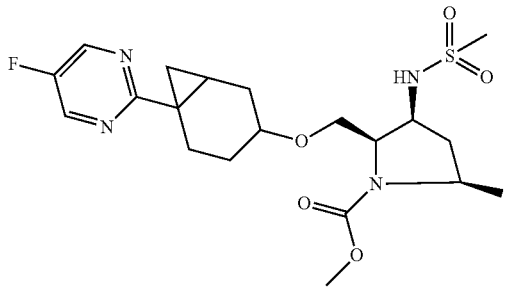 [SMILES: COC(=O)N1[C@H](C)C[C@H](NS(C)(=O)=O)[C@@H]1COC1CCC2(c3ncc(F)cn3)CC2C1]

methyl (2R,3S,5R)-2-(((6-(5-fluoropyrimidin-2-yl)bicyclo[4.1.0]heptan-3-yl)oxy)methyl)-5-methyl-3-(methylsulfonamido)pyrrolidine-1-carboxylate.

34. A pharmaceutical composition which comprises an inert carrier and a compound of claim 30 or a pharmaceutically acceptable salt thereof.

35. A pharmaceutical composition which comprises an inert carrier and a compound of claim 31 or a pharmaceutically acceptable salt thereof.

36. A pharmaceutical composition which comprises an inert carrier and a compound of claim 32 or a pharmaceutically acceptable salt thereof.

37. A pharmaceutical composition which comprises an inert carrier and a compound of claim 33 or a pharmaceutically acceptable salt thereof.

* * * * *